United States Patent
Duffy et al.

(10) Patent No.: US 11,643,397 B2
(45) Date of Patent: *May 9, 2023

(54) PROLYL HYDROXYLASE INHIBITORS

(71) Applicant: GlaxoSmithKline LLC, New Castle, DE (US)

(72) Inventors: Kevin J. Duffy, Collegeville, PA (US); Duke M. Fitch, Collegeville, PA (US); Jian Jin, Collegeville, PA (US); Ronggang Liu, Collegeville, PA (US); Antony N. Shaw, Collegeville, PA (US); Kenneth Wiggall, Collegeville, PA (US)

(73) Assignee: GlaxoSmithKline LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/383,554

(22) Filed: Jul. 23, 2021

(65) Prior Publication Data

US 2021/0347740 A1    Nov. 11, 2021

Related U.S. Application Data

(63) Continuation of application No. 16/455,106, filed on Jun. 27, 2019, now abandoned, which is a continuation of application No. 16/023,058, filed on Jun. 29, 2018, now Pat. No. 10,336,711, which is a continuation of application No. 15/187,075, filed on Jun. 20, 2016, now Pat. No. 10,035,779, which is a continuation of application No. 14/791,152, filed on Jul. 2, 2015, now abandoned, which is a continuation of application No. 14/335,206, filed on Jul. 18, 2014, now abandoned, which is a continuation of application No. 14/026,164, filed on Sep. 13, 2013, now Pat. No. 8,815,884, which is a continuation of application No. 13/667,634, filed on Nov. 2, 2012, now Pat. No. 8,557,834, which is a continuation of application No. 12/305,675, filed as application No. PCT/US2007/071854 on Jun. 22, 2007, now Pat. No. 8,324,208.

(60) Provisional application No. 60/805,602, filed on Jun. 23, 2006.

(51) Int. Cl.
| | |
|---|---|
| *C07D 239/54* | (2006.01) |
| *C07D 239/60* | (2006.01) |
| *A61K 31/515* | (2006.01) |
| *C07D 239/62* | (2006.01) |
| *C07D 401/04* | (2006.01) |
| *C07D 405/04* | (2006.01) |
| *C07D 405/10* | (2006.01) |
| *C07D 409/04* | (2006.01) |
| *C07D 409/10* | (2006.01) |
| *C07D 413/06* | (2006.01) |
| *C07D 413/10* | (2006.01) |
| *C07D 417/10* | (2006.01) |
| *C07D 239/22* | (2006.01) |

(52) U.S. Cl.
CPC .......... *C07D 239/60* (2013.01); *A61K 31/515* (2013.01); *C07D 239/22* (2013.01); *C07D 239/54* (2013.01); *C07D 239/62* (2013.01); *C07D 401/04* (2013.01); *C07D 405/04* (2013.01); *C07D 405/10* (2013.01); *C07D 409/04* (2013.01); *C07D 409/10* (2013.01); *C07D 413/06* (2013.01); *C07D 413/10* (2013.01); *C07D 417/10* (2013.01)

(58) Field of Classification Search
CPC ........................... C07D 239/54; A61K 31/515
USPC ............... 544/122, 299, 300; 514/235.8, 274
See application file for complete search history.

(56) References Cited

U.S. PATENT DOCUMENTS

| | | | |
|---|---|---|---|
| 5,658,933 | A | 8/1997 | Weidmann et al. |
| 7,160,893 | B2 | 1/2007 | Hicks et al. |
| 8,324,208 | B2 | 12/2012 | Duffy et al. |
| 8,557,834 | B2 | 10/2013 | Fitch et al. |
| 8,815,884 | B2 | 8/2014 | Fitch et al. |
| 10,035,779 | B2 | 7/2018 | Fitch et al. |
| 10,336,711 | B2 | 7/2019 | Fitch et al. |

(Continued)

FOREIGN PATENT DOCUMENTS

| | | |
|---|---|---|
| AU | 2018330994 | 3/2019 |
| JP | 2007277096 A | 10/2007 |

(Continued)

OTHER PUBLICATIONS

Bender M.L., et al., "General Basic Catalysis of Ester Hydrolysis and Its Relationship to Enzymatic Hydrolysis 1," *Journal of the American Chemical Society*, 79(7):1656-1662 (1957).

(Continued)

*Primary Examiner* — Deepak R Rao
(74) *Attorney, Agent, or Firm* — Nora L. Stein

(57) ABSTRACT

The invention described herein relates to certain pyrimidinetrione N-substituted glycine derivatives of formula (I)

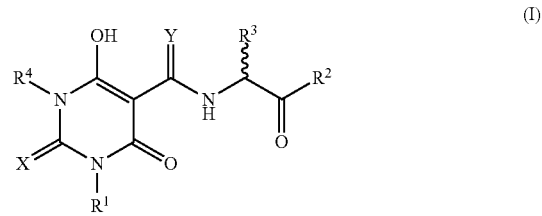

which are antagonists of HIF prolyl hydroxylases and are useful for treating diseases benefiting from the inhibition of this enzyme, anemia being one example.

4 Claims, No Drawings

(56) References Cited

U.S. PATENT DOCUMENTS

| | | |
|---|---|---|
| 2003/0100549 A1 | 5/2003 | Salituro et al. |
| 2003/0114447 A1 | 6/2003 | Choong et al. |
| 2003/0153503 A1 | 8/2003 | Klaus et al. |
| 2005/0020487 A1 | 1/2005 | Klaus et al. |
| 2005/0065145 A1 | 3/2005 | Cao et al. |
| 2006/0276477 A1 | 12/2006 | Klaus et al. |
| 2007/0249550 A1 | 10/2007 | Sitkovsky et al. |
| 2007/0292433 A1 | 12/2007 | Seeley et al. |
| 2007/0293575 A1 | 12/2007 | Seeley et al. |
| 2009/0012059 A1 | 1/2009 | Feng et al. |
| 2009/0170871 A1 | 7/2009 | Busch-Petersen et al. |
| 2009/0176776 A1 | 7/2009 | Prevelige |
| 2010/0003190 A1 | 1/2010 | Kolyada et al. |
| 2014/0024666 A1 | 1/2014 | Fitch et al. |
| 2014/0336383 A1 | 11/2014 | Fitch et al. |
| 2015/0315157 A1 | 11/2015 | Fitch et al. |
| 2016/0297772 A1 | 10/2016 | Fitch et al. |
| 2020/0216399 A1 | 7/2020 | Chen et al. |

FOREIGN PATENT DOCUMENTS

| | | |
|---|---|---|
| WO | WO2003049686 A2 | 6/2003 |
| WO | WO2004108681 A1 | 12/2004 |
| WO | WO2006009054 A1 | 1/2006 |
| WO | WO2008040002 A1 | 4/2008 |
| WO | WO2008089051 A1 | 7/2008 |
| WO | WO2019052133 A1 | 3/2019 |
| WO | WO2020102302 A1 | 5/2020 |

OTHER PUBLICATIONS

U.S. Appl. No. 17/174,006, filed Feb. 11, 2021, Chen, et al.

Bailey et al., PubMed Abstract (Conn Med 67(1):3-5) 2003.

Fu, et al.; Prolyl Hydroxylase EGLN3 Regulates Skeletal Myoblast Differentiation through an NF-kBDependent Pathway; Journal of Biological Chemistry; 2010, 285(12); 8927-8935.

International Search Report and Written Opinion (Translation) for Application No. PCT/CN2018/078766, dated Jun. 2018, 9 pages.

Kakkar, et al., "Isolation and Characterization of Ciprofloxacin-HCL Crystals" Drug Development and Industrial Pharmacy, 23(11): 1063-1067 (1997).

McDonough et al; Cellular Oxygen Sensing: Crystal Structure of Hypoxia-Inducible Factor Prolyl Hydroxylase 9PHD2; PNAS; 2006; 103(26); 9814-9819.

Nurko, Anemia in chronic kidney disease: Causes, diagnosis, treatment, Cleveland Clinic Journal of Medicine, vol. 73, No. 3, pp. 289-297 (2006).

Silverberg,et al; The Use of Subcutaneous Erythropoietin and Intravenous Iron for the Treatment of the Anemia for Severe Resistant Congestive Heart Failure, Improves Cardiac and Renal Function and Functional Cardiac Class and Markedly Reduces Hospitalizations; Journal of American College of Cardiology; 2000; 35(7); 1737-1744.

Tang et al., Anemia in Chronic Heart Failure: Prevalence, Etiology, Clinical Correlates, and Treatment Options, Circulation, 113, pp. 2454-2461 (2006).

Third Party Observation for Application No. EP20180857375 (Publication No. EP3682884), submitted Jan. 11, 2021, and published on EP Register Jan. 22, 2021.

Ulrich; Chapter 4. Crystallization; Kirk-Othmer Encyclopedia of Chemical Technology; 2002; 1-7.

Vippagunta et al.; Crystalline Solids; Advanced Drug Delivery Reviews; 2001; 48; 3-26.

Wang et al., "Recent progress of hypoxia inducible factor-prolyl hydroxylase domain containing enzymes inhibitors." J Int Pharm Res. Apr. 2016; 43(2): 249-259.

West; Solid Solutions; Solid State Chemistiy and Its Applications; 1988; 358, 365.

PROLYL HYDROXYLASE INHIBITORS

CROSS REFERENCE TO PRIOR APPLICATIONS

This application is a Continuation of Ser. No. 16/455,106 filed Jun. 27, 2019, which is Allowed; which is a Continuation of Ser. No. 16/023,058 filed Jun. 29, 2018, which is now U.S. Pat. No. 10,336,711; which is a Continuation of Ser. No. 15/187,075 filed Jun. 20, 2016, which is now U.S. Pat. No. 10,035,779; which is a Continuation of Ser. No. 14/791,152 filed Jul. 2, 2016 which is Abandoned; which is a Continuation of Ser. No. 14/335,206 filed Jul. 18, 2014 which is Abandoned; which is a Continuation of Ser. No. 14/026,164 filed Sep. 13, 2013 which is now U.S. Pat. No. 8,815,884; which is a Continuation of Ser. No. 13/667,634 filed Nov. 2, 2012 which is now U.S. Pat. No. 8,557,834; which is a Continuation of Ser. No. 12/305,675 filed Jan. 13, 2010 which is now U.S. Pat. No. 8,324,208; which is a 371 of PCT/US2007/071854 filed Jun. 22, 2007 which claims the benefit of Provisional Application No. 60/805,602 filed Jun. 23, 2006 which are incorporated herein in their entirety.

FIELD OF THE INVENTION

This invention relates to certain heteroaromatic N-substituted glycine derivatives that are inhibitors of HIF prolyl hydroxylases, and thus have use in treating diseases benefiting from the inhibition of this enzyme, anemia being one example.

BACKGROUND OF THE INVENTION

Anemia occurs when there is a decrease or abnormality in red blood cells, which leads to reduced oxygen levels in the blood. Anemia occurs often in cancer patients, particularly those receiving chemotherapy. Anemia is often seen in the elderly population, patients with renal disease, and in a wide variety of conditions associated with chronic disease.

Frequently, the cause of anemia is reduced erythropoietin (Epo) production resulting in prevention of erythropoiesis (maturation of red blood cells). Epo production can be increased by inhibition of prolyl hydroxylases that regulate hypoxia inducible factor (HIF).

One strategy to increase erythropoietin (Epo) production is to stabilize and thus increase the transcriptional activity of the HIF. HIF-alpha subunits (HIF-1alpha, HIF-2alpha, and HIF-3alpha) are rapidly degraded by proteosome under normoxic conditions upon hydroxylation of proline residues by prolyl hydroxylases (EGLN1, 2, 3). Proline hydroxylation allows interaction with the von Hippel Lindau (VHL) protein, a component of an E3 ubiquitin ligase. This leads to ubiquitination of HIF-alpha and subsequent degradation. Under hypoxic conditions, the inhibitory activity of the prolyl hydroxylases is suppressed, HIF-alpha subunits are therefore stabilized, and HIF-responsive genes, including Epo, are transcribed. Thus, inhibition of prolyl hydroxylases results in increased levels of HIF-alpha and thus increased Epo production.

The compounds of this invention provide a means for inhibiting these hydroxylases, increasing Epo production, and thereby treating anemia. Ischemia, myocardial infarction, stroke, and cytoprotection may also benefit by administering these compounds.

SUMMARY OF THE INVENTION

In the first instance, this invention relates to a compound of formula (I):

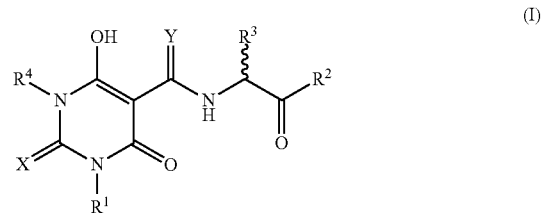

wherein:
$R^1$ and $R^4$ are each independently selected from the group consisting of hydrogen, —$NR^5R^6$, $C_1$-$C_{10}$alkyl, $C_2$-$C_{10}$alkenyl, $C_2$-$C_{10}$alkynyl, $C_3$-$C_8$cycloalkyl, $C_3$-$C_8$cycloalkyl-$C_1$-$C_{10}$alkyl, $C_5$-$C_8$cycloalkenyl, $C_5$-$C_8$cycloalkenyl-$C_1$-$C_{10}$alkyl, $C_3$-$C_8$heterocycloalkyl, $C_3$-$C_8$heterocycloalkyl-$C_1$-$C_{10}$alkyl, aryl, aryl-$C_1$-$C_{10}$alkyl, heteroaryl and heteroaryl-$C_1$-$C_{10}$alkyl;
$R^2$ is —$NR^7R^8$ or —$OR^9$;
$R^3$ is H or $C_1$-$C_4$alkyl;
where $R^5$ and $R^6$ are each independently selected from the group consisting of hydrogen, $C_1$-$C_{10}$alkyl, $C_3$-$C_8$cycloalkyl, $C_3$-$C_8$cycloalkyl-$C_1$-$C_{10}$alkyl, $C_3$-$C_8$heterocycloalkyl, $C_3$-$C_8$heterocycloalkyl-$C_1$-$C_{10}$alkyl, aryl, aryl-$C_1$-$C_{10}$alkyl, heteroaryl, heteroaryl-$C_1$-$C_{10}$alkyl, —$C(O)C_1$-$C_4$alkyl, —$C(O)C_3$-$C_6$cycloalkyl, —$C(O)C_3$-$C_6$heterocycloalkyl, —$C(O)$aryl, —$C(O)$heteroaryl and —$S(O)_2C_1$-$C_4$alkyl, or, when $R^5$ and $R^6$ are attached to the same nitrogen, $R^5$ and $R^6$ taken together with the nitrogen to which they are attached form a 5- or 6- or 7-membered saturated ring optionally containing one other heteroatom selected from oxygen, nitrogen and sulphur,
$R^7$ and $R^8$ are each independently selected from the group consisting of hydrogen, $C_1$-$C_{10}$alkyl, $C_2$-$C_{10}$alkenyl, $C_2$-$C_{10}$alkynyl, $C_3$-$C_8$cycloalkyl, $C_3$-$C_8$heterocycloalkyl, aryl and heteroaryl, and
$R^9$ is H or a cation, or $C_1$-$C_{10}$alkyl which is unsubstituted or substituted with one or more substituents, suitably from 1 to 6 substituents, suitably from 1 to 3 substituents, independently selected from the group consisting of $C_3$-$C_6$cycloalkyl, heterocycloalkyl, aryl and heteroaryl;
X is O or S; and
Y is O or S;
where any carbon or heteroatom of $R^1$, $R^2$, $R^3$, $R^4$, $R^5$, $R^6$, $R^7$, $R^8$, $R^9$ is unsubstituted or, where possible, is substituted with one or more substituents, suitably from 1 to 6 substituents, suitably from 1 to 3 substituents, independently selected from $C_1$-$C_6$alkyl, $C_1$-$C_6$haloalkyl, halogen, —$OR^{10}$, —$NR^5R^6$, oxo, cyano, nitro, —$C(O)R^{10}$, —$C(O)OR^{10}$, —$SR^{10}$, —$S(O)R^{10}$, —$S(O)_2R^{10}$, —$NR^5R^6$, —$CONR^5R^6$, —$N(R^5)C(O)R^{10}$, —$N(R^5)C(O)OR^{10}$, —$OC(O)NR^5R^6$, —$N(R^5)C(O)NR^5R^6$, —$SO_2NR^5R^6$, —$N(R^5)SO_2R^{10}$, $C_2$-$C_{10}$alkenyl, $C_2$-$C_{10}$alkynyl, $C_3$-$C_6$cycloalkyl, $C_3$-$C_6$heterocycloalkyl, aryl, $C_1$-$C_6$alkyl-aryl, heteroaryl and $C_1$-$C_6$alkyl-heteroaryl, wherein $R^1$ and $R^6$ are the same as defined above and R$^{10}$ is selected from hydrogen, C$_1$-C$_{10}$alkyl, C$_2$-C$_{10}$alkenyl, C$_2$-C$_{10}$alkynyl, —C(O) C$_1$-C$_4$alkyl, —C(O)aryl, —C(O)heteroaryl, —C(O) C$_3$-C$_6$cycloalkyl, —C(O)C$_3$-C$_6$heterocycloalkyl, —S(O)$_2$C$_1$-C$_4$alkyl, C$_3$-C$_5$cycloalkyl, C$_3$-C$_5$ heterocycloalkyl, C$_6$-C$_{14}$aryl, aryl-C$_1$-C$_{10}$alkyl, heteroaryl and heteroaryl-C$_1$-C$_{10}$alkyl;

and/or a pharmaceutically acceptable salt or solvate thereof.

In a second aspect of the present invention, there is provided a compound of formula (I) and/or a pharmaceutically acceptable salt or solvate thereof for use in mammalian therapy, including human therapy, e.g. treating amenia. An example of this therapeutic approach is that of a method for treating anemia which is effected by increasing the production of erythropoietin (Epo) by inhibiting HIF prolyl hydroxylases comprising administering a compound of formula (I) and/or a pharmaceutically acceptable salt or solvate thereof, to a patient in need thereof, neat or admixed with a pharmaceutically acceptable excipient or excipients, in an amount sufficient to increase production of Epo.

In a third aspect of the present invention, there is provided a pharmaceutical composition comprising a compound of formula (I), and/or a pharmaceutically acceptable salt or solvate thereof, and one or more of pharmaceutically acceptable carriers, diluents and excipients.

In a fourth aspect, there is provided the use of a compound of formula (I) and/or a pharmaceutically acceptable salt or solvate thereof, in the preparation of a medicament for use in the treatment of a disorder mediated by inhibiting HIF prolyl hydroxylases, such as an anemia, that can be treated by inhibiting HIF prolyl hydroxylases.

In a fifth aspect, there is provided methods of co-administering the presently invented compounds of formula (I) with further active ingredients.

DETAILED DESCRIPTION OF THE INVENTION

For the avoidance of doubt, unless otherwise indicated, the term "substituted" means substituted by one or more defined groups. In the case where groups may be selected from a number of alternative groups the selected groups may be the same or different.

The term "independently" means that where more than one substituent is selected from a number of possible substituents, those substituents may be the same or different.

An "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein the term "alkyl" refers to a straight- or branched-chain hydrocarbon radical having the specified number of carbon atoms, so for example, as used herein, the terms "C$_1$-C$_4$alkyl" and "C$_1$-C$_{10}$ alkyl" refers to an alkyl group having at least 1 and up to 4 or 10 carbon atoms respectively. Examples of such branched or straight-chained alkyl groups useful in the present invention include, but are not limited to, methyl, ethyl, n-propyl, isopropyl, isobutyl, n-butyl, t-butyl, n-pentyl, isopentyl, n-hexyl, n-heptyl, n-octyl, n-nonyl, and n-decyl, and branched analogs of the latter 5 normal alkanes.

When the term "alkenyl" (or "alkenylene") is used it refers to straight or branched hydrocarbon chains containing the specified number of carbon atoms and at least 1 and up to 5 carbon-carbon double bonds. Examples include ethenyl (or ethenylene) and propenyl (or propenylene).

When the term "alkynyl" (or "alkynylene") is used it refers to straight or branched hydrocarbon chains containing the specified number of carbon atoms and at least 1 and up to 5 carbon-carbon triple bonds. Examples include ethynyl (or ethynylene) and propynyl (or propynylene).

"Haloalkyl" refers to an alkyl group that is substituted with one or more halo substituents, suitably from 1 to 6 substituents. Haloalkyl includes trifluoromethyl.

When "cycloalkyl" is used it refers to a non-aromatic, saturated, cyclic hydrocarbon ring containing the specified number of carbon atoms. So, for example, the term "C$_3$-C$_8$cycloalkyl" refers to a non-aromatic cyclic hydrocarbon ring having from three to eight carbon atoms.

Exemplary "C$_3$-C$_8$cycloalkyl" groups useful in the present invention include, but are not limited to, cyclopropyl, cyclobutyl, cyclopentyl, cyclohexyl, cycloheptyl and cyclooctyl.

The term "C$_5$-C$_8$cycloalkenyl" refers to a non-aromatic monocyclic carboxycyclic ring having the specified number of carbon atoms and up to 3 carbon-carbon double bonds. "Cycloalkenyl" includes by way of example cyclopentenyl and cyclohexenyl.

Where "C$_3$-C$_8$heterocycloalkyl" is used, it means a non-aromatic heterocyclic ring containing the specified number of ring atoms being, saturated or having one or more degrees of unsaturation and containing one or more heteroatom substitutions independently selected from O, S and N. Such a ring may be optionally fused to one or more other "heterocyclic" ring(s) or cycloalkyl ring(s). Examples of "heterocyclic" moieties include, but are not limited to, aziridine, thiirane, oxirane, azetidine, oxetane, thietane, tetrahydrofuran, pyran, 1,4-dioxane, 1,3-dioxane, piperidine, piperazine, 2,4-piperazinedione, pyrrolidine, imidazolidine, pyrazolidine, morpholine, thiomorpholine, tetrahydrothiopyran, tetrahydrothiophene, and the like.

"Aryl" refers to optionally substituted monocyclic and polycarbocyclic unfused or fused groups having 6 to 14 carbon atoms and having at least one aromatic ring that complies with Hückel's Rule. Examples of aryl groups are phenyl, biphenyl, naphthyl, anthracenyl, phenanthrenyl and the like.

"Heteroaryl" means an optionally substituted aromatic monocyclic ring or polycarbocyclic fused ring system wherein at least one ring complies with Hückel's Rule, has the specified number of ring atoms, and that ring contains at least one heteroatom independently selected from N, O and S. Examples of "heteroaryl" groups include furanyl, thiophenyl, pyrrolyl, imidazolyl, pyrazolyl, triazolyl, tetrazolyl, thiazolyl, oxazolyl, isoxazolyl, oxadiazolyl, oxo-pyridyl, thiadiazolyl, isothiazolyl, pyridinyl, pyridazinyl, pyrazinyl, pyrimidinyl, quinolinyl, isoquinolinyl, benzofuranyl, benzothiophenyl, indolyl and indazolyl.

The term "optionally" means that the subsequently described event(s) may or may not occur, and includes both event(s), which occur, and events that do not occur.

The term "solvate" refers to a complex of variable stoichiometry formed by a solute and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

Herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

By the term "co-administering" and derivatives thereof as used herein is meant either simultaneous administration or any manner of separate sequential administration of a prolyl hydroxylase inhibiting compound, as described herein, and a further active ingredient or ingredients, known to be useful in treating diseases of the hematopoietic system, particularly anemias, including EPO or a derivative thereof. The term further active ingredient or ingredients, as used herein, includes any compound or therapeutic agent known to or that demonstrates advantageous properties when administered to a patient in need of treatment for diseases of the hematopoietic system, particularly anemias or any compound known to be useful when used in combination with a prolyl hydroxylase inhibiting compound. Preferably, if the administration is not simultaneous, the compounds are administered in a close time proximity to each other. Furthermore, it does not matter if the compounds are administered in the same dosage form, e.g. one compound may be administered topically and another compound may be administered orally.

In certain embodiments, compounds according to Formula I may contain an acidic functional group, one acidic enough to form salts. Representative salts include pharmaceutically-acceptable metal salts such as sodium, potassium, lithium, calcium, magnesium, aluminum, and zinc salts; carbonates and bicarbonates of a pharmaceutically-acceptable metal cation such as sodium, potassium, lithium, calcium, magnesium, aluminum, and zinc; pharmaceutically-acceptable organic primary, secondary, and tertiary amines including aliphatic amines, aromatic amines, aliphatic diamines, and hydroxy alkylamines such as methylamine, ethylamine, 2-hydroxyethylamine, diethylamine, triethylamine, ethylenediamine, ethanolamine, diethanolamine, and cyclohexylamine.

In certain embodiments, compounds according to Formula (I) may contain a basic functional group and are therefore capable of forming pharmaceutically-acceptable acid addition salts by treatment with a suitable acid. Suitable acids include pharmaceutically-acceptable inorganic acids and pharmaceutically-acceptable organic acids. Representative pharmaceutically-acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumnarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate) and napthalene-2-sulfonate.

Compounds of formula (I) that are of particular interest include those wherein:

X is O;

Y is O;

$R^1$ and $R^4$ are each independently selected from the group consisting of hydrogen, $C_1$-$C_{10}$alkyl, $C_2$-$C_{10}$alkenyl, $C_2$-$C_{10}$alkynyl, $C_3$-$C_5$cycloalkyl, $C_3$-$C_8$cycloalkyl-$C_1$-$C_{10}$alkyl, $C_5$-$C_8$cycloalkenyl, $C_5$-$C_8$cycloalkenyl-$C_1$-$C_{10}$alkyl, $C_3$-$C_8$heterocycloalkyl, $C_3$-$C_8$heterocycloalkyl-$C_1$-$C_{10}$alkyl, aryl, aryl-$C_1$-$C_{10}$alkyl, heteroaryl and heteroaryl-$C_1$-$C_{10}$alkyl;

$R^2$ is —$NR^7R^8$ or —$OR^9$;

$R^3$ is H or $C_1$-$C_4$alkyl;

where $R^7$ and Rare each independently selected from the group consisting of hydrogen, $C_1$-$C_{10}$alkyl, $C_2$-$C_{10}$alkenyl, $C_2$-$C_{10}$alkynyl, $C_3$-$C_8$cycloalkyl, $C_3$-$C_8$heterocycloalkyl, aryl and heteroaryl, and $R^9$ is H or a cation, or $C_1$-$C_{10}$alkyl which is unsubstituted or substituted with one or more substituents, suitably from 1 to 6 substituents, suitably from 1 to 3 substituents, independently selected from the group consisting of $C_3$-$C_6$cycloalkyl, heterocycloalkyl, aryl and heteroaryl;

where any carbon or heteroatom of $R^1$, $R^2$, $R^3$, $R^4$, $R^7$, $R^8$, $R^9$ is unsubstituted or, where possible, is substituted with one or more substituents, suitably from 1 to 6 substituents, suitably from 1 to 3 substituents, independently selected from $C_1$-$C_6$alkyl, $C_1$-$C_6$haloalkyl, halogen, —$OR^{10}$, —$NR^5R^6$, oxo, cyano, nitro, —$C(O)R^{10}$, —$C(O)OR^{10}$, —$SR^{10}$, —$S(O)R^{10}$, —$S(O)_2R^{10}$, —$NR^5R^6$, —$CONR^5R^6$, —$N(R^5)C(O)R^{10}$, —$N(R^5)C(O)OR^{10}$, —$OC(O)NR^5R^6$, —$N(R^5)C(O)NR^5R^6$, —$SO_2NR^5R^6$, —$N(R^5)SO_2R^{10}$, $C_2$-$C_{10}$alkenyl, $C_2$-$C_{10}$alkynyl, $C_3$-$C_6$cycloalkyl, $C_3$-$C_6$ heterocycloalkyl, aryl, $C_1$-$C_6$alkyl-aryl, heteroaryl and $C_1$-$C_6$alkyl-heteroaryl, wherein $R^5$, and $R^6$ are the same as defined above and $R^{10}$ is selected from hydrogen, $C_1$-$C_{10}$alkyl, $C_2$-$C_{10}$alkenyl, $C_2$-$C_{10}$alkynyl, —$C(O)C_1$-$C_4$ alkyl, —$C(O)$aryl, —$C(O)$heteroaryl, —$C(O)C_3$-$C_6$cycloalkyl, —$C(O)C_3$-$C_6$heterocycloalkyl, —$S(O)_2C_1$-$C_4$ alkyl, $C_3$-$C_8$cycloalkyl, $C_3$-$C_8$heterocycloalkyl, $C_6$-$C_{14}$aryl, aryl-$C_1$-$C_{10}$alkyl, heteroaryl and heteroaryl-$C_1$-$C_{10}$alkyl;

and/or a pharmaceutically acceptable salt or solvate thereof.

Compounds of formula (I) that are of further interest are those wherein:

X is O;

Y is O;

$R^1$ and $R^4$ are each independently selected from the group consisting of hydrogen, $C_1$-$C_{10}$alkyl, $C_2$-$C_{10}$alkenyl, $C_2$-$C_{10}$alkynyl, $C_3$-$C_8$cycloalkyl, $C_3$-$C_8$cycloalkyl-$C_1$-$C_{10}$alkyl, $C_5$-$C_8$cycloalkenyl, $C_5$-$C_8$cycloalkenyl-$C_1$-$C_{10}$alkyl, $C_3$-$C_8$heterocycloalkyl, $C_3$-$C_8$heterocycloalkyl-$C_1$-$C_{10}$alkyl, aryl, aryl-$C_1$-$C_{10}$alkyl, heteroaryl and heteroaryl-$C_1$-$C_{10}$alkyl;

$R^2$ is —$OR^9$;

$R^3$ is H or $C_1$-$C_4$alkyl;

$R^9$ is H or a cation, or $C_1$-$C_{10}$alkyl which is unsubstituted or is substituted with one or more substituents, suitably from 1 to 6 substituents, suitably from 1 to 3 substituents, independently selected from the group consisting of $C_3$-$C_6$ cycloalkyl, heterocycloalkyl, aryl and heteroaryl;

where any carbon or heteroatom of $R^1$, $R^2$, $R^3$, $R^4$, $R^9$ is unsubstituted or, where possible, is substituted with one or more substituents, suitably from 1 to 6 substituents, suitably from 1 to 3 substituents, independently selected from $C_1$-$C_6$alkyl, $C_1$-$C_6$haloalkyl, halogen, —$OR^{10}$, —$NR^5R^6$, oxo, cyano, nitro, —$C(O)R^{10}$, —$C(O)OR^{10}$, —$SR^{10}$, —$S(O)R^{10}$, —$S(O)_2R^{10}$, —$NR^5R^6$, —$CONR^5R^6$, —$N(R^5)C(O)R^{10}$, —$N(R^5)C(O)OR^{10}$, —$OC(O)NR^5R^6$, —$N(R^5)C(O)NR^5R^6$, —$SO_2NR^5R^6$, —$N(R^5)SO_2R^{10}$, $C_2$-$C_{10}$ alkenyl, $C_2$-$C_{10}$ alkynyl, $C_3$-$C_6$cycloalkyl, $C_3$-$C_6$ heterocycloalkyl, aryl, $C_1$-$C_6$alkyl-aryl, heteroaryl and $C_1$-$C_6$ alkyl-heteroaryl, wherein $R^5$, and $R^6$ are the same as defined above and $R^{10}$ is selected from hydrogen, $C_1$-$C_{10}$alkyl, $C_2$-$C_{10}$alkenyl, $C_2$-$C_{10}$alkynyl, —$C(O)C_1$-$C_4$alkyl, —$C(O)$aryl, —$C(O)$heteroaryl, —$C(O)C_3$-$C_6$cycloalkyl, —$C(O)C_3$-$C_6$heterocycloalkyl, —$S(O)_2C_1$-$C_4$alkyl, $C_3$-$C_5$cycloalkyl, $C_3$-$C_5$heterocycloalkyl, $C_6$-$C_{14}$aryl, aryl-$C_1$-$C_{10}$alkyl, heteroaryl and heteroaryl-$C_1$-$C_{10}$alkyl;

and/or a pharmaceutically acceptable salt or solvate thereof.

Of further interest are those compounds of formula (I) where:

X is O;

Y is O;

$R^1$ and $R^4$ are each independently selected from the group consisting of hydrogen, $C_1$-$C_{10}$alkyl, $C_2$-$C_{10}$alkenyl, $C_2$-$C_{10}$alkynyl, $C_3$-$C_8$cycloalkyl, $C_3$-$C_8$cycloalkyl-$C_1$-$C_{10}$alkyl, $C_5$-$C_8$cycloalkenyl, $C_5$-$C_8$cycloalkenyl-$C_1$-$C_{10}$alkyl, $C_3$-$C_8$heterocycloalkyl, $C_3$-$C_8$heterocycloalkyl-$C_1$-$C_{10}$alkyl, aryl, aryl-$C_1$-$C_{10}$alkyl, heteroaryl and heteroaryl-$C_1$-$C_{10}$alkyl;

$R^2$ is —$OR^9$;

$R^3$ is H;

$R^9$ is H or a cation;

where any carbon or heteroatom of $R^1$, $R^2$, $R^3$, $R^4$ is unsubstituted or, where possible, is substituted with one or more substituents, suitably from 1 to 6 substituents, suitably from 1 to 3 substituents, independently selected from $C_1$-$C_6$alkyl, $C_1$-$C_6$haloalkyl, halogen, —$OR^{10}$, —$NR^5R^6$, oxo, cyano, nitro, —$C(O)R^{10}$, —$C(O)OR^{10}$, —$SR^{10}$, —$S(O)R^{10}$, —$S(O)_2R^{10}$, —$NR^5R^6$, —$CONR^5R^6$, —$N(R^5)C(O)R^{10}$, —$N(R^5)C(O)OR^{10}$, —$OC(O)NR^5R^6$, —$N(R^5)C(O)NR^5R^6$, —$SO_2NR^5R^6$, —$N(R^5)SO_2R^{10}$, $C_2$-$C_{10}$alkenyl, $C_2$-$C_{10}$alkynyl, $C_3$-$C_6$cycloalkyl, $C_3$-$C_6$heterocycloalkyl, aryl, $C_1$-$C_6$alkyl-aryl, heteroaryl and $C_1$-$C_6$ alkyl-heteroaryl, wherein $R^5$, and $R^6$ are the same as defined above and $R^{10}$ is selected from hydrogen, $C_1$-$C_{10}$alkyl, $C_2$-$C_{10}$alkenyl, $C_2$-$C_{10}$alkynyl, —$C(O)C_1$-$C_4$alkyl, —$C(O)$aryl, —$C(O)$heteroaryl, —$C(O)C_3$-$C_6$cycloalkyl, —$C(O)C_3$-$C_6$heterocycloalkyl, —$S(O)_2C_1$-$C_4$ alkyl, $C_3$-$C_8$ cycloalkyl, $C_3$-$C_8$heterocycloalkyl, $C_6$-$C_{14}$ aryl, aryl-$C_1$-$C_{10}$alkyl, heteroaryl and heteroaryl-$C_1$-$C_{10}$alkyl;

and/or a pharmaceutically acceptable salt or solvate thereof.

Specific compounds that are exemplified herein and that are useful in the present invention are:

N-{[1-(4-chlorophenyl)-6-hydroxy-2,4-dioxo-3-(phenylmethyl)-1,2,3,4-tetrahydro-5-pyrimidinyl]carbonyl}glycine;

N-{[1-{[2,4-bis(methyloxy)phenyl]methyl}-6-hydroxy-2,4-dioxo-3-(phenylmethyl)-1,2,3,4-tetrahydro-5-pyrimidinyl]carbonyl}glycine;

N-{[1-(4-chlorophenyl)-6-hydroxy-4-oxo-3-(phenylmethyl)-2-thioxo-1,2,3,4-tetrahydro-5-pyrimidinyl]carbonyl}glycine;

N-({6-hydroxy-2,4-dioxo-3-(phenylmethyl)-1-[3-(trifluoromethyl)phenyl]-1,2,3,4-tetrahydro-5-pyrimidinyl}carbonyl)glycine;

N-{[6-hydroxy-2,4-dioxo-3-(phenylmethyl)-1,2,3,4-tetrahydro-5-pyrimidinyl]carbonyl}glycine;

N-{[6-hydroxy-2,4-dioxo-1-phenyl-3-(phenylmethyl)-1,2,3,4-tetrahydro-5-pyrimidinyl]carbonyl}glycine;

N-[(1-(1,1-dimethylethyl)-3-{[4-(1,1-dimethylethyl)phenyl]methyl}-6-hydroxy-2,4-dioxo-1,2,3,4-tetrahydro-5-pyrimidinyl)carbonyl]glycine;

N-{[6-Hydroxy-2,4-dioxo-3-(phenylmethyl)-1-(2-pyridinyl)-1,2,3,4-tetrahydro-5-pyrimidinyl]carbonyl}glycine;

N-{[6-Hydroxy-1-(2-nitrophenyl)-2,4-dioxo-3-(phenylmethyl)-1,2,3,4-tetrahydro-5-pyrimidinyl]carbonyl}glycine;

N-{[1-Cyclohexyl-6-hydroxy-2,4-dioxo-3-(phenylmethyl)-1,2,3,4-tetrahydro-5-pyrimidinyl]carbonyl}glycine;

N-{[1-[(3-Cyanophenyl)methyl]-6-hydroxy-2,4-dioxo-3-(phenylmethyl)-1,2,3,4-tetrahydro-5-pyrimidinyl]carbonyl}glycine;

N-[(6-Hydroxy-2,4-dioxo-3-(phenylmethyl)-1-{[4-(trifluoromethyl)phenyl]methyl}-1,2,3,4-tetrahydro-5-pyrimidinyl)carbonyl]glycine;

N-{[1-[(3,4-Dichlorophenyl)methyl]-6-hydroxy-2,4-dioxo-3-(phenylmethyl)-1,2,3,4-tetrahydro-5-pyrimidinyl]carbonyl}glycine;

N-{[6-Hydroxy-1-{[3-(methyloxy)phenyl]methyl}-2,4-dioxo-3-(phenylmethyl)-1,2,3,4-tetrahydro-5-pyrimidinyl]carbonyl}glycine;

N-{[1-[(2,6-Dichlorophenyl)methyl]-6-hydroxy-2,4-dioxo-3-(phenylmethyl)-1,2,3,4-tetrahydro-5-pyrimidinyl]carbonyl}glycine;

N-{[6-Hydroxy-1-methyl-2,4-dioxo-3-(phenylmethyl)-1,2,3,4-tetrahydro-5-pyrimidinyl]carbonyl}glycine;

N-{[1-Cyclohexyl-3-(2-cyclopropylethyl)-6-hydroxy-2,4-dioxo-1,2,3,4-tetrahydro-5-pyrimidinyl]carbonyl}glycine;

N-[(1,3-Dicyclohexyl-6-hydroxy-2,4-dioxo-1,2,3,4-tetrahydro-5-pyrimidinyl)carbonyl]glycine;

N-{[1-Hexyl-6-hydroxy-2,4-dioxo-3-(phenylmethyl)-1,2,3,4-tetrahydro-5-pyrimidinyl]carbonyl}glycine;

N-{[1-Ethyl-6-hydroxy-2,4-dioxo-3-(phenylmethyl)-1,2,3,4-tetrahydro-5-pyrimidinyl]carbonyl}glycine;

N-{[6-Hydroxy-2,4-dioxo-3-(phenylmethyl)-1-propyl-1,2,3,4-tetrahydro-5-pyrimidinyl]carbonyl}glycine;

N-{[1-Butyl-6-hydroxy-2,4-dioxo-3-(phenylmethyl)-1,2,3,4-tetrahydro-5-pyrimidinyl]carbonyl}glycine;

N-{[6-Hydroxy-2,4-dioxo-1-(2-phenylethyl)-3-(phenylmethyl)-1,2,3,4-tetrahydro-5-pyrimidinyl]carbonyl}glycine;

N-{[3-{[4-(1,1-Dimethylethyl)phenyl]methyl}-6-hydroxy-1-(1-methylethyl)-2,4-dioxo-1,2,3,4-tetrahydro-5-pyrimidinyl]carbonyl}glycine;

N-[(1-cyclohexyl-3-{[4-(1,1-dimethylethyl)phenyl]methyl}-6-hydroxy-2,4-dioxo-1,2,3,4-tetrahydro-5-pyrimidinyl)carbonyl]glycine;

N-{[6-Hydroxy-1,3-bis(1-methylethyl)-2,4-dioxo-1,2,3,4-tetrahydro-5-pyrimidinyl]carbonyl}glycine;

N-{[3-[(2-Bromophenyl)methyl]-1-(1,1-dimethylethyl)-6-hydroxy-2,4-dioxo-1,2,3,4-tetrahydro-5-pyrimidinyl]carbonyl}glycine;

N-[(1-(2,6-Dichlorophenyl)-3-{[4-(1,1-dimethylethyl)phenyl]methyl}-6-hydroxy-2,4-dioxo-1,2,3,4-tetrahydro-5-pyrimidinyl)carbonyl]glycine;

N-[(1-(2,4-dichlorophenyl)-3-{[4-(1,1-dimethylethyl)phenyl]methyl}-6-hydroxy-2,4-dioxo-1,2,3,4-tetrahydro-5-pyrimidinyl)carbonyl]glycine;

N-[(1-(2-Bromophenyl)-3-{[4-(1,1-dimethylethyl)phenyl]methyl}-6-hydroxy-2,4-dioxo-1,2,3,4-tetrahydro-5-pyrimidinyl)carbonyl]glycine;

N-[(1-(2-Biphenylyl)-3-{[4-(1,1-dimethylethyl)phenyl]methyl}-6-hydroxy-2,4-dioxo-1,2,3,4-tetrahydro-5-pyrimidinyl)carbonyl]glycine;

N-{[6-Hydroxy-2,4-dioxo-3-(phenylmethyl)-1-(tetrahydro-2H-pyran-4-yl)-1,2,3,4-tetrahydro-5-pyrimidinyl]carbonyl}glycine;

N-{[3-Cyclohexyl-6-hydroxy-2,4-dioxo-1-(tetrahydro-2H-pyran-4-yl)-1,2,3,4-tetrahydro-5-pyrimidinyl]carbonyl}glycine;

N-{[3-{[4-(1,1-Dimethylethyl)phenyl]methyl}-6-hydroxy-2,4-dioxo-1-(2-thienyl)-1,2,3,4-tetrahydro-5-pyrimidinyl]carbonyl}glycine;

N-({1-Cyclohexyl-6-hydroxy-3-[3-(4-morpholinyl)propyl]-2,4-dioxo-1,2,3,4-tetrahydro-5-pyrimidinyl}carbonyl)glycine;

N-{[3-{[4-(1,1-Dimethylethyl)phenyl]methyl}-6-hydroxy-2,4-dioxo-1-(3-pyridinyl)-1,2,3,4-tetrahydro-5-pyrimidinyl]carbonyl}glycine;

N-({1-Cyclohexyl-3-[(2-fluorophenyl)methyl]-6-hydroxy-2,4-dioxo-1,2,3,4-tetrahydro-5-pyrimidinyl}carbonyl)glycine;

N-({3-[(2-Chlorophenyl)methyl]-1-cyclohexyl-6-hydroxy-2,4-dioxo-1,2,3,4-tetrahydro-5-pyrimidinyl}carbonyl)glycine;

N-({1-Cyclohexyl-6-hydroxy-2,4-dioxo-3-[(5,5,8,8-tetramethyl-5,6,7,8-tetrahydro-2-naphthalenyl)methyl]-1,2,3,4-tetrahydro-5-pyrimidinyl}carbonyl)glycine;

N-({1-Cyclohexyl-3-[(2,4-dimethylphenyl)methyl]-6-hydroxy-2,4-dioxo-1,2,3,4-tetrahydro-5-pyrimidinyl}carbonyl)glycine;

N-({1-Cyclohexyl-6-hydroxy-2,4-dioxo-3-[(2,4,6-trifluorophenyl)methyl]-1,2,3,4-tetrahydro-5-pyrimidinyl}carbonyl)glycine;

N-[(1-Cyclohexyl-6-hydroxy-3-{[4-(1-methylethyl)phenyl]methyl}-2,4-dioxo-1,2,3,4-tetrahydro-5-pyrimidinyl)carbonyl]glycine;

N-({1-Cyclohexyl-3-[(2-ethylphenyl)methyl]-6-hydroxy-2,4-dioxo-1,2,3,4-tetrahydro-5-pyrimidinyl}carbonyl)glycine;

N-({1-Cyclohexyl-3-[(4-ethylphenyl)methyl]-6-hydroxy-2,4-dioxo-1,2,3,4-tetrahydro-5-pyrimidinyl}carbonyl)glycine;

N-({1-Cyclohexyl-6-hydroxy-2,4-dioxo-3-[(2,4,6-trimethylphenyl)methyl]-1,2,3,4-tetrahydro-5-pyrimidinyl}carbonyl)glycine;

N-{[1-Cyclohexyl-3-(2-cyclohexylethyl)-6-hydroxy-2,4-dioxo-1,2,3,4-tetrahydro-5-pyrimidinyl]carbonyl}glycine;

N-[(3-{[3,5-Bis(methyloxy)phenyl]methyl}-1-cyclohexyl-6-hydroxy-2,4-dioxo-1,2,3,4-tetrahydro-5-pyrimidinyl)carbonyl]glycine;

N-{[1-Cyclohexyl-6-hydroxy-3-(2-naphthalenylmethyl)-2,4-dioxo-1,2,3,4-tetrahydro-5-pyrimidinyl]carbonyl}glycine;

N-({1-Cyclohexyl-6-hydroxy-3-[(4-methylphenyl)methyl]-2,4-dioxo-1,2,3,4-tetrahydro-5-pyrimidinyl}carbonyl)glycine;

N-{[3-(4-Biphenylylmethyl)-1-cyclohexyl-6-hydroxy-2,4-dioxo-1,2,3,4-tetrahydro-5-pyrimidinyl]carbonyl}glycine;

N-[(3-{[4-(1,3-Benzoxazol-2-yl)phenyl]methyl}-1-cyclohexyl-6-hydroxy-2,4-dioxo-1,2,3,4-tetrahydro-5-pyrimidinyl)carbonyl]glycine;

N-({3-[2-(4-Biphenylyl)-2-oxoethyl]-1-cyclohexyl-6-hydroxy-2,4-dioxo-1,2,3,4-tetrahydro-5-pyrimidinyl}carbonyl)glycine;

N-[(1,3-Bis{[4-(1,1-dimethylethyl)phenyl]methyl}-6-hydroxy-2,4-dioxo-1,2,3,4-tetrahydro-5-pyrimidinyl)carbonyl]glycine;

N-{[1-Cyclohexyl-6-hydroxy-3-(4-methylcyclohexyl)-2,4-dioxo-1,2,3,4-tetrahydro-5-pyrimidinyl]carbonyl}glycine;

N-({1-Cyclohexyl-3-[4-(1,1-dimethylethyl)cyclohexyl]-6-hydroxy-2,4-dioxo-1,2,3,4-tetrahydro-5-pyrimidinyl}carbonyl)glycine;

N-[(1-Cyclohexyl-6-hydroxy-2,4-dioxo-3-phenyl-1,2,3,4-tetrahydro-5-pyrimidinyl)carbonyl]glycine;

N-({1-Cyclohexyl-3-[4-(1,1-dimethylethyl)phenyl]-6-hydroxy-2,4-dioxo-1,2,3,4-tetrahydro-5-pyrimidinyl}carbonyl)glycine;

N-{[1-Cyclohexyl-3-(cyclohexylmethyl)-6-hydroxy-2,4-dioxo-1,2,3,4-tetrahydro-5-pyrimidinyl]carbonyl}glycine;

N-[(3-Cycloheptyl-1-cyclohexyl-6-hydroxy-2,4-dioxo-1,2,3,4-tetrahydro-5-pyrimidinyl)carbonyl]glycine;

N-[(3-Cyclohexyl-6-hydroxy-2,4-dioxo-1-tricyclo[3,3,1,1$^{3,7}$]dec-1-yl-1,2,3,4-tetrahydro-5-pyrimidinyl)carbonyl]glycine;

N-({1-[(1R,2R,4S)-Bicyclo[2,2,1]hept-2-yl]-3-cyclohexyl-6-hydroxy-2,4-dioxo-1,2,3,4-tetrahydro-5-pyrimidinyl}carbonyl)glycine;

N-{[1-Cyclohexyl-6-hydroxy-3-(3-methylcyclohexyl)-2,4-dioxo-1,2,3,4-tetrahydro-5-pyrimidinyl]carbonyl}glycine;

N-[(3-Cyclohexyl-1-cyclopropyl-6-hydroxy-2,4-dioxo-1,2,3,4-tetrahydro-5-pyrimidinyl)carbonyl]glycine;

N-[(1-Cyclobutyl-3-cyclohexyl-6-hydroxy-2,4-dioxo-1,2,3,4-tetrahydro-5-pyrimidinyl)carbonyl]glycine;

N-[(3-Cyclohexyl-1-cyclopentyl-6-hydroxy-2,4-dioxo-1,2,3,4-tetrahydro-5-pyrimidinyl)carbonyl]glycine;

N-{[6-Hydroxy-1,3-bis(3-methylbutyl)-2,4-dioxo-1,2,3,4-tetrahydro-5-pyrimidinyl]carbonyl}glycine;

N-[(6-Hydroxy-1,3-bis{[2-(methyloxy)phenyl]methyl}-2,4-dioxo-1,2,3,4-tetrahydro-5-pyrimidinyl)carbonyl]glycine;

N-({1,3-Bis[(2-chlorophenyl)methyl]-6-hydroxy-2,4-dioxo-1,2,3,4-tetrahydro-5-pyrimidinyl}carbonyl)glycine;

N-[(1,3-Dihexyl-6-hydroxy-2,4-dioxo-1,2,3,4-tetrahydro-5-pyrimidinyl)carbonyl]glycine;

N-{[1-Cyclohexyl-6-hydroxy-3-(2-methylcyclohexyl)-2,4-dioxo-1,2,3,4-tetrahydro-5-pyrimidinyl]carbonyl}glycine;

N-{[1-Cyclohexyl-6-hydroxy-3-(2-naphthalenyl)-2,4-dioxo-1,2,3,4-tetrahydro-5-pyrimidinyl]carbonyl}glycine;

N-[(1-Cyclohexyl-3-hexyl-6-hydroxy-2,4-dioxo-1,2,3,4-tetrahydro-5-pyrimidinyl)carbonyl]glycine;

N-[(1,3-Dicycloheptyl-6-hydroxy-2,4-dioxo-1,2,3,4-tetrahydro-5-pyrimidinyl)carbonyl]glycine;

N-[(1,3-Dicyclopentyl-6-hydroxy-2,4-dioxo-1,2,3,4-tetrahydro-5-pyrimidinyl)carbonyl]glycine;

N-{[1-Cyclohexyl-3-(2,3-dimethylcyclohexyl)-6-hydroxy-2,4-dioxo-1,2,3,4-tetrahydro-5-pyrimidinyl]carbonyl}glycine;

4-[5-{[(Carboxymethyl)amino]carbonyl}-3-cyclohexyl-4-hydroxy-2,6-dioxo-3,6-dihydro-1(2H)-pyrimidinyl]cyclohexanecarboxylic acid;

N-{[1-Cyclohexyl-3-(4-ethylcyclohexyl)-6-hydroxy-2,4-dioxo-1,2,3,4-tetrahydro-5-pyrimidinyl]carbonyl}glycine;

cis-4-[3-Cyclohexyl-5-({[2-(ethyloxy)-2-oxoethyl]amino}carbonyl)-4-hydroxy-2,6-dioxo-3,6-dihydro-1(2H)-pyrimidinyl]cyclohexanecarboxylic acid;
N-{[1-Cyclohexyl-6-hydroxy-3-(1-methylcyclohexyl)-2,4-dioxo-1,2,3,4-tetrahydro-5-pyrimidinyl]carbonyl}glycine;
3-[5-{[(Carboxymethyl)amino]carbonyl}-3-cyclohexyl-4-hydroxy-2,6-dioxo-3,6-dihydro-1(2H)-pyrimidinyl]cyclohexanecarboxylic acid;
N-{[1-Cyclohexyl-6-hydroxy-2,4-dioxo-3-(2-oxo-2-phenylethyl)-1,2,3,4-tetrahydro-5-pyrimidinyl]carbonyl}glycine;
N-[(1-Cyclohexyl-6-hydroxy-3-{2-[4-(methyloxy)phenyl]-2-oxoethyl}-2,4-dioxo-1,2,3,4-tetrahydro-5-pyrimidinyl)carbonyl]glycine;
N-({1-Cyclohexyl-6-hydroxy-3-[2-(4-methylphenyl)-2-oxoethyl]-2,4-dioxo-1,2,3,4-tetrahydro-5-pyrimidinyl}carbonyl)glycine;
N-{[1-Cyclohexyl-3-(3,3-dimethyl-2-oxobutyl)-6-hydroxy-2,4-dioxo-1,2,3,4-tetrahydro-5-pyrimidinyl]carbonyl}glycine;
N-({1-Cyclohexyl-3-[2-(4-fluorophenyl)-2-oxoethyl]-6-hydroxy-2,4-dioxo-1,2,3,4-tetrahydro-5-pyrimidinyl}carbonyl)glycine;
N-({3-[2-(4-Cyanophenyl)-2-oxoethyl]-1-cyclohexyl-6-hydroxy-2,4-dioxo-1,2,3,4-tetrahydro-5-pyrimidinyl}carbonyl)glycine;
N-({3-[2-(1-Benzofuran-2-yl)-2-oxoethyl]-1-cyclohexyl-6-hydroxy-2,4-dioxo-1,2,3,4-tetrahydro-5-pyrimidinyl}carbonyl)glycine;
N-{[3-Cyclohexyl-6-hydroxy-1-(1-naphthalenyl)-2,4-dioxo-1,2,3,4-tetrahydro-5-pyrimidinyl]carbonyl}glycine;
N-{[3-Cyclohexyl-1-(4,4-dimethylcyclohexyl)-6-hydroxy-2,4-dioxo-1,2,3,4-tetrahydro-5-pyrimidinyl]carbonyl}glycine;
N-({1-Cyclohexyl-3-[(2,3-difluorophenyl)methyl]-6-hydroxy-2,4-dioxo-1,2,3,4-tetrahydro-5-pyrimidinyl}carbonyl)glycine;
Ethyl N-[(1,3-dicyclohexyl-6-hydroxy-2,4-dioxo-1,2,3,4-tetrahydro-5-pyrimidinyl)carbonothioyl]glycinate;
N-[(1,3-Dicyclohexyl-6-hydroxy-2,4-dioxo-1,2,3,4-tetrahydro-5-pyrimidinyl)carbonothioyl]glycine;
6-[5-{[(Carboxymethyl)amino]carbonyl}-3-cyclohexyl-6-hydroxy-2,4-dioxo-3,4-dihydro-1(2H)-pyrimidinyl]hexanoic acid;
6-[5-{[(Carboxymethyl)amino]carbonothioyl}-3-cyclohexyl-6-hydroxy-2,4-dioxo-3,4-dihydro-1(2H)-pyrimidinyl]hexanoic acid;
N-({1-Cyclohexyl-3-[(3,4-dichlorophenyl)methyl]-6-hydroxy-2,4-dioxo-1,2,3,4-tetrahydro-5-pyrimidinyl}carbonyl)glycine;
N-[(1-Cyclohexyl-6-hydroxy-2,4-dioxo-1,2,3,4-tetrahydro-5-pyrimidinyl)carbonyl]glycine;
N-({3-Cyclohexyl-6-hydroxy-1-[trans-4-(methyloxy)cyclohexyl]-2,4-dioxo-1,2,3,4-tetrahydro-5-pyrimidinyl}carbonyl)glycine;
N-({1-[1,1'-Bi(cyclohexyl)-4-yl]-3-cyclohexyl-6-hydroxy-2,4-dioxo-1,2,3,4-tetrahydro-5-pyrimidinyl}carbonyl)glycine;
N-{[6-Hydroxy-2,4-dioxo-1,3-bis(1-propylbutyl)-1,2,3,4-tetrahydro-5-pyrimidinyl]carbonyl}glycine;
N-({3-(2-Cyclopropylethyl)-6-hydroxy-1-[3-(methyloxy)phenyl]-2,4-dioxo-1,2,3,4-tetrahydro-5-pyrimidinyl}carbonyl)glycine;
N-{[3-Cyclohexyl-6-hydroxy-2,4-dioxo-1-(4-phenylcyclohexyl)-1,2,3,4-tetrahydro-5-pyrimidinyl]carbonyl}glycine;
N-({1-Cyclohexyl-3-[(3,4-difluorophenyl)methyl]-6-hydroxy-2,4-dioxo-1,2,3,4-tetrahydro-5-pyrimidinyl}carbonyl)glycine;
N-({3-(2-Cyclopropylethyl)-6-hydroxy-1-[4-(methyloxy)phenyl]-2,4-dioxo-1,2,3,4-tetrahydro-5-pyrimidinyl}carbonyl)glycine;
N-{[3-(2-Cyclopropylethyl)-6-hydroxy-1-(3-nitrophenyl)-2,4-dioxo-1,2,3,4-tetrahydro-5-pyrimidinyl]carbonyl}glycine;
N-({3-(2-Cyclopropylethyl)-6-hydroxy-2,4-dioxo-1-[4-(2-thienyl)phenyl]-1,2,3,4-tetrahydro-5-pyrimidinyl}carbonyl)glycine;
N-{[1,3-Bis(1-ethylpropyl)-6-hydroxy-2,4-dioxo-1,2,3,4-tetrahydro-5-pyrimidinyl]carbonyl}glycine;
N-[(6-Hydroxy-2,4-dioxo-1,2,3,4-tetrahydro-5-pyrimidinyl)carbonyl]glycine;
N-[(1-Cyclohexyl-6-hydroxy-2,4-dioxo-3-{[4-(trifluoromethyl)phenyl]methyl}-1,2,3,4-tetrahydro-5-pyrimidinyl)carbonyl]glycine;
N-[(1,3-Dibutyl-6-hydroxy-2,4-dioxo-1,2,3,4-tetrahydro-5-pyrimidinyl)carbonyl]glycine;
N-{[1,3-Bis(2-cyclopropylethyl)-6-hydroxy-2,4-dioxo-1,2,3,4-tetrahydro-5-pyrimidinyl]carbonyl}glycine;
N-{[6-Hydroxy-1,3-bis(2-methylpropyl)-2,4-dioxo-1,2,3,4-tetrahydro-5-pyrimidinyl]carbonyl}glycine;
N-({3-(2-Cyclopropylethyl)-6-hydroxy-1-[3-(5-methyl-1,2,4-oxadiazol-3-yl)phenyl]-2,4-dioxo-1,2,3,4-tetrahydro-5-pyrimidinyl}carbonyl)glycine;
N-({3-(2-Cyclopropylethyl)-6-hydroxy-1-[4-(2-methyl-1,3-thiazol-4-yl)phenyl]-2,4-dioxo-1,2,3,4-tetrahydro-5-pyrimidinyl}carbonyl)glycine;
N-{[3-Cyclohexyl-6-hydroxy-2,4-dioxo-1-(4-piperidinyl)-1,2,3,4-tetrahydro-5-pyrimidinyl]carbonyl}glycine;
N-({3-(2-Cyclopropylethyl)-1-[4-(2-furanyl)phenyl]-6-hydroxy-2,4-dioxo-1,2,3,4-tetrahydro-5-pyrimidinyl}carbonyl)glycine;
N-{[1,3-Bis(1,1-dimethylpropyl)-6-hydroxy-2,4-dioxo-1,2,3,4-tetrahydro-5-pyrimidinyl]carbonyl}glycine;
N-{[3-Cyclohexyl-6-hydroxy-2,4-dioxo-1-(3-piperidinyl)-1,2,3,4-tetrahydro-5-pyrimidinyl]carbonyl}glycine;
N-{[3-Cyclohexyl-6-hydroxy-2,4-dioxo-1-(1-{[(phenylmethyl)oxy]carbonyl}-3-piperidinyl)-1,2,3,4-tetrahydro-5-pyrimidinyl]carbonyl}glycine;
N-{[1-(1-Acetyl-3-piperidinyl)-3-cyclohexyl-6-hydroxy-2,4-dioxo-1,2,3,4-tetrahydro-5-pyrimidinyl]carbonyl}glycine;
N-[(1-Cyclohexyl-3-{[4-fluoro-2-(trifluoromethyl)phenyl]methyl}-6-hydroxy-2,4-dioxo-1,2,3,4-tetrahydro-5-pyrimidinyl)carbonyl]glycine;
N-({3-[(2-Bromophenyl)methyl]-1-cyclohexyl-6-hydroxy-2,4-dioxo-1,2,3,4-tetrahydro-5-pyrimidinyl}carbonyl)glycine;
N-({1-Cyclohexyl-3-[(2,6-dichlorophenyl)methyl]-6-hydroxy-2,4-dioxo-1,2,3,4-tetrahydro-5-pyrimidinyl}carbonyl)glycine;
N-[(3-{[2-Bromo-5-(methyloxy)phenyl]methyl}-1-cyclohexyl-6-hydroxy-2,4-dioxo-1,2,3,4-tetrahydro-5-pyrimidinyl)carbonyl]glycine;
N-[(3-{[2,4-Bis(trifluoromethyl)phenyl]methyl}-1-cyclohexyl-6-hydroxy-2,4-dioxo-1,2,3,4-tetrahydro-5-pyrimidinyl)carbonyl]glycine;
N-({3-[(2-Bromo-5-fluorophenyl)methyl]-1-cyclohexyl-6-hydroxy-2,4-dioxo-1,2,3,4-tetrahydro-5-pyrimidinyl}carbonyl)glycine;
N-[(3-{[2-Bromo-4-(1,1-dimethylethyl)phenyl]methyl}-1-cyclohexyl-6-hydroxy-2,4-dioxo-1,2,3,4-tetrahydro-5-pyrimidinyl)carbonyl]glycine;

N-({1-Cyclohexyl-6-hydroxy-3-[(2-methylphenyl)methyl]-2,4-dioxo-1,2,3,4-tetrahydro-5-pyrimidinyl}carbonyl)glycine;

N-{[1-Cyclohexyl-3-(1,1-dimethylpropyl)-6-hydroxy-2,4-dioxo-1,2,3,4-tetrahydro-5-pyrimidinyl]carbonyl}glycine; and N-{[1,3-Bis(2,6-dichlorophenyl)-6-hydroxy-2,4-dioxo-1,2,3,4-tetrahydro-5-pyrimidinyl]carbonyl}glycine.

Processes for preparing the compound of formula (I) are also within the ambit of this invention. To illustrate, a process for preparing a compound of formula (I)

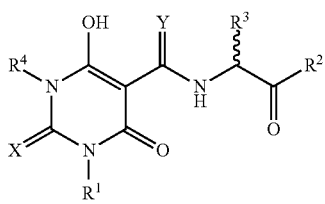
(I)

wherein X, Y, $R^1$, $R^2$, $R^3$ and $R^4$ are the same as defined above for formula (I), the process comprising treating a compound of formula A:

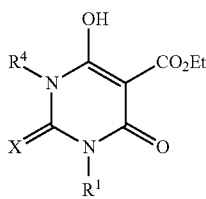
A wherein $R^1$ and $R^4$ are the same as for those groups in formula (I) with glycine and an appropriate base, such as 1,8-diazabicyclo[5.4.0]undec-7-ene, in an appropriate solvent, such as ethanol, under either conventional thermal conditions or by microwave irradiation, to form a compound of formula (I) where Y is O, $R^2$ is —OH, and $R^3$ is H;

or a process for preparing a compound of formula (I) wherein X, Y, $R^1$, $R^2$, $R^3$ and $R^4$ are the same as defined above for formula (I), the process comprising treating a compound of formula B:

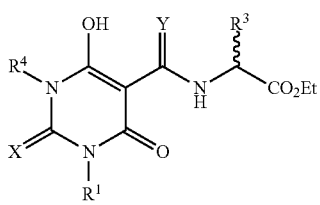
B wherein X, Y, $R^1$, $R^2$, $R^3$ and $R^4$ are the same as for those groups in formula (I) with an alkali such as sodium hydroxide, in an appropriate solvent, such as aqueous ethanol, at a suitable temperature such as room temperature, to form a compound of formula (I) where $R^2$ is —OH;

or a process for preparing a compound of formula (I) wherein X, Y, $R^1$, $R^2$, $R^3$ are as defined above for formula (I) and $R^4$ is piperidinyl, the process comprising treating a compound of formula C:

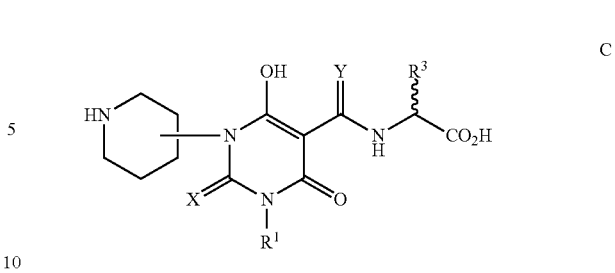
C wherein X, Y, $R^1$, and $R^3$ are the same as for those groups in formula (I) with an acylating agent such as acetic anhydride, in an appropriate solvent, such as acetic acid, at a suitable temperature such as 130° C., to form a compound of formula (I) where $R^2$ is —OH, and $R^4$ is acylpiperidinyl;

It will be appreciated by those skilled in the art that the compounds of formula (I) may exist in one or more tautomeric forms such as:

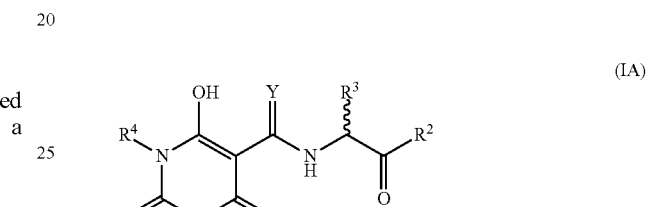
(IA)

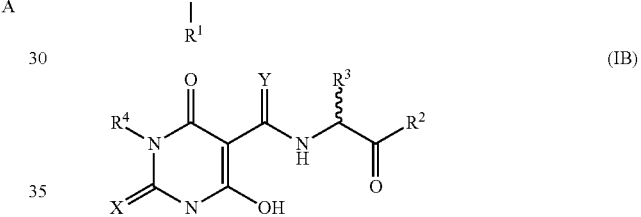
(IB)

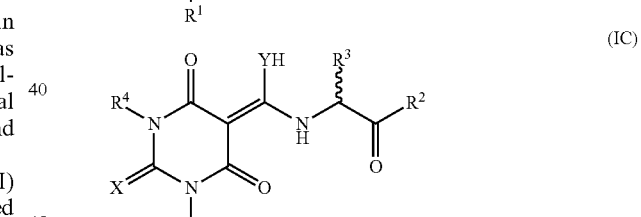
(IC)

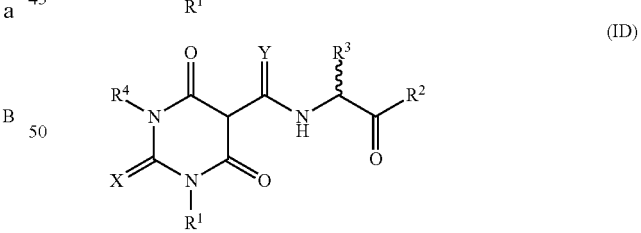
(ID)

All tautomeric forms of the compounds described herein, including mixtures thereof, are intended to be encompassed within the scope of the invention. Generally, the compounds exemplified herein have been assigned names based on the structure of the tautomer of formula (IA). It should be understood that any reference to named compounds of this invention is intended to encompass all tautomers of the named compounds and any mixtures of tautomers of the named compounds.

The compounds of formula (I) may be prepared in crystalline or non-crystalline form, and, if crystalline, may optionally be solvated, e.g. as the hydrate. This invention includes within its scope stoichiometric solvates (e.g. hydrates) as well as compounds containing variable amounts of solvent (e.g. water).

Certain of the compounds described herein may contain one or more chiral atoms, or may otherwise be capable of existing as two enantiomers. The compounds claimed below include mixtures of enantiomers as well as purified enantiomers or enantiomerically enriched mixtures. Also included within the scope of the invention are the individual isomers of the compounds represented by formula (I), or claimed below, as well as any wholly or partially equilibrated mixtures thereof. The present invention also covers the individual isomers of the claimed compounds as mixtures with isomers thereof in which one or more chiral centers are inverted.

Where there are different isomeric forms they may be separated or resolved one from the other by conventional methods, or any given isomer may be obtained by conventional synthetic methods or by stereospecific or asymmetric syntheses.

While it is possible that, for use in therapy, a compound of formula (I), as well as salts, solvates and the like, may be administered as a neat preparation, i.e. no additional carrier, the more usual practice is to present the active ingredient confected with a carrier or diluent. Accordingly, the invention further provides pharmaceutical compositions, which includes a compound of formula (I) and salts, solvates and the like, and one or more pharmaceutically acceptable carriers, diluents, or excipients. The compounds of formula (I) and salts, solvates, etc, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I), or salts, solvates etc, with one or more pharmaceutically acceptable carriers, diluents or excipients.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of the invention may act as prodrugs of other compounds of the invention. All protected derivatives and prodrugs of compounds of the invention are included within the scope of the invention. It will further be appreciated by those skilled in the art, that certain moieties, known to those skilled in the art as "pro-moieties" may be placed on appropriate functionalities when such functionalities are present within compounds of the invention. Preferred prodrugs for compounds of the invention include: esters, carbonate esters, hemi-esters, phosphate esters, nitro esters, sulfate esters, sulfoxides, amides, carbamates, azo-compounds, phosphamides, glycosides, ethers, acetals and ketals.

Pharmaceutical compositions may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula (I), depending on the condition being treated, the route of administration and the age, weight and condition of the patient, or pharmaceutical compositions may be presented in unit dose forms containing a predetermined amount of active ingredient per unit dose. Preferred unit dosage compositions are those containing a daily dose or sub-dose, as herein above recited, or an appropriate fraction thereof, of an active ingredient. Furthermore, such pharmaceutical compositions may be prepared by any of the methods well known in the pharmacy art.

Pharmaceutical compositions may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by bringing into association a compound of formal (I) with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of a compound of formula (I). Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit pharmaceutical compositions for oral administration can be microencapsulated. The formulation can also be prepared to prolong or sustain the release as for example by coating or embedding particulate material in polymers, wax or the like.

Pharmaceutical compositions adapted for rectal administration may be presented as suppositories or as enemas.

Pharmaceutical compositions adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The pharmaceutical compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the pharmaceutical compositions may include other agents conventional in the art having regard to the type of formulation in question, for example those suitable for oral administration may include flavouring agents.

A therapeutically effective amount of a compound of the present invention will depend upon a number of factors including, for example, the age and weight of the intended recipient, the precise condition requiring treatment and its severity, the nature of the formulation, and the route of administration, and will ultimately be at the discretion of the attendant prescribing the medication. However, an effective amount of a compound of formula (I) for the treatment of anemia will generally be in the range of 0.001 to 100 mg/kg body weight of recipient per day, suitably in the range of 0.01 to 10 mg/kg body weight per day. For a 70 kg adult mammal, the actual amount per day would suitably be from 7 to 700 mg and this amount may be given in a single dose per day or in a number (such as two, three, four, five or six) of sub-doses per day such that the total daily dose is the same. An effective amount of a salt or solvate, etc., may be determined as a proportion of the effective amount of the compound of formula (I) per se. It is envisaged that similar dosages would be appropriate for treatment of the other conditions referred to above.

Definitions

CDI—carbonyl di-imidazole
DBU—1,8-diazabicyclo[5.4.0]undec-7-ene
DIAD—diisopropyl azodicarboxylate
DMA—N,N-dimethylacetamide
DMF—N,N-dimethylformamide
DMSO—dimethylsulfoxide
HPLC—high pressure liquid chromatography
LC/MS—liquid chromatography/mass spectrometry
NMR—nuclear magnetic resonance
rt—room temperature
TFA—Trifluoroacetic acid
THF—tetrahydrofuran

Chemical Background

The compounds of this invention may be made by a variety of methods, including standard chemistry. Any previously defined variable will continue to have the previously defined meaning unless otherwise indicated. Illustrative general synthetic methods are set out below and then specific compounds of the invention as prepared are given in the examples.

Compounds of general formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of formula (I). Those skilled in the art will recognize if a stereocenter exists in compounds of formula (I). Accordingly, the present invention includes both possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994).

Illustrated Methods of Preparation

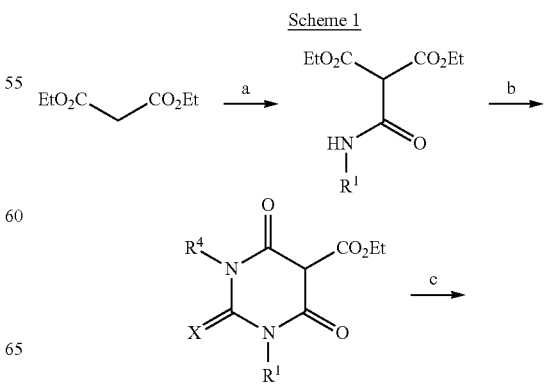

Scheme 1

19

-continued

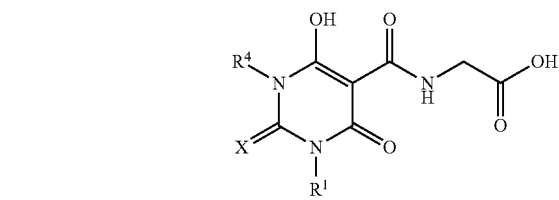

a) 1. NaH, THF, rt 2. R¹NCO, 60° C.; b) 1. NaH, THF or dioxane, rt 2. R⁴NCX, heat; c) H₂NCH₂CO₂H, DBU, EtOH, 160° C., microwave.

Scheme 2

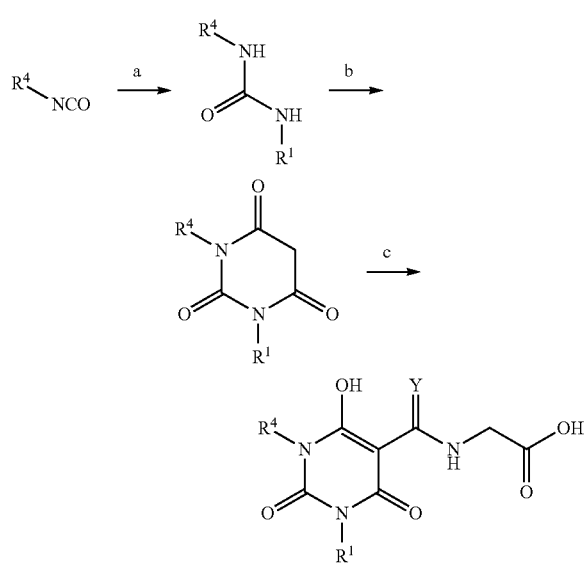

a) R¹NH₂, CH₂Cl₂ or R¹NH₂·HCl, base, CH₂Cl₂; b) CH₂(C(O)Cl)₂, CH₂Cl₂, reflux or CH₂(CO₂Et)₂, NaOEt, MeO(CH₂)₂OH, reflux or 1. EtO₂CCH₂COCl, CHCl₃, 70° C. 2. DBU, CHCl₃, 70° C.; c) 1. YCNCH₂CO₂Et, EtPrⁱ₂N, CHCl₃, CH₂Cl₂ 2. aq NaOH, EtOH, rt.

Scheme 3 (for R¹ = R⁴)

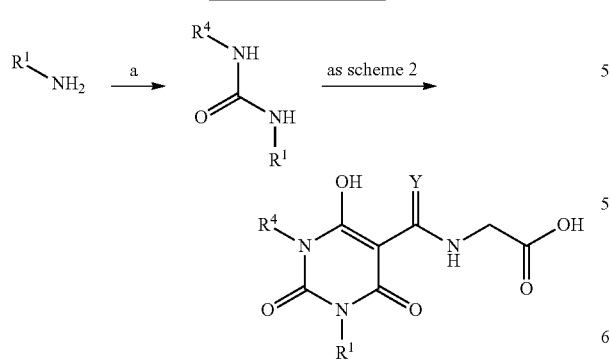

a) CDI, DMF, 70° C. or [benzoxazolethione structure], EtOAc, rt

20

Scheme 4

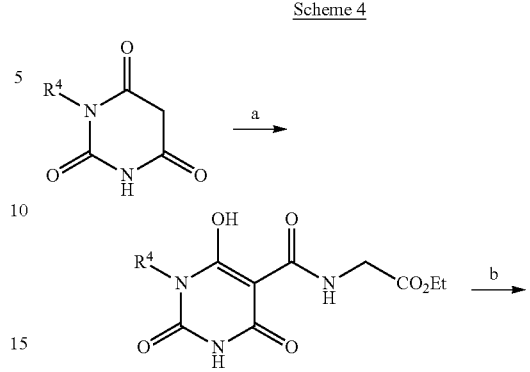

a) OCNCH₂CO₂Et, EtPrⁱ₂N, CHCl³ or CH₂Cl₂;
b) 1. R¹Hal, Na/K₂CO₃, DMF or DMA, 100° C. or R¹Hal, pol-BEMP, DMF, 120° C., microwave 2. aq NaOH, MeOH or EtOH, rt.

Scheme 5

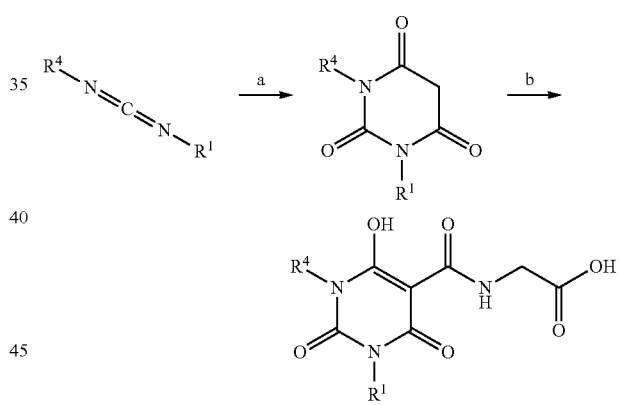

a) 1. CH₂(CO₂H)₂, THF, 0° C. - rt 2. EtOH, reflux;
b) 1. OCNCH₂CO₂Et, EtPrⁱ₂N, CH₂Cl₂ 2. aq NaOH, EtOH, rt.

Scheme 6

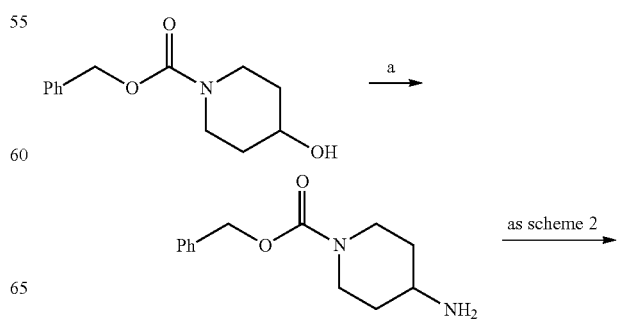

as scheme 2

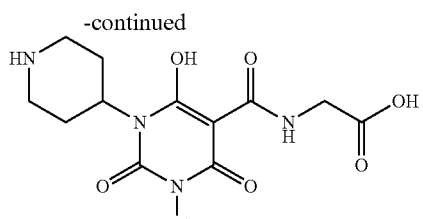

a) 1. Phthalimide, DIAD, PPh₃, THF 2. (NH₂)₂, EtOH, reflux.

Scheme 7

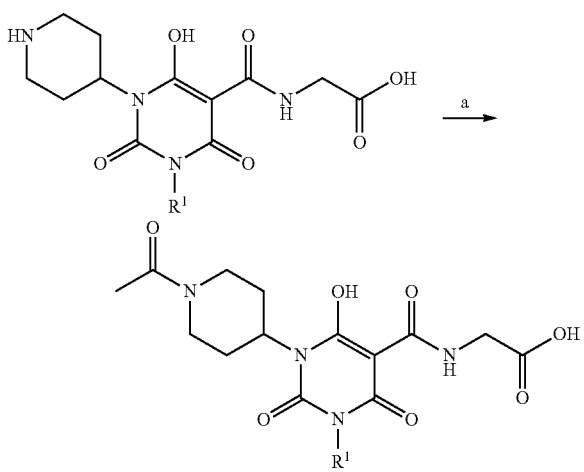

a) Ac₂O, AcOH, 130° C.

EXPERIMENTALS

Example 1

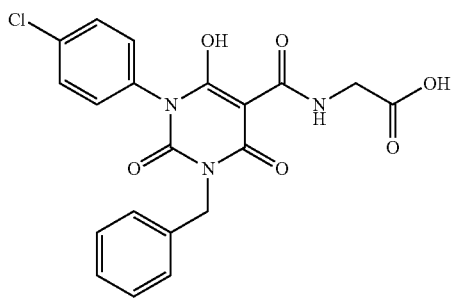 [SMILES: O=C(O)CNC(=O)c1c(O)n(-c2ccc(Cl)cc2)c(=O)n(Cc2ccccc2)c1=O]

N-{[1-(4-Chlorophenyl)-6-hydroxy-2,4-dioxo-3-(phenylmethyl)-1,2,3,4-tetrahydro-5-pyrimidinyl]carbonyl}glycine 1a). Diethyl {[(phenylmethyl)amino]carbonyl} propanedioate. A solution of diethyl malonate (1.52 mL, 10.0 mmoles) in dry tetrahydrofuran (20 mL) was added to a suspension of sodium hydride (60% suspension in mineral oil, 500 mg, 12.5 mmoles) under argon atmosphere at room temperature. After stirring for 15 minutes, a solution of benzyl isocyanate (1.33 mL, 10.0 mmoles) was added and the mixture was heated at 60° C. for 3 hours. The mixture was cooled, carefully acidified with 1 molar hydrochloric acid and the tetrahydrofuran evaporated. The mixture was diluted with water and extracted twice with chloroform. The combined extracts were washed twice with brine, dried and evaporated. Crystallization from ether-hexane afforded the title compound as a white solid, 1.2 g, 40%. 1H NMR (400 MHz, DMSO-d₆) δ ppm 1.20 (t, J=7.20 Hz, 6H) 4.11-4.20 (m, 4H) 4.33 (d, J=6.06 Hz, 2H) 4.56 (s, 1H) 7.24 (s, 1H) 7.25-7.36 (m, 5H) 8.74 (t, J=5.68 Hz, 1H).

1b) Ethyl 1-(4-chlorophenyl)-6-hydroxy-2,4-dioxo-3-(phenylmethyl)-1,2,3,4-tetrahydro-5-pyrimidinecarboxylate. Diethyl {[(phenylmethyl)amino]carbonyl} propanedioate (293 mg, 1.0 mmoles) was added to a suspension of sodium hydride (60% suspension in mineral oil, 100 mg, 2.5 mmoles) in dry tetrahydrofuran (50 mL) and stirred for 10 minutes under argon. 4-Chlorophenyl isocyanate was added and the mixture was heated under reflux for 2 hours, cooled, acidified with 1 molar hydrochloric acid and extracted with ethyl acetate. Flash chromatography (hexane-ethyl acetate) afforded the title compound (225 mg, 56%) 1H NMR (400 MHz, DMSO-d₆) δ ppm 1.06 (t, J=7.07 Hz, 3H) 3.45 (q, J=7.07 Hz, 2H) 5.00 (s, 2H) 7.25-7.28 (m, 1H) 7.30-7.37 (m, 6H) 7.53 (d, J=8.59 Hz, 2H).

1c) N-{[1-(4-Chlorophenyl)-6-hydroxy-2,4-dioxo-3-(phenylmethyl)-1,2,3,4-tetrahydro-5-pyrimidinyl]carbonyl} glycine. A mixture of ethyl 1-(4-chlorophenyl)-6-hydroxy-2,4-dioxo-3-(phenylmethyl)-1,2,3,4-tetrahydro-5-pyrimidinecarboxylate (225 mg, 0.56 mmoles), DBU (200 mg, 1.31 mmoles) and glycine (100 mg, 1.33 mmoles) in ethanol (10 mL) was sealed in a flask and heated in a microwave reactor at 160° C. for 1 hour. The reaction mixture was evaporated, dissolved in chloroform and washed with 1 molar hydrochloric acid. Evaporation of the residue and separation by preparative HPLC (10-80% acetonitrile-water-0.1% TFA) afforded the title compound (25 mg, 10%) 1H NMR (400 MHz, DMSO-d₆) δ ppm 4.13 (d, J=5.81 Hz, 2H) 5.03 (s, 2H) 7.24-7.29 (m, 1H) 7.31-7.38 (m, 4H) 7.42 (d, J=8.34 Hz, 2H) 7.52-7.58 (m, 2H) 10.07 (s, 1H) 13.11 (s, 1H)

Example 2

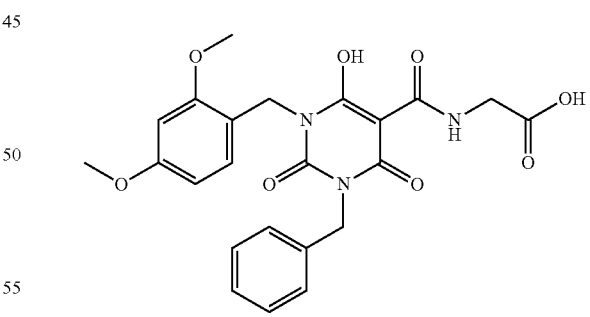

N-{[1-{[2,4-Bis(methyloxy)phenyl]methyl}-6-hydroxy-2,4-dioxo-3-(phenylmethyl)-1,2,3,4-tetrahydro-5-pyrimidinyl]carbonyl}glycine 2a) Ethyl 1-{[2,4-bis(methyloxy)phenyl]methyl}-6-hydroxy-2,4-dioxo-3-(phenylmethyl)-1,2,3,4-tetrahydro-5-pyrimidinecarboxylate. Diethyl {[(phenylmethyl)amino]carbonyl}propanedioate (820 mg, 2.8 mmoles) was added to a suspension of sodium hydride (60% suspension in mineral oil, 280 mg, 7.0 mmoles) in dry tetrahydrofuran (50 mL) and stirred for 10 minutes under argon. 2,4-dimethoxybenzyl isocyanate (1.0 mL, 6.0 mmoles) was added and the mixture heated under reflux for 3 hours, cooled, acidified with 1 molar hydrochloric acid and extracted with ethyl acetate. Flash chromatography (30% methanol in dichloromethane) afforded the title compound (480 mg, 39%) 1H NMR (400 MHz, DMSO-$d_6$) δ ppm 1.15 (t, J=6.69 Hz, 3H) 3.71 (s, 3H) 3.78 (s, 3H) 4.09 (q, J=5.05 Hz, 1H) 4.81 (s, 2H) 4.92 (s, 2H) 6.40-6.59 (m, 3H) 6.62-7.26 (m, 5H).

2b) N-{[1-{[2,4-bis(methyloxy)phenyl]methyl}-6-hydroxy-2,4-dioxo-3-(phenylmethyl)-1,2,3,4-tetrahydro-5-pyrimidinyl]carbonyl}glycine. A mixture of ethyl 1-{[2,4-bis(methyloxy)phenyl]methyl}-6-hydroxy-2,4-dioxo-3-(phenylmethyl)-1,2,3,4-tetrahydro-5-pyrimidinecarboxylate (110 mg, 0.25 mmoles), DBU (76 mg, 0.5 mmoles) and glycine (38 mg, 0.5 mmoles) in ethanol (5 mL) was sealed in a flask and heated in a microwave reactor at 160° C. for 1 hour. The reaction mixture was diluted with 1 molar hydrochloric acid and extracted with ethyl acetate. Purification by preparative HPLC (10-80% acetonitrile-water-0.1% TFA) afforded the title compound (50 mg, 42%) 1H NMR (400 MHz, DMSO-$d_6$) δ ppm 3.71-3.81 (m, 6H) 4.13 (d, J=5.31 Hz, 2H) 4.92 (s, 2H) 5.03 (s, 2H) 6.39-6.49 (m, 1H) 6.56 (s, 1H) 6.81 (d, J=8.08 Hz, 1H) 7.24-7.36 (m, 5H) 10.10 (s, 1H) 13.10 (s, 1H)

Example 3

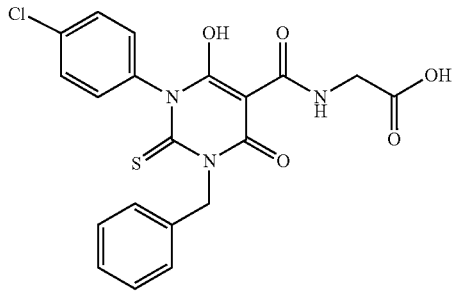 [SMILES: O=C(O)CNC(=O)c1c(O)n(-c2ccc(Cl)cc2)c(=S)n(Cc2ccccc2)c1=O]

N-{[1-(4-Chlorophenyl)-6-hydroxy-4-oxo-3-(phenylmethyl)-2-thioxo-1,2,3,4-tetrahydro-5-pyrimidinyl]carbonyl}glycine 3a) Ethyl 1-(4-chlorophenyl)-6-hydroxy-4-oxo-3-(phenylmethyl)-2-thioxo-1,2,3,4-tetrahydro-5-pyrimidinecarboxylate. Diethyl {[(phenylmethyl)amino]carbonyl} propanedioate (400 mg, 1.36 mmoles) was added to a suspension of sodium hydride (60% suspension in mineral oil, 200 mg, 5.0 mmoles) in dry dioxan (15 mL) and stirred for 10 minutes under argon. 4-Chlorophenyl isothiocyanate (340 mg, 2.0 mmoles) was added and the mixture sealed in a pressure flask heated in a microwave reactor at 100° C. for 1 hour. The mixture was taken up in dichloromethane, washed with 1 molar hydrochloric acid and dried. Flash chromatography (hexane-ethyl acetate) afforded the title compound (85 mg, 20%) 1H NMR (400 MHz, DMSO-$d_6$) δ ppm 1.18 (t, J=7.20 Hz, 3H) 4.01-4.06 (q, J=7.20 Hz, 2H) 4.89 (s, 2H) 7.10 (d, J=8.59 Hz, 2H) 7.26-7.31 (m, 5H) 7.39 (d, J=8.59 Hz, 2H).

3b) N-{[1-(4-Chlorophenyl)-6-hydroxy-4-oxo-3-(phenylmethyl)-2-thioxo-1,2,3,4-tetrahydro-5-pyrimidinyl]carbonyl}glycine. A mixture of ethyl 1-(4-chlorophenyl)-6-hydroxy-4-oxo-3-(phenylmethyl)-2-thioxo-1,2,3,4-tetrahydro-5-pyrimidinecarboxylate (85 mg, 0.21 mmoles), DBU (90 mg, 0.6 mmoles) and glycine (60 mg, 0.8 mmoles) in ethanol (5 mL) was sealed in a flask and heated in a microwave reactor at 160° C. for 1 hour. The reaction mixture was diluted with 1 molar hydrochloric acid and extracted twice with ethyl acetate. The combined extracts were washed with 1 molar hydrochloric acid, dried and evaporated. Purification by preparative HPLC (10-80% acetonitrile-water-0.1% TFA) afforded the title compound (23 mg, 24%) 1H NMR (400 MHz, DMSO-$d_6$) δ ppm 4.14 (d, J=5.81 Hz, 2H) 5.67 (s, 2H) 7.24 (t, J=6.95 Hz, 1H) 7.29-7.40 (m, 7H) 7.54 (d, J=8.59 Hz, 2H) 10.10 (s, 1H) 13.11 (s, 1H)

Example 4

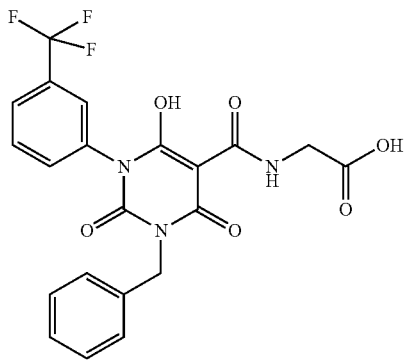 [SMILES: O=C(O)CNC(=O)c1c(O)n(-c2cccc(C(F)(F)F)c2)c(=O)n(Cc2ccccc2)c1=O]

N-({6-Hydroxy-2,4-dioxo-3-(phenylmethyl)-1-[3-(trifluoromethyl)phenyl]-1,2,3,4-tetrahydro-5-pyrimidinyl}carbonyl)glycine 4a) Ethyl 6-hydroxy-2,4-dioxo-3-(phenylmethyl)-1-[3-(trifluoromethyl)phenyl]-1,2,3,4-tetrahydro-5-pyrimidinecarboxylate. Diethyl {[(phenylmethyl)amino]carbonyl} propanedioate (200 mg, 0.68 mmoles) was added to a suspension of sodium hydride (60% suspension in mineral oil, 100 mg, 2.5 mmoles) in dry dioxane (5 mL) and stirred for 10 minutes under argon. 3-Trifluorophenyl isocyanate (140 uL, 1.02 mmoles) was added and the mixture sealed in a pressure flask heated in a microwave reactor at 100° C. for 40 minutes. The mixture was taken up in dichloromethane, washed with 1 molar hydrochloric acid and dried. The mixture was evaporated and azeotroped with ethanol. The residue was slurried in diethyl ether to give the title compound (110 mg, 37%) 1H NMR (400 MHz, DMSO-$d_6$) δ ppm 1.10 (t, J=6.95 Hz, 3H) 3.39 (q, J=6.99 Hz, 2H) 4.89-4.94 (m, 2H) 7.18-7.23 (m, 2H) 7.24-7.31 (m, 3H) 7.44-7.55 (m, 2H) 7.59-7.69 (m, 2H).

4b) N-({6-hydroxy-2,4-dioxo-3-(phenylmethyl)-1-[3-(trifluoromethyl)phenyl]-1,2,3,4-tetrahydro-5-pyrimidinyl}carbonyl)glycine. A mixture of ethyl 6-hydroxy-2,4-dioxo-3-(phenylmethyl)-1-[3-(trifluoromethyl)phenyl]-1,2,3,4-tetrahydro-5-pyrimidinecarboxylate (110 mg, 0.25 mmoles), DBU (100 mg, 0.6 mmoles) and glycine (40 mg, 0.5 mmoles) in ethanol (5 mL) was sealed in a flask and heated in a microwave reactor at 160° C. for 1 hour. The reaction mixture was diluted with 1 molar hydrochloric acid and extracted twice with dichloromethane. Purification by preparative HPLC (10-80% acetonitrile-water-0.1% TFA) afforded the title compound (15 mg, 13%) 1H NMR (400 MHz, DMSO-$d_6$) δ ppm 3.79 (d, J=5.05 Hz, 2H) 4.97 (s, 2H) 7.19-7.30 (m, 5H) 7.46-7.57 (m, 2H) 7.60-7.71 (m, 2H) 8.27 (s, 1H) 9.60 (s, 1H)

Example 5

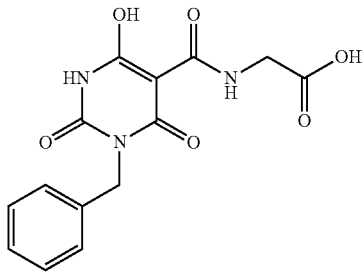 [SMILES: O=C(O)CNC(=O)c1c(O)[nH]c(=O)n(Cc2ccccc2)c1=O]

N-{[6-Hydroxy-2,4-dioxo-3-(phenylmethyl)-1,2,3,4-tetrahydro-5-pyrimidinyl]carbonyl}glycine 5a) Ethyl 6-hydroxy-2,4-dioxo-3-(phenylmethyl)-1,2,3,4-tetrahydro-5-pyrimidinecarboxylate. Ethyl 1-{[2,4-bis(methyloxy)phenyl]methyl}-6-hydroxy-2,4-dioxo-3-(phenylmethyl)-1,2,3,4-tetrahydro-5-pyrimidinecarboxylate (260 mg, 0.59 mmoles) was stirred in a mixture of sulfuric acid (5.0 mL) and water (1.0 mL) for 3 hours. The mixture was poured onto ice and the solid collected.

The aqueous was adjusted to pH3 and extracted three times with ethyl acetate. The extracts were dried, evaporated and combined with the collected solid. Purification by preparative HPLC (acetonitrile-water-0.1% TFA) gave the title compound (106 mg, 62%) 1H NMR (400 MHz, CHLOROFORM-d) δ ppm 1.28 (t, J=7.07 Hz, 3H) 4.14 (q, J=7.16 Hz, 2H) 5.09 (s, 1H) 5.14 (s, 1H) 7.25-7.37 (m, 3H) 7.42-7.52 (m, 2H) 10.22 (s, 1H) 15.53 (s, 1H).

5b) N-{[6-Hydroxy-2,4-dioxo-3-(phenylmethyl)-1,2,3,4-tetrahydro-5-pyrimidinyl]carbonyl}glycine. A mixture of ethyl 6-hydroxy-2,4-dioxo-3-(phenylmethyl)-1,2,3,4-tetrahydro-5-pyrimidinecarboxylate (100 mg, 0.34 mmoles), DBU (106 mg, 0.7 mmoles) and glycine (52 mg, 0.7 mmoles) was sealed in a flask and heated in a microwave reactor at 160° C. for 1 hour. The reaction mixture was taken up in ethyl acetate and washed with 1 molar hydrochloric acid. Purification by preparative HPLC (10-80% acetonitrile-water-0.1% TFA) afforded the title compound (15 mg, 14%) 1H NMR (400 MHz, DMSO-d$_6$) δ ppm 4.11 (s, 2H) 4.95 (s, 2H) 7.23-7.35 (m, 5H) 9.84 (s, 1H) 12.09 (s, 1H)

Example 6

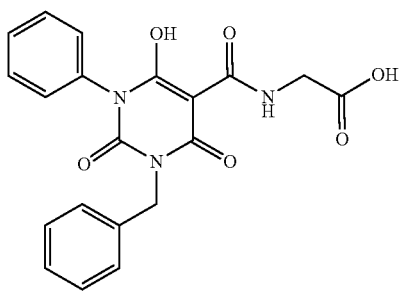 [SMILES: O=C(O)CNC(=O)c1c(O)n(-c2ccccc2)c(=O)n(Cc2ccccc2)c1=O]

N-{[6-Hydroxy-2,4-dioxo-1-phenyl-3-(phenylmethyl)-1,2,3,4-tetrahydro-5-pyrimidinyl]carbonyl}glycine 6a) Ethyl 6-hydroxy-2,4-dioxo-1-phenyl-3-(phenylmethyl)-1,2,3,4-tetrahydro-5-pyrimidinecarboxylate. Diethyl {[(phenylmethyl)amino]carbonyl}propanedioate (420 mg, 1.43 mmoles) was added to a suspension of sodium hydride (60% suspension in mineral oil, 220 mg, 5.5 mmoles) in dry dioxan (10 mL) and stirred for 10 minutes under argon. Phenyl isocyanate (240 uL, 2.21 mmoles) was added and the mixture sealed in a pressure flask heated in a microwave reactor at 110° C. for 1 hour. The mixture was taken up in dichloromethane, washed with 1 molar hydrochloric acid and evaporated onto silica gel. Flash chromatography (ethyl acetate) gave the title compound (300 mg, 57%) 1H NMR (400 MHz, DMSO-d$_6$) δ ppm 1.15 (t, J=7.07 Hz, 3H) 3.99-4.07 (q, J=7.07 Hz, 2H) 4.94 (s, 1H) 7.08-7.13 (m, 2H) 7.21 (ddd, J=8.46, 4.42, 4.29 Hz, 1H) 7.26-7.33 (m, 5H) 7.37 (t, J=7.45 Hz, 2H).

6b) N-{[6-Hydroxy-2,4-dioxo-1-phenyl-3-(phenylmethyl)-1,2,3,4-tetrahydro-5-pyrimidinyl]carbonyl}glycine. A mixture of ethyl 6-hydroxy-2,4-dioxo-1-phenyl-3-(phenylmethyl)-1,2,3,4-tetrahydro-5-pyrimidinecarboxylate (300 mg, 0.82 mmoles), DBU (150 mg, 1.0 mmoles) and glycine (120 mg, 1.6 mmoles) in ethanol (15 mL) was sealed in a flask and heated in a microwave reactor at 160° C. for 1 hour. The reaction mixture was filtered and the filtrate diluted with dichloromethane and washed with 1 molar hydrochloric acid. The aqueous was extracted with dichloromethane and the combined extracts dried and evaporated to give the title compound (50 mg, 15%) 1H NMR (400 MHz, DMSO-d$_6$) δ ppm 3.81 (s, 2H) 4.99 (s, 2H) 7.14 (d, J=7.33 Hz, 2H) 7.19-7.23 (m, 1H) 7.25-7.34 (m, 5H) 7.39 (t, J=7.45 Hz, 2H) 9.84 (s, 1H)

Example 7

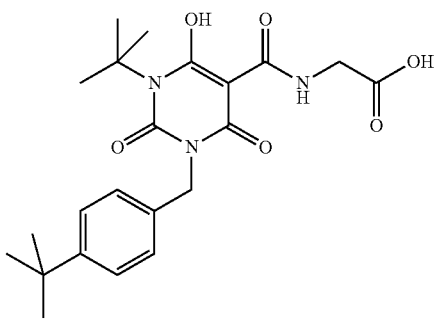 [SMILES: CC(C)(C)c1ccc(Cn2c(=O)c(C(=O)NCC(=O)O)c(O)n(C(C)(C)C)c2=O)cc1]

N-[(1-(1,1-Dimethylethyl)-3-{[4-(1,1-dimethylethyl)phenyl]methyl}-6-hydroxy-2,4-dioxo-1,2,3,4-tetrahydro-5-pyrimidinyl)carbonyl]glycine 7a) 1-(1,1-Dimethylethyl)-3-{[4-(1,1-dimethylethyl)phenyl]methyl}-2,4,6(1H,3H,5H)-pyrimidinetrione. A mixture of t-butyl isocyanate (571 uL, 5.0 mmoles) and 4-t-butylbenzylamine (880 uL, 5.0 mmoles) in dry dichloromethane was stirred for 1 hour. Dichloromalonate (486 uL, 5.0 mmoles) was added and the mixture heated under reflux for 1 hour. The mixture was washed with 1N hydrochloric acid and evaporated onto silica gel. Flash chromatography (10-35% ethyl acetate-hexane) gave the title compound (1.3 g, 79%) 1H NMR (400 MHz, CHLOROFORM-d) δ ppm 1.32 (s, 9H) 1.63 (s, 9H) 3.60 (s, 2H) 4.99 (s, 2H) 7.37 (d, J=2.78 Hz, 4H).

7b) Ethyl N-[(1-(1,1-dimethylethyl)-3-{[4-(1,1-dimethylethyl)phenyl]methyl}-6-hydroxy-2,4-dioxo-1,2,3,4-tetrahydro-5-pyrimidinyl)carbonyl]glycinate. 1-(1,1-Dimethylethyl)-3-{[4-(1,1-dimethylethyl)phenyl]methyl}-2,4,6(1H,3H,5H)-pyrimidinetrione (1.3 g, 3.93 mmoles) and diisopropylethylamine (1.36 mL, 7.86 mmoles) were stirred together in dry chloroform (25 mL) and treated with ethyl isocyanatoacetate (335 uL, 3.93 mmoles). The mixture was stirred for 3 hours, washed twice with 1 molar hydrochloric acid, dried and evaporated to give the title compound (1.8 g, quant.) 1H NMR (400 MHz, CHLOROFORM-d) δ ppm 1.32 (t, J=7.07 Hz, 3H) 1.71 (s, 9H) 1.73 (s, 9H) 4.28-4.34 (m, 2H) 5.03-5.07 (m, 2H) 7.33-7.39 (m, 4H) 10.21-10.30 (m, 1H).

7c) N-[(1-(1,1-Dimethylethyl)-3-{[4-(1,1-dimethylethyl)phenyl]methyl}-6-hydroxy-2,4-dioxo-1,2,3,4-tetrahydro-5-pyrimidinyl)carbonyl]glycine. A mixture of ethyl N-[(1-(1,1-dimethylethyl)-3-{[4-(1,1-dimethylethyl)phenyl]methyl}-6-hydroxy-2,4-dioxo-1,2,3,4-tetrahydro-5-pyrimidinyl)carbonyl]glycinate (1.8 g, 3.9 mmoles) and 1 molar sodium hydroxide solution (6.0 mL) in ethanol (5.0 mL) was stirred overnight. The reaction was incomplete; therefore 6 molar sodium hydroxide was added. After 2 hours, the mixture was partitioned between ethyl acetate and 1 molar hydrochloric acid, the organic solution washed with 1 molar hydrochloric acid, dried and evaporated. The title compound was obtained by crystallization from cold hexane (700 mg, 41%) 1H NMR (400 MHz, DMSO-$d_6$) δ ppm 1.25 (s, 9H) 1.65 (s, 9H) 4.11 (d, J=5.81 Hz, 2H) 4.93 (s, 2H) 7.20 (d, J=8.59 Hz, 2H) 7.34 (d, J=8.34 Hz, 2H) 10.06 (t, J=5.56 Hz, 1H) 13.06 (s, 1H).

Example 8

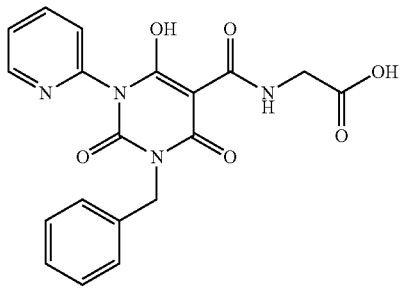 [SMILES: O=C(O)CNC(=O)c1c(O)n(-c2ccccn2)c(=O)n(Cc2ccccc2)c1=O]

N-{[6-Hydroxy-2,4-dioxo-3-(phenylmethyl)-1-(2-pyridinyl)-1,2,3,4-tetrahydro-5-pyrimidinyl]carbonyl}glycine 8a) 2-Isocyanatopyridine. 2-Picolinic acid (1.0 g, 8.0 mmoles) was stirred in toluene (25 mL) and treated with diphenylphosphoryl azide (2.0 mL, 9.3 mmoles) at room temperature under argon. Triethylamine (1.34 mL, 9.6 mmoles) was added dropwise, stirred for 30 minutes then heated to 80° C. for 2 hours. The mixture was cooled, the solid collected, washed with a little ethyl acetate, hexane and vacuum dried to give the title compound (750 mg, 78%) 1H NMR (400 MHz, DMSO-$d_6$) δ ppm 8.62 (dd, J=4.93, 1.14 Hz, 1H), 8.44 (d, J=6.32 Hz, 1H), 8.04 (td, J=7.71, 2.02 Hz, 1H), 7.91 (ddd, J=8.84, 6.95, 1.64 Hz, 1H), 7.55 (s, 1H), 7.51-7.55 (m, 1H), 7.17 (d, J=8.84 Hz, 1H), 7.00 (td, J=6.95, 1.26 Hz, 1H).

8b) Ethyl 6-hydroxy-2,4-dioxo-3-(phenylmethyl)-1-(2-pyridinyl)-1,2,3,4-tetrahydro-5-pyrimidinecarboxylate. 2-Isocyanatopyridine (265 mg, 2.2 mmoles) was added to a suspension of sodium hydride (200 mg, 5 mmoles) and diethyl {[(phenylmethyl)amino]carbonyl}propanedioate (example 1a, 425 mg, 1.45 mmoles) in anhydrous dioxane (10 mL). The mixture was heated in a microwave reactor at 110° C. for 1 hour, cooled, dissolved in dichloromethane, washed with 1 molar hydrochloric acid and purified by flash chromatography (ethyl acetate-10% methanol in ethyl acetate) to give the title compound (90 mg, 12%) 1H NMR (400 MHz, DMSO-$d_6$) δ ppm 8.93 (dd, J=7.20, 1.39 Hz, 1H), 8.11-8.26 (m, 1H), 7.19-7.45 (m, 7H), 4.78-5.01 (m, 2H), 4.15 (q, J=7.24 Hz, 2H), 1.24 (t, J=7.07 Hz, 3H).

8c) N-{[6-hydroxy-2,4-dioxo-3-(phenylmethyl)-1-(2-pyridinyl)-1,2,3,4-tetrahydro-5-pyrimidinyl]carbonyl}glycine. A mixture of N-{[6-hydroxy-2,4-dioxo-3-(phenylmethyl)-1-(2-pyridinyl)-1,2,3,4-tetrahydro-5-pyrimidinyl]carbonyl}glycine (90 mg, 0.24 mmoles), glycine (90 mg, 1.2 mg) and DBU (150 mg, 1.0 mmoles) in ethanol (5 mL) was heated at 170° C. for 1 hour in a microwave reactor. Purification by preparative HPLC (acetonitrile-0.1% TFA in water, 20-100%) gave the title compound (17 mg, 18%). 1H NMR (400 MHz, DMSO-$d_6$) δ ppm 13.13 (s, 1H), 10.07 (s, 1H), 8.58 (dd, J=4.93, 1.14 Hz, 1H), 8.01 (td, J=7.71, 1.77 Hz, 1H), 7.49-7.58 (m, 2H), 7.26-7.36 (m, 6H), 5.02 (s, 2H), 4.15 (d, J=5.81 Hz, 2H).

Example 9

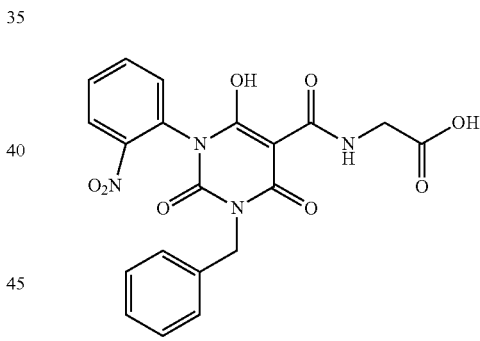

N-{[6-Hydroxy-1-(2-nitrophenyl)-2,4-dioxo-3-(phenylmethyl)-1,2,3,4-tetrahydro-5-pyrimidinyl]carbonyl}glycine 9a) Ethyl 6-hydroxy-1-(2-nitrophenyl)-2,4-dioxo-3-(phenylmethyl)-1,2,3,4-tetrahydro-5-pyrimidinecarboxylate. Diethyl {[(phenylmethyl)amino]carbonyl}propanedioate (420 mg, 1.43 mmoles) was added to a suspension of sodium hydride (60% suspension in mineral oil, 220 mg, 5.5 mmoles) in dry dioxan (10 mL) and stirred for 10 minutes under argon. 2-Nitrophenyl isocyanate (360 mg, 2.20 mmoles) was added and the mixture sealed in a pressure flask heated in a microwave reactor at 110° C. for 1 hour. The mixture was taken up in dichloromethane, washed with 1 molar hydrochloric acid and evaporated onto silica gel. Flash chromatography (hexane to 0.5% formic acid in ethyl acetate) gave the title compound (59 mg, 7%) 1H NMR (400 MHz, DMSO-$d_6$) δ ppm 8.16 (s, 1H), 7.81 (s, 1H), 7.68 (s, 1H), 7.47 (s, 1H), 7.08-7.38 (m, 5H), 4.77-5.16 (m, 2H), 4.12 (q, J=5.31 Hz, 2H), 0.97-1.31 (m, 3H)

9b) N-{[6-Hydroxy-2,4-dioxo-1-phenyl-3-(phenylmethyl)-1,2,3,4-tetrahydro-5-pyrimidinyl]carbonyl}glycine. A mixture of ethyl 6-hydroxy-1-(2-nitrophenyl)-2,4-dioxo-3-(phenylmethyl)-1,2,3,4-tetrahydro-5-pyrimidinecarboxylate (59 mg, 0.14 mmoles), DBU (80 mg, 0.52 mmoles) and glycine (40 mg, 0.53 mmoles) in ethanol (3 mL) was sealed in a flask and heated in a microwave reactor at 170° C. for 1 hour. The reaction mixture was poured into 1 molar hydrochloric acid and extracted with dichloromethane (×2) and washed with 1 molar hydrochloric acid. The title compound was obtained by purification by preparative HPLC (10-80% acetonitrile-water-0.1% TFA)(17 mg, 28%) 1H NMR (400 MHz, DMSO-$d_6$) δ ppm 13.14 (br. s., 1H), 10.04 (br. s., 1H), 8.25 (dd, J=8.21, 1.14 Hz, 1H), 7.93 (dt, J=7.71, 1.26 Hz, 1H), 7.71-7.81 (m, 2H), 5.06 (s, 2H), 4.14 (d, J=5.56 Hz, 2H)

Example 10

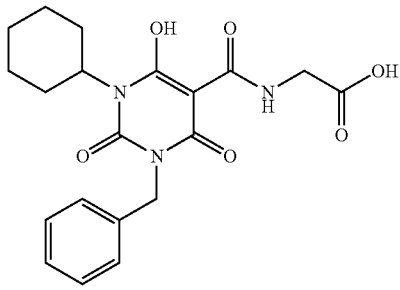 [SMILES: O=C(O)CNC(=O)c1c(O)n(C2CCCCC2)c(=O)n(Cc2ccccc2)c1=O]

N-{[1-Cyclohexyl-6-hydroxy-2,4-dioxo-3-(phenylmethyl)-1,2,3,4-tetrahydro-5-pyrimidinyl]carbonyl}glycine A microwave tube containing sodium hydride (60% suspension in oil, 46 mg, 1.15 mmoles) in dioxan (3 mL) was treated with diethyl {[(phenylmethyl)amino]carbonyl}-propanedioate (example 1a, 100 mg, 0.34 mmoles) and stirred under argon until evolution ceased. Cyclohexyl isocyanate (90 uL, 0.7 mmoles) was added and the mixture was heated at 100° C. for 30 minutes in a microwave reactor. Glycine (48 mg, 0.65 mmoles) and DBU (4 drops) was added, the flask re-sealed and heated at 160° C. for 1 hour in a microwave reactor. The mixture was poured into 1 molar hydrochloric acid and extracted with dichloromethane (×3). The combined extracts were washed with 1 molar hydrochloric acid and brine, dried and evaporated to give the crude product. Purification by preparative HPLC (acetonitrile-water-0.1% TFA, 20-100%) gave the title compound (10 mg, 7%). 1H NMR (400 MHz, DMSO-$d_6$) δ ppm 10.12 (t, J=5.18 Hz, 1H), 7.23-7.34 (m, 6H), 4.99 (s, 2H), 4.65 (t, J=11.62 Hz, 1H), 4.10 (d, J=5.81 Hz, 2H), 2.21-2.32 (m, 2H), 1.78 (d, J=12.63 Hz, 2H), 1.62 (s, 3H), 1.22-1.33 (m, 3H), 1.06-1.17 (m, 1H)

Example 11

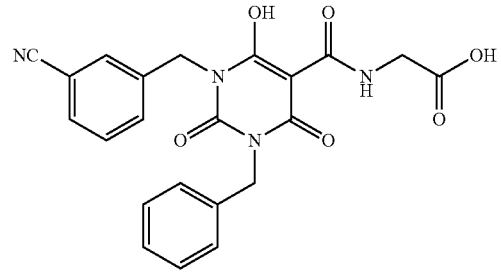 [SMILES: N#Cc1cccc(Cn2c(O)c(C(=O)NCC(=O)O)c(=O)n(Cc3ccccc3)c2=O)c1]

N-{[1-[(3-Cyanophenyl)methyl]-6-hydroxy-2,4-dioxo-3-(phenylmethyl)-1,2,3,4-tetrahydro-5-pyrimidinyl]carbonyl}glycine 11a) Ethyl N-{[6-hydroxy-2,4-dioxo-3-(phenylmethyl)-1,2,3,4-tetrahydro-5-pyrimidinyl]carbonyl}glycinate. Ethyl isocyanatoacetate (2.24 mL, 20 mmoles) was added dropwise to a solution of 1-(phenylmethyl)-2,4,6(1H,3H,5H)-pyrimidinetrione (4.4 g, 20 mmoles) and ethyl diisopropylamine (6.9 mL, 40 mmoles) in dichloromethane (120 mL) and stirred overnight under argon. The mixture was washed with 1 molar hydrochloric acid, water and brine, dried and evaporated. The solid was slurried in diethyl ether, collected, washed with diethyl ether and hexane, dried to give the title compound (5.1 g, 73%). 1H NMR (400 MHz, DMSO-$d_6$) δ ppm 12.13 (br. s., 1H), 9.84 (br. s., 1H), 7.13-7.48 (m, 5H), 4.95 (s, 2H), 4.17 (d, 2H), 4.15 (q, 2H), 1.21 (t, J=7.20 Hz, 3H)

11b) Ethyl N-{[1-[(3-cyanophenyl)methyl]-6-hydroxy-2,4-dioxo-3-(phenylmethyl)-1,2,3,4-tetrahydro-5-pyrimidinyl]carbonyl}glycinate. A mixture of ethyl N-{[6-hydroxy-2,4-dioxo-3-(phenylmethyl)-1,2,3,4-tetrahydro-5-pyrimidinyl]carbonyl}glycinate (350 mg, 1.0 mmoles), 3-cyanobenzyl bromide (250 mg, 1.22 mmoles) and sodium carbonate (300 mg, 2.9 mmoles) in dimethylformamide (5.0 mL) was stirred under argon at 100° C. for 2 hours. The mixture was cooled, poured into 1 molar hydrochloric acid and extracted with ethyl acetate (×2). The combined extracts were washed with water and brine. Purification by preparative HPLC (acetonitrile-water-0.1% TFA, 20-100%) gave the title compound (300 mg, 65%). 1H NMR (400 MHz, DMSO-$d_6$) δ ppm 10.12 (t, J=5.81 Hz, 1H), 7.79 (s, 1H), 7.71-7.76 (m, 1H), 7.66 (d, J=8.34 Hz, 1H), 7.54 (t. J=7.83 Hz, 1H), 7.32 (d, J=4.29 Hz, 4H), 7.23-7.29 (m, 1H), 5.07 (s, 2H), 5.03 (s, 2H), 4.22 (d, J=6.06 Hz, 2H), 4.15 (q, J=7.07 Hz, 2H), 1.21 (t, J=7.20 Hz, 3H)

11c) N-{[1-[(3-Cyanophenyl)methyl]-6-hydroxy-2,4-dioxo-3-(phenylmethyl)-1,2,3,4-tetrahydro-5-pyrimidinyl]carbonyl}glycine. Ethyl N-{[1-[(3-cyanophenyl)methyl]-6-hydroxy-2,4-dioxo-3-(phenylmethyl)-1,2,3,4-tetrahydro-5-pyrimidinyl]carbonyl}glycinate (280 mg, 0.6 mmoles) was dissolved in methanol (5 mL) and treated with 1 molar sodium hydroxide solution (4 mL) and stirred for 3 hours. The mixture was acidified and extracted into ethyl acetate. Purification by preparative HPLC (acetonitrile-water-0.1% TFA, 20-100%) and crystallization from ethanol-water gave the title compound (50 mg, 20%). 1H NMR (400 MHz, DMSO-$d_6$) δ ppm 13.11 (s, 1H), 10.11 (s, 1H), 7.79 (s, 1H), 7.74 (d, J=7.58 Hz, 1H), 7.66 (d, J=8.34 Hz, 1H), 7.55 (t, J=7.71 Hz, 1H), 7.29-7.35 (m, 4H), 7.23-7.29 (m, 1H), 5.07 (s, 2H), 5.03 (s, 2H), 4.14 (d, J=5.81 Hz, 2H).

Example 12

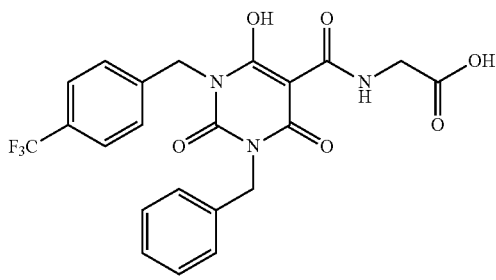 [SMILES: O=C(O)CNC(=O)c1c(O)n(Cc2ccc(C(F)(F)F)cc2)c(=O)n(Cc2ccccc2)c1=O]

N-[(6-Hydroxy-2,4-dioxo-3-(phenylmethyl)-1-{[4-(trifluoromethyl)phenyl]methyl}-1,2,3,4-tetrahydro-5-pyrimidinyl)carbonyl]glycine A mixture of ethyl N-{[6-hydroxy-2,4-dioxo-3-(phenylmethyl)-1,2,3,4-tetrahydro-5-pyrimidinyl]carbonyl} glycinate (example 11a, 356 mg, 1.03 mmoles), 4-trifluoromethylbenzyl bromide (175 uL, 1.13 mmoles) and sodium carbonate (330 mg, 3.1 mmoles) in dimethylformamide (6.0 mL) was stirred under argon at 100° C. for 2.5 hours. The mixture was cooled, poured into 1 molar hydrochloric acid and extracted with ethyl acetate (×2). The ester was hydrolysed by stirring in a mixture of ethanol (3 mL) and 1 molar sodium hydroxide solution (3 mL) for 3 hours. The mixture was acidified and extracted with ethyl acetate. Purification by preparative HPLC (acetonitrile-water-0.1% TFA, 20-100%) and crystallization from ethanol-water gave the title compound (150 mg, 30%). 1H NMR (400 MHz, DMSO-$d_6$) δ ppm 13.12 (s, 1H), 10.12 (t, J=5.56 Hz, 1H), 7.69 (d, J=8.08 Hz, 2H), 7.53 (d, J=8.08 Hz, 2H), 7.24-7.35 (m, 5H), 5.11 (s, 2H), 5.03 (s, 2H), 4.14 (d, J=5.81 Hz, 2H).

Example 13

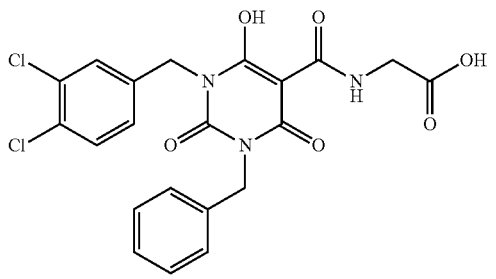 [SMILES: O=C(O)CNC(=O)c1c(O)n(Cc2ccc(Cl)c(Cl)c2)c(=O)n(Cc2ccccc2)c1=O]

N-{[1-[(3,4-Dichlorophenyl)methyl]-6-hydroxy-2,4-dioxo-3-(phenylmethyl)-1,2,3,4-tetrahydro-5-pyrimidinyl]carbonyl}glycine A mixture of ethyl N-{[6-hydroxy-2,4-dioxo-3-(phenylmethyl)-1,2,3,4-tetrahydro-5-pyrimidinyl]carbonyl} glycinate (example 11a, 357 mg, 1.03 mmoles), 3,4-dichlorobenzyl bromide (193 uL, 1.13 mmoles) and sodium carbonate (330 mg, 3.1 mmoles) in dimethylformamide (6.0 mL) was stirred under argon at 100° C. for 2.5 hours. The mixture was cooled, poured into 1 molar hydrochloric acid and extracted with ethyl acetate (×2). The ester was hydrolysed by stirring in a mixture of ethanol (3 mL) and 1 molar sodium hydroxide solution (3 mL) for 3 hours. The mixture was acidified and extracted with ethyl acetate. Purification by preparative HPLC (acetonitrile-water-0.1% TFA, 20-100%) and crystallization from ethanol-water gave the title compound (50 mg, 10%). 1H NMR (400 MHz, DMSO-$d_6$) δ ppm 13.13 (s, 1H), 10.11 (t, J=5.68 Hz, 1H), 7.59 (dd, J=5.18, 3.16 Hz, 2H), 7.24-7.34 (m, 6H), 5.01 (s, 2H), 5.02 (s, 2H), 4.14 (d, J=5.81 Hz, 2H).

Example 14

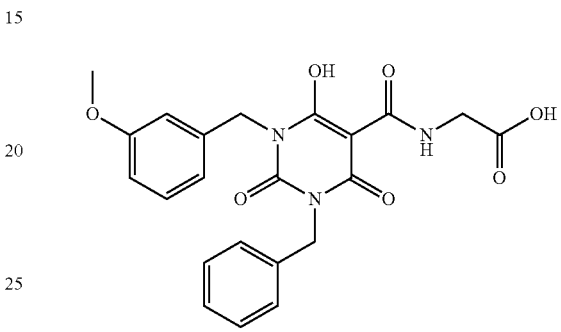

N-{[6-Hydroxy-1-{[3-(methyloxy)phenyl]methyl}-2,4-dioxo-3-(phenylmethyl)-1,2,3,4-tetrahydro-5-pyrimidinyl]carbonyl}glycine A mixture of ethyl N-{[6-hydroxy-2,4-dioxo-3-(phenylmethyl)-1,2,3,4-tetrahydro-5-pyrimidinyl] carbonyl}glycinate (example 11a, 369 mg, 1.06 mmoles), 3-methoxybenzyl bromide (163 uL, 1.17 mmoles) and sodium carbonate (330 mg, 3.1 mmoles) in dimethylformamide (6.0 mL) was stirred under argon at 100° C. for 2.5 hours. The mixture was cooled, poured into 1 molar hydrochloric acid and extracted with ethyl acetate (×2). The ester was hydrolysed by stirring in a mixture of ethanol (3 mL) and 1 molar sodium hydroxide solution (3 mL) for 3 hours. The mixture was acidified and extracted with ethyl acetate. Purification by preparative HPLC (acetonitrile-water-0.1% TFA, 20-100%) and crystallization from ethanol-water gave the title compound (50 mg, 11%). 1H NMR (400 MHz, DMSO-$d_6$) δ ppm 13.10 (br. s., 1H), 10.12 (t, 1H), 7.14-7.47 (m, 6H), 6.69-6.97 (m, 3H), 5.00 (s, 2H), 5.03 (s, 2H), 4.13 (d, J=5.56 Hz, 2H), 3.71 (s, 3H).

Example 15

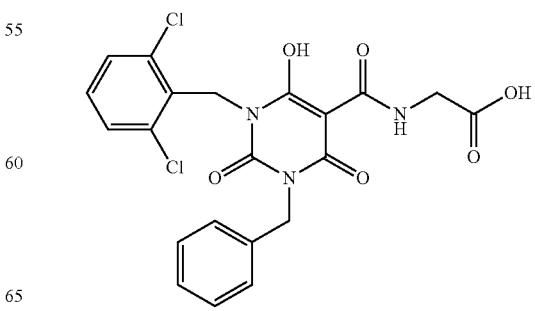

N-{[1-[(2,6-Dichlorophenyl)methyl]-6-hydroxy-2,4-dioxo-3-(phenylmethyl)-1,2,3,4-tetrahydro-5-pyrimidinyl]carbonyl}glycine A mixture of ethyl N-{[6-hydroxy-2,4-dioxo-3-(phenylmethyl)-1,2,3,4-tetrahydro-5-pyrimidinyl]carbonyl}glycinate (example 11a, 388 mg, 1.12 mmoles), 2,6-dichlorobenzyl bromide (295 uL, 1.23 mmoles) and sodium carbonate (330 mg, 3.1 mmoles) in dimethylformamide (6.0 mL) was stirred under argon at 100° C. for 2.5 hours. The mixture was cooled, poured into 1 molar hydrochloric acid and extracted with ethyl acetate (×2). The ester was hydrolysed by stirring in a mixture of ethanol (3 mL) and 1 molar sodium hydroxide solution (3 mL) for 3 hours. The mixture was acidified and extracted with ethyl acetate. Purification by preparative HPLC (acetonitrile-water-0.1% TFA, 20-100%) and crystallization from ethanol-water gave the title compound (60 mg, 11%). 1H NMR (400 MHz, DMSO-$d_6$) δ ppm 13.12 (br. s., 1H), 10.02 (br. s., 1H), 7.42 (d, 2H), 7.22-7.35 (m, 6H), 5.30 (s, 2H), 5.01 (s, 2H), 4.12 (d, J=5.81 Hz, 2H).

Example 16

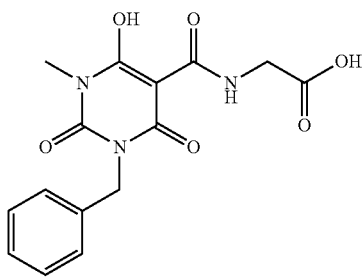 [SMILES: Cn1c(O)c(C(=O)NCC(=O)O)c(=O)n(Cc2ccccc2)c1=O]

N-{[6-Hydroxy-1-methyl-2,4-dioxo-3-(phenylmethyl)-1,2,3,4-tetrahydro-5-pyrimidinyl]carbonyl}glycine A mixture of ethyl N-{[6-hydroxy-2,4-dioxo-3-(phenylmethyl)-1,2,3,4-tetrahydro-5-pyrimidinyl]carbonyl}glycinate (295 mg, 0.85 mmoles), methyl iodide (62 uL, 1.0 mmoles) and sodium carbonate (320 mg, 3.0 mmoles) in dimethylformamide (5.0 mL) was stirred under argon at 100° C. for 2.5 hours. The mixture was cooled, poured into 1 molar hydrochloric acid and extracted with ethyl acetate (×2). The ester was hydrolysed by stirring in a mixture of ethanol (5 mL) and 1 molar sodium hydroxide solution (4 mL) for 4 hours. The mixture was acidified and extracted with ethyl acetate. Purification by preparative HPLC (acetonitrile-water-0.1% TFA, 20-100%) and crystallization from ether-hexane gave the title compound (80 mg, 28%). 1H NMR (400 MHz, DMSO-$d_6$) δ ppm 13.11 (br. s., 1H), 10.09 (br. s., 1H), 7.28-7.36 (m, 4H), 7.19-7.29 (m, 1H), 5.01 (s, 2H), 4.14 (d, J=5.81 Hz, 2H), 3.21 (s, 3H).

Example 17

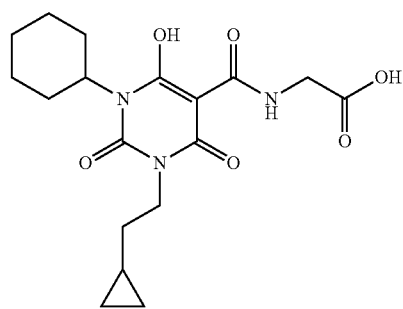 [SMILES: O=C(O)CNC(=O)c1c(O)n(C2CCCCC2)c(=O)n(CCC2CC2)c1=O]

N-{[1-Cyclohexyl-3-(2-cyclopropylethyl)-6-hydroxy-2,4-dioxo-1,2,3,4-tetrahydro-5-pyrimidinyl]carbonyl}glycine 17a) N-Cyclohexyl-N'-(2-cyclopropylethyl)urea. Cyclohexyl isocyanate (564 uL, 4.7 mmoles) was added to a solution of cyclopropylethylamine hydrochloride (537 mg, 4.4 mmoles) and triethylamine (615 uL, 4.4 mmoles) in chloroform (10 mL) under argon at room temperature. The mixture was stirred for 1 hour, washed with 1 molar hydrochloric acid, dried and evaporated. Trituration with hexane gave a solid (550 mg, 59%). 1H NMR (400 MHz, CHLOROFORM-d) δ ppm 4.55 (br. s., 1H), 3.47-3.59 (m, 1H), 3.27 (t, J=6.95 Hz, 2H), 1.95 (dd, J=12.63, 3.54 Hz, 2H), 1.67-1.79 (m, 2H), 1.58-1.67 (m, 1H), 1.43 (q, J=6.99 Hz, 2H), 1.30-1.40 (m, 2H), 1.07-1.24 (m, 3H), 0.63-0.77 (m, 1H), 0.44-0.51 (m, 2H), 0.05-0.12 (m, 2H)

17b) 1-Cyclohexyl-3-(2-cyclopropylethyl)-2,4,6(1H,3H,5H)-pyrimidinetrione. Malonyl dichloride (250 uL, 2.57 mmoles) was added dropwise to a solution of N-cyclohexyl-N-(2-cyclopropylethyl)urea (500 mg, 2.38 mmoles) in dichloromethane under argon. The mixture was stirred overnight then heated under reflux for 2 hours. Flash chromatography (hexane to 20% ethyl acetate-hexane) gave the title compound (230 mg, 35%). 1H NMR (400 MHz, CHLOROFORM-d) δ ppm 4.57-4.71 (m, 1H), 3.94-4.04 (m, 2H), 3.60-3.68 (m, 2H), 2.20-2.36 (m, 2H), 1.86 (d, J=13.39 Hz, 2H), 1.60-1.73 (m, 3H), 1.45-1.60 (m, 2H), 1.29-1.44 (m, 2H), 1.15-1.29 (m, 1H), 0.62-0.77 (m, 1H), 0.40-0.51 (m, 2H), −0.00-0.12 (m, 2H).

17c) N-{[1-cyclohexyl-3-(2-cyclopropylethyl)-6-hydroxy-2,4-dioxo-1,2,3,4-tetrahydro-5-pyrimidinyl]carbonyl}glycine. A solution of 1-cyclohexyl-3-(2-cyclopropylethyl)-2,4,6(1H,3H,5H)-pyrimidinetrione (225 mg, 0.8 mmoles) and diisopropylethylamine (280 uL, 1.6 mmoles) in chloroform (10 mL) was treated with ethyl 2-isocyanatoacetate (91 uL, 0.81 mmoles) and stirred for 1 hour. The mixture was washed with hydrochloric acid (×2) and evaporated. The residue was dissolved in ethanol (3 mL) and treated with 1 molar sodium hydroxide solution and stirred for 3 hours. The mixture was partitioned between ethyl acetate and 1 molar hydrochloric acid, separated and the organic solution washed with brine, dried and evaporated. The solid residue was reprecipitated from ether-hexane to give the title compound (190 mg, 63%). 1H NMR (400 MHz, DMSO-$d_6$) δ ppm 13.07 (br. s, 1H), 10.14 (t, J=5.81 Hz, 1H), 4.64 (s, 1H), 4.12 (d, J=5.81 Hz, 2H), 3.87-3.92 (m, 2H), 2.22-2.34 (m, 2H), 1.79 (d, J=13.14 Hz, 2H), 1.61 (t, J=12.13 Hz, 3H), 1.45 (q, J=7.16 Hz, 2H), 1.23-1.33 (m, 2H), 1.08-1.18 (m, 1H), 0.62-0.70 (m, 1H), 0.35-0.40 (m, 2H), −0.04-0.00 (m, 2H)

Example 18

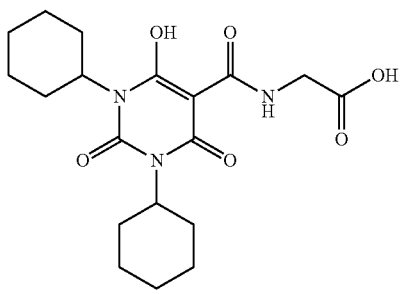

N-[(1,3-Dicyclohexyl-6-hydroxy-2,4-dioxo-1,2,3,4-tetrahydro-5-pyrimidinyl)carbonyl]glycine Method 1

18.1a) 1,3-Dicyclohexyl-2,4,6(1H,3H,5H)-pyrimidinetrione. Dicyclohexylurea (3.0 g, 13.39 mmoles) was stirred in chloroform (80 mL) and treated with a solution of malonyl dichloride (1.3 mL, 13.39 mmoles) in chloroform (20 mL), added dropwise under argon. The mixture was heated at 50° C. for 4 hours, washed with 1 molar hydrochloric acid and evaporated onto silica gel. Flash chromatography (10-30% ethyl acetate in hexane) to give the title compound (2.13 g, 55%). 1H NMR (400 MHz, DMSO-$d_6$) δ ppm 4.46 (tt, J=12.13, 3.54 Hz, 2H), 3.69 (s, 2H), 2.15 (qd, J=12.46, 3.28 Hz, 4H), 1.77 (d, J=13.14 Hz, 4H), 1.59 (t, J=12.76 Hz, 6H), 1.26 (q, J=12.97 Hz, 4H), 1.04-1.16 (m, 2H)

18.1b) N-[(1,3-Dicyclohexyl-6-hydroxy-2,4-dioxo-1,2,3,4-tetrahydro-5-pyrimidinyl)carbonyl]glycine. Ethyl isocyanatoacetate (802 uL, 7.15 mmoles) was added to a mixture of 1,3-dicyclohexyl-2,4,6(1H,3H,5H)-pyrimidinetrione (2.1 g, 7.15 mmoles) and diisopropylethylamine (2.47 mL, 14.3 mmoles) in dichloromethane (100 mL) and stirred overnight. The reaction mixture was washed with 1 molar hydrochloric acid (×2) and evaporated. The residue was dissolved in ethanol (10 mL) and treated with 1.0 molar sodium hydroxide (5 mL). The mixture was stirred for 72 hours, acidified and extracted into ethyl acetate. Some ester remained, therefore the solution was evaporated and the residue was dissolved in 1 molar sodium hydroxide solution with warming and stirred for 2 hours. The mixture was acidified with 1M HCl and extracted with ethyl acetate (×2). The combined extracts were washed with 1 molar hydrochloric acid, dried and evaporated to a solid which was slurried in a mixture of diethyl ether and hexane, collected, washed with the same solvent mixture and dried to give the title compound (1.86 g, 66%). 1H NMR (400 MHz, DMSO-$d_6$) δ ppm 13.07 (br. s., 1H), 10.19 (t, J=5.31 Hz, 1H), 4.63 (t, J=10.99 Hz, 2H), 4.12 (d, J=5.56 Hz, 2H), 2.27 (q, J=11.71 Hz, 4H), 1.79 (d, J=12.88 Hz, 4H), 1.50-1.69 (m, 6H), 1.28 (q, J=12.97 Hz, 4H), 1.12 (q, J=12.72 Hz, 2H)

Method 2

18.2a) 1,3-Dicyclohexyl-2,4,6(1H,3H,5H)-pyrimidinetrione. A solution of N,N-dicyclohexylcarbodiimide (254 g; 1.23 mol.) in anhydrous THF (700 mL) was added dropwise to a cold (0° C.) solution of malonic acid (64.1 g; 0.616 mol.) in anhydrous THF (300 mL) over a period of ~30 minutes. The mixture was stirred and allowed to warm to room temperature over 2 h. (After 1 h, the mixture became very thick with precipitate so further anhydrous THF (500 mL) was added to facilitate agitation.). The mixture was filtered and the filtrate evaporated to afford a yellow solid which was immediately slurried in ethanol (1 L) and heated to reflux temperature. The mixture was then allowed to cool to room temperature then filtered and the solid washed with cold ethanol (250 mL) to afford the title compound (129.4 g; 72%) as a colorless solid. 1H NMR (400 MHz, DMSO-$d_6$) δ ppm 1.03-1.18 (m, 2H) 1.18-1.34 (m, 4H) 1.59 (t, J=13.14 Hz, 6H) 1.76 (d, J=12.88 Hz, 4H) 2.04-2.24 (m, 4H) 3.69 (s, 2H) 4.35-4.54 (m, 2H).

18.2b) Ethyl N-[(1,3-dicyclohexyl-6-hydroxy-2,4-dioxo-1,2,3,4-tetrahydro-5-pyrimidinyl)carbonyl]glycinate. A solution of 1,3-dicyclohexyl-2,4,6(1H,3H,5H)-pyrimidinetrione (120.0 g; 0.41 mol.) and diisopropylethylamine (105.8 g; 0.82 mol.) in dichloromethane (1 L) was stirred and treated dropwise with a solution of ethyl isocyanatoacetate (53.0 g; 0.41 mol.) in dichloromethane (500 mL) and the mixture was then stirred at room temperature overnight. The mixture was then treated dropwise with 6M aq. hydrochloric acid (500 mL) and the separated organic layer was dried and evaporated. The resulting solid was slurried in hexanes (500 mL) and heated to reflux temperature. The mixture was then allowed to cool and filtered to afford ethyl N-[(1,3-dicyclohexyl-6-hydroxy-2,4-dioxo-1,2,3,4-tetrahydro-5-pyrimidinyl)carbonyl]glycinate (159.1 g; 92%) as a cream powder. 1H NMR (400 MHz, CHLOROFORM-d) δ ppm 1.24 (s, 2H) 1.37 (s, 7H) 1.52-1.76 (m, 6H) 1.78-1.94 (m, 4H) 2.25-2.48 (m, 4H) 4.17 (d, J=5.81 Hz, 2H) 4.28 (q, J=7.24 Hz, 2H) 4.74 (s, 2H) 10.37 (t, J=4.67 Hz, 1H).

18.2c) N-[(1,3-Dicyclohexyl-6-hydroxy-2,4-dioxo-1,2,3,4-tetrahydro-5-pyrimidinyl)carbonyl]glycine. A stirred suspension of ethyl N-[(1,3-dicyclohexyl-6-hydroxy-2,4-dioxo-1,2,3,4-tetrahydro-5-pyrimidinyl)carbonyl]glycinate (159.0 g; 0.377 mol.) in ethanol (1.5 L) was treated dropwise with 6M aq. Sodium hydroxide (250 mL) and stirred at room temperature for 3 h. The solution was then acidified by the dropwise addition of 6M aq. hydrochloric acid (300 mL), diluted with water (1 L) and then filtered. The crude solid was slurried in water (2 L) then stirred vigorously and heated at 35° C. for 1 h and filtered and dried. The solid material (~138 g) was then crystallized from glacial acetic acid (1.5 L) (with hot filtration to remove a small amount of insoluble material). The solid, which crystallized upon cooling, was collected and washed with cold glacial acetic acid (3×100 mL) to afford N-[(1,3-dicyclohexyl-6-hydroxy-2,4-dioxo-1,2,3,4-tetrahydro-5-pyrimidinyl)carbonyl]glycine (116.2 g; 78%) as a colorless solid. 1H NMR (400 MHz, DMSO-$d_6$) δ ppm 1.11 (d, J=12.88 Hz, 2H) 1.27 (q, J=12.80 Hz, 4H) 1.62 (s, 6H) 1.70-1.90 (m, J=12.88 Hz, 4H) 2.11-2.44 (m, 4H) 4.11 (d, J=5.81 Hz, 2H) 4.45-4.77 (m, 2H) 10.19 (t, J=5.81 Hz, 1H) 13.08 (s, 1H).

Example 19

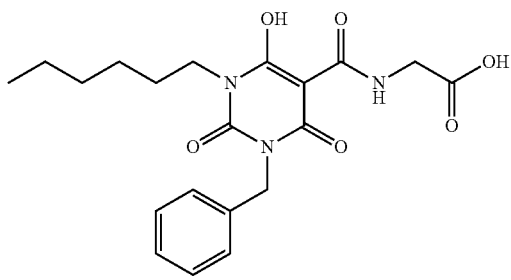 [SMILES: CCCCCCn1c(O)c(C(=O)NCC(=O)O)c(=O)n(Cc2ccccc2)c1=O]

N-{[1-Hexyl-6-hydroxy-2,4-dioxo-3-(phenylmethyl)-1,2,3,4-tetrahydro-5-pyrimidinyl]carbonyl}glycine 19a) N-Hexyl-N'-(phenylmethyl)urea. n-Hexyl isocyanate (620 uL, 4.24 mmoles) was added to a solution of benzylamine hydrochloride (610 mg, 4.24 mmoles) and diisopropylethylamine (735 uL, 4.24 mmoles) in chloroform (10 mL). The mixture was stirred for 1 hour, washed with 1 molar hydrochloric acid (×2), dried and evaporated to give the title compound (993 mg, 91%). 1H NMR (400 MHz, CHLOROFORM-d) δ ppm 7.18-7.45 (m, 5H), 4.37 (s, 2H), 3.15 (t, J=7.20 Hz, 2H), 1.42-1.53 (m, 2H), 1.23-1.36 (m, 6H), 0.84-0.94 (m, 3H).

19b) 1-Hexyl-3-(phenylmethyl)-2,4,6(1H,3H,5H)-pyrimidinetrione. Malonyl dichloride (411 uL, 4.2 mmoles) was added to a solution of N-hexyl-M-(phenylmethyl)urea (900 mg, 3.8 mmoles) in dichloromethane (25 mL) and the mixture was heated under reflux for 3 hours. The mixture was washed with 1 molar hydrochloric acid and evaporated. Flash chromatography (10-15% ethyl acetate in hexane) gave the title compound (480 mg, 42%). 1H NMR (400 MHz, CHLOROFORM-d) δ ppm 7.46 (dd, J=7.83, 1.52 Hz, 2H), 7.28-7.41 (m, 3H), 5.07 (s, 2H), 3.82-3.91 (m, 2H), 3.70 (s, 2H), 1.52-1.66 (m, 2H), 1.19-1.38 (m, 6H), 0.79-0.97 (m, 3H).

19c) N-{[1-Hexyl-6-hydroxy-2,4-dioxo-3-(phenylmethyl)-1,2,3,4-tetrahydro-5-pyrimidinyl]carbonyl}glycine. A mixture of 1-hexyl-3-(phenylmethyl)-2,4,6(1H,3H,5H)-pyrimidinetrione (470 mg, 1.55 mmoles), diisopropylethylamine (280 uL, 1.6 mmoles) and ethyl 2-isocyanatoacetate (132 uL, 1.55 mmoles) was stirred in chloroform (10 mL) for 3 hours. The mixture was washed with hydrochloric acid (×2) and evaporated. The residue was dissolved in ethanol (15 mL), treated with 1 molar sodium hydroxide solution and stirred for 4 hours. The mixture was partitioned between ethyl acetate and 1 molar hydrochloric acid. The aqueous was extracted with ethyl acetate and the combined extracts washed with 1 molar hydrochloric acid and brine, dried and evaporated. A solid was obtained from diethyl ether-hexane and recrystallized from toluene-hexane to give the title compound (280 mg, 46%). 1H NMR (400 MHz, DMSO-$d_6$) δ ppm 13.11 (s, 1H), 10.10 (s, 1H), 7.24-7.34 (m, 5H), 5.01 (s, 2H), 4.13 (d, J=5.81 Hz, 2H), 3.77-3.86 (m, 2H), 1.54 (d, J=6.82 Hz, 2H), 1.26 (s, 6H), 0.81-0.89 (m, 3H).

Example 20

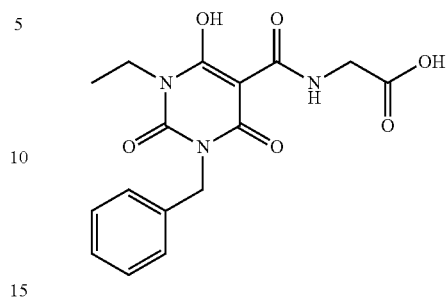

N-{[1-Ethyl-6-hydroxy-2,4-dioxo-3-(phenylmethyl)-1,2,3,4-tetrahydro-5-pyrimidinyl]carbonyl}glycine 20a) 1-Ethyl-3-(phenylmethyl)-2,4,6(1H,3H,5H)-pyrimidinetrione. Malonyl dichloride (411 uL, 4.2 mmoles) was added to a solution of N-ethyl-M-(phenylmethyl)urea (685 mg, 3.84 mmoles) in dichloromethane (25 mL) and the mixture was heated under reflux for 1 hour. The mixture was washed with 1 molar hydrochloric acid and evaporated. Flash chromatography (10-30% ethyl acetate in hexane) gave the title compound (390 mg, 42%). 1H NMR (400 MHz, CHLOROFORM-d) δ ppm 7.41-7.49 (m, 2H), 7.25-7.34 (m, 3H), 5.03 (s, 2H), 3.92 (q, J=7.07 Hz, 2H), 3.64 (s, 2H), 1.20 (t, J=7.07 Hz, 3H).

20b) N-{[1-Ethyl-6-hydroxy-2,4-dioxo-3-(phenylmethyl)-1,2,3,4-tetrahydro-5-pyrimidinyl]carbonyl}glycine. A solution of 1-ethyl-3-(phenylmethyl)-2,4,6(1H,3H,5H)-pyrimidinetrione (390 mg, 1.58 mmoles) and diisopropylethylamine (546 uL, 3.16 mmoles) in chloroform (10 mL) was treated with ethyl isocyanatoacetate (135 uL, 1.58 mmoles) and stirred for 2 hours under argon. The mixture was washed with 1 molar hydrochloric acid (×2), dried and evaporated. The residue was dissolved in ethanol (10 mL), treated with 1 molar sodium hydroxide solution (5 mL) and stirred overnight. The mixture was acidified and extracted into ethyl acetate and the organic solution dried and evaporated. Crystallization from methanol-water gave the title compound (350 mg, 64%). 1H NMR (400 MHz, DMSO-$d_6$) δ ppm 13.12 (br. s, 1H), 10.10 (s, 1H), 7.24-7.35 (m, 5H), 5.01 (s, 2H), 4.14 (d, J=5.56 Hz, 2H), 3.87 (q, J=6.99 Hz, 2H), 1.14 (t, J=6.95 Hz, 3H).

Example 21

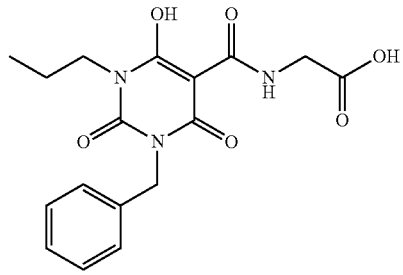 [SMILES: CCCn1c(O)c(C(=O)NCC(=O)O)c(=O)n(Cc2ccccc2)c1=O]

N-{[6-Hydroxy-2,4-dioxo-3-(phenylmethyl)-1-propyl-1,2,3,4-tetrahydro-5-pyrimidinyl]carbonyl}glycine 21a) 1-(Phenylmethyl)-3-propyl-2,4,6(1H,3H,5H)-pyrimidinetrione. Malonyl dichloride (427 uL, 4.4 mmoles) was added to a solution of N-(phenylmethyl)-N'-propylurea (778 mg, 4.04 mmoles) in dichloromethane (25 mL) and the mixture was heated under reflux for 1 hour. The mixture was washed with 1 molar hydrochloric acid and evaporated. Flash chromatography (10-20% ethyl acetate in hexane) gave the title compound (730 mg, 70%). 1H NMR (400 MHz, CHLOROFORM-d) δ ppm 7.46 (dd, J=8.08, 1.52 Hz, 2H), 7.29-7.38 (m, 3H), 5.07 (s, 2H), 3.79-3.87 (m, 2H), 3.69 (s, 2H), 1.57-1.69 (m, 2H), 0.94 (t, J=7.45 Hz, 3H).

21b) N-{[6-Hydroxy-2,4-dioxo-3-(phenylmethyl)-1-propyl-1,2,3,4-tetrahydro-5-pyrimidinyl]carbonyl}glycine. A solution of 1-(phenylmethyl)-3-propyl-2,4,6(1H,3H,5H)-pyrimidinetrione (730 mg, 2.8 mmoles) and diisopropylethylamine (970 uL, 5.6 mmoles) in chloroform (12 mL) was treated with ethyl isocyanatoacetate (239 uL, 2.8 mmoles) and stirred for 2 hours under argon. The mixture was washed with 1 molar hydrochloric acid (×2), dried and evaporated. The residue was dissolved in ethanol (10 mL), treated with 1 molar sodium hydroxide solution (5 mL) and stirred overnight. The mixture was acidified and extracted into ethyl acetate and the organic solution dried and evaporated. Crystallization from ethanol-water gave the title compound (800 mg, 71%). 1H NMR (400 MHz, DMSO-$d_6$) δ ppm 13.11 (s, 1H), 10.11 (s, 1H), 7.24-7.34 (m, 5H), 5.01 (s, 2H), 4.13 (d, J=5.81 Hz, 2H), 3.75-3.84 (m, 2H), 1.52-1.63 (m, 2H), 0.86 (t, J=7.45 Hz, 3H)

Example 22

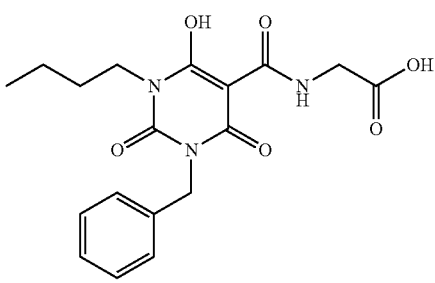 [SMILES: CCCCn1c(O)c(C(=O)NCC(=O)O)c(=O)n(Cc2ccccc2)c1=O]

N-{[1-Butyl-6-hydroxy-2,4-dioxo-3-(phenylmethyl)-1,2,3,4-tetrahydro-5-pyrimidinyl]carbonyl}glycine 22a) 1-Butyl-3-(phenylmethyl)-2,4,6(1H,3H,5H)-pyrimidinetrione. Malonyl dichloride (497 uL, 5.1 mmoles) was added to a solution of N-butyl-N-(phenylmethyl)urea (959 mg, 4.65 mmoles) in dichloromethane (25 mL) and the mixture was heated under reflux for 1 hour. The mixture was washed with 1 molar hydrochloric acid and evaporated. Flash chromatography (0-15% ethyl acetate in hexane) gave the title compound (676 mg, 53%). 1H NMR (400 MHz, DMSO-$d_6$) δ ppm 7.29-7.35 (m, 4H), 7.20-7.28 (m, 1H), 4.92 (s, 2H), 3.82 (s, 2H), 3.71 (t, 2H), 1.48 (tt, 2H), 1.28 (tq, J=7.49, 7.33 Hz, 2H), 0.88 (t, J=7.33 Hz, 3H).

22b) N-{[6-Hydroxy-2,4-dioxo-3-(phenylmethyl)-1-propyl-1,2,3,4-tetrahydro-5-pyrimidinyl]carbonyl}glycine. A solution of 1-butyl-3-(phenylmethyl)-2,4,6(1H,3H,5H)-pyrimidinetrione (676 mg, 2.46 mmoles) and diisopropylethylamine (826 uL, 4.93 mmoles) in chloroform (12 mL) was treated with ethyl isocyanatoacetate (211 uL, 2.46 mmoles) and stirred for 3 hours under argon. The mixture was washed with 1 molar hydrochloric acid (×2), dried and evaporated. The residue was dissolved in ethanol (10 mL), treated with 1 molar sodium hydroxide solution (7 mL) and stirred overnight. The mixture was acidified and extracted into ethyl acetate and the organic solution dried and evaporated. Crystallization from ethanol-water gave the title compound (580 mg, 63%). 1H NMR (400 MHz, DMSO-$d_6$) δ ppm 13.10 (s, 1H), 10.11 (s, 1H), 7.24-7.35 (m, 5H), 5.01 (s, 2H), 4.13 (d, J=5.81 Hz, 2H), 3.79-3.87 (m, 2H), 1.54 (dq, J=7.58, 7.41 Hz, 2H), 1.29 (dq, J=14.97, 7.39 Hz, 2H), 0.89 (t, J=7.45 Hz, 3H).

Example 23

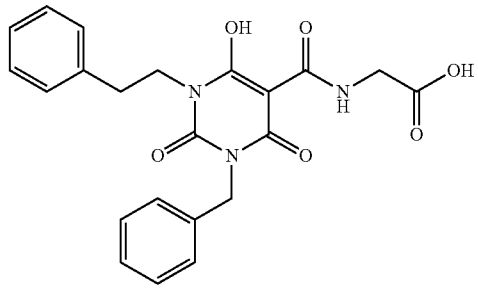 [SMILES: O=C(O)CNC(=O)c1c(O)n(CCc2ccccc2)c(=O)n(Cc2ccccc2)c1=O]

N-{[6-Hydroxy-2,4-dioxo-1-(2-phenylethyl)-3-(phenylmethyl)-1,2,3,4-tetrahydro-5-pyrimidinyl]carbonyl}glycine 23a) N-(2-Phenylethyl)-N-(phenylmethyl)urea. Phenethyl isocyanate (612 uL, 4.42 mmoles) was added to a stirred solution of benzylamine hydrochloride (635 mg, 4.42 mmoles) and diisopropylamine (766 uL, 4.42 mmoles) in chloroform under argon and stirred for 1 hour. The mixture was washed with 1 molar hydrochloric acid (×2), dried and evaporated to give the title compound (1.0 g, 89%). 1H NMR (400 MHz, CHLOROFORM-d) δ ppm 7.20-7.41 (m, 8H), 7.18 (d, J=6.82 Hz, 2H), 4.34 (s, 1H), 3.47 (t, J=6.82 Hz, 2H), 2.82 (t, J=6.95 Hz, 2H).

23b) 1-(2-Phenylethyl)-3-(phenylmethyl)-2,4,6(1H,3H,5H)-pyrimidinetrione. Malonyl dichloride (546 uL, 5.6 mmoles) was added to a solution of N-(2-phenylethyl)-N-(phenylmethyl)urea (1.0 g, 3.93 mmoles) in dichloromethane (25 mL) and the mixture was heated under reflux for 1 hour. The mixture was washed with 1 molar hydrochloric acid and evaporated. Flash chromatography (10-25% ethyl acetate in hexane) gave the title compound (930 mg, 73%). 1H NMR (400 MHz, CHLOROFORM-d) δ ppm 7.43 (dd, J=7.96, 1.64 Hz, 2H), 7.14-7.40 (m, 8H), 5.06 (s, 2H), 4.08-4.17 (m, 2H), 3.64 (s, 2H), 2.87-2.97 (m, 2H)

23c) N-{[6-Hydroxy-2,4-dioxo-1-(2-phenylethyl)-3-(phenylmethyl)-1,2,3,4-tetrahydro-5-pyrimidinyl]carbonyl}glycine. A solution of 1-(2-phenylethyl)-3-(phenylmethyl)-2,4,6(1H,3H,5H)-pyrimidinetrione (930 mg, 2.89 mmoles) and diisopropylethylamine (1.0 mL, 5.78 mmoles) in chloroform (15 mL) was treated with ethyl isocyanatoacetate (250 uL, 2.89 mmoles) and stirred for 3 hours under argon. The mixture was washed with 1 molar hydrochloric acid (×2), dried and evaporated. The residue was dissolved in ethanol (10 mL), treated with 1 molar sodium hydroxide solution (10 mL) and stirred overnight. The mixture was acidified and extracted into ethyl acetate and the organic solution dried and evaporated to a solid. The solid was slurried in diethyl ether, collected, washed with diethyl ether and hexane and dried to afford the title compound (580 mg, 47%). 1H NMR (400 MHz, DMSO-$d_6$) δ ppm 13.11 (br. s., 1H), 10.10 (br. s., 1H), 7.08-7.44 (m, 10H), 5.00 (s, 2H), 4.14 (d, J=5.81 Hz, 2H), 3.98-4.10 (m, 2H), 2.87 (t, 2H)

Example 24

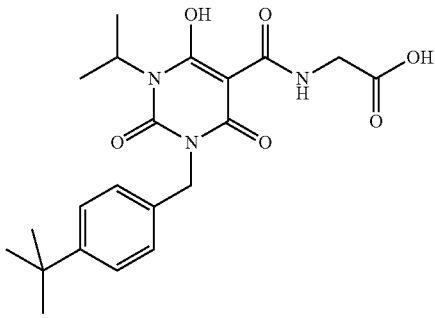 [SMILES: CC(C)n1c(O)c(C(=O)NCC(=O)O)c(=O)n(Cc2ccc(C(C)(C)C)cc2)c1=O]

N-{[3-{[4-(1,1-Dimethylethyl)phenyl]methyl}-6-hydroxy-1-(1-methylethyl)-2,4-dioxo-1,2,3,4-tetrahydro-5-pyrimidinyl]carbonyl}glycine 24a) 1-{[4-(1,1-Dimethylethyl)phenyl]methyl}-3-(1-methylethyl)-2,4,6(1H,3H,5H)-pyrimidinetrione. A mixture of 4-t-butylbenzylamine (704 uL, 4.0 mmoles) and isopropyl isocyanate (392 uL, 4.0 mmoles) was stirred in chloroform (10 mL) for 1 hour. Malonyl dichloride (388 uL, 4.0 mmoles) was added and the mixture was heated at 45° C. for 1 hour. The mixture was washed with 1 molar hydrochloric acid and purified by flash chromatography (10-25% ethyl acetate-hexane) to give the title compound (385 mg, 30%). 1H NMR (400 MHz, CHLOROFORM-d) δ ppm 7.34-7.43 (m, 4H), 5.03-5.09 (m, 1H), 5.03 (s, 2H), 3.66 (s, 2H), 1.45 (d, J=7.07 Hz, 6H), 1.32 (s, 9H).

24b) N-{[3-{[4-(1,1-dimethylethyl)phenyl]methyl}-6-hydroxy-1-(1-methylethyl)-2,4-dioxo-1,2,3,4-tetrahydro-5-pyrimidinyl]carbonyl}glycine. A solution of 1-{[4-(1,1-dimethylethyl)phenyl]methyl}-3-(1-methylethyl)-2,4,6(1H,3H,5H)-pyrimidinetrione (385 mg, 1.21 mmoles) and diisopropylethylamine (418 uL, 2.42 mmoles) in chloroform (10 mL) was treated with ethyl isocyanatoacetate (103 uL, 1.21 mmoles) and stirred for 3 hours under argon. The mixture was washed with 1 molar hydrochloric acid (×2), dried and evaporated. The residue was dissolved in ethanol (5 mL), treated with 1 molar sodium hydroxide solution (8 mL) and stirred for 3 hours. The mixture was acidified and extracted into ethyl acetate and the organic solution dried and evaporated. A solid was obtained by trituration in hexane plus a little diethyl ether, collected, washed with hexane to give the title compound (338 mg, 67%). 1H NMR (400 MHz, DMSO-$d_6$) δ ppm 13.09 (br.s, 1H), 10.12 (br.s, 1H), 7.34 (d, J=8.34 Hz, 2H), 7.22 (d, J=8.59 Hz, 2H), 5.06 (ddd, J=13.52, 6.69, 6.57 Hz, 1H), 4.96 (s, 2H), 4.13 (d, J=5.81 Hz, 2H), 1.41 (d, J=7.07 Hz, 6H), 1.25 (s, 9H)

Example 25

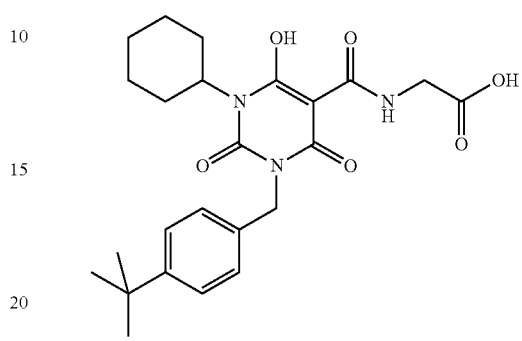

N-[(1-cyclohexyl-3-{[4-(1,1-dimethylethyl)phenyl]methyl}-6-hydroxy-2,4-dioxo-1,2,3,4-tetrahydro-5-pyrimidinyl)carbonyl]glycine 25a) 1-Cyclohexyl-3-{[4-(1,1-dimethylethyl)phenyl]methyl}-2,4,6(1H,3H,5H)-pyrimidinetrione. A mixture of 4-t-butylbenzylamine (880 uL, 5.0 mmoles) and cyclohexyl isocyanate (638 uL, 5.0 mmoles) was stirred in dichloromethane (40 mL) for 1 hour. Malonyl dichloride (388 uL, 4.0 mmoles) was added and the mixture was heated under gentle reflux for 1 hour. The mixture was washed with 1 molar hydrochloric acid and purified by flash chromatography (10-25% ethyl acetate-hexane) to give the title compound (1.23 g, 69%). 1H NMR (400 MHz, CHLOROFORM-d) δ ppm 7.33-7.43 (m, 4H), 5.02 (s, 2H), 4.56-4.70 (m, 1H), 3.65 (s, 2H), 2.20-2.35 (m, 2H), 1.85 (d, J=13.39 Hz, 2H), 1.65 (t, J=16.42 Hz, 3H), 1.20-1.43 (m, 11H)

25b) N-[(1-Cyclohexyl-3-{[4-(1,1-dimethylethyl)phenyl]methyl}-6-hydroxy-2,4-dioxo-1,2,3,4-tetrahydro-5-pyrimidinyl)carbonyl]glycine. A solution 1-cyclohexyl-3-{[4-(1,1-dimethylethyl)phenyl]methyl}-2,4,6(1H,3H,5H)-pyrimidinetrione (1.23 g, 3.45 mmoles) and diisopropylethylamine (1.2 mL, 6.9 mmoles) in chloroform (20 mL) was treated with ethyl isocyanatoacetate (295 uL, 3.45 mmoles) and stirred overnight under argon. The mixture was washed with 1 molar hydrochloric acid (×2), dried and evaporated. The residue was dissolved in ethanol (8 mL), treated with 1 molar sodium hydroxide solution (8 mL) and stirred for 3 hours. The mixture was diluted with ethyl acetate, washed with 1 molar hydrochloric acid (×2), dried and evaporated. A solid was obtained from ethanol-water to give the title compound (1.3 g, 82%). 1H NMR (400 MHz, DMSO-$d_6$) δ ppm 13.10 (br. s., 1H), 10.14 (br. s., 1H), 7.34 (d, J=8.34 Hz, 2H), 7.22 (d, J=8.34 Hz, 2H), 4.95 (s, 2H), 4.65 (t, J=11.75 Hz, 1H), 4.13 (d, J=5.81 Hz, 2H), 2.14-2.37 (m, 2H), 1.79 (d, J=12.63 Hz, 2H), 1.62 (d, J=11.62 Hz, 3H), 1.19-1.37 (m, 11H), 1.04-1.19 (m, 1H)

Example 26

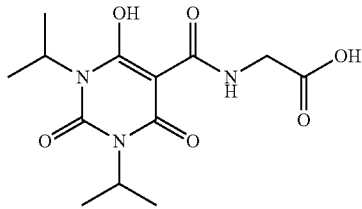 [SMILES: CC(C)n1c(O)c(C(=O)NCC(=O)O)c(=O)n(C(C)C)c1=O]

N-{[6-Hydroxy-1,3-bis(1-methylethyl)-2,4-dioxo-1,2,3,4-tetrahydro-5-pyrimidinyl]carbonyl}glycine 26a) 1,3-Bis(1-methylethyl)-2,4,6(1H,3H,5H)-pyrimidinetrione. A solution of isopropylamine (520 uL, 6.11 mmoles) was stirred in dichloromethane (25 mL) under nitrogen, treated with isopropyl isocyanate (600 uL, 6.11 mmoles) in dichloromethane (25 mL) and stirred for 1 hour. Malonyl dichloride (593 uL, 6.11 mmoles) was added and the mixture was heated under gentle reflux for 1 hour. The mixture was washed with 1 molar hydrochloric acid and purified by flash chromatography (10-30% ethyl acetate-hexane) to give the title compound (900 mg, 69%). 1H NMR (400 MHz, CHLOROFORM-d) δ ppm 5.04 (dt, J=13.89, 6.95 Hz, 2H), 3.61 (s, 2H), 1.45 (d, J=7.07 Hz, 12H).

26b) N-{[6-Hydroxy-1,3-bis(1-methylethyl)-2,4-dioxo-1,2,3,4-tetrahydro-5-pyrimidinyl]carbonyl}glycine. A solution 1,3-bis(1-methylethyl)-2,4,6(1H,3H,5H)-pyrimidinetrione (900 mg, 4.24 mmoles) and diisopropylethylamine (1.47 mL, 8.48 mmoles) in chloroform (15 mL) was treated with ethyl isocyanatoacetate (362 uL, 4.24 mmoles) and stirred for 4 hours under nitrogen. The mixture was washed with 1 molar hydrochloric acid (×2), dried and evaporated. The residue was dissolved in ethanol (6 mL), treated with 1 molar sodium hydroxide solution (8 mL) and stirred overnight. The mixture was diluted with ethyl acetate, washed with 1 molar hydrochloric acid (×2), dried and evaporated to a solid that crystallized from diethyl ether-hexane to give the title compound (925 mg, 69%). 1H NMR (400 MHz, DMSO-d$_6$) δ ppm 13.06 (s, 1H), 10.14 (t, J=5.81 Hz, 1H), 4.98-5.09 (m, 2H), 4.12 (d, J=5.81 Hz, 2H), 1.39 (d, J=6.82 Hz, 12H)

Example 27

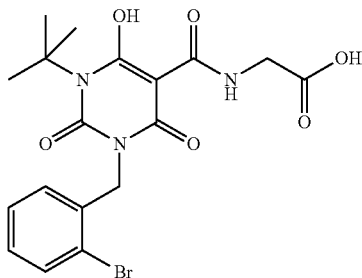 [SMILES: CC(C)(C)n1c(O)c(C(=O)NCC(=O)O)c(=O)n(Cc2ccccc2Br)c1=O]

N-{[3-[(2-Bromophenyl)methyl]-1-(1,1-dimethylethyl)-6-hydroxy-2,4-dioxo-1,2,3,4-tetrahydro-5-pyrimidinyl]carbonyl}glycine 27a) 1-[(2-Bromophenyl)methyl]-3-(1,1-dimethylethyl)-2,4,6(1H,3H,5H)-pyrimidinetrione. t-Butyl isocyanate (571 uL, 5.0 mmoles) was added to a solution of 2-bromobenzylamine hydrochloride (1.112 g, 5.0 mmoles) and diisopropylethylamine (864 uL, 5.0 mmoles) in chloroform (50 mL) and the mixture stirred for 1 hour. Malonyl dichloride (486 uL, 5.0 mmoles) was added and the mixture was stirred at 50° C. for 1 hour. The mixture was washed with 1 molar hydrochloric acid and evaporated. Flash chromatography (10-35% ethyl acetate-hexane) afforded the title compound (500 mg, 28%). 1H NMR (400 MHz, CHLOROFORM-d) δ ppm 7.59 (dd, J=8.08, 1.26 Hz, 1H), 7.26-7.32 (m, 1H), 7.12-7.19 (m, 1H), 6.99 (dd, J=7.58, 1.52 Hz, 1H), 5.12 (s, 2H), 3.72 (s, 2H), 1.63 (s, 9H)

27b) N-{[3-[(2-Bromophenyl)methyl]-1-(1,1-dimethylethyl)-6-hydroxy-2,4-dioxo-1,2,3,4-tetrahydro-5-pyrimidinyl]carbonyl}glycine. 1-[(2-Bromophenyl)methyl]-3-(1,1-dimethylethyl)-2,4,6(1H,3H,5H)-pyrimidinetrione (500 mg, 1.41 mmoles) and diisopropylethylamine (490 uL, 2.82 mmoles) were stirred together in dry chloroform (15 mL) and treated with ethyl isocyanatoacetate (121 uL, 1.41 mmoles). The mixture was stirred for 3 hours, washed twice with 1 molar hydrochloric acid, dried and evaporated. The residue was dissolved in ethanol (5.0 mL) and treated with 1 molar sodium hydroxide solution (6.0 mL)) and stirred overnight. The mixture was partitioned between ethyl acetate and 1 molar hydrochloric acid, the organic solution washed with 1 molar hydrochloric acid, dried and evaporated. The title compound was obtained by crystallization from ethanol-water (390 mg, 61%). 1H NMR (400 MHz, DMSO-d$_6$) δ ppm 13.08 (s, 1H), 10.05 (s, 1H), 7.65 (dd, J=8.08, 1.01 Hz, 1H), 7.34 (t, J=6.95 Hz, 1H), 7.22 (td, J=7.71, 1.52 Hz, 1H), 7.03 (d, J=6.57 Hz, 1H), 4.96 (s, 2H), 4.12 (d, J=5.81 Hz, 2H), 1.66 (s, 9H).

Example 28

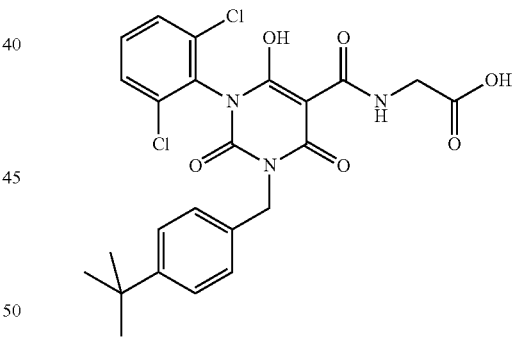

N-[(1-(2,6-Dichlorophenyl)-3-{[4-(1,1-dimethylethyl)phenyl]methyl}-6-hydroxy-2,4-dioxo-1,2,3,4-tetrahydro-5-pyrimidinyl)carbonyl]glycine 28a) 1-(2,6-Dichlorophenyl)-3-{[4-(1,1-dimethylethyl)phenyl]methyl}-2,4,6(1H,3H,5H)-pyrimidinetrione. A mixture of 2,6-dichlorophenlisocyanate (1.47 g, 7.82 mmoles) and 4-t-butylbenzylamine (1.38 g, 7.82 mmoles) in dichloromethane (100 mL) was stirred under argon for 1 hour. Malonyl dichloride (760 uL, 7.82 mmoles) was added and the mixture was heated at 40° C. for 1 hour. The mixture was washed with 1 molar hydrochloric acid and evaporated. Flash chromatography (10-25% ethyl acetate-hexane) afforded the title compound (2.2 g, 67%). 1H NMR (400

MHz, CHLOROFORM-d) δ ppm 7.50 (d, J=1.26 Hz, 1H), 7.48 (d, J=0.51 Hz, 2H), 7.35-7.41 (m, 5H), 5.11 (s, 2H), 3.92 (s, 2H), 1.33 (s, 9H).

28b) N-[(1-(2,6-Dichlorophenyl)-3-{[4-(1,1-dimethylethyl)phenyl]methyl}-6-hydroxy-2,4-dioxo-1,2,3,4-tetrahydro-5-pyrimidinyl)carbonyl]glycine. 1-(2,6-Dichlorophenyl)-3-{[4-(1,1-dimethylethyl)phenyl]methyl}-2,4,6(1H,3H,5H)-pyrimidinetrione (2.3 g, 5.48 mmoles) and diisopropylethylamine (1.9 mL, 10.97 mmoles) were stirred together in dry chloroform (50 mL) and treated with ethyl isocyanatoacetate (469 uL, 5.48 mmoles). The mixture was stirred overnight, washed twice with 1 molar hydrochloric acid, dried and evaporated. Flash chromatography (dichloromethane) gave pure ester which was dissolved in ethanol (10 mL) and treated with 6 molar sodium hydroxide solution (5.0 mL)) and stirred overnight. The mixture was partitioned between ethyl acetate and 1 molar hydrochloric acid, the organic solution washed with 1 molar hydrochloric acid, dried and evaporated. The title compound was obtained by crystallization from ethanol-water (1.8 g, 63%). 1H NMR (400 MHz, DMSO-$d_6$) δ ppm 13.20 (s, 1H), 10.08 (s, 1H), 7.67-7.74 (m, 2H), 7.54-7.61 (m, 1H), 7.37 (d, J=8.34 Hz, 2H), 7.22 (d, J=8.59 Hz, 2H), 5.06 (s, 2H), 4.15 (d, J=5.56 Hz, 2H), 1.26 (s, 9H).

Example 29

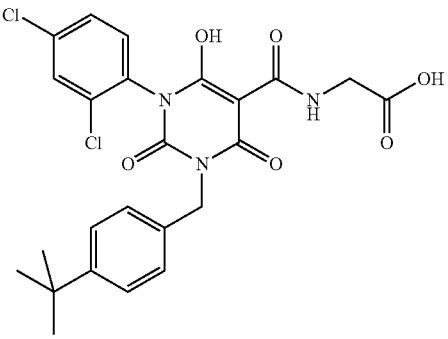 [SMILES: CC(C)(C)c1ccc(Cn2c(=O)c(C(=O)NCC(=O)O)c(O)n(-c3ccc(Cl)cc3Cl)c2=O)cc1]

N-[(1-(2,4-dichlorophenyl)-3-{[4-(1,1-dimethylethyl)phenyl]methyl}-6-hydroxy-2,4-dioxo-1,2,3,4-tetrahydro-5-pyrimidinyl)carbonyl]glycine 29a) 1-(2,4-Dichlorophenyl)-3-{[4-(1,1-dimethylethyl)phenyl]methyl}-2,4,6(1H,3H,5H)-pyrimidinetrione. A mixture of 2,4-dichlorophenlisocyanate (1.43 g, 7.6 mmoles) and 4-t-butylbenzylamine (1.34 ml, 7.6 mmoles) in dichloromethane (100 mL) was stirred under argon for 1 hour. Malonyl dichloride (739 uL, 7.6 mmoles) was added and the mixture was heated at 40° C. for 1 hour. The mixture was washed with 1 molar hydrochloric acid and evaporated. Flash chromatography (10-25% ethyl acetate-hexane) afforded the title compound (2.6 g, 82%). 1H NMR (400 MHz, CHLOROFORM-d) δ ppm 7.58 (d, J=2.27 Hz, 1H), 7.35-7.43 (m, 5H), 7.21 (d, J=8.59 Hz, 1H), 5.10-5.17 (m, 1H), 5.01-5.07 (m, 1H), 3.89 (d, J=5.81 Hz, 2H), 1.33 (s, 9H)

29b) N-[(1-(2,4-Dichlorophenyl)-3-{[4-(1,1-dimethylethyl)phenyl]methyl}-6-hydroxy-2,4-dioxo-1,2,3,4-tetrahydro-5-pyrimidinyl)carbonyl]glycine. 1-(2,4-Dichlorophenyl)-3-{[4-(1,1-dimethylethyl)phenyl]methyl}-2,4,6(1H,3H,5H)-pyrimidinetrione (2.57 g, 6.13 mmoles) and diisopropylethylamine (2.12 mL, 12.26 mmoles) were stirred together in dry chloroform (50 mL) and treated with ethyl isocyanatoacetate (524 uL, 6.13 mmoles). The mixture was stirred overnight, washed twice with 1 molar hydrochloric acid, dried and evaporated. Flash chromatography (dichloromethane) gave pure ester which was dissolved in ethanol (10 mL) and treated with 6 molar sodium hydroxide solution (5.0 mL)) and stirred overnight. The mixture was partitioned between ethyl acetate and 1 molar hydrochloric acid, the organic solution washed with 1 molar hydrochloric acid, dried and evaporated. The title compound was obtained as a solid by trituration with hexane (680 mg, 51%). 1H NMR (400 MHz, DMSO-$d_6$) δ ppm 7.87 (d, J=2.27 Hz, 1H), 7.56-7.68 (m, 2H), 7.62 (none, 2H), 7.36 (d, 2H), 7.26 (d, J=8.59 Hz, 2H), 5.02 (d, J=2.27 Hz, 2H), 4.15 (d, J=5.81 Hz, 2H), 1.26 (s, 9H).

Example 30

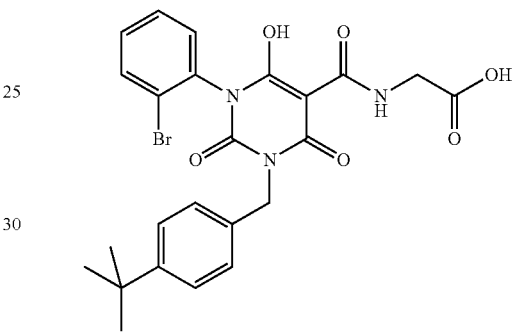

N-[(1-(2-Bromophenyl)-3-{[4-(1,1-dimethylethyl)phenyl]methyl}-6-hydroxy-2,4-dioxo-1,2,3,4-tetrahydro-5-pyrimidinyl)carbonyl]glycine 30a) 1-(2-Bromophenyl)-3-{[4-(1,1-dimethylethyl)phenyl]methyl}-2,4,6(1H,3H,5H)-pyrimidinetrione. A mixture of 2-bromophenylisocyanate (1.11 g, 5.6 mmoles) and 4-t-butylbenzylamine (1.0 ml, 5.6 mmoles) in dichloromethane (100 mL) was stirred under argon for 2 hours. Malonyl dichloride (739 uL, 7.6 mmoles) was added and the mixture was heated at 40° C. for 3 hour. The mixture was washed with 1 molar hydrochloric acid and evaporated. Flash chromatography (10-35% ethyl acetate-hexane) afforded the title compound (1.75 g, 72%). 1H NMR (400 MHz, CHLOROFORM-d) δ ppm 7.74 (dd, J=7.96, 1.39 Hz, 1H), 7.47 (td, J=7.71, 1.52 Hz, 1H), 7.41-7.44 (m, 2H), 7.35-7.40 (m, 3H), 7.28 (dd, J=7.83, 1.77 Hz, 1H), 5.11-5.18 (m, 1H), 5.02-5.09 (m, 1H), 3.90 (d, J=6.57 Hz, 2H), 1.33 (s, 9H)

30b) N-[(1-(2-Bromophenyl)-3-{[4-(1,1-dimethylethyl)phenyl]methyl}-6-hydroxy-2,4-dioxo-1,2,3,4-tetrahydro-5-pyrimidinyl)carbonyl]glycine. 1-(2-Bromophenyl)-3-{[4-(1,1-dimethylethyl)phenyl]methyl}-2,4,6(1H,3H,5H)-pyrimidinetrione (1.7 g, 3.96 mmoles) and diisopropylethylamine (1.37 mL, 7.92 mmoles) were stirred together in dry dichloromethane (20 mL) and treated with ethyl isocyanatoacetate (338 uL, 3.96 mmoles). The mixture was stirred for 4 hours, washed twice with 1 molar hydrochloric acid, dried and evaporated. The residue was dissolved in ethanol (10 mL) and treated with 1 molar sodium hydroxide solution (6.0 mL) and stirred overnight. The mixture was partitioned between ethyl acetate and 1 molar hydrochloric acid, the organic solution washed with 1 molar hydrochloric acid, dried and evaporated to a foam. The title compound was obtained as a solid by trituration with hexane and standing overnight (1.3 mg, 62%). 1H NMR (400 MHz, DMSO-d$_6$) δ ppm 13.14 (s, 1H), 10.09 (s, 1H), 7.80 (dd, J=8.08, 1.26 Hz, 1H), 7.55-7.61 (m, 1H), 7.53 (td, J=7.58, 1.26 Hz, 1H), 7.43 (td, J=7.58, 1.77 Hz, 1H), 7.33-7.40 (m, 2H), 7.24-7.31 (m, 2H), 4.98-5.08 (m, 2H), 4.15 (d, J=5.81 Hz, 2H), 1.26 (s, 9H).

in hexane (1.3 mg, 58%). 1H NMR (400 MHz, DMSO-d$_6$) δ ppm 13.09 (br. s, 1H), 10.01 (t, J=5.68 Hz, 1H), 7.49-7.58 (m, 2H), 7.41-7.47 (m, 1H), 7.26-7.37 (m, 5H), 7.15 (d, J=6.57 Hz, 2H), 6.89 (d, J=8.08 Hz, 2H), 4.89 (s, 2H), 4.11 (d, J=5.81 Hz, 2H), 1.28 (s, 9H).

Example 31

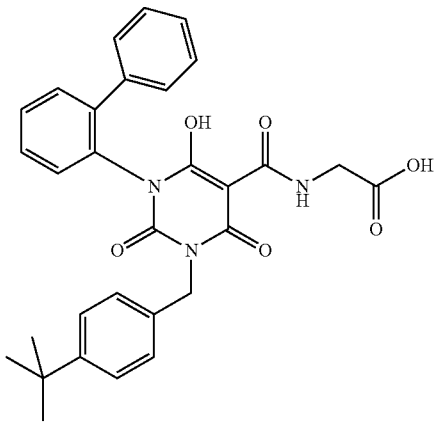 [SMILES: CC(C)(C)c1ccc(Cn2c(=O)c(C(=O)NCC(=O)O)c(O)n(-c3ccccc3-c3ccccc3)c2=O)cc1]

N-[(1-(2-Biphenylyl)-3-{[4-(1,1-dimethylethyl)phenyl]methyl}-6-hydroxy-2,4-dioxo-1,2,3,4-tetrahydro-5-pyrimidinyl)carbonyl]glycine 31a) 1-(2-Biphenylyl)-3-{[4-(1,1-dimethylethyl)phenyl]methyl}-2,4,6(1H,3H,5H)-pyrimidinetrione. A mixture of 2-biphenylisocyanate (858 uL, 5.0 mmoles) and 4-t-butylbenzylamine (881 uL, 5.0 mmoles) in dichloromethane (50 mL) was stirred under argon overnight. Malonyl dichloride (486 uL, 5.0 mmoles) was added and the mixture was heated at 40° C. for 3 hours. The mixture was washed with 1 molar hydrochloric acid and evaporated. Flash chromatography (10-35% ethyl acetate-hexane) afforded the title compound as a gum (1.86 g, 87%). 1H NMR (400 MHz, DMSO-d$_6$) δ ppm 7.48-7.57 (m, 2H), 7.44 (dd, J=7.07, 2.02 Hz, 1H), 7.30-7.41 (m, 4H), 7.26 (d, J=8.34 Hz, 2H), 7.13 (d, J=6.82 Hz, 2H), 6.89 (d, J=8.08 Hz, 2H), 4.74-4.85 (m, 2H), 3.92 (s, 2H), 1.28 (s, 9H).

31b) N-[(1-(2-Biphenylyl)-3-{[4-(1,1-dimethylethyl)phenyl]methyl}-6-hydroxy-2,4-dioxo-1,2,3,4-tetrahydro-5-pyrimidinyl)carbonyl]glycine. 1-(2-Biphenylyl)-3-{[4-(1,1-dimethylethyl)phenyl]methyl}-2,4,6(1H,3H,5H)-pyrimidinetrione (1.8 g, 4.22 mmoles) and diisopropylethylamine (730 uL, 4.22 mmoles) were stirred together in dry dichloromethane (50 mL) and treated with ethyl isocyanatoacetate (474 uL, 4.22 mmoles). The mixture was stirred for under argon overnight, washed twice with 1 molar hydrochloric acid, dried and evaporated. The residue was dissolved in ethanol (10 mL) and treated with 1 molar sodium hydroxide solution (1.0 mL) and 6 molar sodium hydroxide solution (2.0 mL) and stirred for 24 hours. The mixture was partitioned between ethyl acetate and 1 molar hydrochloric acid, the organic solution washed with 1 molar hydrochloric acid, dried and evaporated. The title compound was obtained as a solid by trituration with a small amount of dichloromethane Example 32

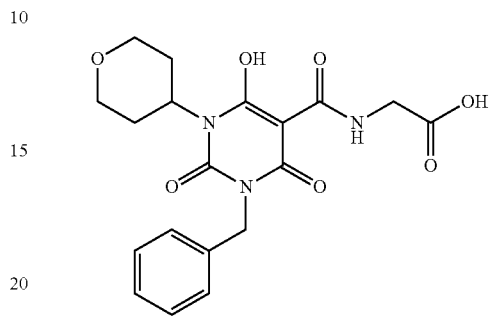

N-{[6-Hydroxy-2,4-dioxo-3-(phenylmethyl)-1-(tetrahydro-2H-pyran-4-yl)-1,2,3,4-tetrahydro-5-pyrimidinyl]carbonyl}glycine 32a) 1-(Phenylmethyl)-3-(tetrahydro-2H-pyran-4-yl)-2,4,6(1H,3H,5H) pyrimidinetrione. A mixture of tetrahydro-2H-pyran-4-ylamine (400 mg, 3.96 mmoles) and benzyl isocyanate (490 uL, 3.96 mmoles) in chloroform (40 mL) was stirred under inert atmosphere for 4 hours. Malonyl dichloride (388 uL, 4.0 mmoles) was added and the mixture was heated at 50° C. for 3 hours. The mixture was washed with 1 molar hydrochloric acid and evaporated. Flash chromatography (10-40% ethyl acetate-hexane) afforded the title (980 mg, 82%). 1H NMR (400 MHz, DMSO-d$_6$) δ ppm 7.23-7.35 (m, 5H), 4.91 (s, 2H), 4.69-4.79 (m, J=12.06, 12.06, 3.92, 3.79 Hz, 1H), 3.91 (dd, J=11.12, 4.29 Hz, 2H), 3.82 (s, 2H), 3.33 (t, J=11.12 Hz, 2H), 2.41 (qd, J=12.38, 4.55 Hz, 2H), 1.49 (dd, J=12.00, 2.15 Hz, 2H).

32b) N-{[6-Hydroxy-2,4-dioxo-3-(phenylmethyl)-1-(tetrahydro-2H-pyran-4-yl)-1,2,3,4-tetrahydro-5-pyrimidinyl]carbonyl}glycine. 1-(Phenylmethyl)-3-(tetrahydro-2H-pyran-4-yl)-2,4,6(1H,3H,5H) pyrimidinetrione (970 mg, 3.21 mmoles) and diisopropylethylamine (1.11 mL, 6.42 mmoles) were stirred together in dry dichloromethane (50 mL) and treated with ethyl isocyanatoacetate (360 uL, 3.21 mmoles). The mixture was stirred for under argon overnight, washed twice with 1 molar hydrochloric acid, dried and evaporated. The residue was dissolved in ethanol (15 mL) and treated with 1 molar sodium hydroxide solution (2.0 mL) and 6 molar sodium hydroxide solution (2.0 mL) and stirred for 4 hours. The mixture was partitioned between ethyl acetate and 1 molar hydrochloric acid, the organic solution washed with 1 molar hydrochloric acid, dried and evaporated to a solid. The solid was triturated with diethyl ether, collected, washed with a small amount of diethyl ether and hexane to afford the title compound (1.05 g, 81%). 1H NMR (400 MHz, DMSO-d$_6$) δ ppm 13.11 (br. s, 1H), 10.15 (t, J=4.93 Hz, 1H), 7.24-7.35 (m, 5H), 5.00 (s, 2H), 4.86-4.96 (m, J=11.91, 11.91, 3.85, 3.66 Hz, 1H), 4.14 (d, J=5.81 Hz, 2H), 3.93 (dd, J=11.12, 4.04 Hz, 2H), 3.37 (d, J=11.37 Hz, 2H), 3.32 (s, 1H), 2.53-2.59 (m, 1H), 1.55 (d, J=10.36 Hz, 2H).

Example 33

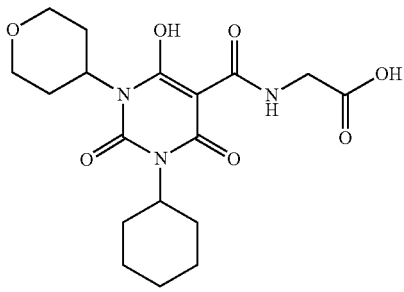 [SMILES: O=C(O)CNC(=O)c1c(O)n(C2CCOCC2)c(=O)n(C2CCCCC2)c1=O]

N-{[3-Cyclohexyl-6-hydroxy-2,4-dioxo-1-(tetrahydro-2H-pyran-4-yl)-1,2,3,4-tetrahydro-5-pyrimidinyl]carbonyl}glycine 33a) 1-Cyclohexyl-3-(tetrahydro-2H-pyran-4-yl)-2,4,6 (1H,3H,5H)-pyrimidinetrione. A mixture of tetrahydro-2H-pyran-4-ylamine (400 mg, 3.96 mmoles) and cyclohexyl isocyanate (505 uL, 3.96 mmoles) in chloroform (40 mL) was stirred under inert atmosphere for 4 hours. Malonyl dichloride (388 uL, 4.0 mmoles) was added and the mixture was heated at 50° C. for 3 hours. The mixture was washed with 1 molar hydrochloric acid and evaporated. Flash chromatography (10-35% ethyl acetate-hexane) afforded the title (900 mg, 77%). 1H NMR (400 MHz, DMSO-$d_6$) δ ppm 4.72 (tt, J=12.09, 3.95 Hz, 1H), 4.42-4.51 (m, J=12.16, 12.16, 3.60, 3.41 Hz, 1H), 3.91 (dd, J=11.12, 4.29 Hz, 2H), 3.70 (s, 2H), 3.33 (t, J=10.99 Hz, 3H), 2.42 (qd, J=12.38, 4.80 Hz, 2H), 2.15 (qd, J=12.51, 3.41 Hz, 2H), 1.77 (d, J=13.14 Hz, 2H), 1.55-1.65 (m, 3H), 1.48 (dd, J=11.87, 2.27 Hz, 2H), 1.21-1.32 (m, 2H), 1.12 (tt, J=12.85, 3.06 Hz, 1H).

33b) N-{[3-Cyclohexyl-6-hydroxy-2,4-dioxo-1-(tetrahydro-2H-pyran-4-yl)-1,2,3,4-tetrahydro-5-pyrimidinyl]carbonyl}glycine. 1-Cyclohexyl-3-(tetrahydro-2H-pyran-4-yl)-2,4,6(1H,3H,5H)-pyrimidinetrione (900 mg, 3.06 mmoles) and diisopropylethylamine (1.06 mL, 6.12 mmoles) were stirred together in dry dichloromethane (50 mL) and treated with ethyl isocyanatoacetate (360 uL, 3.21 mmoles). The mixture was stirred for under argon overnight, washed twice with 1 molar hydrochloric acid, dried and evaporated. The residue was dissolved in ethanol (15 mL) and treated with 1 molar sodium hydroxide solution (2.0 mL) and 6 molar sodium hydroxide solution (2.0 mL) and stirred for 4 hours. The mixture was partitioned between ethyl acetate and 1 molar hydrochloric acid, the organic solution washed with 1 molar hydrochloric acid, dried and evaporated to a solid. The solid was triturated with diethyl ether, collected, washed with a small amount of diethyl ether and hexane to afford the title compound (570 mg, 47%). 1H NMR (400 MHz, DMSO-$d_6$) δ ppm 13.10 (br. s, 1H), 10.19 (t, J=5.56 Hz, 1H), 4.83-4.94 (m, 1H), 4.63 (t, J=11.49 Hz, 1H), 4.13 (d, J=5.81 Hz, 2H), 3.93 (dd, J=11.12, 4.04 Hz, 2H), 3.30-3.37 (m, 2H), 2.56 (m, 2H), 2.21-2.33 (m, 2H), 1.79 (d, J=12.88 Hz, 2H), 1.61 (s, 3H), 1.52 (d, J=10.61 Hz, 2H), 1.28 (q, J=12.97 Hz, 2H), 1.11-1.18 (m, 1H).

Example 34

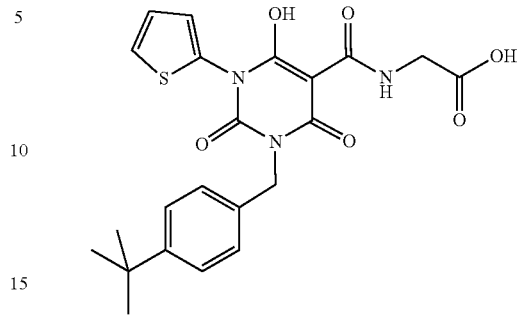

N-{[3-{[4-(1,1-Dimethylethyl)phenyl]methyl}-6-hydroxy-2,4-dioxo-1-(2-thienyl)-1,2,3,4-tetrahydro-5-pyrimidinyl]carbonyl}glycine 34a) 1-{[4-(1,1-Dimethylethyl)phenyl]methyl}-3-(2-thienyl)-2,4,6(1H,3H,5H)-pyrimidinetrione. A mixture of 2-thienyl isocyanate (970 mg, 7.76 mmoles) and 4-t-butylbenzylamine (1.38 mL, 7.76 mmoles) in dichloromethane (100 mL) was stirred under inert atmosphere for 2 hours. Malonyl dichloride (754 uL, 7.76 mmoles) was added (became dark on addition) and the mixture was heated under reflux for 1.5 hours. The mixture was washed with 1 molar hydrochloric acid and evaporated. Flash chromatography (10-35% ethyl acetate-hexane) afforded the title (274 mg, 10%). 1H NMR (400 MHz, DMSO-$d_6$) δ ppm 7.57 (dd, J=5.56, 1.52 Hz, 1H), 7.27-7.36 (m, 4H), 7.04 (dd, J=5.43, 3.66 Hz, 1H), 6.96 (dd, J=3.66, 1.39 Hz, 1H), 4.90 (s, 2H), 3.94 (s, 2H), 1.26 (s, 9H).

34b) N-{[3-{[4-(1,1-Dimethylethyl)phenyl]methyl}-6-hydroxy-2,4-dioxo-1-(2-thienyl)-1,2,3,4-tetrahydro-5-pyrimidinyl]carbonyl}glycine. 1-{[4-(1,1-Dimethylethyl)phenyl]methyl}-3-(2-thienyl)-2,4,6(1H,3H,5H)-pyrimidinetrione (270 mg, 0.66 mmoles) and diisopropylethylamine (228 uL, 1.32 mmoles) were stirred together in dry chloroform (5 mL) and treated with ethyl isocyanatoacetate (56.4 uL, 0.66 mmoles). The mixture was stirred under argon overnight, washed twice with 1 molar hydrochloric acid, dried and evaporated. The residue was dissolved in ethanol (5 mL) and treated with 6 molar sodium hydroxide solution (1.5 mL) and stirred overnight. The mixture was partitioned between ethyl acetate and 1 molar hydrochloric acid, the organic solution washed with 1 molar hydrochloric acid and evaporated, taken up in diethyl ether and warmed with decolorizing charcoal. The mixture was filtered and evaporated to a foam. The solid was triturated with hexane and collected. Preparative HPLC (10-100% acetonitrile-water-0.1% TFA) gave the title compound (120 mg, 40%). 1H NMR (400 MHz, DMSO-$d_6$) δ ppm 13.15 (br. s, 1H), 10.09 (br. s, 1H), 7.60 (dd, J=5.05, 1.77 Hz, 1H), 7.32-7.38 (m, 2H), 7.26-7.31 (m, 2H), 7.04-7.10 (m, 2H), 4.98 (s, 2H), 4.12-4.19 (m, 2H), 1.26 (s, 9H).

Example 35

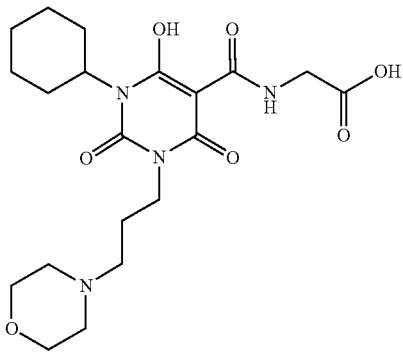 [SMILES: O=C(O)CNC(=O)c1c(O)n(C2CCCCC2)c(=O)n(CCCN2CCOCC2)c1=O]

N-({1-Cyclohexyl-6-hydroxy-3-[3-(4-morpholinyl)
propyl]-2,4-dioxo-1,2,3,4-tetrahydro-5-
pyrimidinyl}carbonyl)glycine 35a) 1-Cyclohexyl-3-[3-(4-morpholinyl)propyl]-2,4,6 (1H,3H,5H)-pyrimidinetrione. A mixture of cyclohexyl isocyanate (638 mg, 5.0 mmoles) and 3-morpholinopropylamine (730 mL, 5.0 mmoles) in dichloromethane (50 mL) was stirred under inert atmosphere for 3 hours. Malonyl dichloride (486 uL, 5.0 mmoles) was added and the mixture was heated under reflux for 3 hours. The mixture was washed with water, sodium bicarbonate solution and evaporated. Flash chromatography (0-5% methanol-dichloromethane) afforded the title (785 mg, 47%).

35b) N-({1-Cyclohexyl-6-hydroxy-3-[3-(4-morpholinyl) propyl]-2,4-dioxo-1,2,3,4-tetrahydro-5-pyrimidinyl}carbonyl)glycine. 1-Cyclohexyl-3-[3-(4-morpholinyl)propyl]-2, 4,6(1H,3H,5H)-pyrimidinetrione (785 mg, 2.32 mmoles) and diisopropylethylamine (805 uL, 4.65 mmoles) were stirred together in dry dichloromethane (50 mL) and treated with ethyl isocyanatoacetate (260 uL, 2.32 mmoles). The mixture was stirred under argon overnight, washed with water and brine, dried and evaporated. The residue was dissolved in ethanol (10 mL) and treated with 1 molar sodium hydroxide solution (2.0 mL) and 6 molar sodium hydroxide solution (1.0 mL) and stirred for 2 hours. The mixture was diluted with 1 molar hydrochloric acid and extracted with ethyl acetate (×3), the organic solution washed with brine and evaporated. The residue was purified by preparative HPLC (10-70% acetonitrile-water-0.1% TFA) to give the title compound (90 mg, 9%). 1H NMR (400 MHz, DMSO-$d_6$) δ ppm 13.16 (br. s., 1H), 10.15 (br. s., 1H), 4.64 (t, J=11.62 Hz, 1H), 4.15 (d, J=3.28 Hz, 2H), 3.88 (t, J=6.44 Hz, 6H), 2.86-3.31 (br. m, 6H), 2.18-2.39 (m, 2H), 1.90-2.05 (m, 2H), 1.88-2.05 (m, 2H), 1.80 (d, J=12.88 Hz, 2H), 1.63 (s, 3H), 1.21-1.38 (m, 2H), 1.03-1.20 (m, 1H)

Example 36

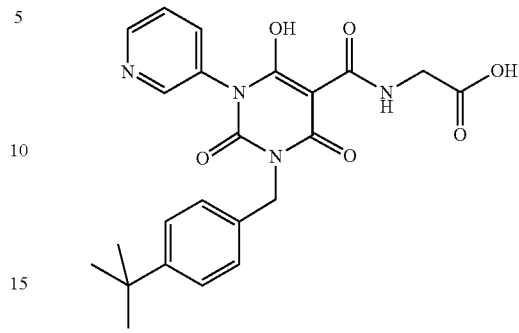

N-{[3-{[4-(1,1-Dimethylethyl)phenyl]methyl}-6-
hydroxy-2,4-dioxo-1-(3-pyridinyl)-1,2,3,4-tetra-
hydro-5-pyrimidinyl]carbonyl}glycine 36a) 1-{[4-(1,1-Dimethylethyl)phenyl]methyl}-3-(3-pyridinyl)-2,4,6(1H,3H,5H)-pyrimidinetrione. A mixture of pyridine 3-isocyanate (622 mg, 5.18 mmoles) and 4-t-butylbenzylamine (912 uL, 5.18 mmoles) in dichloromethane (50 mL) was stirred overnight. The urea was purified by flash chromatography (ethyl acetate), taken up in methoxyethanol (10 mL), treated with diethyl malonate (1.0 mL, 6.58 mmoles) and sodium ethoxide (1.0 mL of a 21 molar solution in ethanol) and heated under reflux for 24 hours in an inert atmosphere. The mixture was cooled, diluted with ethyl acetate and washed with brine. The organic solution was evaporated and purified by flash chromatography (10-100% ethyl acetate in hexane) to give the title compound (340 mg, 19%). 1H NMR (400 MHz, DMSO-$d_6$) δ ppm 8.62 (dd, J=4.80, 1.52 Hz, 1H), 8.48 (d, J=2.02 Hz, 1H), 7.75 (d, J=8.08 Hz, 1H), 7.57 (dd, J=8.21, 4.93 Hz, 1H), 7.29-7.36 (m, 4H), 3.55 (s, 2H), 1.26 (s, 9H).

36b) N-{[3-{[4-(1,1-Dimethylethyl)phenyl]methyl}-6-hydroxy-2,4-dioxo-1-(3-pyridinyl)-1,2,3,4-tetrahydro-5-pyrimidinyl]carbonyl}glycine. 1-{[4-(1,1-Dimethylethyl)phenyl]methyl}-3-(3-pyridinyl)-2,4,6(1H,3H,5H)-pyrimidinetrione (340 mg, 0.96 mmoles) and diisopropylethylamine (334 uL, 1.93 mmoles) were stirred together in dry chloroform (25 mL) and treated with ethyl isocyanatoacetate (108 uL, 0.96 mmoles). The mixture was stirred under argon overnight, washed with 1 molar hydrochloric acid and brine, dried and evaporated. The residue was dissolved in ethanol (5 mL) and treated with 1 molar sodium hydroxide solution (2.0 mL) and 6 molar sodium hydroxide solution (2.0 mL) and stirred overnight. The mixture was diluted with 1 molar hydrochloric acid and extracted with ethyl acetate (×2), the organic solution washed with brine and evaporated. The solid residue was slurried in hot ethanol, collected and recrystallized from ethanol-water to give the title compound (100 mg, 23%). 1H NMR (400 MHz, DMSO-$d_6$) δ ppm 13.11 (s, 1H), 10.09 (s, 1H), 8.62 (dd, J=4.67, 1.39 Hz, 1H), 8.58 (s, 1H), 7.86 (d, J=7.83 Hz, 1H), 7.55 (dd, J=8.08, 4.80 Hz, 1H), 7.28-7.37 (m, 4H), 5.00 (s, 2H), 4.11-4.19 (m, 2H), 1.26 (s, 9H).

Example 37

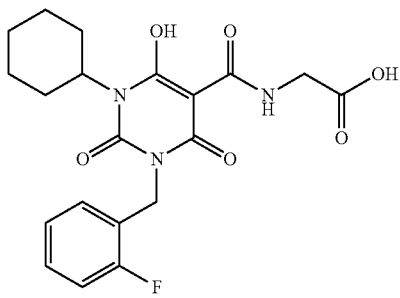 [SMILES: O=C(O)CNC(=O)c1c(O)n(C2CCCCC2)c(=O)n(Cc2ccccc2F)c1=O]

N-({1-Cyclohexyl-3-[(2-fluorophenyl)methyl]-6-hydroxy-2,4-dioxo-1,2,3,4-tetrahydro-5-pyrimidinyl}carbonyl)glycine 37a) Ethyl N-[(1-cyclohexyl-6-hydroxy-2,4-dioxo-1,2,3,4-tetrahydro-5-pyrimidinyl)carbonyl]glycinate. Ethyl isocyanatoacetate (9.7 mL, 86.32 mmoles) in dichloromethane (80 mL) was added dropwise to a stirred solution of 1-cyclohexylpyrimidinetrione (16.5 g, 78.5 mmoles) and diisopropylethylamine (27.2 mL, 157 mmoles) in dichloromethane (120 mL). The mixture was stirred for 3 hours, 1 molar hydrochloric acid was added, causing the title compound to precipitate. The solid was collected and washed with 1 molar hydrochloric acid. The solid was slurried in diethyl ether, collected, washed with diethyl ether and hexane then dried to give the title compound (23 g, 86%). 1H NMR (400 MHz, DMSO-$d_6$) δ ppm 11.92 (br. s., 1H), 9.91 (br. s., 1H), 4.57 (s, 1H), 4.15 (q, J=6.99 Hz, 4H), 2.26 (d, J=11.62 Hz, 2H), 1.78 (d, J=12.63 Hz, 2H), 1.50-1.68 (m, 3H), 1.17-1.36 (m, 5H), 1.11 (q, J=13.05 Hz, 1H)

37b) N-({1-Cyclohexyl-3-[(2-fluorophenyl)methyl]-6-hydroxy-2,4-dioxo-1,2,3,4-tetrahydro-5-pyrimidinyl}carbonyl)glycine. A mixture of ethyl N-[(1-cyclohexyl-6-hydroxy-2,4-dioxo-1,2,3,4-tetrahydro-5-pyrimidinyl)carbonyl]glycinate (340 mg, 1.0 mmoles), pulv. Potassium carbonate (740 mg, 5.35 mmoles) and 2-fluorobenzyl bromide (380 mg, 2.0 mmoles) in dimethylformamide (5 mL) was vigorously stirred at 100° C. for 3 hours. The mixture was poured into 1 molar hydrochloric acid and extracted with ethyl acetate. The organic solution was washed with 1 molar hydrochloric acid and evaporated. The residue was purified by flash chromatography (10-50% ethyl acetate in hexane), the required fractions evaporated, dissolved in ethanol (5 mL) and 1 molar sodium hydroxide solution (1.0 mL) and 6 molar sodium hydroxide solution (1.0 mL) added. The mixture was stirred overnight, acidified and extracted with ethyl acetate (×2), the combined extracts washed with 1 molar hydrochloric acid, dried and evaporated to give the title compound (163 mg, 39%). 1H NMR (400 MHz, DMSO-$d_6$) δ ppm 13.09 (br. s, 1H), 10.13 (br. s, 1H), 7.28-7.34 (m, 1H), 7.12-7.22 (m, 3H), 5.05 (s, 2H), 4.64 (t, J=12.13 Hz, 1H), 4.10-4.16 (m, 2H), 2.26 (qd, J=12.38, 2.78 Hz, 2H), 1.78 (d, J=12.88 Hz, 2H), 1.63 (s, 3H), 1.28 (q, J=12.88 Hz, 2H), 1.06-1.17 (m, 1H).

Example 38

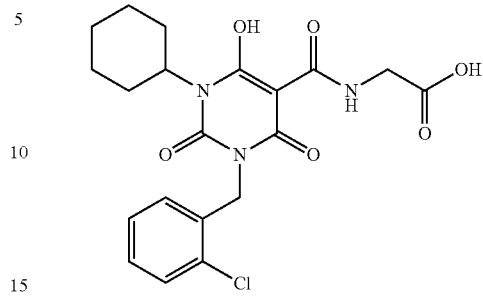

N-({3-[(2-Chlorophenyl)methyl]-1-cyclohexyl-6-hydroxy-2,4-dioxo-1,2,3,4-tetrahydro-5-pyrimidinyl}carbonyl)glycine A mixture of ethyl N-[(1-cyclohexyl-6-hydroxy-2,4-dioxo-1,2,3,4-tetrahydro-5-pyrimidinyl)carbonyl]glycinate (340 mg, 1.0 mmoles), pulv. Potassium carbonate (740 mg, 5.35 mmoles) and 2-chlorobenzyl bromide (300 mg, 1.5 mmoles) in dimethylformamide (5 mL) was vigorously stirred at 100° C. for 3 hours. The mixture was poured into 1 molar hydrochloric acid and extracted with ethyl acetate. The organic solution was washed with 1 molar hydrochloric acid and evaporated. The residue was purified by flash chromatography (10-50% ethyl acetate in hexane), the required fractions evaporated, dissolved in ethanol (5 mL) and 1 molar sodium hydroxide solution (1.0 mL) and 6 molar sodium hydroxide solution (1.0 mL) added. The mixture was stirred overnight, acidified and extracted with ethyl acetate (×2), the combined extracts washed with 1 molar hydrochloric acid, dried and evaporated to give the title compound (193 mg, 44%). 1H NMR (400 MHz, DMSO-$d_6$) δ ppm 13.11 (br. s, 1H), 10.13 (br. s, 1H), 7.45-7.50 (m, 1H), 7.26-7.32 (m, 2H), 7.05-7.09 (m, 1H), 5.05 (s, 2H), 4.65 (t, J=11.87 Hz, 1H), 4.13 (d, J=5.56 Hz, 2H), 2.20-2.30 (m, 2H), 1.79 (d, J=13.14 Hz, 2H), 1.59-1.69 (m, 3H), 1.28 (q, J=12.97 Hz, 2H), 1.06-1.16 (m, 1H).

Example 39

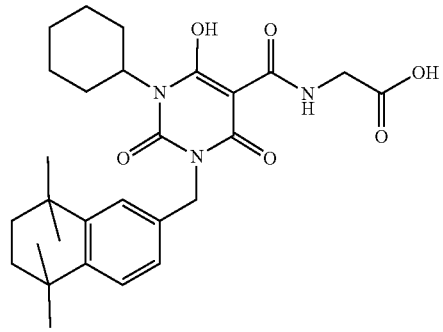

N-({1-Cyclohexyl-6-hydroxy-2,4-dioxo-3-[(5,5,8,8-tetramethyl-5,6,7,8-tetrahydro-2-naphthalenyl)methyl]-1,2,3,4-tetrahydro-5-pyrimidinyl}carbonyl)glycine A mixture of ethyl N-[(1-cyclohexyl-6-hydroxy-2,4-dioxo-1,2,3,4-tetrahydro-5-pyrimidinyl)carbonyl]glycinate (340 mg, 1.0 mmoles), pulv. Potassium carbonate (740 mg, 5.35 mmoles) and 6-(bromomethyl)-1,1,4,4-tetramethyl-1,2,3,4-tetrahydronaphthalene (250 mg, 0.89 mmoles) in dimethylformamide (5 mL) was vigorously stirred at 100° C. for 3 hours. The mixture was poured into 1 molar hydrochloric acid and extracted with ethyl acetate. The organic solution was washed with 1 molar hydrochloric acid and evaporated. The residue was purified by flash chromatography (10-50% ethyl acetate in hexane), the required fractions evaporated, dissolved in ethanol (5 mL) and 1 molar sodium hydroxide solution (1.0 mL) and 6 molar sodium hydroxide solution (1.0 mL) added. The mixture was stirred overnight, acidified and extracted with ethyl acetate (×2), the combined extracts washed with 1 molar hydrochloric acid, dried and evaporated to give the title compound (156 mg, 35%). 1H NMR (400 MHz, DMSO-$d_6$) δ ppm 13.07 (br. s., 1H), 7.24 (dd, J=4.80, 3.28 Hz, 2H), 6.98 (dd, J=8.21, 1.39 Hz, 1H), 4.93 (s, 2H), 4.66 (t, J=11.87 Hz, 1H), 4.13 (d, J=5.56 Hz, 2H), 2.19-2.36 (m, 2H), 1.79 (d, J=12.63 Hz, 2H), 1.62 (s, 7H), 1.01-1.37 (m, 15H).

Example 40

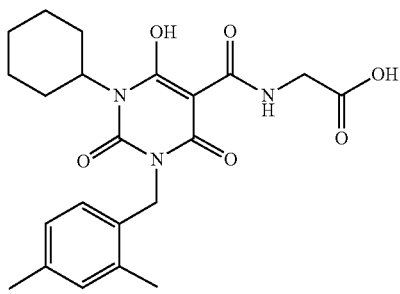 [SMILES: Cc1ccc(Cn2c(=O)c(C(=O)NCC(=O)O)c(O)n(C3CCCCC3)c2=O)c(C)c1]

N-({1-Cyclohexyl-3-[(2,4-dimethylphenyl)methyl]-6-hydroxy-2,4-dioxo-1,2,3,4-tetrahydro-5-pyrimidinyl}carbonyl)glycine A mixture of ethyl N-[(1-cyclohexyl-6-hydroxy-2,4-dioxo-1,2,3,4-tetrahydro-5-pyrimidinyl)carbonyl]glycinate (340 mg, 1.0 mmoles), pulv. Potassium carbonate (740 mg, 5.35 mmoles) and 2,4-dimethylbenzyl bromide (400 mg, 2.0 mmoles) in dimethylformamide (5 mL) was vigorously stirred at 100° C. for 3 hours. The mixture was poured into 1 molar hydrochloric acid and extracted with ethyl acetate. The organic solution was washed with 1 molar hydrochloric acid and evaporated. The residue was purified by flash chromatography (10-50% ethyl acetate in hexane), the required fractions evaporated, dissolved in ethanol (5 mL) and 1 molar sodium hydroxide solution (1.0 mL) and 6 molar sodium hydroxide solution (1.0 mL) added. The mixture was stirred overnight, acidified and extracted with ethyl acetate (×2), the combined extracts washed with 1 molar hydrochloric acid, dried and evaporated to give the title compound (173 mg, 40%). 1H NMR (400 MHz, DMSO-$d_6$) δ ppm 13.10 (br. s., 1H), 10.15 (br. s., 1H), 2.31 (s, 3H), 2.18-2.29 (m, 5H), 1.78 (d, J=13.14 Hz, 2H), 1.62 (d, J=10.36 Hz, 3H), 1.28 (q, J=12.72 Hz, 2H), 1.12 (t, J=12.88 Hz, 1H).

Example 41

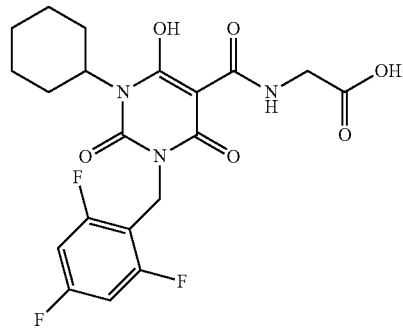 [SMILES: O=C(O)CNC(=O)c1c(O)n(C2CCCCC2)c(=O)n(Cc2c(F)cc(F)cc2F)c1=O]

N-({1-Cyclohexyl-6-hydroxy-2,4-dioxo-3-[(2,4,6-trifluorophenyl)methyl]-1,2,3,4-tetrahydro-5-pyrimidinyl}carbonyl)glycine A mixture of ethyl N-[(1-cyclohexyl-6-hydroxy-2,4-dioxo-1,2,3,4-tetrahydro-5-pyrimidinyl)carbonyl]glycinate (340 mg, 1.0 mmoles), pulv. Potassium carbonate (740 mg, 5.35 mmoles) and 2,4,6-trifluorobenzyl bromide (337 mg, 1.5 mmoles) in dimethylformamide (5 mL) was vigorously stirred at 100° C. for 3 hours. The mixture was poured into 1 molar hydrochloric acid and extracted with ethyl acetate. The organic solution was washed with 1 molar hydrochloric acid and evaporated. The residue was purified by flash chromatography (10-50% ethyl acetate in hexane), the required fractions evaporated, dissolved in ethanol (5 mL) and 1 molar sodium hydroxide solution (1.0 mL) and 6 molar sodium hydroxide solution (1.0 mL) added. The mixture was stirred overnight, acidified and extracted with ethyl acetate (×2), the combined extracts washed with 1 molar hydrochloric acid, dried and evaporated to give the title compound (240 mg, 53%). 1H NMR (400 MHz, DMSO-$d_6$) δ ppm 13.06 (br. s, 1H), 10.08 (br. s, 1H), 7.11-7.19 (m, 2H), 5.06 (s, 2H), 4.61 (t, J=12.00 Hz, 1H), 4.12 (d, J=5.81 Hz, 2H), 2.19-2.30 (m, J=12.25, 12.25, 12.13, 2.53 Hz, 2H), 1.78 (d, J=12.88 Hz, 2H), 1.59 (t, J=13.01 Hz, 3H), 1.28 (q, J=12.88 Hz, 2H), 1.06-1.17 (m, 1H).

Example 42

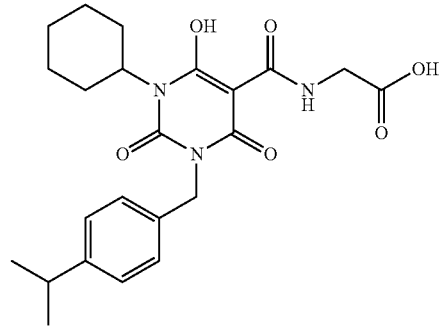 [SMILES: CC(C)c1ccc(Cn2c(=O)c(C(=O)NCC(=O)O)c(O)n(C3CCCCC3)c2=O)cc1]

N-[(1-Cyclohexyl-6-hydroxy-3-{[4-(1-methylethyl)phenyl]methyl}-2,4-dioxo-1,2,3,4-tetrahydro-5-pyrimidinyl)carbonyl]glycine A mixture of ethyl N-[(1-cyclohexyl-6-hydroxy-2,4-dioxo-1,2,3,4-tetrahydro-5-pyrimidinyl)carbonyl]glycinate (340 mg, 1.0 mmoles), pulv. Potassium carbonate (1.0 g, 7.24 mmoles) and 4-isopropylbenzyl chloride (250 mg, 1.5 mmoles) in dimethylacetamide (5 mL) was vigorously stirred at 100° C. for 3 hours. The mixture was poured into 1 molar hydrochloric acid and extracted with ethyl acetate. The organic solution was washed with 1 molar hydrochloric acid and evaporated. The residue was purified by flash chromatography (10-50% ethyl acetate in hexane), the required fractions evaporated, dissolved in ethanol (5 mL) and 1 molar sodium hydroxide solution (1.0 mL) and 6 molar sodium hydroxide solution (1.0 mL) added. The mixture was stirred overnight, acidified and extracted with ethyl acetate (×2), the combined extracts washed with 1 molar hydrochloric acid, dried and evaporated to give the title compound (161 mg, 36%). 1H NMR (400 MHz, DMSO-d$_6$) δ ppm 13.10 (s, 1H), 10.14 (s, 1H), 7.16-7.24 (m, 4H), 4.95 (s, 2H), 4.64 (t, J=11.37 Hz, 1H), 4.13 (d, J=5.56 Hz, 2H), 2.79-2.90 (m, J=6.86, 6.86, 6.86, 6.86, 6.86, 6.86 Hz, 1H), 2.20-2.32 (m, 2H), 1.78 (d, J=12.88 Hz, 2H), 1.62 (d, J=11.12 Hz, 3H), 1.22-1.34 (m, 2H), 1.09-1.20 (m, 7H).

Example 43

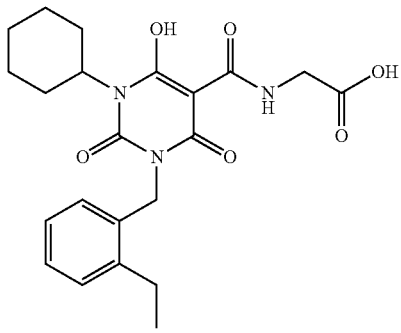 [SMILES: CCc1ccccc1Cn1c(=O)c(C(=O)NCC(=O)O)c(O)n(C2CCCCC2)c1=O]

N-({1-Cyclohexyl-3-[(2-ethylphenyl)methyl]-6-hydroxy-2,4-dioxo-1,2,3,4-tetrahydro-5-pyrimidinyl}carbonyl)glycine A mixture of ethyl N-[(1-cyclohexyl-6-hydroxy-2,4-dioxo-1,2,3,4-tetrahydro-5-pyrimidinyl)carbonyl]glycinate (680 mg, 2.0 mmoles), pulv. potassium carbonate (2.0 g, 14.46 mmoles) and a mixture of both 2- and 4-ethylbenzyl chloride (464 mg, 3.0 mmoles) in dimethylacetamide (8.0 mL) was vigorously stirred at 100° C. for 3 hours. The mixture was poured into 1 molar hydrochloric acid and extracted with ethyl acetate. The organic solution was washed with 1 molar hydrochloric acid and evaporated. The residue was separated by preparative HPLC (80% acetonitrile-water-0.1% TFA), to give a) ethyl N-({1-cyclohexyl-3-[(2-ethylphenyl)methyl]-6-hydroxy-2,4-dioxo-1,2,3,4-tetrahydro-5-pyrimidinyl}carbonyl)glycinate (100 mg, 11%) and b) ethyl N-({1-cyclohexyl-3-[(4-ethylphenyl)methyl]-6-hydroxy-2,4-dioxo-1,2,3,4-tetrahydro-5-pyrimidinyl}carbonyl)glycinate (300 mg, 33%). Product a) was dissolved in ethanol (5 mL) and 1 molar sodium hydroxide solution (1.0 mL) and 6 molar sodium hydroxide solution (1.0 mL) added. The mixture was stirred overnight, acidified and extracted with ethyl acetate (×2), the combined extracts washed with 1 molar hydrochloric acid, dried and evaporated to give the title compound (58 mg, 62%). 1H NMR (400 MHz, DMSO-d$_6$) δ ppm 13.00 (br. s., 1H), 10.15 (br. s., 1H), 7.14-7.23 (m, 2H), 7.07-7.15 (m, 1H), 6.88 (d, J=7.58 Hz, 1H), 5.03 (s, 2H), 4.65 (t, J=11.75 Hz, 1H), 4.13 (d, J=5.56 Hz, 2H), 2.72 (q, J=7.49 Hz, 2H), 2.17-2.35 (m, 2H), 1.78 (d, J=12.63 Hz, 2H), 1.56-1.69 (m, 3H), 1.23-1.35 (m, 2H), 1.20 (t, J=7.58 Hz, 3H), 1.04-1.17 (m, 1H).

Example 44

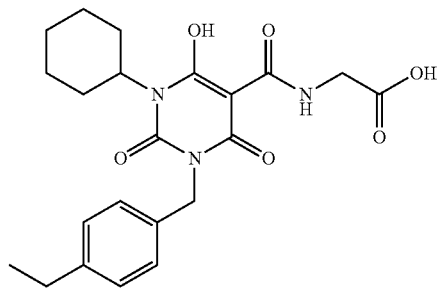 [SMILES: CCc1ccc(Cn2c(=O)c(C(=O)NCC(=O)O)c(O)n(C3CCCCC3)c2=O)cc1]

N-({1-Cyclohexyl-3-[(4-ethylphenyl)methyl]-6-hydroxy-2,4-dioxo-1,2,3,4-tetrahydro-5-pyrimidinyl}carbonyl)glycine Ethyl N-({1-cyclohexyl-3-[(4-ethylphenyl)methyl]-6-hydroxy-2,4-dioxo-1,2,3,4-tetrahydro-5-pyrimidinyl}carbonyl)glycinate (product b from example 43) was dissolved in ethanol (5 mL) and 1 molar sodium hydroxide solution (1.0 mL) and 6 molar sodium hydroxide solution (1.0 mL) added. The mixture was stirred overnight, acidified and extracted with ethyl acetate (×2), the combined extracts washed with 1 molar hydrochloric acid, dried and evaporated to give the title compound (195 mg, 69%). 1H NMR (400 MHz, DMSO-d$_6$) δ ppm 13.13 (br. s., 1H), 10.15 (s, 1H), 7.18-7.24 (m, 2H), 7.13-7.18 (m, 2H), 4.95 (s, 2H), 4.64 (t, J=11.62 Hz, 1H), 4.13 (d, J=5.81 Hz, 2H), 2.56 (q, J=7.58 Hz, 2H), 2.20-2.31 (m, 2H), 1.78 (d, J=12.13 Hz, 2H), 1.61 (d, J=10.36 Hz, 3H), 1.28 (q, J=12.72 Hz, 2H), 1.06-1.17 (m, 4H).

Example 45

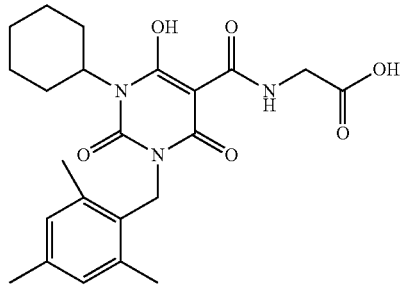 [SMILES: Cc1cc(C)c(Cn2c(=O)c(C(=O)NCC(=O)O)c(O)n(C3CCCCC3)c2=O)c(C)c1]

N-({1-Cyclohexyl-6-hydroxy-2,4-dioxo-3-[(2,4,6-trimethylphenyl)methyl]-1,2,3,4-tetrahydro-5-pyrimidinyl}carbonyl)glycine A mixture of ethyl N-[(1-cyclohexyl-6-hydroxy-2,4-dioxo-1,2,3,4-tetrahydro-5-pyrimidinyl)carbonyl]glycinate (340 mg, 1.0 mmoles), pulv. potassium carbonate (1.0 g, 7.24 mmoles) and 2,4,6-trimethylbenzyl chloride (339 mg, 1.5 mmoles) in dimethylacetamide (5 mL) was vigorously stirred at 100° C. for 3 hours. The mixture was poured into 1 molar hydrochloric acid and extracted with ethyl acetate. The organic solution was washed with 1 molar hydrochloric acid and evaporated. The residue was purified by flash chromatography (10-50% ethyl acetate in hexane), the required fractions evaporated, dissolved in ethanol (5 mL) and 1 molar sodium hydroxide solution (1.0 mL) and 6 molar sodium hydroxide solution (1.0 mL) added. The mixture was stirred overnight, acidified and extracted with ethyl acetate (×2), the combined extracts washed with 1 molar hydrochloric acid, dried and evaporated to give the title compound (61 mg, 13%). 1H NMR (400 MHz, DMSO-$d_6$) δ ppm 13.07 (s, 1H), 10.07 (s, 1H), 6.77 (s, 2H), 4.99 (s, 2H), 4.59 (t, J=12.00 Hz, 1H), 4.08-4.14 (m, 2H), 2.21-2.29 (m, 8H), 2.14-2.20 (m, 4H), 1.77 (d, J=12.63 Hz, 2H), 1.52-1.64 (m, 3H), 1.27 (q, J=12.88 Hz, 2H), 1.05-1.17 (m, 1H).

Example 46

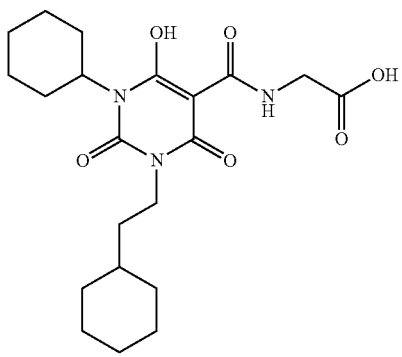 [SMILES: O=C(O)CNC(=O)c1c(O)n(C2CCCCC2)c(=O)n(CCC2CCCCC2)c1=O]

N-{[1-Cyclohexyl-3-(2-cyclohexylethyl)-6-hydroxy-2,4-dioxo-1,2,3,4-tetrahydro-5-pyrimidinyl]carbonyl}glycine A mixture of ethyl N-[(1-cyclohexyl-6-hydroxy-2,4-dioxo-1,2,3,4-tetrahydro-5-pyrimidinyl)carbonyl]glycinate (340 mg, 1.0 mmoles), pulv. potassium carbonate (1.0 g, 7.24 mmoles) and 2-cyclohexylethyl bromide (287 mg, 1.5 mmoles) in dimethylacetamide (8 mL) was vigorously stirred at 100° C. for 3 hours. The mixture was poured into 1 molar hydrochloric acid and extracted with ethyl acetate. The organic solution was washed with 1 molar hydrochloric acid and evaporated. The residue was purified by flash chromatography (10-50% ethyl acetate in hexane), the required fractions evaporated, dissolved in ethanol (5 mL) and 1 molar sodium hydroxide solution (1.0 mL) and 6 molar sodium hydroxide solution (1.0 mL) added. The mixture was stirred overnight, acidified and extracted with ethyl acetate (×2), the combined extracts washed with 1 molar hydrochloric acid, dried and evaporated. Recrystallization from toluene gave the title compound (180 mg, 42%). 1H NMR (400 MHz, DMSO-$d_6$) δ ppm 10.15 (br. s., J=5.43, 5.43 Hz, 1H), 4.63 (t, J=11.62 Hz, 1H), 4.07-4.19 (m, 2H), 3.72-3.88 (m, 2H), 2.18-2.36 (m, 2H), 1.50-1.87 (m, 10H), 1.35-1.47 (m, 2H), 1.04-1.35 (m, 7H), 0.91 (q, J=11.62 Hz, 2H).

Example 47

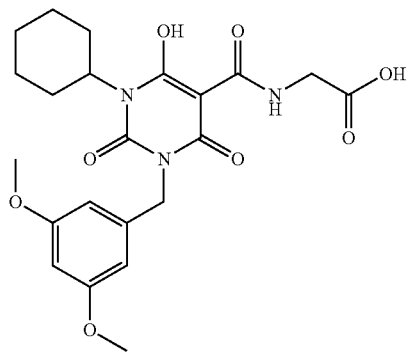 [SMILES: COc1cc(Cn2c(=O)c(C(=O)NCC(=O)O)c(O)n(C3CCCCC3)c2=O)cc(OC)c1]

N-[(3-{[3,5-Bis(methyloxy)phenyl]methyl}-1-cyclohexyl-6-hydroxy-2,4-dioxo-1,2,3,4-tetrahydro-5-pyrimidinyl)carbonyl]glycine A mixture of ethyl N-[(1-cyclohexyl-6-hydroxy-2,4-dioxo-1,2,3,4-tetrahydro-5-pyrimidinyl)carbonyl]glycinate (340 mg, 1.0 mmoles), pulv. potassium carbonate (1.5 g, 11 mmoles) and 3,5-dimethoxybenzyl bromide (300 mg, 1.3 mmoles) in dimethylacetamide (5 mL) was vigorously stirred at 100° C. for 3 hours. The mixture was poured into 1 molar hydrochloric acid and extracted with ethyl acetate. The organic solution was washed with 1 molar hydrochloric acid and evaporated. The residue was purified by flash chromatography (10-50% ethyl acetate in hexane), the required fractions evaporated, dissolved in ethanol (5 mL) and 1 molar sodium hydroxide solution (1.0 mL) and 6 molar sodium hydroxide solution (1.0 mL) added. The mixture was stirred overnight, acidified and extracted with ethyl acetate (×2), the combined extracts washed with 1 molar hydrochloric acid, dried and evaporated. Recrystallization from toluene gave the title compound (190 mg, 41%). 1H NMR (400 MHz, DMSO-$d_6$) δ ppm 13.11 (s, 1H), 10.15 (s, 1H), 6.40 (s, 3H), 4.92 (s, 2H), 4.64 (t, J=11.87 Hz, 1H), 4.09-4.17 (m, 2H), 3.70 (s, 6H), 2.26 (s, 2H), 1.78 (d, J=12.63 Hz, 2H), 1.62 (d, J=11.62 Hz, 3H), 1.28 (q, J=13.05 Hz, 2H), 1.06-1.17 (m, 1H).

Example 48

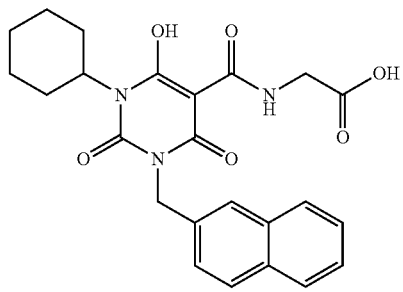 [SMILES: O=C(O)CNC(=O)c1c(O)n(C2CCCCC2)c(=O)n(Cc2ccc3ccccc3c2)c1=O]

N-{[1-Cyclohexyl-6-hydroxy-3-(2-naphthalenylmethyl)-2,4-dioxo-1,2,3,4-tetrahydro-5-pyrimidinyl]carbonyl}glycine A mixture of ethyl N-[(3-cyclohexyl-6-hydroxy-2,4-dioxo-1,2,3,4-tetrahydro-5-pyrimidinyl)carbonyl]glycinate (100 mg, 0.29 mmoles), 2-bromomethylnaphthalene (195 mg, 0.88 mmoles) and polymer-bound 2-tert-butylimino-2-diethylamine-1,3-dimethyl-perhydro-1,3,2-diazaphosphorine (pol-BEMP, 0.88 mmoles) in DMF (3 mL) was heated in a microwave synthesiser at 120° C. for 20 minutes. After cooling, the mixture was filtered, and the solids washed with dichloromethane (3×3 mL). The combined filtrate was evaporated and purified by flash chromatography (ethyl acetate-hexane) to obtain the desired intermediate ester. The crude ester was dissolved in ethanol (4 mL) and 1M aqueous NaOH (1 mL) and the solution stirred for 2 hours, then neutralized by addition of 1M aqueous HCl. The solid was collected, washed with water (3×4 mL) and dried under vacuum overnight to give the title compound (77 mg, 29%). 1H NMR (400 MHz, CDCl$_3$) δ ppm 1.13-1.42 (m, 4H) 1.56-1.72 (m, 3H) 1.77-1.90 (m, 2H) 2.26-2.44 (m, 2H) 4.24 (dd, J=2.2, 5.7 Hz, 2H) 4.64-4.84 (m, 1H) 5.24 (s, 2H) 7.40-7.50 (m, 2H) 7.55 (dt, J=2.1, 8.3 Hz, 1H) 7.75-7.90 (m, 4H) 10.21-10.34 (m, 1H)

Example 49

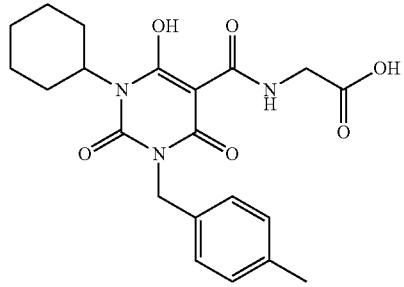 [SMILES: Cc1ccc(Cn2c(=O)c(C(=O)NCC(=O)O)c(O)n(C3CCCCC3)c2=O)cc1]

N-({1-Cyclohexyl-6-hydroxy-3-[(4-methylphenyl)methyl]-2,4-dioxo-1,2,3,4-tetrahydro-5-pyrimidinyl}carbonyl)glycine Using 4-methylbenzyl bromide in place of 2-bromomethylnaphthylene, the title compound was prepared in 27% yield (67 mg) following the procedures described in example 48. 1H NMR (400 MHz, CDCl$_3$) δ ppm 1.10-1.43 (m, 4H) 1.52-1.72 (m, 3H) 1.76-1.93 (m, 2H) 2.20-2.43 (m, 5H) 4.22 (dd, J=3.4, 5.7 Hz, 2H) 4.64-4.82 (m, 1H) 5.04 (s, 2H) 7.06-7.16 (m, 2H) 7.29-7.36 (m, 2H) 10.15-10.36 (m, 1H)

Example 50

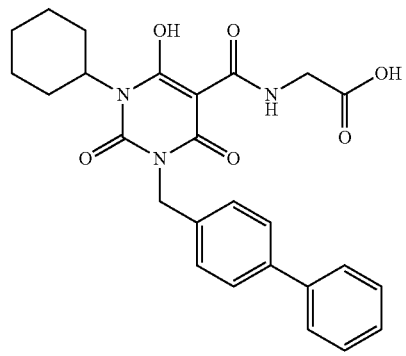 [SMILES: O=C(O)CNC(=O)c1c(O)n(C2CCCCC2)c(=O)n(Cc2ccc(-c3ccccc3)cc2)c1=O]

N-{[3-(4-Biphenylylmethyl)-1-cyclohexyl-6-hydroxy-2,4-dioxo-1,2,3,4-tetrahydro-5-pyrimidinyl]carbonyl}glycine Using 4-bromomethylbiphenyl in place of 2-bromomethylnaphthylene, the title compound was prepared in 17% yield (48 mg) following the procedures described in example 48. 1H NMR (400 MHz, CDCl$_3$) δ ppm 1.13-1.45 (m, 3H) 1.55-1.75 (m, 3H) 1.76-1.91 (m, 2H) 2.24-2.46 (m, 2H) 4.23 (dd, J=3.4, 5.7 Hz, 2H) 4.62-4.92 (m, 1H) 5.12 (s, 2H) 5.42-5.97 (m, 2H) 7.29-7.38 (m, 1H) 7.38-7.46 (m, 2H) 7.46-7.61 (m, 6H) 10.14-10.42 (m, 1H)

Example 51

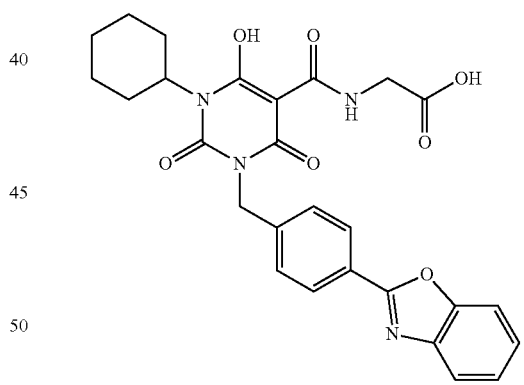

N-[(3-{[4-(1,3-Benzoxazol-2-yl)phenyl]methyl}-1-cyclohexyl-6-hydroxy-2,4-dioxo-1,2,3,4-tetrahydro-5-pyrimidinyl)carbonyl]glycine Using 2-[4-(bromomethyl)phenyl]-1,3-benzoxazole in place of 2-bromomethylnaphthylene, the title compound was prepared in 10% yield (30 mg) following the procedures described in example 48. 1H NMR (400 MHz, CDCl$_3$) δ ppm 1.11-1.42 (m, 3H) 1.57-1.72 (m, 3H) 1.74-1.91 (m, 2H) 2.27-2.43 (m, 2H) 4.16 (dd, J=3.4, 5.7 Hz, 2H) 4.67-4.95 (m, 3H) 5.09-5.23 (m, 2H) 7.32-7.42 (m, 3H) 7.53-7.62 (m, 3H) 7.74-7.79 (m, 1H) 8.18-8.27 (m, 1H) 10.22-10.42 (m, 1H)

Example 52

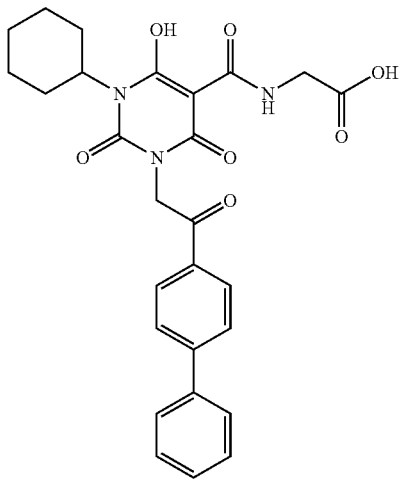 [SMILES: O=C(O)CNC(=O)c1c(O)n(C2CCCCC2)c(=O)n(CC(=O)c2ccc(-c3ccccc3)cc2)c1=O]

N-({3-[2-(4-Biphenylyl)-2-oxoethyl]-1-cyclohexyl-6-hydroxy-2,4-dioxo-1,2,3,4-tetrahydro-5-pyrimidinyl}carbonyl)glycine Using 2-bromo-4'-phenylacetophenone in place of 2-bromomethylnaphthylene, the title compound was prepared in 8% yield (24 mg) following the procedures described in example 48. 1H NMR (400 MHz, CDCl$_3$) δ ppm 1.11-1.27 (m, 1H) 1.27-1.43 (m, 2H) 1.59-1.78 (m, 3H) 1.78-1.20 (m, 2H) 2.25-2.43 (m, 2H) 4.15-4.31 (m, 2H) 4.62-4.87 (m, 1H) 5.36-5.42 (m, 2H) 7.39-7.45 (m, 1H) 7.45-7.53 (m, 2H) 7.61-7.67 (m, 2H) 7.69-7.76 (m, 2H) 8.08 (d, J=8.3 Hz, 2H) 10.07-10.42 (m, 1H)

Example 53

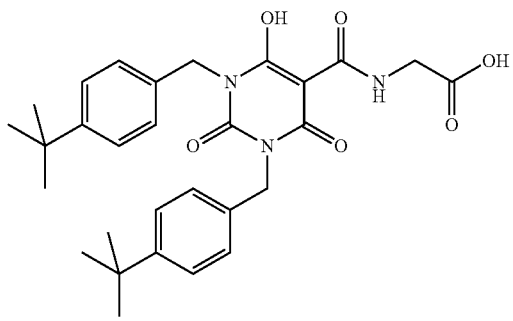 [SMILES: CC(C)(C)c1ccc(Cn2c(O)c(C(=O)NCC(=O)O)c(=O)n(Cc3ccc(C(C)(C)C)cc3)c2=O)cc1]

N-[(1,3-Bis{[4-(1,1-dimethylethyl)phenyl]methyl}-6-hydroxy-2,4-dioxo-1,2,3,4-tetrahydro-5-pyrimidinyl)carbonyl]glycine 53a) N,N'-Bis{[4-(1,1-dimethylethyl)phenyl]methyl}urea. Diphosgene (725 uL, 6.0 mmoles) was added to a solution of 4-t-butylbenzylamine (880 uL, 5.0 mmoles) in ethyl acetate (20 mL) under nitrogen atmosphere at room temperature. A solid precipitated and the mixture was then heated to 70° C. until the solid dissolved. After stirring for 1 hour, 4-t-butylbenzylamine (880 uL, 5.0 mmoles) was added and the mixture was stirred for 2 hours. Diisopropylethylamine (1.0 mL, 5.75 uL) was added and the mixture was stirred for 1 hour, washed with 1 molar hydrochloric acid, dried and evaporated to an oil which solidified on standing overnight to give the title compound (710 mg, 40%). 1H NMR (400 MHz, DMSO-d$_6$) δ ppm 7.30-7.38 (m, 4H), 7.17 (d, J=8.34 Hz, 4H), 6.34 (t, J=5.94 Hz, 2H), 4.18 (d, J=5.81 Hz, 4H), 1.27 (s, 18H).

53b) 1,3-Bis{[4-(1,1-dimethylethyl)phenyl]methyl}-2,4,6(1H,3H,5H)-pyrimidinetrione. Malonyl dichloride (195 uL, 2.0 mmoles) was added to a stirred solution of N,N'-bis{[4-(1,1-dimethylethyl)phenyl]methyl}urea in dichloromethane (80 mL) and the mixture was heated under reflux for 2 hours. The mixture was washed with 1 molar hydrochloric acid, and purified by flash chromatography (0-30% ethyl acetate in hexane) to give the title compound (700 mg, 84%). 1H NMR (400 MHz, DMSO-d$_6$) δ ppm 7.29-7.35 (m, 4H), 7.21-7.29 (m, 4H), 4.87 (s, 4H), 3.86-3.93 (s, 2H), 1.25 (s, 18H).

53c) N-[(1,3-Bis{[4-(1,1-dimethylethyl)phenyl]methyl}-6-hydroxy-2,4-dioxo-1,2,3,4-tetrahydro-5-pyrimidinyl)carbonyl]glycine. A mixture of 1,3-bis{[4-(1,1-dimethylethyl)phenyl]methyl}-2,4,6(1H,3H,5H)-pyrimidinetrione (700 mg, 1.66 mmoles) and diisopropylethylamine (574 uL, 3.32 mmoles) was stirred in dichloromethane (50 mL) and treated with ethyl isocyanatoacetate (202 uL, 1.8 mmoles). The mixture was stirred for 5 hours, then warmed to complete reaction. The mixture was washed with 1 molar hydrochloric acid, evaporated, taken up in ethanol-6 molar sodium hydroxide solution, stirred and gently warmed to complete hydrolysis. The mixture was acidified and extracted into ethyl acetate. The extracts were evaporated and a solid obtained from aqueous ethanol to give the title compound (700 mg, 81%). 1H NMR (400 MHz, DMSO-d$_6$) δ ppm 9.67 (s, 1H), 7.24-7.30 (m, 4H), 7.16 (d, J=8.59 Hz, 4H), 4.94 (s, 4H), 3.42 (d, J=4.04 Hz, 2H), 1.25 (s, 18H).

Example 54

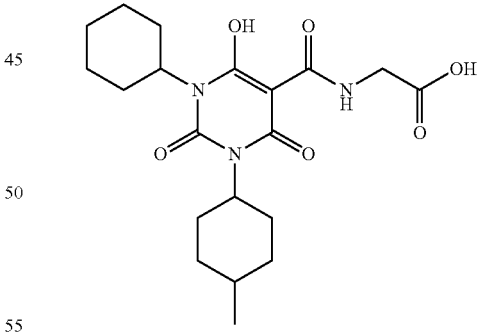

N-{[1-Cyclohexyl-6-hydroxy-3-(4-methylcyclohexyl)-2,4-dioxo-1,2,3,4-tetrahydro-5-pyrimidinyl]carbonyl}glycine A solution of cyclohexylisocyanate (1252 mg, 10 mmoles) in dichloromethane (20 mL) was added dropwise to a solution of 4-methylcyclohexylamine (1132 mg, 10 mmoles) in dichloromethane (100 mL). The solution was allowed to stir at room temperature for 2 hours, then the solvent evaporated and the residue dissolved in dichloromethane (10 mL) along with malonyl chloride (10 mmol). The mixture was heated in a microwave synthesiser (80° C./20 min). All volatiles were evaporated and the residue dissolved in of chloroform (10 mL) along with ethyl isocyanatoacetate (10 mmol), then the mixture was stirred at room temperature for 2 hours. Solvent was evaporated and the residue was purified by flash chromatography (ethyl acetate-hexane) to obtain the intermediate ester. The ester was dissolved in a mixture of ethanol (4 mL) and 1M aqueous NaOH (1 mL). The solution was stirred for 2 hours and neutralized by addition of 1M aqueous HCl. The solid was collected, washed with water (3×4 mL) and dried under vacuum overnight to give the title compound (443 mg, 11%). 1H NMR (400 MHz, CDCl$_3$) δ ppm 0.85-0.96 (m, 2H) 1.10-1.13 (m, 3H) 1.16-1.50 (m, 6H), 1.53-1.72 (m, 6H) 1.73-1.89 (m, 3H) 2.25-2.47 (m, 3H) 2.50-2.66 (m, 1H) 4.01-4.08 (m, 1H) 4.23 (d, J=5.8 Hz, 1H) 4.60-4.82 (m, 2H) 10.25-10.36 (m, 1H)

Example 55

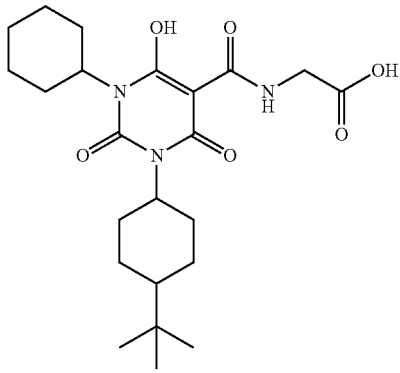 [SMILES: CC(C)(C)C1CCC(n2c(=O)c(C(=O)NCC(=O)O)c(O)n(C3CCCCC3)c2=O)CC1]

N-({1-Cyclohexyl-3-[4-(1,1-dimethylethyl)cyclohexyl]-6-hydroxy-2,4-dioxo-1,2,3,4-tetrahydro-5-pyrimidinyl}carbonyl)glycine Using 4-tert-butylcyclohexylamine in place of 4-methylcyclohexylamine, the title compound was prepared in 21% yield (931 mg) following the procedures described in example 54. 1H NMR (400 MHz, CDCl$_3$) δ ppm 0.77-0.94 (m, 13H) 1.03-1.45 (m, 6H) 1.45-1.77 (m, 5H) 1.77-1.97 (m, 3H) 2.18-2.48 (m, 3H) 4.01-4.10 (m, 1H) 4.24 (d, J=5.6 Hz, 1H) 4.58-4.82 (m, 2H) 10.26-10.36 (m, 1H)

Example 56

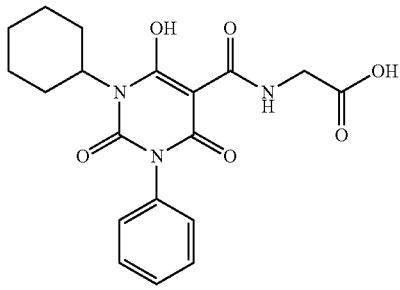 [SMILES: O=C(O)CNC(=O)c1c(O)n(C2CCCCC2)c(=O)n(-c2ccccc2)c1=O]

N-[(1-Cyclohexyl-6-hydroxy-2,4-dioxo-3-phenyl-1,2,3,4-tetrahydro-5-pyrimidinyl)carbonyl]glycine Using aniline in place of 4-methylcyclohexylamine, the title compound was prepared in 5% yield (198 mg) following the procedures described in example 54. 1H NMR (400 MHz, CDCl$_3$) δ ppm 1.02-1.46 (m, 5H) 1.54-1.78 (m, 3H) 1.78-1.98 (m, 2H) 2.26-2.47 (m, 2H) 4.21 (dd, J=5.8, 19 Hz, 2H) 4.69-4.87 (m, 1H) 7.16-7.31 (m, 2H) 7.40-7.46 (m, 3H) 10.06-10.42 (m, 1H)

Example 57

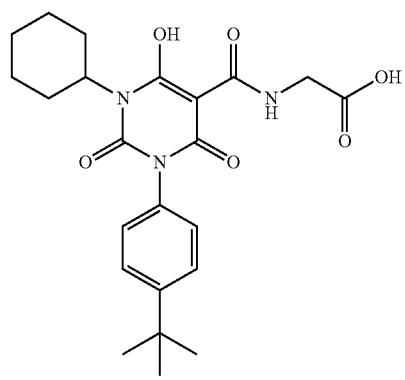 [SMILES: CC(C)(C)c1ccc(-n2c(=O)c(C(=O)NCC(=O)O)c(O)n(C3CCCCC3)c2=O)cc1]

N-({1-Cyclohexyl-3-[4-(1,1-dimethylethyl)phenyl]-6-hydroxy-2,4-dioxo-1,2,3,4-tetrahydro-5-pyrimidinyl}carbonyl)glycine Using 4-tert-butylaniline in place of 4-methylcyclohexylamine, the title compound was prepared in 7% yield (321 mg) following the procedures described in example 54. 1H NMR (400 MHz, CDCl$_3$) δ ppm 1.09-1.24 (m, 1H) 1.26-1.43 (m, 13H) 1.58-1.77 (m, 3H) 1.78-1.91 (m, 2H) 2.27-2.49 (m, 2H) 4.22 (dd, J=14.7, 20.2 Hz, 2H) 4.68-4.88 (m, 1H) 7.16 (dd, J=8.6, 14.4 Hz, 2H) 7.51 (dd, J=14.4 Hz, 2H) 10.10-10.42 (m, 1H)

Example 58

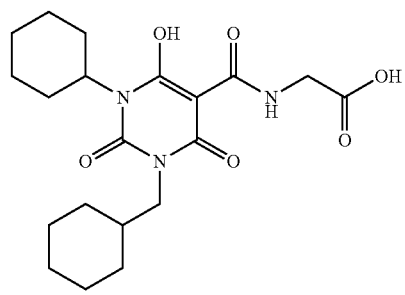 [SMILES: O=C(O)CNC(=O)c1c(O)n(C2CCCCC2)c(=O)n(CC2CCCCC2)c1=O]

N-{[1-Cyclohexyl-3-(cyclohexylmethyl)-6-hydroxy-2,4-dioxo-1,2,3,4-tetrahydro-5-pyrimidinyl]carbonyl}glycine Using cyclohexylmethylamine in place of 4-methylcyclohexylamine, the title compound was prepared in 22% yield (442 mg) following the procedures described in example 54. 1H NMR (400 MHz, CDCl$_3$) δ ppm 0.85-1.11 (m, 2H) 1.11-1.28 (m, 5H) 1.28-1.48 (m, 2H) 1.55-1.79 (m, 10H) 1.79-1.91 (m, 2H) 2.35 (dq, J=3.0, 12.4 Hz, 2H) 3.76 (d, J=1.4, 7.2 Hz, 2H) 4.24 (dd, J=3.0, 7.2 Hz, 2H) 4.65-4.83 (m, 1H) 10.17-10.33 (m, 1H)

Example 59

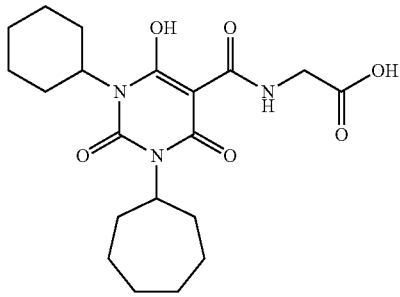 [SMILES: O=C(O)CNC(=O)c1c(O)n(C2CCCCC2)c(=O)n(C2CCCCCC2)c1=O]

N-[(3-Cycloheptyl-1-cyclohexyl-6-hydroxy-2,4-dioxo-1,2,3,4-tetrahydro-5-pyrimidinyl)carbonyl]glycine Using cycloheptylamine in place of 4-methylcyclohexylamine, the title compound was prepared in 29% yield (583 mg) following the procedures described in example 54. 1H NMR (400 MHz, DMSO-d$_6$) ppm 1.03-1.19 (m, 2H) 1.19-1.34 (m, 3H) 1.34-1.84 (m, 14H) 2.14-2.36 (m, 4H) 3.17 (s, 1H) 4.06 (d, J=5.6 Hz, 2H) 4.56-4.71 (m, 1H) 4.73-4.89 (m, 1H) 10.11-10.23 (m, 1H)

Example 60

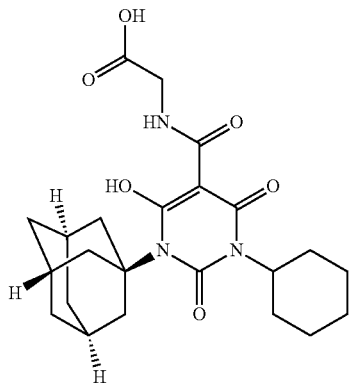 [SMILES: O=C(O)CNC(=O)c1c(O)n([C@]23C[C@H]4C[C@H](C[C@H](C4)C2)C3)c(=O)n(C2CCCCC2)c1=O]

N-[(3-Cyclohexyl-6-hydroxy-2,4-dioxo-1-tricyclo[3,3,1,1$^{3,7}$]dec-1-yl-1,2,3,4-tetrahydro-5-pyrimidinyl)carbonyl]glycine Using 1-adamantanamine hydrochloride in place of 4-methylcyclohexylamine, the title compound was prepared in 3% yield (66 mg) following the procedures described in example 54. 1H NMR (400 MHz, CDCl$_3$) δ ppm 1.12-1.43 (m, 4H) 1.54-1.88 (m, 12H) 2.03-2.20 (m, 3H) 2.23-2.28 (m, 2H) 2.45-2.57 (m, 6H) 4.21 (d, J=5.8 Hz, 2H) 4.50-4.70 (m, 1H) 10.16-10.31 (m, 1H)

Example 61

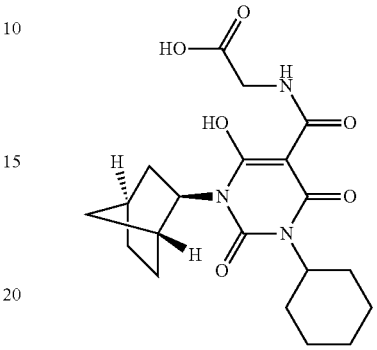

N-({1-[(1R,2R,4S)-Bicyclo[2,2,1]hept-2-yl]-3-cyclohexyl-6-hydroxy-2,4-dioxo-1,2,3,4-tetrahydro-5-pyrimidinyl}carbonyl)glycine Using exo-2-aminonorbornane in place of 4-methylcyclohexylamine, the title compound was prepared in 30% yield (604 mg) following the procedures described in example 54. 1H NMR (400 MHz, DMSO-d$_6$) δ ppm 0.96-1.34 (m, 9H) 1.35-1.67 (m, 6H) 1.67-1.84 (m, 3H) 2.20-2.36 (m, 4H) 4.01 (d, J=5.6 Hz, 2H) 4.55-4.72 (m, 2H) 10.11-10.20 (m, 1H)

Example 62

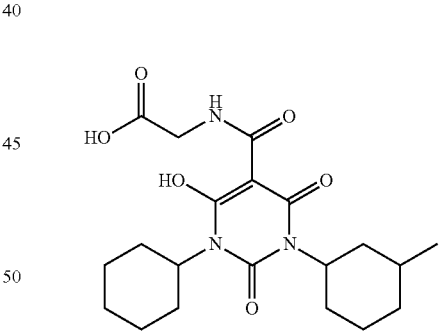

N-{[1-Cyclohexyl-6-hydroxy-3-(3-methylcyclohexyl)-2,4-dioxo-1,2,3,4-tetrahydro-5-pyrimidinyl]carbonyl}glycine Using 3-methylcyclohexylamine in place of 4-methylcyclohexylamine, the title compound was prepared in 41% yield (836 mg) following the procedures described in example 54. 1H NMR (400 MHz, DMSO-d$_6$) δ ppm 0.89 (d, J=6.6 Hz, 3H) 0.97-1.48 (m, 8H) 1.49-1.67 (m, 6H) 1.69-1.86 (m, 3H) 2.08-2.37 (m, 4H) 4.06 (d, J=5.6 Hz, 2H) 4.55-4.76 (m, 2H) 10.12-10.26 (m, 1H)

Example 63

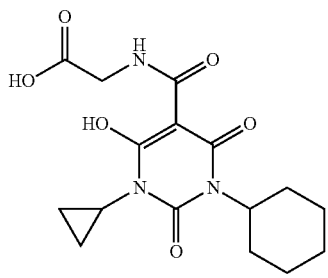 [SMILES: O=C(O)CNC(=O)c1c(O)n(C2CC2)c(=O)n(C2CCCCC2)c1=O]

N-[(3-Cyclohexyl-1-cyclopropyl-6-hydroxy-2,4-dioxo-1,2,3,4-tetrahydro-5-pyrimidinyl)carbonyl]glycine Using cyclopropylamine in place of 4-methylcyclohexylamine, the title compound was prepared in 20% yield (351 mg) following the procedures described in example 54. 1H NMR (400 MHz, CDCl$_3$) δ ppm 0.95-1.08 (m, 1H), 1.12-1.28 (m, 4H), 1.29-1.42 (m, 1H), 1.57-1.80 (m, 6H), 1.80-1.89 (m, 1H), 2.28-2.42 (m, 2H), 3.76 (d, J=7.1 Hz, 2H), 4.24 (dd, J=5.6, 3.5 Hz, 2H), 4.66-4.82 (m, 1H), 10.21-10.31 (m, 1H).

Example 64

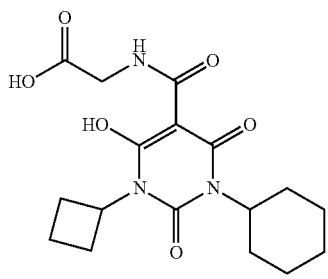 [SMILES: O=C(O)CNC(=O)c1c(O)n(C2CCC2)c(=O)n(C2CCCCC2)c1=O]

N-[(1-Cyclobutyl-3-cyclohexyl-6-hydroxy-2,4-dioxo-1,2,3,4-tetrahydro-5-pyrimidinyl)carbonyl]glycine Using cyclobutylamine in place of 4-methylcyclohexylamine, the title compound was prepared in 23% yield (424 mg) following the procedures described in example 54. 1H NMR (400 MHz, CDCl$_3$) δ ppm 1.14-1.46 (m, 4H) 1.56-1.98 (m, 7H) 2.14-2.46 (m, 4H) 2.80-3.00 (m, 2H) 4.24 (d, J=5.6 Hz, 2H) 4.58-4.83 (m, 1H) 5.08-5.33 (m, 2H) 10.22-10.32 (m, 1H)

Example 65

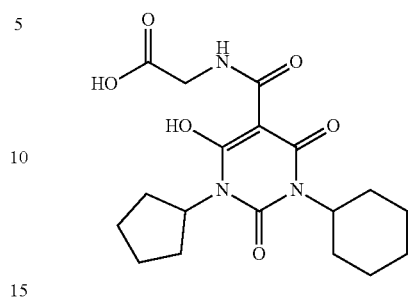

N-[(3-Cyclohexyl-1-cyclopentyl-6-hydroxy-2,4-dioxo-1,2,3,4-tetrahydro-5-pyrimidinyl)carbonyl]glycine Method 1

65.1 Using cyclopentylamine in place of 4-methylcyclohexylamine, the title compound was prepared in 19% yield (357 mg) generally following the procedures described in example 54. 1H NMR (400 MHz, CDCl$_3$) δ ppm 1.14-1.45 (m, 4H) 1.52-1.73 (m, 5H) 1.75-2.00 (m, 7H) 2.00-2.16 (m, 2H) 2.24-2.43 (m, 2H) 4.24 (dd, J=1.3, 5.8 Hz, 2H) 4.64-4.82 (m, 1H) 5.11-5.38 (m, 1H) 10.23-10.35 (m, 1H)

Method 2

65.2a) 1-Cyclohexyl-3-cyclopentyl-2,4,6(1H,3H,5H)-pyrimidinetrione. Cyclohexyl isocyanate (14.7 g, 117.34 mmoles) in dichloromethane (500 mL) under argon was treated with a solution of cyclopentylamine (11.58 mL, 117.34 mmoles) in dichloromethane (300 mL) and stirred overnight to leave a thick suspension of the urea. Malonyl dichloride (12.55 mL, 129 mmoles) in dichloromethane (200 mL) was added and the mixture was heated under gentle reflux for 3.5 hours. The mixture was washed with 1 molar hydrochloric acid (×2) dried and evaporated. Crystallization from ethanol and flash chromatography of the liquors (hexane to ethyl acetate) gave the title compound (18.9 g, 58%). 1H NMR (400 MHz, DMSO-d$_6$) δ ppm 4.96-5.12 (m, 1H), 4.46 (tt, J=12.13, 3.54 Hz, 1H), 3.69 (s, 2H), 2.15 (ddd, 2H), 1.67-2.00 (m, 8H), 1.41-1.66 (m, 5H), 1.27 (m, 2H), 1.11 (m, 1H).

65.2b) N-[(1-Cyclohexyl-3-cyclopentyl-6-hydroxy-2,4-dioxo-1,2,3,4-tetrahydro-5-pyrimidinyl)carbonyl]glycine. Ethyl isocyanatoacetate (8.33 mL, 74.3 mmoles) was added to a mixture of 1-cyclohexyl-3-cyclopentyl-2,4,6(1H,3H,5H)-pyrimidinetrione (18.8 g, 67.54 mmoles) and diisopropylethylamine (23.53 mL, 135.08 mmoles) in dichloromethane (800 mL) and stirred for 2 hours. Reaction mixture from a prior run (approx 25% scale) was added. The combined reaction mixture was washed with 2 molar hydrochloric acid (2×1.0 L) and evaporated. The residue was dissolved in ethanol (200 mL) and treated with 3.0 molar sodium hydroxide (100 mL). The mixture was stirred for 2 hours. Ethyl acetate (500 mL) was added and the mixture acidified with 6 molar hydrochloric acid (200 mL), water (500 mL) was added and the layers separated. The aqueous layer was extracted with ethyl acetate (500 mL) and the organic solution was washed with 1 molar hydrochloric acid. The organic solution was dried and evaporated to a solid residue which recrystallized from acetic acid (300 mL) to afford the title compound (15.5 g, 49%). Mp 222-224° C. 1H NMR (400 MHz, DMSO-d$_6$) δ ppm 13.08 (s, 1H), 10.17 (t, J=5.43

Hz, 1H), 5.08-5.33 (m, 1H), 4.63 (t, J=12.25 Hz, 1H), 4.12 (d, J=5.81 Hz, 2H), 2.18-2.36 (m, 2H), 1.93-2.06 (m, 2H), 1.69-1.91 (m, 6H), 1.46-1.68 (m, 5H), 1.28 (q, J=12.88 Hz, 2H), 1.12 (q, J=13.05 Hz, 1H).

Example 66

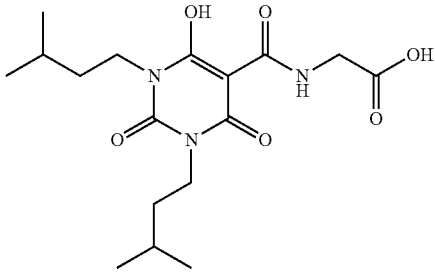 [SMILES: CC(C)CCn1c(O)c(C(=O)NCC(=O)O)c(=O)n(CCC(C)C)c1=O]

N-{[6-Hydroxy-1,3-bis(3-methylbutyl)-2,4-dioxo-1, 2,3,4-tetrahydro-5-pyrimidinyl]carbonyl}glycine 66a) N,N'-Bis(3-methylbutyl)urea. Isoamylamine (1.4 mL, 12 mmoles) was added to a solution of [1,3]oxathiolo [4,5-b]pyridin-2-one (765 mg, 5.0 mmoles) in ethyl acetate (15 mL). The mixture was stirred for 2 hours, the solid collected, washed with ethyl acetate and dried to give the title compound (1.1 g, 91%). 1H NMR (400 MHz, CHLOROFORM-d) δ ppm 4.86 (br. s, 2H), 3.20 (td, J=7.33, 5.81 Hz, 4H), 1.61-1.72 (m, J=13.39, 6.69, 6.69, 6.69, 6.69 Hz, 2H), 1.40-1.48 (m, 4H), 0.93 (d, J=6.57 Hz, 12H).

66b), 3-Bis(3-methylbutyl)-2,4,6(1H,3H,5H)-pyrimidinetrione. Ethyl malonyl chloride (768 uL, 6.0 mmoles) was added to a solution of N,N'-bis(3-methylbutyl)urea (1.1 g, 5.5 mmoles) in chloroform (70 mL) and the mixture was stirred at 70° C. for 2 hours. The mixture was washed with 1 molar hydrochloric acid, dried and evaporated to give ethyl 3-((3-methylbutyl){[(3-methylbutyl)amino] carbonyl}amino)-3-oxopropanoate. The intermediate was dissolved in ethanol (30 mL), DBU (900 uL, 6 mmoles) and heated to 70° C. for 5 minutes. The mixture was cooled, diluted with ethyl acetate and washed with 1 molar hydrochloric acid, dried and evaporated to give the title compound (1.2 g, 81%). 1H NMR (400 MHz, DMSO-$d_6$) δ ppm 3.65-3.78 (m, 3H), 1.56 (dt, J=20.02, 13.33, 6.57 Hz, 1H), 1.32-1.44 (m, 2H), 0.90 (d, J=6.57 Hz, 6H).

66c) -{[6-Hydroxy-1,3-bis(3-methylbutyl)-2,4-dioxo-1,2, 3,4-tetrahydro-5-pyrimidinyl]carbonyl}glycine. A mixture of 1,3-bis(3-methylbutyl)-2,4,6(1H,3H,5H)-pyrimidinetrione (1.2 g, 4.47 mmoles) and diisopropylethylamine (1.56 mL, 8.94 mmoles) was stirred in dichloromethane (30 mL) and treated with ethyl isocyanatoacetate (501 uL, 4.47 mmoles). The mixture was stirred for 5 hours, washed with 1 molar hydrochloric acid (×2), evaporated, taken up in ethanol-6 molar sodium hydroxide and stirred overnight. The mixture was acidified and extracted into ethyl acetate (×2). The extracts were washed with 1 molar hydrochloric acid evaporated, dried and evaporated. The title compound was recrystallized from acetic acid (430 mg, 26%). 1H NMR (400 MHz, DMSO-$d_6$) δ ppm 13.09 (br. s, 1H), 10.11 (s, 1H), 4.09-4.16 (m, 2H), 3.77-3.86 (m, 4H), 1.51-1.62 (dt, J=13.29, 6.59, 6.59, 6.59, 6.59 Hz, 2H), 1.42 (q, J=7.07 Hz, 4H), 0.91 (d, J=6.57 Hz, 12H).

Example 67

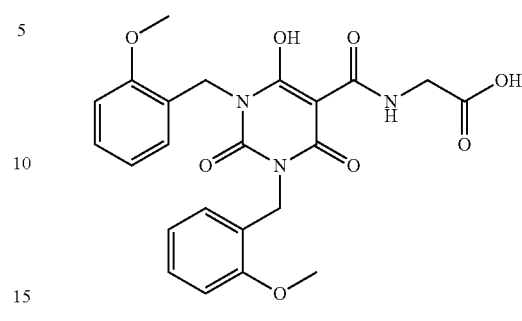

N-[(6-Hydroxy-1,3-bis{[2-(methyloxy)phenyl] methyl}-2,4-dioxo-1,2,3,4-tetrahydro-5-pyrimidinyl) carbonyl]glycine 67a) 1,3-Bis{[2-(methyloxy)phenyl]methyl}-2,4,6(1H, 3H,5H)-pyrimidinetrione. 2-Methoxybenzyl isocyanate (923 uL, 6.0 mmoles) was added to a solution of 2-methoxybenzylamine (775 uL, 6.0 mmoles) in chloroform (100 mL) and the mixture stirred for 1 hour. Ethyl malonyl chloride (768 uL, 6.0 mmoles) was added and the mixture was heated to 70° C. for 2 hours. DBU (1.0 mL) was added and the mixture was heated for a further 1 hour. The mixture was cooled and washed with 1 molar hydrochloric acid (×2), dried and evaporated. The title compound was obtained as a solid by trituration in diethyl ether (1.65 g, 75 1H NMR (400 MHz, DMSO-$d_6$) δ ppm 7.22 (t, 2H), 7.15 (d, J=7.58 Hz, 2H), 6.98 (d, J=7.58 Hz, 2H), 6.86 (t, 2H), 4.88 (s, 4H), 3.81 (s, 6H), 3.79-3.80 (s, 2H).

67b) N-[(6-hydroxy-1,3-bis{[2-(methyloxy)phenyl] methyl}-2,4-dioxo-1,2,3,4-tetrahydro-5-pyrimidinyl)carbonyl]glycine. A mixture of 1,3-bis{[2-(methyloxy)phenyl] methyl}-2,4,6(1H,3H,5H)-pyrimidinetrione (1.64 g, 4.45 mmoles) and diisopropylethylamine (1.56 mL, 8.94 mmoles) was stirred in dichloromethane (30 mL) and treated with ethyl isocyanatoacetate (500 uL, 4.45 mmoles). The mixture was stirred for 5 hours, washed with 1 molar hydrochloric acid (×2), evaporated, taken up in ethanol-6 molar sodium hydroxide and stirred overnight. The mixture was acidified and extracted into ethyl acetate (×2). The extracts were washed with 1 molar hydrochloric acid evaporated, dried and evaporated. The title compound was recrystallized from acetic acid (1.0 g, 48%). 1H NMR (400 MHz, DMSO-$d_6$) δ ppm 12.51 (br. s., 1H), 10.11 (t, J=4.93 Hz, 1H), 7.20-7.28 (m, 2H), 7.00 (d, J=7.83 Hz, 2H), 6.86-6.96 (m, 4H), 5.00 (s, 4H), 4.10-4.18 (m, 2H), 3.82 (s, 6H).

Example 68

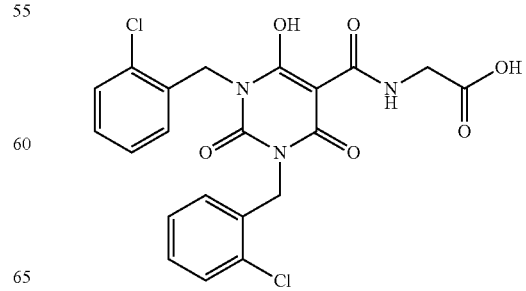

N-({1,3-Bis[(2-chlorophenyl)methyl]-6-hydroxy-2,4-dioxo-1,2,3,4-tetrahydro-5-pyrimidinyl}carbonyl)glycine 68a) 1,3-Bis[(2-chlorophenyl)methyl]-2,4,6(1H,3H,5H)-pyrimidinetrione. 2-Chlorobenzyl isocyanate (875 uL, 6.0 mmoles) was added to a solution of 2-chlorobenzylamine (725 uL, 6.0 mmoles) in chloroform (100 mL) and the mixture stirred for 1 hour. Ethyl malonyl chloride (768 uL, 6.0 mmoles) was added and the mixture was heated to 70° C. for 2 hours. DBU (1.0 mL) was added and the mixture was heated for a further 1 hour. The mixture was cooled and washed with 1 molar hydrochloric acid (×2), dried and evaporated to an oil (2.0 g, 88%). 1H NMR (400 MHz, DMSO-$d_6$) δ ppm 7.45-7.49 (m, 2H), 7.40-7.45 (m, 2H), 7.28-7.32 (m, 4H), 4.98 (s, 4H), 4.02 (s, 2H).

68b) N-({1,3-Bis[(2-chlorophenyl)methyl]-6-hydroxy-2,4-dioxo-1,2,3,4-tetrahydro-5-pyrimidinyl}carbonyl)glycine. A mixture of 1,3-bis[(2-chlorophenyl)methyl]-2,4,6(1H,3H,5H)-pyrimidinetrione (2.0 g, 5.3 mmoles) and diisopropylethylamine (1.85 mL, 10.6 mmoles) was stirred in dichloromethane (35 mL) and treated with ethyl isocyanatoacetate (594 uL, 5.3 mmoles). The mixture was stirred for 5 hours, washed with 1 molar hydrochloric acid (×2), evaporated, taken up in ethanol-6 molar sodium hydroxide and stirred overnight. The mixture was acidified and extracted into ethyl acetate (×2). The extracts were washed with 1 molar hydrochloric acid evaporated, dried and evaporated. The title compound was recrystallized from acetic acid (1.59 g, 62%). 1H NMR (400 MHz, DMSO-$d_6$) δ ppm 13.06 (br. s., 1H), 10.13 (s, 1H), 7.41-7.60 (m, 2H), 7.30 (dd, J=5.81, 3.28 Hz, 4H), 7.21 (dd, J=5.31, 3.79 Hz, 2H), 5.09 (s, 4H), 4.15 (s, 2H).

Example 69

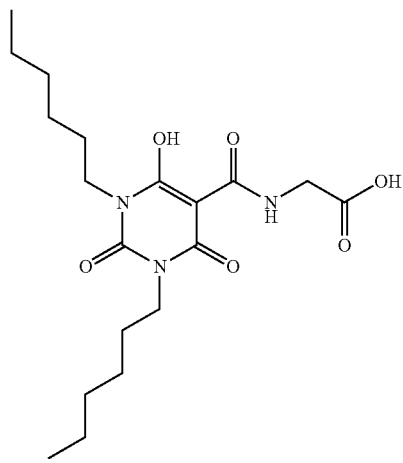 [SMILES: CCCCCCn1c(O)c(C(=O)NCC(=O)O)c(=O)n(CCCCCC)c1=O]

N-[(1,3-Dihexyl-6-hydroxy-2,4-dioxo-1,2,3,4-tetrahydro-5-pyrimidinyl)carbonyl]glycine Hexyl isocyanate (728 uL, 5.0 mmoles) was added to a solution of n-hexylamine (660 uL, 5.0 mmoles) in dichloromethane (100 mL) and the mixture stirred for 1 hour. Malonyl dichloride (486 uL, 5.0 mmoles) was added and the mixture was heated to gentle reflux for 1 hour. The mixture was washed with 1 molar hydrochloric acid (×2), dried and evaporated. The residue was redissolved in dichloromethane (50 mL) and diisopropylethylamine (1.73 mL, 10 mmoles) and the mixture was treated with ethyl isocyanatoacetate (561 uL, 5.0 mmoles). After stirring overnight the mixture was washed with 1 molar hydrochloric acid, dried and evaporated. The residue was dissolved in ethanol (5 mL) and treated with 6 molar sodium hydroxide (2.0 mL). The mixture was stirred for 1 hour, acidified and extracted into ethyl acetate. The organic solution was washed with 1 molar hydrochloric acid, dried and evaporated. The crude product was slurried in hexane to afford the title compound (890 mg, 45%). 1H NMR (400 MHz, DMSO-$d_6$) δ ppm 13.10 (br. s, 1H), 10.10 (t, J=4.80 Hz, 1H), 4.13 (d, J=5.81 Hz, 2H), 3.75-3.84 (m, 4H), 1.53 (s, 4H), 1.26 (s, 12H), 0.82-0.90 (m, 6H).

Example 70

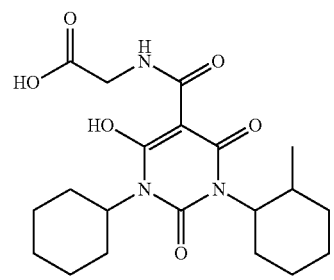 [SMILES: CC1CCCCC1n1c(=O)c(C(=O)NCC(=O)O)c(O)n(C2CCCCC2)c1=O]

N-{[1-Cyclohexyl-6-hydroxy-3-(2-methylcyclohexyl)-2,4-dioxo-1,2,3,4-tetrahydro-5-pyrimidinyl]carbonyl}glycine Using 2-methylcyclohexylamine in place of 4-methylcyclohexylamine, the title compound was prepared in 19% yield (390 mg) following the procedures described in example 54. 1H NMR (400 MHz, CDCl$_3$) δ ppm 0.68-0.84 (m, 3H) 1.14-1.43 (m, 8H) 1.53-1.76 (m, 5H) 1.76-1.90 (m, 4H) 2.14-2.43 (m, 3H) 4.18-4.27 (m, 2H) 4.38-4.54 (m, 1H) 4.62-4.87 (m, 2H) 10.21-10.43 (m, 1H)

Example 71

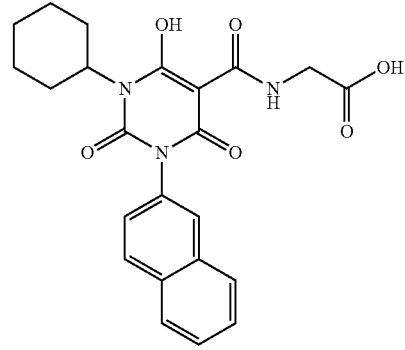 [SMILES: O=C(O)CNC(=O)c1c(O)n(C2CCCCC2)c(=O)n(-c2ccc3ccccc3c2)c1=O]

N-{[1-Cyclohexyl-6-hydroxy-3-(2-naphthalenyl)-2,4-dioxo-1,2,3,4-tetrahydro-5-pyrimidinyl]carbonyl}glycine Using 2-aminonaphthalene in place of 4-methylcyclohexylamine, the title compound was prepared in 0.6% yield (12.9 mg) following the procedures described in example 54. 1H NMR (400 MHz, CDCl$_3$) δ ppm 1.04-1.19 (m, 1H) 1.27-1.46 (m, 2H) 1.57-1.93 (m, 6H) 2.26-2.48 (m, 2H) 4.06-4.21 (m, 1H) 4.23 (d, J=5.6 Hz, 1H) 4.72-4.91 (m, 1H) 7.39 (dd, J=1.0, 7.3 Hz, 1H) 7.47-7.65 (m, 4H) 7.84-8.03 (m, 2H) 10.21 (t, J=5.6 Hz, 1H)

Example 72

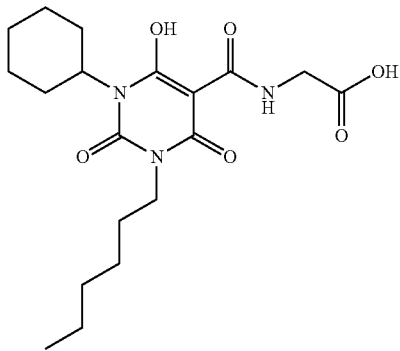 [SMILES: CCCCCCn1c(=O)c(C(=O)NCC(=O)O)c(O)n(C2CCCCC2)c1=O]

N-[(1-Cyclohexyl-3-hexyl-6-hydroxy-2,4-dioxo-1,2,3,4-tetrahydro-5-pyrimidinyl)carbonyl]glycine Cyclohexyl isocyanate (635 uL, 5.0 mmoles) was added to a solution of n-hexylamine (660 uL, 5.0 mmoles) in dichloromethane (100 mL) and the mixture stirred for 1 hour. Malonyl dichloride (486 uL, 5.0 mmoles) was added and the mixture was heated to gentle reflux for 1 hour. The mixture was washed with 1 molar hydrochloric acid (×2), dried and evaporated. The residue was redissolved in dichloromethane (50 mL) and diisopropylethylamine (1.73 mL, 10 mmoles) and the mixture was treated with ethyl isocyanatoacetate (561 uL, 5.0 mmoles). After stirring overnight the mixture was washed with 1 molar hydrochloric acid, dried and evaporated. The residue was dissolved in ethanol (5 mL) and treated with 6 molar sodium hydroxide (2.0 mL). The mixture was stirred for 1 hour, acidified and extracted into ethyl acetate. The organic solution was washed with 1 molar hydrochloric acid, dried and evaporated to a brown oil. The crude material was stood in a freezer overnight in hexane to afford some solid. The liquors were concentrated and purified by preparative HPLC (acetonitrile-water-0.1% TFA) to give additional material which was combined with the previously obtained solid and recrystallized from ethanol-water to give the title compound (480 mg, 24%). 1H NMR (400 MHz, DMSO-d$_6$) δ ppm 13.09 (br. s., 1H), 10.15 (t, J=5.56 Hz, 1H), 4.53-4.73 (m, 1H), 4.05-4.18 (m, 2H), 3.78 (t, 2H), 2.16-2.36 (m, 2H), 1.79 (d, J=12.38 Hz, 2H), 1.42-1.71 (m, 5H), 1.26 (s, 8H), 1.03-1.19 (m, 1H), 0.79-0.92 (m, 3H).

Example 73

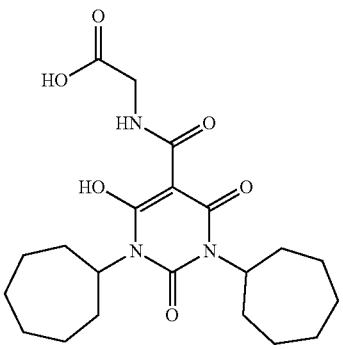 [SMILES: O=C(O)CNC(=O)c1c(O)n(C2CCCCCC2)c(=O)n(C2CCCCCC2)c1=O]

N-[(1,3-Dicycloheptyl-6-hydroxy-2,4-dioxo-1,2,3,4-tetrahydro-5-pyrimidinyl)carbonyl]glycine Using cycloheptylamine in place of 4-methylcyclohexylamine and cycloheptylisocyanate in place of cyclohexylisocyanate, the title compound was prepared in 7% yield (142.6 mg) following the procedures described in example 54. 1H NMR (400 MHz, CDCl$_3$) δ ppm 1.19-1.36 (m, 2H) 1.37-1.92 (m, 17H) 2.20-2.42 (m, 6H) 4.15 (d, J=5.8 Hz, 2H) 4.69-5.03 (m, 3H) 10.20-10.46 (m, 1H)

Example 74

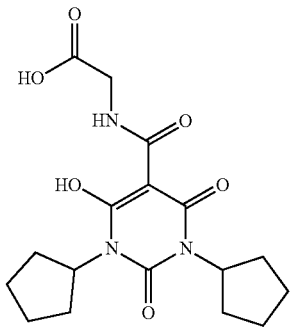 [SMILES: O=C(O)CNC(=O)c1c(O)n(C2CCCC2)c(=O)n(C2CCCC2)c1=O]

N-[(1,3-Dicyclopentyl-6-hydroxy-2,4-dioxo-1,2,3,4-tetrahydro-5-pyrimidinyl)carbonyl]glycine Method 1

Using cyclopentylamine in place of 4-methylcyclohexylamine and cyclopentylisocyanate in place of cyclohexylisocyanate, the title compound was prepared in 14% yield (263 mg) following the procedures described in example 54. 1H NMR (400 MHz, CDCl$_3$) δ ppm 1.50-1.66 (m, 4H) 1.75-1.88 (m, 4H) 1.88-2.00 (m, 4H) 2.01-2.16 (m, 4H) 2.56-2.71 (m, 1H) 3.06-3.27 (m, 1H) 4.14 (d, J=5.6 Hz, 2H) 5.12-5.40 (m, 2H) 10.28-10.41 (m, 1H)

Example 75

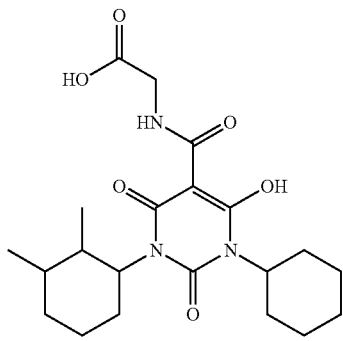 [SMILES: CC1CCCC(n2c(=O)c(C(=O)NCC(=O)O)c(O)n(C3CCCCC3)c2=O)C1C]

N-{[1-Cyclohexyl-3-(2,3-dimethylcyclohexyl)-6-hydroxy-2,4-dioxo-1,2,3,4-tetrahydro-5-pyrimidinyl]carbonyl}glycine Using 2,3-dimethylcyclohexylamine in place of 4-methylcyclohexylamine, the title compound was prepared in 5% yield (85 mg) following the procedures described in example 54. LC/MS m/z 422 (M+H$^+$).

Example 76

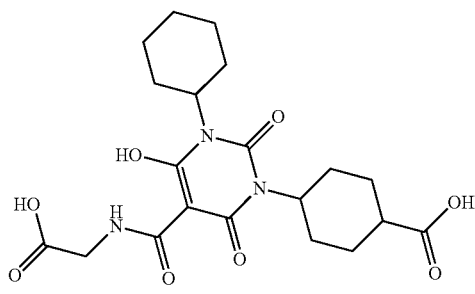 [SMILES: O=C(O)CNC(=O)c1c(O)n(C2CCCCC2)c(=O)n(C2CCC(C(=O)O)CC2)c1=O]

4-[5-{[(Carboxymethyl)amino]carbonyl}-3-cyclohexyl-4-hydroxy-2,6-dioxo-3,6-dihydro-1(2H)-pyrimidinyl]cyclohexanecarboxylic Acid Using 4-aminocyclohexanecarboxylic acid in place of 4-methylcyclohexylamine, the title compound was prepared in 16% yield (151 mg) following the procedures described in example 54. LC/MS m/z 438 (M+H$^+$).

Example 77

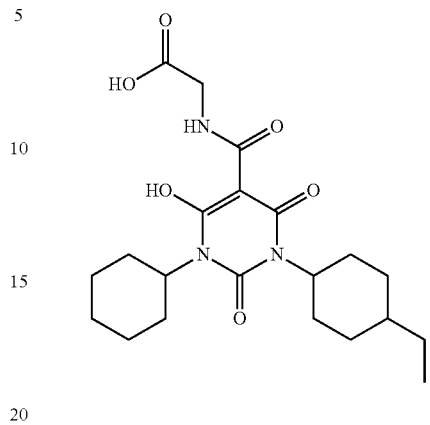

N-{[1-Cyclohexyl-3-(4-ethylcyclohexyl)-6-hydroxy-2,4-dioxo-1,2,3,4-tetrahydro-5-pyrimidinyl]carbonyl}glycine Using 4-ethylcyclohexylamine in place of 4-methylcyclohexylamine, the title compound was prepared in 20% yield (185 mg) following the procedures described in example 54. 1H NMR (400 MHz, CDCl$_3$) δ ppm 0.85-0.96 (m, 3H) 1.10-1.40 (m, 8H) 1.53-1.72 (m, 6H) 1.73-1.89 (m, 3H) 2.19-2.61 (m, 3H) 3.85-4.04 (m, 1H) 4.09-4.34 (m, 2H) 4.59-4.85 (m, 2H) 5.07-5.32 (m, 2H) 10.30-10.426 (m, 1H).

Example 78

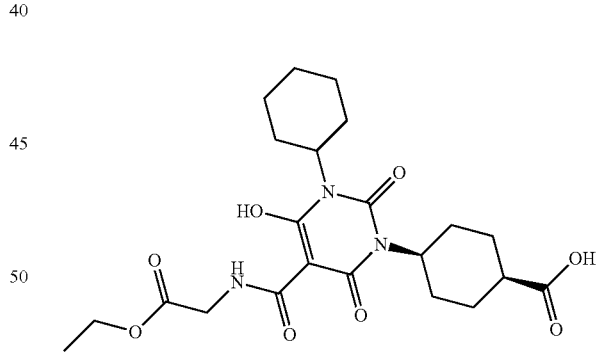

cis-4-[3-Cyclohexyl-5-({[2-(ethyloxy)-2-oxoethyl]amino}carbonyl)-4-hydroxy-2,6-dioxo-3,6-dihydro-1(2H)-pyrimidinyl]cyclohexanecarboxylic Acid Using cis-4-aminocyclohexanecarboxylic acid 1 in place of 4-methylcyclohexylamine, the title compound was prepared in 9% yield (114 mg) following the procedures described in example 54. LC/MS m/z 466 (M+H$^+$).

Example 79

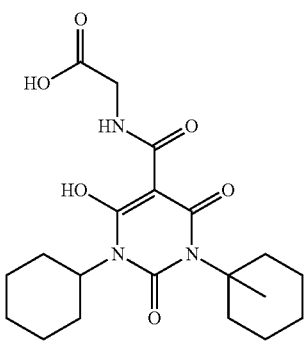

N-{[1-Cyclohexyl-6-hydroxy-3-(1-methylcyclohexyl)-2,4-dioxo-1,2,3,4-tetrahydro-5-pyrimidinyl]carbonyl}glycine Using 1-amino-1-methylcyclohexane in place of 4-methylcyclohexylamine, the title compound was prepared in 18% yield (595 mg) following the procedures described in example 54. 1H NMR (400 MHz, CDCl$_3$) δ ppm 0.97-1.18 (m, 3H) 1.19-1.44 (m, 9H) 1.46-1.74 (m, 5H) 1.77-1.99 (m, 4H) 2.22-2.40 (m, 2H) 3.11-3.30 (m, 2H) 4.07-4.37 (m, 2H) 4.50-4.78 (m, 1H) 10.15-10.35 (m, 1H)

Example 80

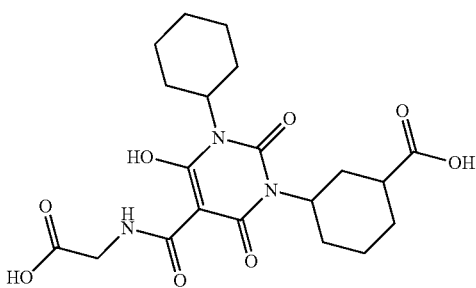 [SMILES: O=C(O)CNC(=O)c1c(O)n(C2CCCCC2)c(=O)n(C2CCCC(C(=O)O)C2)c1=O]

3-[5-{[(Carboxymethyl)amino]carbonyl}-3-cyclohexyl-4-hydroxy-2,6-dioxo-3,6-dihydro-1(2H)-pyrimidinyl]cyclohexanecarboxylic Acid Using 3-aminocyclohexanecarboxylic acid in place of 4-methylcyclohexylamine, the title compound was prepared in 18% yield (184 mg) following the procedures described in example 54. LC/MS m/z 438 (M+H$^+$).

Example 81

N-{[1-Cyclohexyl-6-hydroxy-2,4-dioxo-3-(2-oxo-2-phenylethyl)-1,2,3,4-tetrahydro-5-pyrimidinyl]carbonyl}glycine A mixture of ethyl N-[(3-cyclohexyl-6-hydroxy-2,4-dioxo-1,2,3,4-tetrahydro-5-pyrimidinyl)carbonyl]glycinate (300 mg, 0.88 mmoles), 2-bromoacetophenone (350 mg, 1.76 mmoles) and potassium carbonate (243 mg, 1.76 mmoles) in DMF (4 mL) was heated in a microwave synthesiser at 100° C. for 15 minutes, then cooled and filtered. The residue was washed with dichloromethane (3×3 mL) and the combined filtrate was evaporated and purified by flash chromatography (ethyl acetate-hexane) to obtain the desired crude ester. The ester was dissolved in ethanol (3 mL) and 1M aqueous NaOH (1 mL) and the solution stirred for 2 hours, then neutralized by addition of 1M aqueous HCl. The solid was collected, washed with water (3×4 mL) and dried under vacuum overnight to give the title compound (51 mg, 20%). 1H NMR (400 MHz, CDCl$_3$) δ ppm 1.10-1.27 (m, 1H) 1.27-1.45 (m, 2H) 1.58-1.77 (m, 3H) 1.77-1.91 (m, 2H) 2.24-2.43 (m, 2H) 3.56-5.09 (br s, 2H), 4.19-4.26 (m, 2H) 4.62-4.85 (m, 1H) 5.31-5.41 (m, 2H) 7.45-7.55 (m, 2H) 7.58-7.66 (m, 1H) 7.97-8.03 (m, 2H) 10.04-10.42 (m, 1H)

Example 82

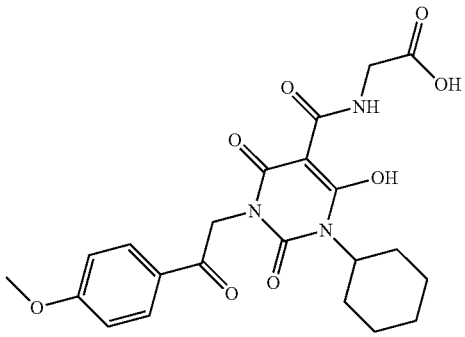 [SMILES: COc1ccc(C(=O)Cn2c(=O)c(C(=O)NCC(=O)O)c(O)n(C3CCCCC3)c2=O)cc1]

N-[(1-Cyclohexyl-6-hydroxy-3-{2-[4-(methyloxy)phenyl]-2-oxoethyl}-2,4-dioxo-1,2,3,4-tetrahydro-5-pyrimidinyl)carbonyl]glycine Using 2-bromo-4'-methoxyacetophenone in place of 2-bromoacetophenone, the title compound was prepared in 48% yield (196 mg) following the procedures described in example 81. LC/MS m/z 460 (M+H$^+$).

Example 83

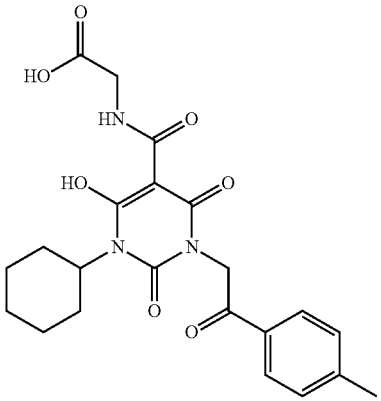 [SMILES: Cc1ccc(C(=O)Cn2c(=O)c(C(=O)NCC(=O)O)c(O)n(C3CCCCC3)c2=O)cc1]

N-({1-Cyclohexyl-6-hydroxy-3-[2-(4-methylphenyl)-2-oxoethyl]-2,4-dioxo-1,2,3,4-tetrahydro-5-pyrimidinyl}carbonyl)glycine Using 2-bromo-4'-methylacetophenone in place of 2-bromoacetophenone, the title compound was prepared in 61% yield (241 mg) following the procedures described in example 81. 1H NMR (400 MHz, CDCl$_3$) δ ppm 1.10-1.43 (m, 4H) 1.57-1.75 (m, 4H) 1.77-1.90 (m, 2H) 2.21-2.52 (m, 5H) 4.11-4.29 (m, 2H) 4.64-4.85 (m, 1H) 5.26-5.39 (m, 2H) 7.20-7.35 (m, 2H) 7.89 (d, J=8.3 Hz, 2H) 10.02-10.41 (m, 1H)

Example 84

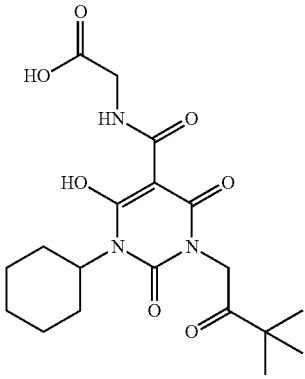 [SMILES: CC(C)(C)C(=O)Cn1c(=O)c(C(=O)NCC(=O)O)c(O)n(C2CCCCC2)c1=O]

N-{[1-Cyclohexyl-3-(3,3-dimethyl-2-oxobutyl)-6-hydroxy-2,4-dioxo-1,2,3,4-tetrahydro-5-pyrimidinyl]carbonyl}glycine Using 1-bromopinacolone in place of 2-bromoacetophenone, the title compound was prepared in 31% yield (114 mg) following the procedures described in example 81. 1H NMR (400 MHz, CDCl$_3$) δ ppm 1.01-1.45 (m, 5H) 1.26 (s, 9H) 1.57-1.76 (m, 3H) 1.76-1.91 (m, 2H) 2.22-2.43 (m, 2H) 4.15-4.30 (m, 2H) 4.62-4.79 (m, 1H) 4.82-4.97 (m, 2H) 9.97-10.39 (m, 1H)

Example 85

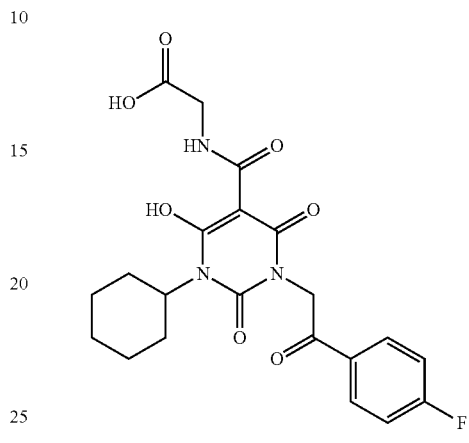

N-({1-Cyclohexyl-3-[2-(4-fluorophenyl)-2-oxoethyl]-6-hydroxy-2,4-dioxo-1,2,3,4-tetrahydro-5-pyrimidinyl}carbonyl)glycine Using 2-bromo-4'-fluoroacetophenone in place of 2-bromoacetophenone, the title compound was prepared in 69% yield (275 mg) following the procedures described in example 81. 1H NMR (400 MHz, CDCl$_3$) δ ppm 1.06-1.43 (m, 5H) 1.55-1.76 (m, 3H) 1.76-1.93 (m, 2H) 2.23-2.43 (m, 2H) 4.09-4.33 (m, 2H) 4.65-4.84 (m, 1H) 5.28-5.38 (m, 2H) 7.13-7.23 (m, 2H) 7.99-8.08 (m, 2H) 10.01-10.52 (m, 1H)

Example 86

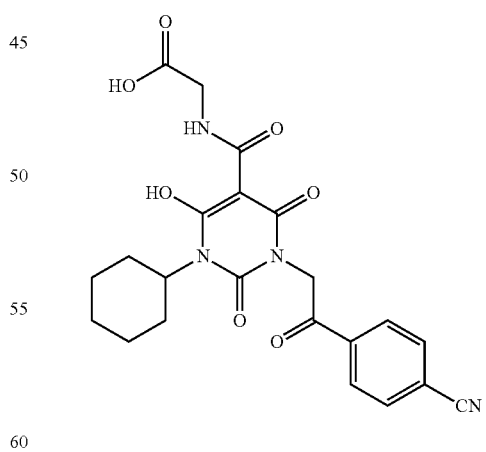

N-({3-[2-(4-Cyanophenyl)-2-oxoethyl]-1-cyclohexyl-6-hydroxy-2,4-dioxo-1,2,3,4-tetrahydro-5-pyrimidinyl}carbonyl)glycine Using 2-bromo-4'-cyanoacetophenone in place of 2-bromoacetophenone, the title compound was prepared in 65% yield (259 mg) following the procedures described in example 81. 1H NMR (400 MHz, CDCl$_3$) δ ppm 1.05-1.45 (m, 5H) 1.59-1.77 (m, 3H) 1.77-1.91 (m, 2H) 2.21-2.40 (m, 2H) 4.18-4.29 (m, 2H) 4.64-4.83 (m, 1H) 5.29-5.41 (m, 2H) 7.79-7.85 (m, 2H) 8.09 (d, J=8.6 Hz, 2H) 9.99-10.45 (m, 1H)

Example 87

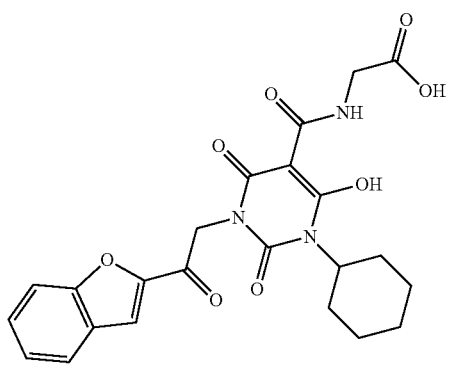 [SMILES: O=C(O)CNC(=O)c1c(O)n(C2CCCCC2)c(=O)n(CC(=O)c2cc3ccccc3o2)c1=O]

N-({3-[2-(1-Benzofuran-2-yl)-2-oxoethyl]-1-cyclohexyl-6-hydroxy-2,4-dioxo-1,2,3,4-tetrahydro-5-pyrimidinyl}carbonyl)glycine Using 1-(1-benzofuran-2-yl)-2-bromoethan-1-one in place of 2-bromoacetophenone, the title compound was prepared in 44% yield (183 mg) following the procedures described in example 81. 1H NMR (400 MHz, CDCl$_3$) δ ppm 1.04-1.44 (m, 5H) 1.59-1.77 (m, 3H) 1.77-1.91 (m, 2H) 2.25-2.43 (m, 2H) 4.16-4.28 (m, 2H) 4.65-4.84 (m, 1H) 5.30-5.40 (m, 2H) 7.30-7.38 (m, 1H) 7.46-7.56 (m, 1H) 7.56-7.67 (m, 2H) 7.69-7.78 (m, 1H) 10.02-10.45 (m, 1H)

Example 88

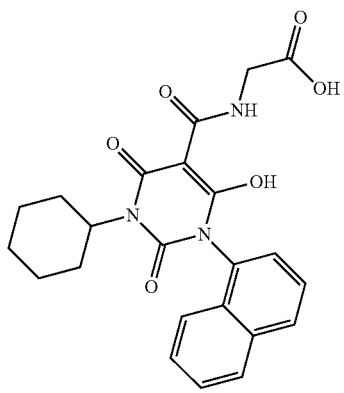 [SMILES: O=C(O)CNC(=O)c1c(O)n(-c2cccc3ccccc23)c(=O)n(C2CCCCC2)c1=O]

N-{[3-Cyclohexyl-6-hydroxy-1-(1-naphthalenyl)-2,4-dioxo-1,2,3,4-tetrahydro-5-pyrimidinyl]carbonyl}glycine Using 1-aminonaphthalene in place of 4-methylcyclohexylamine, the title compound was prepared in 20% yield (257 mg) following the procedures described in example 54. 1H NMR (400 MHz, CDCl$_3$) δ ppm 1.07-1.43 (m, 4H) 1.56-1.90 (m, 5H) 2.27-2.48 (m, 2H) 4.05-4.19 (m, 2H) 4.23 (d, J=5.8 Hz, 1H) 4.71-4.92 (m, 1H) 7.37-7.46 (m, 1H) 7.48-7.61 (m, 4H) 7.87-8.00 (m, 2H) 9.99-10.46 (m, 1H)

Example 89

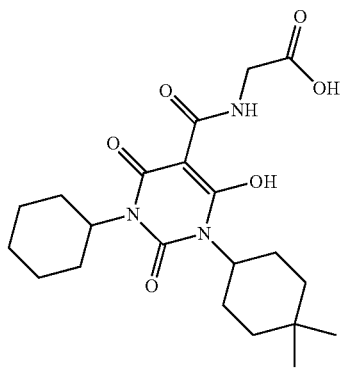 [SMILES: CC1(C)CCC(n2c(O)c(C(=O)NCC(=O)O)c(=O)n(C3CCCCC3)c2=O)CC1]

N-{[3-Cyclohexyl-1-(4,4-dimethylcyclohexyl)-6-hydroxy-2,4-dioxo-1,2,3,4-tetrahydro-5-pyrimidinyl]carbonyl}glycine Using 4,4-dimethylcyclohexylamine in place of 4-methylcyclohexylamine, the title compound was prepared in 3% yield (45 mg) following the procedures described in example 54. 1H NMR (400 MHz, CDCl$_3$) δ ppm 0.93 (s, 3H) 1.02 (s, 3H) 1.14-1.53 (m, 11H) 1.56-1.72 (m, 3H) 1.77-1.89 (m, 2H) 2.26-2.43 (m, 2H) 2.45-2.65 (m, 2H) 4.15-4.32 (m, 2H) 4.57-4.84 (m, 2H) 10.20-10.40 (m, 1H)

Example 90

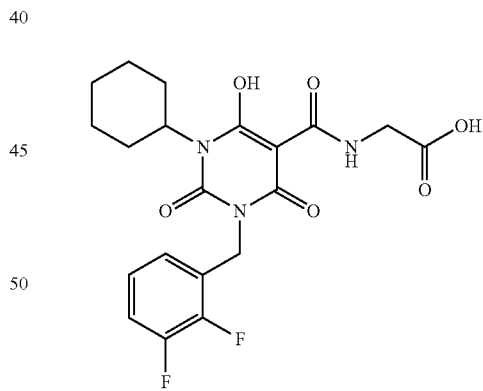

N-({1-Cyclohexyl-3-[(2,3-difluorophenyl)methyl]-6-hydroxy-2,4-dioxo-1,2,3,4-tetrahydro-5-pyrimidinyl}carbonyl)glycine A mixture of ethyl N-[(1-cyclohexyl-6-hydroxy-2,4-dioxo-1,2,3,4-tetrahydro-5-pyrimidinyl)carbonyl]glycinate (340 mg, 1.0 mmoles), pulv. potassium carbonate (750 mg, 5.35 mmoles) and 2,3-difluorobenzyl bromide (255 uL, 2.0 mmoles) in dimethylacetamide (5 mL) was vigorously stirred at 100° C. for 3 hours. The mixture was poured into 1 molar hydrochloric acid and extracted with ethyl acetate (×2). The combined organic solutions were washed with 1 molar hydrochloric acid and evaporated. The residue was purified by flash chromatography (10-50% ethyl acetate in hexane), the required fractions evaporated, dissolved in ethanol (5 mL) and 1 molar sodium hydroxide solution (3.0 mL) added. The mixture was stirred overnight, acidified and extracted with ethyl acetate (×2), the combined extracts washed with 1 molar hydrochloric acid, dried and evaporated. Recrystallization from ethanol-water gave the title compound (140 mg, 32%). 1H NMR (400 MHz, DMSO-$d_6$) δ ppm 13.10 (br. s., 1H), 10.11 (br. s., 1H), 7.25-7.43 (m, 1H), 7.08-7.23 (m, 1H), 7.03 (t, J=7.07 Hz, 1H), 5.08 (s, 2H), 4.55-4.73 (m, 1H), 4.13 (d, J=5.81 Hz, 2H), 2.12-2.35 (m, 2H), 1.78 (d, J=12.63 Hz, 2H), 1.63 (s, 3H), 1.20-1.38 (m, 2H), 1.02-1.18 (m, 1H)

Example 91

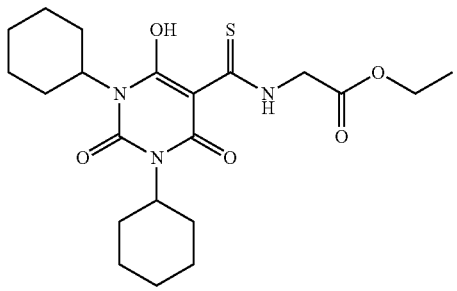 [SMILES: CCOC(=O)CNC(=S)c1c(O)n(C2CCCCC2)c(=O)n(C2CCCCC2)c1=O]

Ethyl N-[(1,3-dicyclohexyl-6-hydroxy-2,4-dioxo-1,2,3,4-tetrahydro-5-pyrimidinyl)carbonothioyl]glycinate A mixture of 1,3-dicyclohexyl-2,4,6(1H,3H,5H)-pyrimidinetrione (660 mg, 2.25 mmoles), diisopropylethylamine (780 uL, 4.5 mmoles) and ethyl isocyanatoacetate (340 uL, 2.75 mmoles) in chloroform (20 mL) was stirred for 6 hours. The mixture was washed with 1 molar hydrochloric acid (×2), dried and evaporated. The solid residue was purified by flash chromatography (0-20% ethyl acetate in hexane) and crystallization from ethanol to give the title compound (250 mg, 25%). 1H NMR (400 MHz, DMSO-$d_6$) δ ppm 12.57 (t, J=5.18 Hz, 1H), 4.69 (t, 2H), 4.44 (d, J=5.31 Hz, 2H), 4.17 (q, J=7.24 Hz, 2H), 2.25 (q, 4H), 1.79 (d, J=12.88 Hz, 4H), 1.55-1.72 (m, 6H), 1.24-1.38 (m, 4H), 1.22 (t, J=7.07 Hz, 3H), 1.12 (q, J=12.88 Hz, 2H).

Example 92

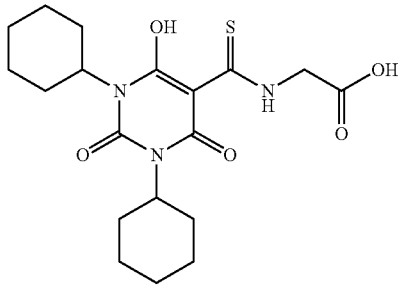 [SMILES: O=C(O)CNC(=S)c1c(O)n(C2CCCCC2)c(=O)n(C2CCCCC2)c1=O]

N-[(1,3-Dicyclohexyl-6-hydroxy-2,4-dioxo-1,2,3,4-tetrahydro-5-pyrimidinyl)carbonothioyl]glycine A mixture of 1,3-dicyclohexyl-2,4,6(1H,3H,5H)-pyrimidinetrione (660 mg, 2.25 mmoles), diisopropylethylamine (780 uL, 4.5 mmoles) and ethyl isothiocyanatoacetate (340 uL, 2.75 mmoles) in chloroform (20 mL) was stirred overnight. The mixture was washed with 1 molar hydrochloric acid (×2), dried and evaporated. The solid residue was purified by flash chromatography (dichloromethane) and the fractions evaporated, dissolved in ethanol (5 mL, some heating) and treated with 1 molar sodium hydroxide (3 mL). The mixture was stirred for 30 minutes and acidified to give a solid which recrystallized from ethanol-water to give the title compound (135 mg, 15%). 1H NMR (400 MHz, DMSO-$d_6$) δ ppm 13.16 (s, 1H), 12.54 (t, J=4.80 Hz, 1H), 4.69 (t, J=12.00 Hz, 2H), 4.35 (d, J=5.05 Hz, 2H), 2.25 (q, 4H), 1.79 (d, J=12.38 Hz, 4H), 1.63 (d, J=12.38 Hz, 6H), 1.29 (q, 4H), 1.13 (q, 2H).

Example 93

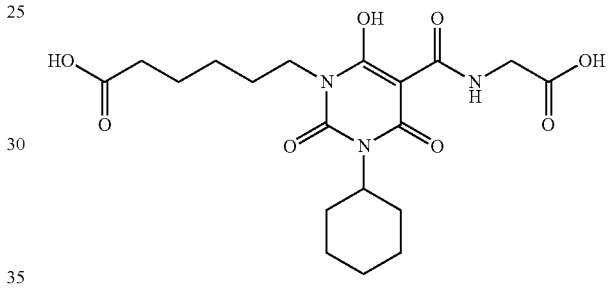

6-[5-{[(Carboxymethyl)amino]carbonyl}-3-cyclohexyl-6-hydroxy-2,4-dioxo-3,4-dihydro-1(2H)-pyrimidinyl]hexanoic Acid 93a) Ethyl 6-(3-cyclohexyl-2,4,6-trioxotetrahydro-1(2H)-pyrimidinyl)hexanoate. Ethyl isocyanatohexanoate (790 mg, 4.26 mmoles) and cyclohexylamine (490 uL, 4.26 mmoles) were stirred together in dichloromethane (100 mL) for 2 hours. Malonyl dichloride (414 uL, 4.26 mmoles) was added and the mixture was heated under gentle reflux for 2 hours. The mixture was purified by flash chromatography (dichloromethane to 5% methanol in dichloromethane) to give the title compound (1.07 g, 71%). 1H NMR (400 MHz, CHLOROFORM-d) δ ppm 4.56-4.67 (m, 1H), 4.62 (tt, J=12.25, 3.79 Hz, 1H), 4.13 (q, J=7.24 Hz, 2H), 3.85 (t, 2H), 2.31 (t, 2H), 2.26 (dq, 2H), 1.85 (d, J=13.39 Hz, 2H), 1.57-1.73 (m, 7H), 1.29-1.43 (m, 4H), 1.26 (t, J=7.07 Hz, 3H), 1.06-1.24 (m, 2H).

93b) 6-[5-{[(Carboxymethyl)amino]carbonyl}-3-cyclohexyl-6-hydroxy-2,4-dioxo-3,4-dihydro-1(2H)-pyrimidinyl]hexanoic acid. A mixture of ethyl 6-(3-cyclohexyl-2,4,6-trioxotetrahydro-1(2H)-pyrimidinyl)hexanoate (330 mg, 0.936 mmoles) and diisopropylethylamine (324 uL, 1.87 mmoles) in chloroform (30 mL) was treated with ethyl isocyanatoacetate (126 uL, 1.12 mmoles) and stirred overnight. The mixture was washed with 1 molar hydrochloric acid (×2), dried and evaporated. The residue was taken up in ethanol and treated with 1 molar sodium hydroxide (2 mL) and stirred for 1 hour. The mixture was acidified and extracted into ethyl acetate. The organic solution was washed with 1 molar hydrochloric acid, dried and evaporated. Crystallization from acetic acid afforded the title compound (160 mg, 40%). 1H NMR (400 MHz, DMSO-$d_6$) δ ppm 13.06 (br. s., 1H), 12.08 (br. s., 1H), 10.15 (t, J=5.81 Hz, 1H), 4.63 (t, J=9.22 Hz, 1H), 4.12 (d, J=5.81 Hz, 2H), 3.66-3.87 (m, 2H), 2.26 (d, J=11.37 Hz, 2H), 2.20 (t, J=7.33 Hz, 2H), 1.79 (d, J=12.88 Hz, 2H), 1.57-1.68 (m, 3H), 1.46-1.57 (m, 4H), 1.21-1.35 (m, 4H), 1.04-1.19 (m, 1H).

Example 94

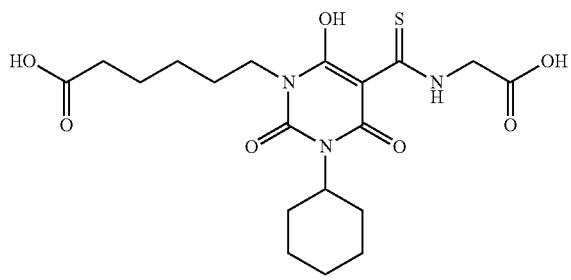 [SMILES: O=C(O)CCCCCn1c(O)c(C(=O)NCC(=O)O)c(=O)n(C2CCCCC2)c1=O]

6-[5-{[(Carboxymethyl)amino]carbonothioyl}-3-cyclohexyl-6-hydroxy-2,4-dioxo-3,4-dihydro-1(2H)-pyrimidinyl]hexanoic Acid A mixture of ethyl 6-(3-cyclohexyl-2,4,6-trioxotetrahydro-1(2H)-pyrimidinyl)hexanoate (330 mg, 0.94 mmoles), diisopropylethylamine (324 uL, 1.87 mmoles) and ethyl isothiocyanatoacetate (139 uL, 1.12 mmoles) in chloroform (20 mL) was stirred for 7 days. The mixture was washed with 1 molar hydrochloric acid (×2), dried and evaporated. The residue was purified by flash chromatography (hexane-20% ethyl acetate in hexane) to give the title compound as a clear oil (250 mg, 60%). The diester was dissolved in ethanol (3 mL) and treated with 1 molar sodium hydroxide (2 mL). The mixture was stirred overnight, taken up in ethyl acetate and washed with 1 molar hydrochloric acid (×2), dried and evaporated. Crystallization from acetic acid afforded the title compound (160 mg, 40%). 1H NMR (400 MHz, DMSO-$d_6$) δ ppm 13.13 (br s, 1H), 12.50 (s, 1H), 12.03 (br s, 1H), 4.71 (m, 1H), 4.35 (d, J=5.05 Hz, 2H), 3.84 (t, J=7.20 Hz, 2H), 2.10-2.38 (m, 4H), 1.80 (d, J=12.63 Hz, 2H), 1.42-1.71 (m, 7H), 1.21-1.42 (m, 4H), 1.01-1.22 (m, 1H).

Example 95

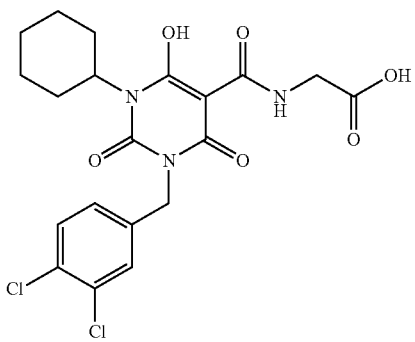 [SMILES: O=C(O)CNC(=O)c1c(O)n(C2CCCCC2)c(=O)n(Cc2ccc(Cl)c(Cl)c2)c1=O]

N-({1-Cyclohexyl-3-[(3,4-dichlorophenyl)methyl]-6-hydroxy-2,4-dioxo-1,2,3,4-tetrahydro-5-pyrimidinyl}carbonyl)glycine A mixture of ethyl N-[(1-cyclohexyl-6-hydroxy-2,4-dioxo-1,2,3,4-tetrahydro-5-pyrimidinyl)carbonyl]glycinate (340 mg, 1.0 mmoles), pulv. potassium carbonate (750 mg, 5.35 mmoles) and 3,4-dichlorobenzyl bromide (480 uL, 2.0 mmoles) in dimethylacetamide (5 mL) was vigorously stirred at 100° C. for 3 hours. The mixture was poured into 1 molar hydrochloric acid and extracted with ethyl acetate (×2). The combined organic solutions were washed with 1 molar hydrochloric acid and evaporated. The residue was purified by flash chromatography (10-50% ethyl acetate in hexane), the required fractions evaporated, dissolved in ethanol (5 mL) and 1 molar sodium hydroxide solution (3.0 mL) added. The mixture was stirred overnight, acidified and extracted with ethyl acetate (×2), the combined extracts washed with 1 molar hydrochloric acid, dried and evaporated. Recrystallization from ethanol-water gave the title compound (154 mg, 33%). 1H NMR (400 MHz, DMSO-$d_6$) δ ppm 13.11 (br. s., 1H), 10.12 (br. s., 1H), 7.58 (dd, J=5.05, 3.03 Hz, 2H), 7.29 (dd, J=8.34, 2.02 Hz, 1H), 4.97 (s, 2H), 4.62 (t, J=12.00 Hz, 1H), 4.13 (d, J=5.81 Hz, 2H), 2.24 (q, 2H), 1.78 (d, J=12.63 Hz, 2H), 1.63 (s, 3H), 1.27 (q, J=12.88 Hz, 2H), 1.11 (q, 1H)

Example 96

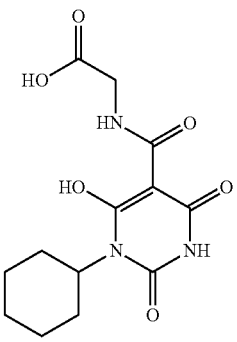 [SMILES: O=C(O)CNC(=O)c1c(O)n(C2CCCCC2)c(=O)[nH]c1=O]

N-[(1-Cyclohexyl-6-hydroxy-2,4-dioxo-1,2,3,4-tetrahydro-5-pyrimidinyl)carbonyl]glycine Ethyl N-[(1-cyclohexyl-6-hydroxy-2,4-dioxo-1,2,3,4-tetrahydro-5-pyrimidinyl)carbonyl]glycinate (270 mg, 0.80 mmol)) was dissolved in ethanol (2 mL) and 1M aqueous NaOH solution was added. The solution was stirred one hour at room temperature, then neutralized by addition of 1M aqueous HCl. The resulting solid was collected, washed with water, and dried under vacuum overnight to give the title compound (208 mg, 84%). LC/MS m/z 312 (M+H$^+$).

Example 97

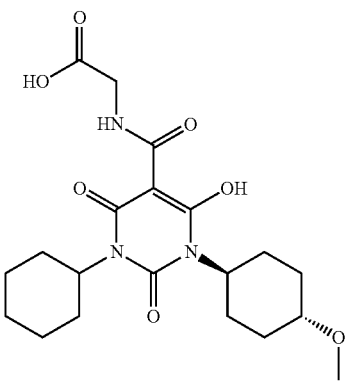 [SMILES: CO[C@H]1CC[C@H](n2c(O)c(C(=O)NCC(=O)O)c(=O)n(C3CCCCC3)c2=O)CC1]

N-({3-Cyclohexyl-6-hydroxy-1-[trans-4-(methyloxy)cyclohexyl]-2,4-dioxo-1,2,3,4-tetrahydro-5-pyrimidinyl}carbonyl)glycine Using trans-4-(methyloxy)cyclohexanamine hydrochloride in place of 4-methylcyclohexylamine, the title compound was prepared in 11% yield (541.6 mg) following the procedures described in example 54. 1H NMR (400 MHz, CDCl$_3$) δ ppm 1.12-1.50 (m, 6H) 1.56-1.77 (m, 6H) 1.78-1.90 (m, 2H) 2.09-2.22 (m, 2H) 2.25-2.55 (m, 4H) 3.18-3.31 (m, 1H) 3.37 (s, 3H) 4.22 (d, J=5.3 Hz, 2H) 4.62-4.89 (m, 2H) 10.22-10.41 (m, 1H)

Example 98

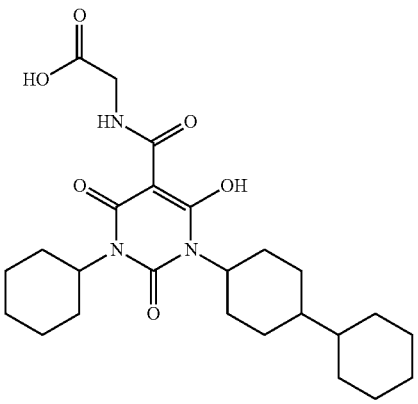 [SMILES: O=C(O)CNC(=O)c1c(O)n(C2CCC(C3CCCCC3)CC2)c(=O)n(C2CCCCC2)c1=O]

N-({1-[1,1'-Bi(cyclohexyl)-4-yl]-3-cyclohexyl-6-hydroxy-2,4-dioxo-1,2,3,4-tetrahydro-5-pyrimidinyl}carbonyl)glycine Using 1,1'-bi(cyclohexyl)-4-amine hydrochloride in place of 4-methylcyclohexylamine, the title compound was prepared in 19% yield (84 mg) following the procedures described in example 54. 1H NMR (400 MHz, CDCl$_3$) δ ppm 0.88-1.43 (m, 13H) 1.56-1.76 (m, 11H) 1.76-1.91 (m, 4H) 2.26-2.43 (m, 4H) 4.24 (d, J=5.8 Hz, 2H) 4.59-4.82 (m, 2H) 10.24-10.38 (m, 1H)

Example 99

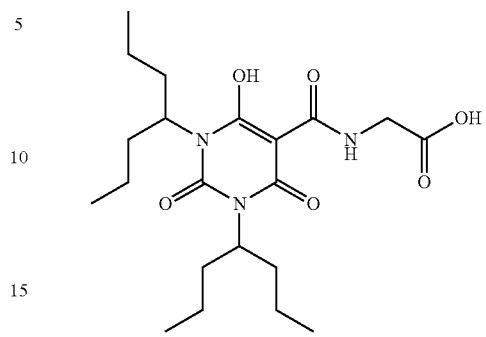

N-{[6-Hydroxy-2,4-dioxo-1,3-bis(1-propylbutyl)-1,2,3,4-tetrahydro-5-pyrimidinyl]carbonyl}glycine 99a) N,N'-Bis(1-propylbutyl)urea. A mixture of carbonyldiimidazole (3.0 g, 18.5 mmoles) and 4-heptylamine (6.0 mL, 40 mmoles) in dimethylformamide (25 mL) was heated at 70° C. for 3 hours. The mixture was cooled and partitioned between ethyl acetate and 1 molar hydrochloric acid. The aqueous was extracted with ethyl acetate and the combined extracts washed with 1 molar hydrochloric acid, dried and evaporated to a solid (4.18 g, 88%). 1H NMR (400 MHz, DMSO-d$_6$) δ ppm 5.34 (d, J=8.59 Hz, 2H), 1.12-1.38 (m, 16H), 0.85 (t, J=6.19 Hz, 12H).

99b) 1,3-Bis(1-propylbutyl)-2,4,6(1H,3H,5H)-pyrimidinetrione. N,N'-bis(1-propylbutyl)urea (1.87 g, 7.29 mmoles) in chloroform (70 mL) was treated with malonyl dichloride (851 uL, 8.75 mmoles) and heated at 70° C. for 3 hours. The mixture was washed with 1 molar hydrochloric acid (×2), dried and evaporated. Flash chromatography (hexane-50% ethyl acetate in hexane) gave the title compound (660 mg, 28%). 1H NMR (400 MHz, CHLOROFORM-d) δ ppm 4.78 (s, 2H), 3.61 (s, 2H), 1.94-2.04 (m, 4H), 1.58-1.67 (m, 4H), 1.17-1.28 (m, 8H), 0.90 (t, J=7.33 Hz, 12H)

99c) N-{[1,3-Bis(1-ethylpropyl)-6-hydroxy-2,4-dioxo-1,2,3,4-tetrahydro-5-pyrimidinyl]carbonyl}glycine. A mixture of 1,3-bis(1-ethylpropyl)-2,4,6(1H,3H,5H)-pyrimidinetrione (660 mg, 2.0 mmoles) and diisopropylethylamine (690 uL, 4.0 mmoles) in dichloromethane (50 mL) was treated with ethyl isocyanatoacetate (270 uL, 2.4 mmoles) and stirred overnight. The mixture was washed with 1 molar hydrochloric acid (×2), dried and evaporated. The residue was dissolved in ethanol (6 mL) and treated with 6 molar sodium hydroxide (4.0 mL). The mixture was stirred for 72 hour, acidified and extracted with ethyl acetate (×2), dried and evaporated. The residue was stored at −10° C. overnight to crystallize. The solid produced was slurried in hexane, collected and washed with hexane to give the title compound (310, 36%). 1H NMR (400 MHz, DMSO-d$_6$) δ ppm 13.09 (s, 1H), 10.19 (d, J=21.47 Hz, 1H), 4.82 (s, 2H), 4.12 (d, J=3.54 Hz, 2H), 2.02 (s, 4H), 1.58 (s, 4H), 1.16 (s, 8H), 0.84 (t, J=7.33 Hz, 12H)

Example 100

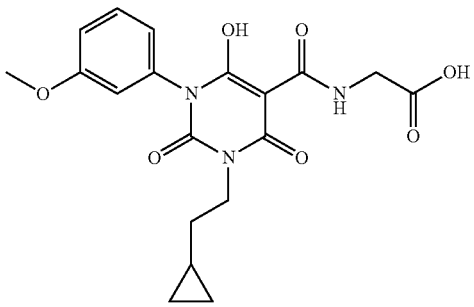 [SMILES: COc1cccc(-n2c(O)c(C(=O)NCC(=O)O)c(=O)n(CCC3CC3)c2=O)c1]

N-({3-(2-Cyclopropylethyl)-6-hydroxy-1-[3-(methyloxy)phenyl]-2,4-dioxo-1,2,3,4-tetrahydro-5-pyrimidinyl}carbonyl)glycine 100a) 1-(2-Cyclopropylethyl)-3-{[3-(methyloxy)phenyl]methyl}-2,4,6(1H,3H,5H)-pyrimidinetrione. Cyclopropylethylamine hydrochloride (2.0 g, 16.44 mmoles) in dichloromethane (60 mL) was treated with diisopropylethylamine (2.84 mL, 16.44 mmoles) followed by 3-methoxyphenyl isocyanate (2.12 mL, 16.44 mmoles). The mixture was stirred for 1 hour, malonyl dichloride (1.92 mL, 19.73 mmoles) was added and the mixture heated under gentle reflux for 4 hours. The mixture was washed with 1 molar hydrochloric acid and purified by flash chromatography (hexane to 30% ethyl acetate in hexane) to give the title compound which was obtained as a solid from hexane-diethyl ether (2.12 g, 42%). 1H NMR (400 MHz, DMSO-$d_6$) δ ppm 7.37 (t, J=8.21 Hz, 1H), 6.94-7.12 (m, 1H), 6.69-6.88 (m, 2H), 3.86 (s, 2H), 3.78-3.85 (m, 2H), 3.76 (s, 3H), 1.43 (q, J=7.07 Hz, 2H), 0.69 (dt, 1H), 0.29-0.47 (m, 2H), −0.09-0.12 (m, 2H)

100b) N-({3-(2-Cyclopropylethyl)-6-hydroxy-1-[3-(methyloxy)phenyl]-2,4-dioxo-1,2,3,4-tetrahydro-5-pyrimidinyl}carbonyl)glycine. A mixture 1-(2-cyclopropylethyl)-3-{[3-(methyloxy)phenyl]methyl}-2,4,6(1H,3H,5H)-pyrimidinetrione (2.12 g, 7.0 mmole) and diisopropylethylamine (2.42 mL, 14.0 mmoles) in dichloromethane (80 mL) was treated with ethyl isocyanatoacetate (942 uL, 8.4 mmoles) and stirred for 72 hours. The mixture was washed with 1 molar hydrochloric acid (×2), dried and evaporated. The residue was dissolved in ethanol (10 mL) and treated with 6 molar sodium hydroxide (6.0 mL). The mixture was stirred for 2 hours, acidified and extracted with ethyl acetate (×2), dried and evaporated. The residue was purified by flash chromatography (1.0% methanol-0.1% acetic acid in dichloromethane to 3.0% methanol-0.1% acetic acid in dichloromethane) to give the title compound (1.4 g, 50%). 1H NMR (400 MHz, DMSO-$d_6$) δ ppm 13.12 (br. s, 1H), 10.04 (s, 1H), 8.35 (s, 1H), 8.32 (d, J=8.08 Hz, 1H), 7.76-7.87 (m, 2H), 4.14 (d, J=5.56 Hz, 2H), 3.87-3.97 (m, 2H), 2.50 (s, 3H), 1.50 (q, J=7.16 Hz, 2H), 0.66-0.76 (m, 1H), 0.37-0.46 (m, 2H), 0.05 (q, J=4.80 Hz, 2H)

Example 101

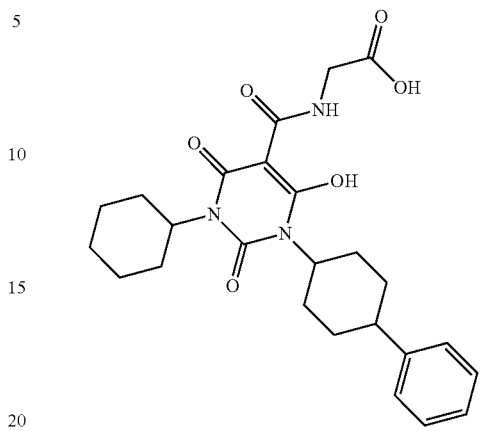

N-{[3-Cyclohexyl-6-hydroxy-2,4-dioxo-1-(4-phenylcyclohexyl)-1,2,3,4-tetrahydro-5-pyrimidinyl]carbonyl}glycine Using 4-phenylcyclohexylamine in place of 4-methylcyclohexylamine, the title compound was prepared in 29% yield (173 mg) following the procedures described in example 54. 1H NMR (400 MHz, CDCl$_3$) δ ppm 1.16-1.44 (m, 4H) 1.56-1.91 (m, 8H) 1.95-2.07 (m, 3H) 2.27-2.43 (m, 2H) 2.51-2.68 (m, 4H) 4.26 (d, J=5.6 Hz, 2H) 4.65-4.96 (m, 2H) 7.15-7.25 (m, 3H) 7.27-7.35 (m, 2H) 10.27-10.38 (m, 1H)

Example 102

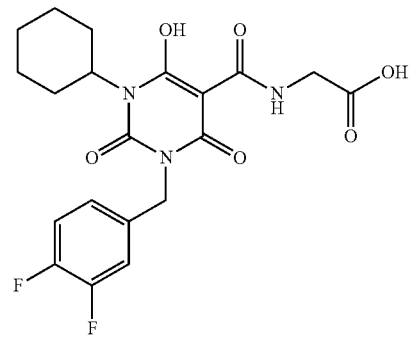 [SMILES: O=C(O)CNC(=O)c1c(O)n(C2CCCCC2)c(=O)n(Cc2ccc(F)c(F)c2)c1=O]

N-({1-Cyclohexyl-3-[(3,4-difluorophenyl)methyl]-6-hydroxy-2,4-dioxo-1,2,3,4-tetrahydro-5-pyrimidinyl}carbonyl)glycine A mixture of ethyl N-[(1-cyclohexyl-6-hydroxy-2,4-dioxo-1,2,3,4-tetrahydro-5-pyrimidinyl)carbonyl]glycinate (340 mg, 1.0 mmoles), pulv. potassium carbonate (750 mg, 5.35 mmoles) and 3,4-difluorobenzyl bromide (256 uL, 2.0 mmoles) in dimethylacetamide (5 mL) was vigorously stirred at 100° C. for 3 hours. The mixture was poured into 1 molar hydrochloric acid and extracted with ethyl acetate (×2). The combined organic solutions were washed with 1 molar hydrochloric acid and evaporated. The residue was purified by flash chromatography (10-50% ethyl acetate in hexane), the required fractions evaporated, dissolved in ethanol (5 mL) and 1 molar sodium hydroxide solution (3.0 mL) added. The mixture was stirred overnight, acidified and extracted with ethyl acetate (×2), the combined extracts washed with 1 molar hydrochloric acid, dried and evaporated. Recrystallization from ethanol-water gave the title compound (138 mg, 32%). 1H NMR (400 MHz, DMSO-$d_6$) δ ppm 13.11 (br. s., 1H), 10.12 (br. s., 1H), 7.28-7.52 (m, 2H), 7.05-7.23 (m, J=5.43, 3.16 Hz, 1H), 4.96 (s, 2H), 4.63 (t, J=12.00 Hz, 1H), 4.13 (d, J=5.81 Hz, 2H), 2.25 (q, 2H), 1.78 (d, J=12.88 Hz, 2H), 1.63 (s, 3H), 1.28 (q, J=12.97 Hz, 2H), 1.11 (q, 1H)

Example 103

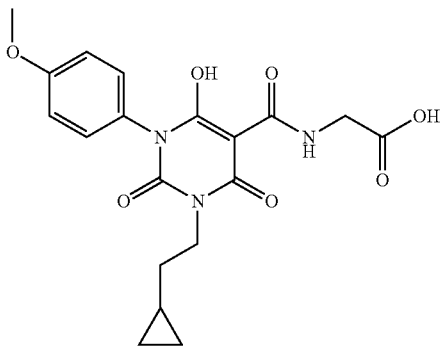 [SMILES: COc1ccc(-n2c(O)c(C(=O)NCC(=O)O)c(=O)n(CCC3CC3)c2=O)cc1]

N-({3-(2-Cyclopropylethyl)-6-hydroxy-1-[4-(methyloxy)phenyl]-2,4-dioxo-1,2,3,4-tetrahydro-5-pyrimidinyl}carbonyl)glycine 103a) 1-(2-Cyclopropylethyl)-3-{[4-(methyloxy)phenyl]methyl}-2,4,6(1H,3H5H)-pyrimidinetrione. Cyclopropylethylamine hydrochloride (1.62 g, 13.32 mmoles) in chloroform (80 mL) was treated with diisopropylethylamine (2.3 mL, 13.32 mmoles) followed by 4-methoxyphenyl isocyanate (1.73 mL, 13.32 mmoles). The mixture was stirred for 2 hours, malonyl dichloride (1.55 mL, 16.0 mmoles) was added and the mixture heated at 43° C. for 4 hours. The mixture was washed with 1 molar hydrochloric acid and purified by flash chromatography (hexane to 35% ethyl acetate in hexane) to give the title compound which was obtained as a solid from hexane-diethyl ether (2.2 g, 54%). 1H NMR (400 MHz, DMSO-$d_6$) δ ppm 7.13 (d, 2H), 7.00 (d, J=9.09 Hz, 2H), 3.85 (s, 2H), 3.80-3.84 (m, 2H), 3.79 (s, 3H), 1.42 (q, J=7.07 Hz, 2H), 0.62-0.77 (m, 1H), 0.36-0.44 (m, 2H), −0.00-0.06 (m, 2H)

103b) N-({3-(2-Cyclopropylethyl)-6-hydroxy-1-[4-(methyloxy)phenyl]-2,4-dioxo-1,2,3,4-tetrahydro-5-pyrimidinyl}carbonyl)glycine. A mixture 1-(2-cyclopropylethyl)-3-{[4-(methyloxy)phenyl]methyl}-2,4,6(1H,3H,5H)-pyrimidinetrione (2.2 g, 7.27 mmole) and diisopropylethylamine (2.50 mL, 14.5 mmoles) in dichloromethane (80 mL) was treated with ethyl isocyanatoacetate (979 uL, 8.7 mmoles) and stirred overnight. The mixture was washed with 1 molar hydrochloric acid (×2), dried and evaporated. The residue was dissolved in ethanol (6 mL) and treated with 6 molar sodium hydroxide (5.0 mL). The mixture was stirred for 2 hours, acidified and extracted with ethyl acetate (×2), dried and evaporated. The residue was purified by flash chromatography (1.0% methanol-0.1% acetic acid in dichloromethane to 3.0% methanol-0.1% acetic acid in dichloromethane) to give the title compound (1.3 g, 44%). 1H NMR (400 MHz, DMSO-$d_6$) δ ppm 13.10 (s, 1H), 10.08 (s, 1H), 7.21 (d, J=5.31 Hz, 2H), 6.97-7.04 (m, 2H), 4.13 (d, J=5.81 Hz, 2H), 3.89-3.97 (m, 2H), 3.80 (s, 3H), 1.48 (q, J=6.91 Hz, 2H), 0.64-0.74 (m, J=15.22, 12.25, 7.39, 5.05 Hz, 1H), 0.41 (ddd, J=7.96, 5.68, 4.04 Hz, 2H), 0.02 (td, J=5.18, 4.29 Hz, 2H)

Example 104

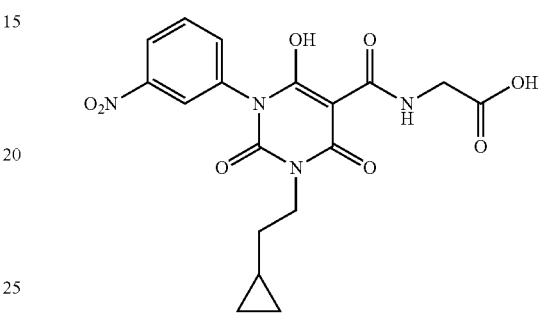

N-{[3-(2-Cyclopropylethyl)-6-hydroxy-1-(3-nitrophenyl)-2,4-dioxo-1,2,3,4-tetrahydro-5-pyrimidinyl]carbonyl}glycine 104a) 1-(2-Cyclopropylethyl)-3-(3-nitrophenyl)-2,4,6(1H,3H,5H)-pyrimidinetrione. Cyclopropylethylamine hydrochloride (1.62 g, 13.32 mmoles) in chloroform (80 mL) was treated with diisopropylethylamine (2.3 mL, 13.32 mmoles) followed by 3-nitrophenyl isocyanate (2.19 g, 13.32 mmoles). The mixture was stirred for 2 hours, malonyl dichloride (1.55 mL, 16.0 mmoles) was added and the mixture heated at 43° C. for 4 hours. The mixture was washed with 1 molar hydrochloric acid and purified by flash chromatography (hexane to 50% ethyl acetate in hexane) to give the title compound (1.66 g, 40%). 1H NMR (400 MHz, DMSO-$d_6$) δ ppm 8.27-8.36 (m, 1H), 8.22 (t, J=2.02 Hz, 1H), 7.80 (d, J=8.08 Hz, 1H), 7.71-7.77 (m, 1H), 3.90 (s, 2H), 3.84 (t, 2H), 1.44 (q, J=7.16 Hz, 2H), 0.62-0.80 (m, 1H), 0.31-0.47 (m, 2H), 0.05 (q, J=4.80 Hz, 2H)

104b) N-{[1-(2-Cyclopropylethyl)-6-hydroxy-3-(3-nitrophenyl)-2,4-dioxo-1,2,3,4-tetrahydro-5-pyrimidinyl]carbonyl}glycine. A mixture 1-(2-cyclopropylethyl)-3-(3-nitrophenyl)-2,4,6(1H,3H,5H)-pyrimidinetrione (1.66 g, 5.23 mmole) and diisopropylethylamine (1.80 mL, 10.5 mmoles) in dichloromethane (80 mL) was treated with ethyl isocyanatoacetate (704 uL, 6.27 mmoles) and stirred overnight. The mixture was washed with 1 molar hydrochloric acid (×2), dried and evaporated. The residue was dissolved in ethanol (6 mL) and treated with 6 molar sodium hydroxide (5.0 mL). The mixture was stirred for 1 hour, acidified and extracted with ethyl acetate (×2), dried and evaporated. A solid was obtained from acetic acid-water, which was purified by trituration in boiling chloroform to give the title compound (800 mg, 37%). 1H NMR (400 MHz, DMSO-$d_6$) δ ppm 13.12 (br. s, 1H), 10.03 (s, 1H), 8.35 (s, 1H), 8.32 (ddd, J=8.40, 1.64, 1.33 Hz, 1H), 7.82-7.88 (m, 1H), 7.79 (t, J=8.08 Hz, 1H), 4.14 (d, J=5.81 Hz, 2H), 3.88-3.97 (m, 2H), 1.50 (q, J=7.16 Hz, 2H), 0.66-0.76 (m, 1H), 0.42 (ddd, J=7.96, 5.68, 4.04 Hz, 2H), 0.05 (td, J=5.18, 4.29 Hz, 2H).

Example 105

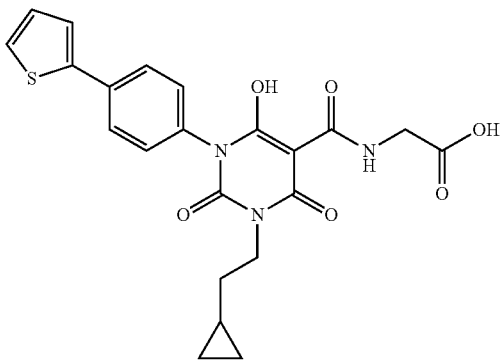

N-({3-(2-Cyclopropylethyl)-6-hydroxy-2,4-dioxo-1-[4-(2-thienyl)phenyl]-1,2,3,4-tetrahydro-5-pyrimidinyl}carbonyl)glycine 105a) 1-(2-Cyclopropylethyl)-3-[4-(2-thienyl)phenyl]-2,4,6(1H,3H,5H)-pyrimidinetrione. Cyclopropylethylamine hydrochloride (608 mg, 4.96 mmoles) in chloroform (50 mL) was treated with diisopropylethylamine (2.1 mL, 12.0 mmoles) followed by 2-(4-isocyanatophenyl) thiophene (1.0 g, 4.96 mmoles). The mixture was stirred for 2 hours, malonyl dichloride (583 uL, 6.0 mmoles) was added and the mixture heated at 63° C. for 2 hours. The mixture was washed with 1 molar hydrochloric acid and purified by flash chromatography (0-4.0% methanol in dichloromethane) to give the title compound (630 mg, 36%) 1H NMR (400 MHz, DMSO-d$_6$) δ ppm 7.75 (d, J=8.59 Hz, 2H), 7.61 (dd, J=5.05, 1.26 Hz, 1H), 7.57 (dd, J=3.54, 1.01 Hz, 1H), 7.27 (d, J=8.59 Hz, 2H), 7.18 (dd, J=5.18, 3.66 Hz, 1H), 3.89 (s, 2H), 3.84 (t, 2H), 1.44 (q, 2H), 0.63-0.76 (m, 1H), 0.37-0.46 (m, 2H), 0.05 (q, J=4.80 Hz, 2H)

105b) N-({3-(2-Cyclopropylethyl)-1-[4-(2-thienyl)phenyl]-6-hydroxy-2,4-dioxo-1,2,3,4-tetrahydro-5-pyrimidinyl}carbonyl)glycine. A mixture of 1-(2-cyclopropylethyl)-3-[4-(2-thienyl)phenyl]-2,4,6(1H,3H,5H)-pyrimidinetrione (630 mg, 1.78 mmoles) and diisopropylethylamine (616 uL, 2.13 mmoles) in dichloromethane (50 mL) was treated with ethyl isocyanatoacetate (239 uL, 2.13 mmoles) and stirred overnight. The mixture was washed with 1 molar hydrochloric acid (×2), dried and evaporated. The residue was dissolved in ethanol (5 mL) and treated with 6 molar sodium hydroxide (2.0 mL). The mixture was stirred for 2 hour, acidified and extracted with ethyl acetate (×2), dried and evaporated. Flash chromatography (dichloromethane to 3.5% methanol-0.1% acetic acid) gave the title compound which was recrystallized from dichloromethane (300 mg, 37%). 1H NMR (400 MHz, DMSO-d$_6$) δ ppm 13.11 (s, 1H), 10.07 (s, 1H), 7.75 (ddd, J=8.72, 2.53, 2.15 Hz, 2H), 7.60 (ddd, J=9.79, 4.36, 1.01 Hz, 2H), 7.36 (d, J=6.82 Hz, 2H), 7.18 (dd, J=5.05, 3.54 Hz, 1H), 4.14 (d, J=5.81 Hz, 2H), 3.90-3.99 (m, 2H), 1.50 (q, J=7.07 Hz, 2H), 0.65-0.75 (m, 1H), 0.42 (ddd, J=7.96, 5.68, 4.04 Hz, 2H), 0.03 (td, J=5.18, 4.29 Hz, 2H)

Example 106

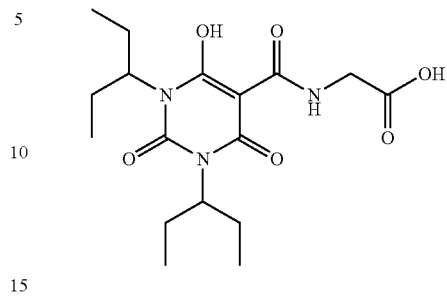

N-{[1,3-Bis(1-ethylpropyl)-6-hydroxy-2,4-dioxo-1,2,3,4-tetrahydro-5-pyrimidinyl]carbonyl}glycine 106a) N,N'-Bis(1-ethylpropyl)urea. A mixture of carbonyldiimidazole (3.0 g, 18.5 mmoles) and 3-aminopentane (4.66 mL, 40 mmoles) in dimethylformamide (25 mL) was heated at 70° C. for 3 hours. The mixture was cooled and partitioned between ethyl acetate and 1 molar hydrochloric acid. The aqueous was extracted with ethyl acetate and the combined extracts washed with 1 molar hydrochloric acid, dried and evaporated to a solid (3.6 g, 97%). 1H NMR (400 MHz, DMSO-d$_6$) δ ppm 5.37 (s, 2H), 1.55 (q, J=7.33 Hz, 4H), 1.13 (s, 12H), 0.76 (t, J=7.45 Hz, 6H).

106b) 1,3-Bis(1-ethylpropyl)-2,4,6(1H,3H,5H)-pyrimidinetrione. N,N'-bis(1-ethylpropyl)urea (1.03 g, 5.15 mmoles) in chloroform (60 mL) was treated with malonyl dichloride (600 uL, 6.2 mmoles) and heated at 70° C. for 3 hours. The mixture was washed with 1 molar hydrochloric acid (×2), dried and evaporated. Flash chromatography (hexane-50% ethyl acetate in hexane) gave the title compound (540 mg, 39%). 1H NMR (400 MHz, CHLOROFORM-d) δ ppm 4.45-4.76 (m, 2H), 3.66 (s, 2H), 1.91-2.14 (m, 4H), 1.55-1.87 (m, 4H), 0.85 (t, J=7.45 Hz, 12H)

106c) N-{[1,3-Bis(1-ethylpropyl)-6-hydroxy-2,4-dioxo-1,2,3,4-tetrahydro-5-pyrimidinyl]carbonyl}glycine. A mixture of 1,3-bis(1-ethylpropyl)-2,4,6(1H,3H,5H)-pyrimidinetrione (540 mg, 2.0 mmoles) and diisopropylethylamine (690 uL, 4.0 mmoles) in dichloromethane (50 mL) was treated with ethyl isocyanatoacetate (270 uL, 2.4 mmoles) and stirred overnight. The mixture was washed with 1 molar hydrochloric acid (×2), dried and evaporated. The residue was dissolved in ethanol (6 mL) and treated with 6 molar sodium hydroxide (4.0 mL). The mixture was stirred for 72 hour, acidified and extracted with ethyl acetate (×2), dried and evaporated. The residue was stored at −10° C. overnight, crystallized. The solid was slurried in hexane, collected, washed with hexane to give the title compound (300 mg, 40%). 1H NMR (400 MHz, DMSO-d$_6$) δ ppm 13.10 (br. s, 1H), 10.20 (br s, 1H), 4.65 (br. s, 2H), 4.13 (d, J=5.81 Hz, 2H), 2.02 (br. s, 4H), 1.69 (br. s, 4H), 0.77 (t, J=7.33 Hz, 12H)

Example 107

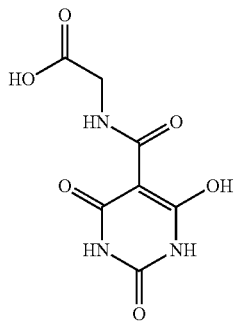 [SMILES: O=C(O)CNC(=O)c1c(O)[nH]c(=O)[nH]c1=O]

N-[(6-Hydroxy-2,4-dioxo-1,2,3,4-tetrahydro-5-pyrimidinyl)carbonyl]glycine

Barbituric acid (512 mg, 4 mmol) was dissolved in a mixture of dichloromethane (3 mL) and DMF (5 mL). N,N-Diisopropylethylamine (2 mL) was added followed by ethyl isocyanatoacetate (645 mg, 5 mmol) and the solution was stirred overnight. After evaporation of all volatiles, the residue was re-dissolved in a mixture of ethanol (5 mL) and 1M aqueous NaOH (5 mL). After stirring at room temperature for one hour, this solution was neutralized by addition of 1M aqueous HCl. The resulting solid was collected, washed with water, and dried under vacuum overnight to give the title compound (202 mg, 22%). LC/MS m/z 230 (M+H$^+$).

Example 108

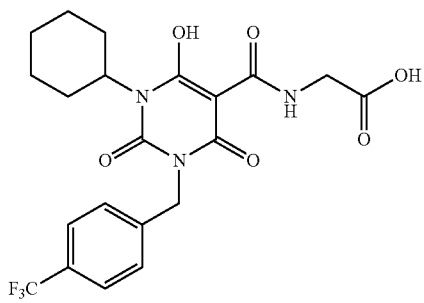 [SMILES: O=C(O)CNC(=O)c1c(O)n(C2CCCCC2)c(=O)n(Cc2ccc(C(F)(F)F)cc2)c1=O]

N-[(1-Cyclohexyl-6-hydroxy-2,4-dioxo-3-{[4-(trifluoromethyl)phenyl]methyl}-1,2,3,4-tetrahydro-5-pyrimidinyl)carbonyl]glycine A mixture of ethyl N-[(1-cyclohexyl-6-hydroxy-2,4-dioxo-1,2,3,4-tetrahydro-5-pyrimidinyl)carbonyl]glycinate (340 mg, 1.0 mmoles), pulv. potassium carbonate (750 mg, 5.35 mmoles) and 4-trifluoromethylbenzyl bromide (478 uL, 2.0 mmoles) in dimethylacetamide (5 mL) was vigorously stirred at 100° C. for 3 hours. The mixture was poured into 1 molar hydrochloric acid and extracted with ethyl acetate (×2). The combined organic solutions were washed with 1 molar hydrochloric acid and evaporated. The residue was purified by flash chromatography (10-50% ethyl acetate in hexane), the required fractions evaporated, dissolved in ethanol (5 mL) and 1 molar sodium hydroxide solution (3.0 mL) added. The mixture was stirred overnight, acidified and extracted with ethyl acetate (×2), the combined extracts washed with 1 molar hydrochloric acid, dried and evaporated. Recrystallization from ethanol-water gave the title compound (176 mg, 37.5%). 1H NMR (400 MHz, DMSO-d$_6$) δ ppm 13.10 (br. s., 1H), 10.13 (br. s., 1H), 7.69 (d, J=8.08 Hz, 2H), 7.51 (d, J=8.08 Hz, 2H), 5.07 (s, 2H), 4.64 (t, J=12.13 Hz, 1H), 4.13 (d, J=5.81 Hz, 2H), 2.13-2.32 (m, 2H), 1.78 (d, J=12.63 Hz, 2H), 1.50-1.72 (m, 3H), 1.28 (q, 2H), 1.11 (q, J=13.22 Hz, 1H).

Example 109

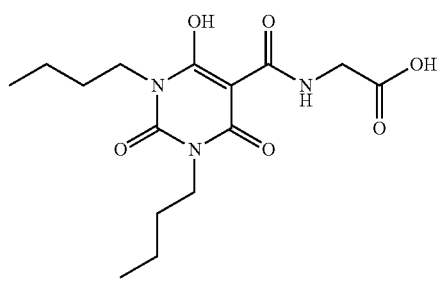 [SMILES: CCCCn1c(O)c(C(=O)NCC(=O)O)c(=O)n(CCCC)c1=O]

N-[(1,3-Dibutyl-6-hydroxy-2,4-dioxo-1,2,3,4-tetrahydro-5-pyrimidinyl)carbonyl]glycine 109a) 1,3-Dibutyl-2,4,6(1H,3H,5H)-pyrimidinetrione. 1-Butylisocyanate (2.25 ml, 20 mmoles) and butylamine (1.98 mL, 20 mmoles) were stirred together in dichloromethane (100 mL) for 2 hours. Malonyl dichloride (2.14 mL, 22 mmoles) was added and the mixture was heated under gentle reflux for 2 hours. The mixture was washed with 1 molar hydrochloric acid (×2), dried and evaporated. Flash chromatography (hexane-25% ethyl acetate-hexane) gave the title compound (1.32 g, 27%). 1H NMR (400 MHz, DMSO-d$_6$) δ ppm 3.65-3.77 (m, 6H), 1.48 (tt, 4H), 1.28 (tq, J=7.49, 7.33 Hz, 4H), 0.89 (t, J=7.33 Hz, 6H)

109b) N-[(1,3-Dibutyl-6-hydroxy-2,4-dioxo-1,2,3,4-tetrahydro-5-pyrimidinyl)carbonyl]glycine. A mixture of 1,3-dibutyl-2,4,6(1H,3H,5H)-pyrimidinetrione (1.3 g mg, 5.5 mmoles) and diisopropylethylamine (1.9 mL, 11.0 mmoles) in dichloromethane (20 mL) was treated with ethyl isocyanatoacetate (673 uL, 6.0 mmoles) and stirred for 24 hours. The mixture was washed with 1 molar hydrochloric acid (×2), dried and evaporated. The residue was taken up in ethanol (5 mL) and treated with 6 molar sodium hydroxide (3 mL) and stirred for 2 hours. The mixture was acidified with 1 molar hydrochloric acid and stirred for 30 minutes to give a solid which was recrystallized from acetic acid-water to afford the title compound (1.2 g, 64%). 1H NMR (400 MHz, DMSO-d$_6$) δ ppm 13.10 (br. s., 1H), 10.11 (t, J=6.19 Hz, 1H), 4.13 (d, J=5.81 Hz, 2H), 3.81 (t, 4H), 1.43-1.63 (m, 4H), 1.14-1.41 (m, 4H), 0.89 (t, J=7.33 Hz, 6H).

Example 110

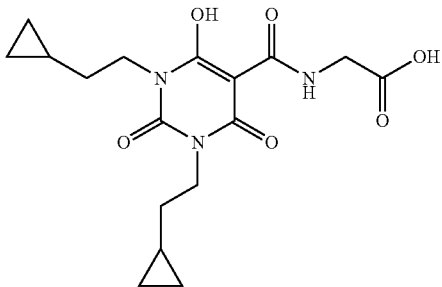 [SMILES: O=C(O)CNC(=O)c1c(O)n(CCC2CC2)c(=O)n(CCC2CC2)c1=O]

N-{[1,3-Bis(2-cyclopropylethyl)-6-hydroxy-2,4-dioxo-1,2,3,4-tetrahydro-5-pyrimidinyl]carbonyl}glycine 110a) N,N'-Bis(2-cyclopropylethyl)urea. A mixture of cyclopropylethylamine hydrochloride (5.15 g, 42.35 mmoles), sodium carbonate (4.56 g, 43 mmoles) and carbonyldiimidazole (2.99 g, 18.4 mmoles) in dimethylformamide (30 mL) was sealed in a pressure flask and heated at 100° C. for 2 hours. The mixture was acidified with 1 molar hydrochloric acid and extracted into ethyl acetate (×2). The combined extracts were washed with 1 molar hydrochloric acid, dried and evaporated to give the title compound (3.28 g, 79%). 1H NMR (400 MHz, DMSO-$d_6$) δ ppm 5.77 (br. s., 2H), 3.03 (t, J=6.95 Hz, 4H), 1.25 (q, J=7.07 Hz, 4H), 0.50-0.76 (m, 2H), 0.26-0.48 (m, 4H), −0.17-0.16 (m, 4H)

110b) 1,3-Bis(2-cyclopropylethyl)-2,4,6(1H,3H,5H)-pyrimidinetrione. Malonyl dichloride (2.02 mL, 20.8 mmoles) was added to a solution of N,N'-bis(2-cyclopropylethyl)urea (3.26 g, 16.6 mmoles) in dichloromethane (200 mL) and the mixture was heated under gentle reflux for 2 hours. The mixture was washed with 1 molar hydrochloric acid, evaporated and purified by flash chromatography (hexane-25% ethyl acetate-hexane) gave the title compound (1.05 g, 24%). 1H NMR (400 MHz, CHLOROFORM-d) δ ppm 3.94 (t, 4H), 3.61 (s, 2H), 1.46 (q, 4H), 0.55-0.75 (m, 2H), 0.33-0.49 (m, 4H), −0.04-0.08 (m, 4H)

110c) N-{[1,3-Bis(2-cyclopropylethyl)-6-hydroxy-2,4-dioxo-1,2,3,4-tetrahydro-5-pyrimidinyl]carbonyl}glycine. A mixture of 1,3-bis(2-cyclopropylethyl)-2,4,6(1H,3H,5H)-pyrimidinetrione (1.05 g, 3.97 mmoles) and diisopropylethylamine (1.51 mL, 8.7 mmoles) in dichloromethane (50 mL) was treated with ethyl isocyanatoacetate (980 uL, 8.7 mmoles) and stirred overnight. The mixture was washed with 1 molar hydrochloric acid (×2), dried and evaporated. The residue was taken up in ethanol (6 mL) and treated with 6 molar sodium hydroxide (4 mL) and stirred for 2 hours. The mixture was acidified with 1 molar hydrochloric acid and stirred for 30 minutes to give a solid which was recrystallized from acetic acid-water to afford the title compound (1.1 g, 76%). 1H NMR (400 MHz, DMSO-$d_6$) δ ppm 13.09 (br. s, 1H), 10.10 (t, J=5.81 Hz, 1H), 4.13 (d, J=5.81 Hz, 2H), 3.86-3.95 (m, 4H), 1.45 (q, J=7.07 Hz, 4H), 0.62-0.72 (m, J=15.13, 12.28, 7.33, 4.93 Hz, 2H), 0.38 (ddd, J=7.96, 5.68, 4.04 Hz, 4H), −0.00 (q, J=4.80 Hz, 4H)

Example 111

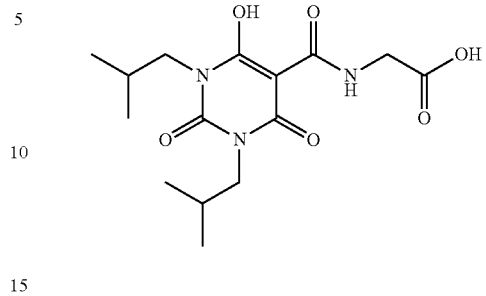

N-{[6-Hydroxy-1,3-bis(2-methylpropyl)-2,4-dioxo-1,2,3,4-tetrahydro-5-pyrimidinyl]carbonyl}glycine 111a) N,N'-Bis(2-methylpropyl)urea. A mixture of isobutylamine (3.98 mL, 40 mmoles) and carbonyldiimidazole (3.0 g, 18.5 mmoles) in dimethylformamide (6 mL) was sealed in a pressure flask and heated at 75° C. for 2 hours. The mixture was acidified with 1 molar hydrochloric acid and extracted into ethyl acetate (×2). The combined extracts were washed with 1 molar hydrochloric acid, dried and evaporated to give the title compound (3.2 g, 93%). 1H NMR (400 MHz, DMSO-$d_6$) δ ppm 5.79 (br. s., 2H), 2.81 (d, J=6.82 Hz, 4H), 1.59 (dq, J=13.39, 6.69 Hz, 2H), 0.82 (d, J=6.82 Hz, 12H)

111b) 1,3-Bis(2-methylpropyl)-2,4,6(1H,3H,5H)-pyrimidinetrione. Malonyl dichloride (2.2 mL, 22.3 mmoles) was added to a solution of N,N'-bis(2-methylpropyl)urea (3.2 g, 18.6 mmoles) in dichloromethane (175 mL) and the mixture was heated under gentle reflux for 2 hours. The mixture was washed with 1 molar hydrochloric acid, evaporated and purified by flash chromatography (hexane-25% ethyl acetate-hexane) gave the title compound (3.38 g, 76%). 1H NMR (400 MHz, CHLOROFORM-d) δ ppm 3.75 (d, J=7.33 Hz, 4H), 3.70 (s, 2H), 2.07 (dq, J=13.89, 7.07 Hz, 2H), 0.92 (d, J=6.82 Hz, 12H)

111c) N-{[6-Hydroxy-1,3-bis(2-methylpropyl)-2,4-dioxo-1,2,3,4-tetrahydro-5-pyrimidinyl]carbonyl}glycine. A mixture of 1,3-bis(2-methylpropyl)-2,4,6(1H,3H,5H)-pyrimidinetrione (3.3 g, 13.73 mmoles) and diisopropylethylamine (5.2 mL, 30 mmoles) in dichloromethane (100 mL) was treated with ethyl isocyanatoacetate (3.36 mL, 30 mmoles) and stirred overnight. The mixture was washed with 1 molar hydrochloric acid (×2), dried and evaporated to a solid which was slurried in hexane and collected. The solid was taken up in ethanol (10 mL) and treated with 6 molar sodium hydroxide (6 mL) and stirred for 2 hours. The mixture was acidified with 6 molar hydrochloric acid and diluted with 6 molar hydrochloric acid stirred for 30 minutes to give a solid which was recrystallized from acetic acid-water to afford the title compound (3.15 g, 67%). 1H NMR (400 MHz, DMSO-$d_6$) δ ppm 13.11 (br. s, 1H), 10.13 (t, J=5.81 Hz, 1H), 4.13 (d, J=5.81 Hz, 2H), 3.67 (d, J=7.33 Hz, 4H), 2.02 (dq, J=13.80, 6.92 Hz, 2H), 0.85 (d, J=6.82 Hz, 12H)

Example 112

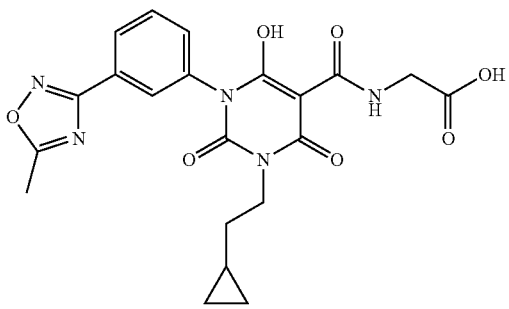 [SMILES: Cc1nc(-c2cccc(-n3c(O)c(C(=O)NCC(=O)O)c(=O)n(CCC4CC4)c3=O)c2)no1]

N-({3-(2-Cyclopropylethyl)-6-hydroxy-1-[3-(5-methyl-1,2,4-oxadiazol-3-yl)phenyl]-2,4-dioxo-1,2,3,4-tetrahydro-5-pyrimidinyl}carbonyl)glycine 112a) 1-(2-Cyclopropylethyl)-3-[3-(5-methyl-1,2,4-oxadiazol-3-yl)phenyl]-2,4,6(1H,3H,5H)-pyrimidinetrione. Cyclopropylethylamine hydrochloride (588 mg, 4.84 mmoles) in chloroform (50 mL) was treated with diisopropylethylamine (2.1 mL, 12.0 mmoles) followed by 3-(3-isocyanatophenyl)-5-methyl-1,2,4-oxadiazole (973 mg, 4.84 mmoles). The mixture was stirred for 2 hours, malonyl dichloride (583 uL, 6.0 mmoles) was added and the mixture heated at 63° C. for 2 hours. The mixture was washed with 1 molar hydrochloric acid and purified by flash chromatography (0-4.0% methanol in dichloromethane) to give the title compound (425 mg, 25%) 1H NMR (400 MHz, CHLOROFORM-d) δ ppm 8.19 (ddd, J=7.96, 1.39, 1.26 Hz, 1H), 7.95 (t, J=1.77 Hz, 1H), 7.64 (t, J=8.08 Hz, 1H), 7.36 (ddd, J=7.96, 2.15, 1.01 Hz, 1H), 4.03-4.09 (m, 2H), 3.89 (s, 2H), 2.68 (s, 3H), 1.54-1.57 (m, 1H), 0.67-0.77 (m, 1H), 0.46-0.52 (m, 2H), 0.10 (td, J=5.24, 4.42 Hz, 2H)

112b) N-({3-(2-Cyclopropylethyl)-6-hydroxy-1-[3-(5-methyl-1,2,4-oxadiazol-3-yl)phenyl]-2,4-dioxo-1,2,3,4-tetrahydro-5-pyrimidinyl}carbonyl)glycine. A mixture of 1-(2-cyclopropylethyl)-3-[3-(5-methyl-1,2,4-oxadiazol-3-yl)phenyl]-2,4,6(1H,3H,5H)-pyrimidinetrione (418 mg, 1.18 mmoles) and diisopropylethylamine (408 uL, 2.36 mmoles) in dichloromethane (50 mL) was treated with ethyl isocyanatoacetate (160 uL, 1.41 mmoles) and stirred overnight. The mixture was washed with 1 molar hydrochloric acid (×2), dried and evaporated. The residue was dissolved in ethanol (5 mL) and treated with 6 molar sodium hydroxide (2.0 mL). The mixture was stirred for 2 hour, acidified and extracted with ethyl acetate (×2), dried and evaporated. Flash chromatography (dichloromethane to 3.5% methanol-0.1% acetic acid) gave the title compound which was recrystallized from acetic acid-water (290 mg, 54%). 1H NMR (400 MHz, DMSO-d$_6$) δ ppm 13.10 (br. s, 1H), 10.06 (br. s, 1H), 8.05 (d, J=7.83 Hz, 1H), 7.98 (s, 1H), 7.67 (t, J=7.83 Hz, 1H). 7.55 (d, J=7.33 Hz, 1H), 4.14 (d, J=5.81 Hz, 2H), 3.88-3.98 (m, 2H), 2.68 (s, 3H), 1.50 (q, J=7.16 Hz, 2H), 0.66-0.76 (m, 1H), 0.42 (ddd, J=7.83, 5.68, 4.17 Hz, 2H), −0.01-0.08 (m, 2H).

Example 113

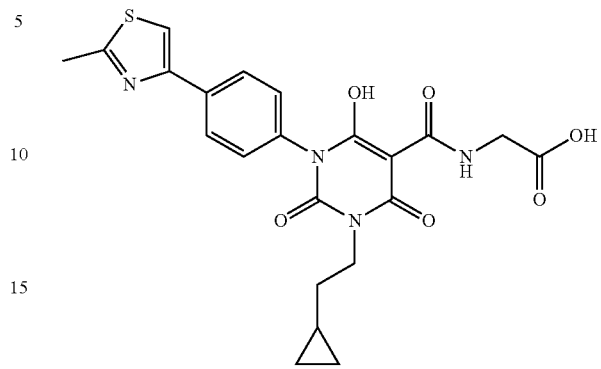

N-({3-(2-Cyclopropylethyl)-6-hydroxy-1-[4-(2-methyl-1,3-thiazol-4-yl)phenyl]-2,4-dioxo-1,2,3,4-tetrahydro-5-pyrimidinyl}carbonyl)glycine 113a) 1-(2-Cyclopropylethyl)-3-[4-(2-methyl-1,3-thiazol-4-yl)phenyl]-2,4,6(1H,3H,5H)-pyrimidinetrione. Cyclopropylethylamine hydrochloride (620 mg, 5.1 mmoles) in chloroform (50 mL) was treated with diisopropylethylamine (2.1 mL, 12.0 mmoles) followed by 4-(4-isocyanatophenyl)-2-methyl-1,3-thiazole (1.1 g, 5.1 mmoles). The mixture was stirred for 2 hours, malonyl dichloride (583 uL, 6.0 mmoles) was added and the mixture heated at 63° C. for 2 hours. The mixture was washed with 1 molar hydrochloric acid and purified by flash chromatography (0-7.0% methanol in dichloromethane) to give the title compound (620 mg, 33%) 1H NMR (400 MHz, CHLOROFORM-d) δ ppm 8.03 (d, J=8.59 Hz, 2H), 7.39 (s, 1H), 7.26 (d, J=8.84 Hz, 2H), 4.01-4.10 (m, 2H), 3.88 (s, 2H), 2.81 (s, 3H), 1.58 (q, 2H), 0.67-0.78 (m, 1H), 0.44-0.50 (m, 2H), 0.06-0.13 (m, 2H)

113b) N-({3-(2-Cyclopropylethyl)-6-hydroxy-1-[4-(2-methyl-1,3-thiazol-4-yl)phenyl]-2,4-dioxo-1,2,3,4-tetrahydro-5-pyrimidinyl}carbonyl)glycine. A mixture of 1-(2-cyclopropylethyl)-3-[4-(2-methyl-1,3-thiazol-4-yl)phenyl]-2,4,6(1H,3H,5H)-pyrimidinetrione (618 mg, 1.67 mmoles) and and diisopropylethylamine (578 uL, 3.34 mmoles) in dichloromethane (50 mL) was treated with ethyl isocyanatoacetate (224 uL, 2.0 mmoles) and stirred overnight. The mixture was washed with 1 molar hydrochloric acid (×2), dried and evaporated. The residue was dissolved in ethanol (5 mL) and treated with 6 molar sodium hydroxide (2.0 mL). The mixture was stirred for 2 hour, acidified and extracted with ethyl acetate (×2), dried and evaporated. Flash chromatography (dichloromethane to 3.5% methanol-0.1% acetic acid) gave the title compound which was obtained as a solid from diethyl ether. (210 mg, 27%). 1H NMR (400 MHz, DMSO-d$_6$) δ ppm 13.11 (br. s, 1H), 10.08 (br. s, 1H), 7.97-8.05 (m, 3H), 7.37 (d, J=6.82 Hz, 2H), 4.14 (d, J=5.56 Hz, 2H), 3.88-3.98 (m, 2H), 2.74 (s, 3H), 1.50 (q, J=7.07 Hz, 2H), 0.65-0.75 (m, 1H), 0.37-0.46 (m, 2H), 0.03 (q, J=4.72 Hz, 2H).

Example 114

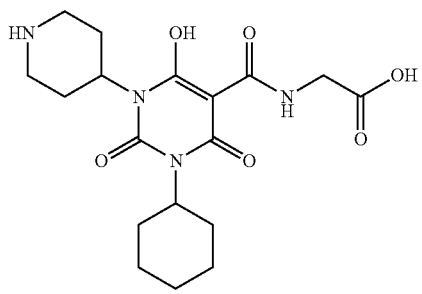 [SMILES: O=C(O)CNC(=O)c1c(O)n(C2CCNCC2)c(=O)n(C2CCCCC2)c1=O]

N-{[3-Cyclohexyl-6-hydroxy-2,4-dioxo-1-(4-piperidinyl)-1,2,3,4-tetrahydro-5-pyrimidinyl]carbonyl}glycine 114a) Phenylmethyl 4-(1,3-dioxo-1,3-dihydro-2H-isoindol-2-yl)-1-piperidinecarboxylate. A mixture of benzyl 4-hydroxy-1-piperidine carboxylate (2.0 g, 8.5 mmoles), phthalimide (2.5 g, 17 mmoles), triphenylphosphine (4.46 g, 17 mmoles) and diisopropyl azodicarboxylate (3.345 mL, 17 mmoles) were stirred together in tetrahydrofuran (60 mL) for 5 hours. The mixture was evaporated onto silica gel and chromatographed (hexane to 60% ethyl acetate-hexane). The fractions afforded crystalline product on standing (1.5 g, 48%). 1H NMR (400 MHz, DMSO-$d_6$) δ ppm 7.76-7.94 (m, 5H), 7.37-7.41 (m, 3H), 7.30-7.37 (m, 1H), 4.71-4.83 (m, 1H), 4.18-4.29 (m, 1H), 4.14 (d, J=13.64 Hz, 2H), 2.16 (dd, 2H), 1.73 (d, J=10.36 Hz, 2H), 1.18 (d, J=6.32 Hz, 2H)

114b) Phenylmethyl 4-amino-1-piperidinecarboxylate. A mixture of phenylmethyl 4-(1,3-dioxo-1,3-dihydro-2H-isoindol-2-yl)-1-piperidinecarboxylate (1.5 g, 4.11 mmoles) and 25% hydrazine hydrate (10.0 mL) in ethanol (20 mL) was heated under reflux for 30 minutes. The mixture was evaporated, re-diluted with ethanol and re-evaporated to a solid. The solid was slurried in diethyl ether, collected, washed with diethyl ether and the filtrate evaporated to give the title compound as an oil (quant.) 1H NMR (400 MHz, CHLOROFORM-d) δ ppm 7.25-7.45 (m, 5H), 5.14 (s, 2H), 4.89-5.07 (m, 1H), 3.18-3.42 (m, 2H), 2.76-2.95 (m, 2H), 1.74-1.94 (m, 2H), 1.51-1.68 (m, 2H), 1.28 (d, J=6.06 Hz, 2H).

114c) Phenylmethyl 4-(3-cyclohexyl-2,4,6-trioxotetrahydro-1(2H)-pyrimidinyl)-1-piperidinecarboxylate. A mixture of phenylmethyl 4-amino-1-piperidinecarboxylate (700 mg, 2.98 mmoles) and cyclohexyl isocyanate (457 uL, 3.6 mmoles) was stirred in chloroform (60 mL) for 2 hours. Malonyl dichloride (350 uL, 3.6 mmoles) was added and the mixture was stirred at 50° C. for 2 hours. The mixture was washed with 1 molar hydrochloric acid (×2) and evaporated onto silica gel. Flash chromatography (dichloromethane to 30% methanol in dichloromethane) gave the title compound (350 mg, 80%). 1H NMR (400 MHz, DMSO-$d_6$) δ ppm 7.24-7.47 (m, 5H), 5.10 (s, 2H), 4.61-4.78 (m, 1H), 4.35-4.52 (m, 1H), 4.09 (d, J=10.86 Hz, 2H), 3.70 (s, 2H), 2.85 (d, J=26.02 Hz, 2H), 2.20-2.33 (m, 2H), 2.14 (dd, 1H), 1.78 (d, 2H), 1.58 (d, J=11.12 Hz, 4H), 1.00-1.34 (m, 5H).

114d) N-{[3-Cyclohexyl-6-hydroxy-2,4-dioxo-1-(4-piperidinyl)-1,2,3,4-tetrahydro-5-pyrimidinyl]carbonyl} glycine. A mixture of phenylmethyl 4-(3-cyclohexyl-2,4,6-trioxotetrahydro-1(2H)-pyrimidinyl)-1-piperidinecarboxylate (530 mg, 1.24 mmoles) and diisopropylethylamine (536 uL, 3.1 mmoles) in chloroform (50 mL) was treated with ethyl isocyanatoacetate (225 uL, 2.0 mmoles) and stirred overnight. The mixture was washed with 1 molar hydrochloric acid (×2), dried and evaporated. The residue was dissolved in isopropanol (30 mL), the solution flushed with argon and 10% palladium on charcoal catalyst (100 mg) added. The mixture was shaken in a hydrogen atmosphere at 50 psi for 2 hours. The mixture was filtered, evaporated and treated with 1 molar sodium hydroxide solution overnight. Acidified and extracted into ethyl acetate. Preparative HPLC (10 to 80% acetonitrile-water-0.1% TFA) gave the title compound (120 mg, 24%). 1H NMR (400 MHz, DMSO-$d_6$) δ ppm 13.17 (s, 1H), 10.18 (s, 1H), 8.74 (d, J=11.12 Hz, 1H), 8.32-8.40 (m, 1H), 8.29 (s, 1H), 4.95 (t, J=12.63 Hz, 1H), 4.63 (t, J=12.63 Hz, 1H), 4.15 (d, J=5.81 Hz, 2H), 3.36 (d, J=12.13 Hz, 2H), 3.02 (q, J=12.55 Hz, 2H), 2.61-2.73 (m, 2H), 2.20-2.31 (m, 2H), 1.79 (d, J=12.38 Hz, 4H), 1.62 (s, 3H), 1.22-1.34 (m, 2H), 1.10 (d, J=16.42 Hz, 1H).

Example 115

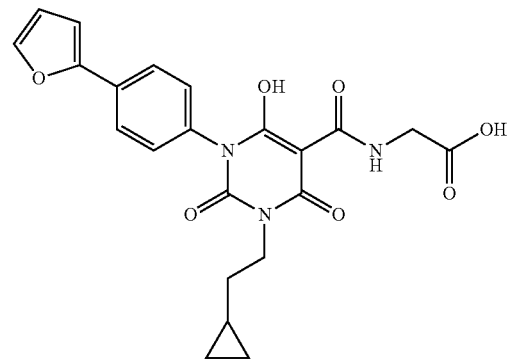 [SMILES: O=C(O)CNC(=O)c1c(O)n(-c2ccc(-c3ccco3)cc2)c(=O)n(CCC2CC2)c1=O]

N-({3-(2-Cyclopropylethyl)-1-[4-(2-furanyl)phenyl]-6-hydroxy-2,4-dioxo-1,2,3,4-tetrahydro-5-pyrimidinyl}carbonyl)glycine 115a) 1-(2-Cyclopropylethyl)-3-[4-(2-furanyl)phenyl]-2,4,6(1H,3H,5H)-pyrimidinetrione. Cyclopropylethylamine hydrochloride (693 mg, 5.67 mmoles) in chloroform (50 mL) was treated with diisopropylethylamine (1.04 mL, 6.0 mmoles) followed by 2-(4-isocyanatophenyl) furan (1.05 g, 5.67 mmoles). The mixture was stirred for 2 hours, malonyl dichloride (665 uL, 6.84 mmoles) was added and the mixture heated at 63° C. for 2 hours. The mixture was washed with 1 molar hydrochloric acid and purified by flash chromatography (0-3.5% methanol in dichloromethane) to give the title compound (330 mg, 17%) 1H NMR (400 MHz, DMSO-$d_6$) δ ppm 7.75 (d, J=8.59 Hz, 2H), 7.59-7.63 (m, 1H), 7.55-7.59 (m, 1H), 7.27 (d, J=8.59 Hz, 2H), 7.18 (dd, J=5.05, 3.54 Hz, 1H), 3.88 (s, 2H), 3.84 (t, 2H), 1.44 (q, J=7.33 Hz, 2H), 0.63-0.76 (m, 1H), 0.36-0.44 (m, 2H), 0.01-0.07 (m, 2H)

115b) N-({3-(2-Cyclopropylethyl)-1-[4-(2-furanyl)phenyl]-6-hydroxy-2,4-dioxo-1,2,3,4-tetrahydro-5-pyrimidinyl} carbonyl)glycine. A mixture 1-(2-cyclopropylethyl)-3-[4-(2-furanyl)phenyl]-2,4,6(1H,3H,5H)-pyrimidinetrione (330 mg, 0.976 mmoles) and diisopropylethylamine (337 uL, 1.95 mmoles) in dichloromethane (80 mL) was treated with ethyl isocyanatoacetate (131 uL, 1.17 mmoles) and stirred overnight. The mixture was washed with 1 molar hydrochloric acid (×2), dried and evaporated. The residue was dissolved in ethanol (5 mL) and treated with 6 molar sodium hydroxide (2.0 mL). The mixture was stirred for 2 hour, acidified and extracted with ethyl acetate (×2), dried and evaporated. Flash chromatography (dichloromethane to 3.5% methanol-0.1% acetic acid); material still impure, re-chromatographed (hexane-ethyl acetate) gave the title compound (30 mg, 7%). 1H NMR (400 MHz, DMSO-$d_6$) δ ppm 13.10 (s, 1H), 10.08 (br. s., 1H), 7.80 (s, 2H), 7.78 (s, 1H), 7.36 (d, J=7.33 Hz, 2H), 7.04 (d, J=3.28 Hz, 1H), 6.64 (dd, J=3.28, 1.77 Hz, 1H), 4.14 (d, J=5.81 Hz, 2H), 3.94 (t, 2H), 1.50 (q, J=6.65 Hz, 2H), 0.63-0.77 (m, 1H), 0.36-0.46 (m, 2H), −0.01-0.07 (m, 2H).

Example 116

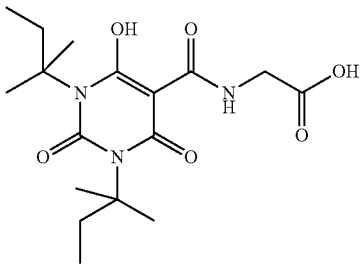 [SMILES: CCC(C)(C)n1c(O)c(C(=O)NCC(=O)O)c(=O)n(C(C)(C)CC)c1=O]

N-{[1,3-Bis(1,1-dimethylpropyl)-6-hydroxy-2,4-dioxo-1,2,3,4-tetrahydro-5-pyrimidinyl]carbonyl}glycine 116a) N,N'-Bis(1,1-dimethylpropyl)urea. A mixture of carbonyldiimidazole (3.0 g, 18.5 mmoles) and t-amylamine (4.7 mL, 40 mmoles) in dimethylformamide (25 mL) was heated at 70° C. for 3 hours. The mixture was cooled and partitioned between ethyl acetate and 1 molar hydrochloric acid. The aqueous was extracted with ethyl acetate and the combined extracts washed with 1 molar hydrochloric acid, dried and evaporated to a solid (2.9 g, 78%). 1H NMR (400 MHz, DMSO-$d_6$) δ ppm 5.37 (s, 2H), 1.55 (q, J=7.33 Hz, 4H), 1.13 (s, 12H), 0.76 (t, J=7.45 Hz, 6H).

116b) 1,3-Bis(1,1-dimethylpropyl)-2,4,6(1H,3H,5H)-pyrimidinetrione. N,N'-bis(1,1-dimethylpropyl)urea (1.6 g, 8.0 mmoles) in chloroform (60 mL) was treated with malonyl dichloride (935 uL, 9.6 mmoles) and heated at 70° C. for 3 hours. The mixture was washed with 1 molar hydrochloric acid (×2), dried and evaporated. Flash chromatography (hexane-50% ethyl acetate in hexane) gave the title compound (960 mg, 44%). 1H NMR (400 MHz, CHLOROFORM-d) δ ppm 3.49 (s, 2H), 2.04 (q, J=7.41 Hz, 4H), 1.55 (s, 12H), 0.85 (t, J=7.45 Hz, 6H).

116c) N-{[1,3-Bis(1,1-dimethylpropyl)-6-hydroxy-2,4-dioxo-1,2,3,4-tetrahydro-5-pyrimidinyl]carbonyl}glycine. A mixture of 1,3-bis(1,1-dimethylpropyl)-2,4,6(1H,3H,5H)-pyrimidinetrione (960 mg, 3.5 mmoles) and diisopropylethylamine (1.21 mL, 7.0 mmoles) in dichloromethane (50 mL) was treated with ethyl isocyanatoacetate (482 uL, 4.3 mmoles) and stirred overnight. The mixture was washed with 1 molar hydrochloric acid (×2), dried and evaporated. The residue was dissolved in ethanol (10 mL) and treated with 6 molar sodium hydroxide (5.0 mL). The mixture was stirred for 72 hour, acidified and extracted with ethyl acetate (×2), dried and evaporated. The residue was stored at −10° C. overnight, crystallized. The solid was slurried in hexane, collected, washed with hexane to give the title compound (600 mg, 46%). 1H NMR (400 MHz, DMSO-$d_6$) δ ppm 12.71 (br. s, 1H), 10.12 (t, J=6.06 Hz, 1H), 4.08 (d, J=5.81 Hz, 2H), 2.00-2.10 (m, 4H), 1.54 (s, 12H), 0.79 (m, 6H).

Example 117

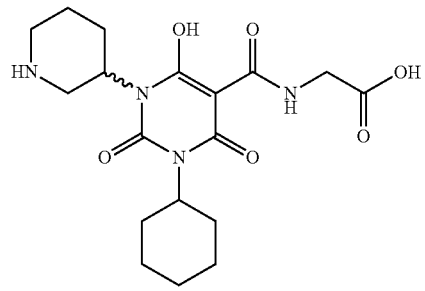 [SMILES: O=C(O)CNC(=O)c1c(O)n(C2CCCNC2)c(=O)n(C2CCCCC2)c1=O]

N-{[3-Cyclohexyl-6-hydroxy-2,4-dioxo-1-(3-piperidinyl)-1,2,3,4-tetrahydro-5-pyrimidinyl]carbonyl}glycine 117a) Phenylmethyl 3-(3-cyclohexyl-2,4,6-trioxotetrahydro-1(2H)-pyrimidinyl)-1-piperidinecarboxylate. A mixture of benzyl 3-aminopiperidine-1-carboxylate hydrochloride (1.51 g, 5.57 mmoles), diisopropylethylamine (965 uL, 5.57 mmoles) and cyclohexylisocyanate (708 uL, 5.57 mmoles) were stirred together in dichloromethane (60 mL) overnight. The mixture was washed with 1 molar hydrochloric acid (×2) and the solution dried. Malonyl dichloride (650 uL, 6.68 mmoles) was added and the mixture was heated under gentle reflux for 4 hours. The mixture was washed with 1 molar hydrochloric acid (×2) and the solution dried and evaporated. The title compound was obtained as a solid from diethyl ether (1.0 g, 42%). 1H NMR (400 MHz, DMSO-$d_6$) δ ppm 7.24-7.47 (m, 5H), 5.09 (s, 2H), 4.35-4.58 (m, 2H), 3.98 (d, 2H), 3.68 (d, J=4.29 Hz, 2H), 3.35-3.60 (m, 1H), 2.32 (q, 1H), 2.07-2.21 (m, 2H), 1.66-1.87 (m, 5H), 1.53-1.65 (m, 3H), 1.36-1.50 (m, 1H), 1.26 (q, J=13.05 Hz, 2H), 1.03-1.15 (m, 1H).

117b) Phenylmethyl 3-[3-cyclohexyl-5-({[2-(ethyloxy)-2-oxoethyl]amino}carbonyl)-6-hydroxy-2,4-dioxo-3,4-dihydro-1(2H)-pyrimidinyl]-1-piperidinecarboxylate. A mixture of phenylmethyl 3-(3-cyclohexyl-2,4,6-trioxotetrahydro-1(2H)-pyrimidinyl)-1-piperidinecarboxylate (1.0 g, 3.5 mmole) and diisopropylethylamine (1.2 mL, 7.0 mmoles) in dichloromethane (60 mL) was treated with ethyl isocyanatoacetate (450 uL, 4.0 mmoles) and stirred overnight. The mixture was washed with 1 molar hydrochloric acid (×2), dried and evaporated to a glassy solid (1.3 g, 67%). 1H NMR (400 MHz, DMSO-$d_6$) δ ppm 10.17 (br. s., 1H), 7.15-7.51 (m, 5H), 4.93-5.26 (m, 2H), 4.50-4.79 (m, 2H), 4.17-4.27 (m, 2H), 4.08-4.17 (m, 2H), 3.93-4.07 (m, 2H), 3.51-3.73 (m, 1H), 2.58-2.85 (m, 1H), 2.33-2.48 (m, 1H), 2.11-2.34 (m, 2H), 1.68-1.86 (m, 4H), 1.62 (d, J=11.62 Hz, 3H), 1.35-1.53 (m, 1H), 1.24-1.34 (m, 2H), 1.16-1.26 (m, 4H), 1.02-1.18 (m, 1H)

117c) N-{[3-Cyclohexyl-6-hydroxy-2,4-dioxo-1-(3-piperidinyl)-1,2,3,4-tetrahydro-5-pyrimidinyl]carbonyl} glycine hydrobromide. Phenylmethyl 3-[3-cyclohexyl-5-({[2-(ethyloxy)-2-oxoethyl]amino}carbonyl)-6-hydroxy-2,4-dioxo-3,4-dihydro-1(2H)-pyrimidinyl]-1-piperidinecarboxylate (1.2 g, 2.15 mmoles) was stirred in a mixture of acetic acid (30 mL) and 48% hydrobromic acid (5.0 mL) for 40 hours—reaction incomplete. The mixture was then heated at 60° C. for 2 hours, diluted with water and extracted with ethyl acetate (×5). The combined extracts were dried and evaporated, and recrystallized from diethyl ether-hexane to give the title compound (160 mg, 20%). 1H NMR (400 MHz, DMSO-$d_6$) δ ppm 12.84 (br. s., 1H), 10.11 (s, 1H), 8.86 (s, 1H), 5.12 (s, 1H), 4.63 (t, J=12.00 Hz, 1H), 4.09 (s, 2H), 3.66 (t, J=11.37 Hz, 1H), 3.28 (d, J=10.61 Hz, 2H), 2.77 (t, J=11.12 Hz, 1H), 2.36 (dd, J=12.38, 3.54 Hz, 1H), 2.22-2.32 (m, 2H), 1.89 (d, J=12.63 Hz, 1H), 1.69-1.81 (m, 4H), 1.55-1.67 (m, 4H), 1.27 (q, J=12.88 Hz, 2H), 1.11 (q, J=12.97 Hz, 1H)

Example 118

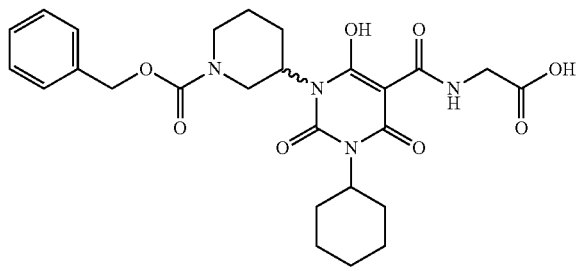 [SMILES: O=C(O)CNC(=O)c1c(O)n(C2CCCN(C(=O)OCc3ccccc3)C2)c(=O)n(C2CCCCC2)c1=O]

N-{[3-Cyclohexyl-6-hydroxy-2,4-dioxo-1-(1-{[(phenylmethyl)oxy]carbonyl}-3-piperidinyl)-1,2,3,4-tetrahydro-5-pyrimidinyl]carbonyl}glycine Phenylmethyl 3-[3-cyclohexyl-5-({[2-(ethyloxy)-2-oxoethyl]amino}carbonyl)-6-hydroxy-2,4-dioxo-3,4-dihydro-1(2H)-pyrimidinyl]-1-piperidinecarboxylate (100 mg, 0.18 mmoles) was dissolved in ethanol (3.0 mL) and treated with 6 molar sodium hydroxide (1.5 mL). The mixture was stirred for 2 hours, acidified and extracted with ethyl acetate (×2). The combined extracts were washed with 1 molar hydrochloric acid, dried and evaporated to a foam (80 mg, 84%). 1H NMR (400 MHz, DMSO-$d_6$) δ ppm 13.11 (s, 1H), 10.17 (s, 1H), 7.30-7.40 (m, 5H), 5.10 (s, 2H), 4.57-4.69 (m, 2H), 4.13 (d, J=5.81 Hz, 2H), 3.95-4.05 (m, 2H), 3.64 (s, 1H), 3.37 (s, 1H), 2.73 (s, 1H), 2.36-2.48 (m, 1H), 2.25 (q, J=11.62 Hz, 2H), 1.70-1.82 (m, 4H), 1.62 (d, J=11.37 Hz, 3H), 1.38-1.50 (m, 1H), 1.21-1.33 (m, 2H), 1.06-1.18 (m, 1H)

Example 119

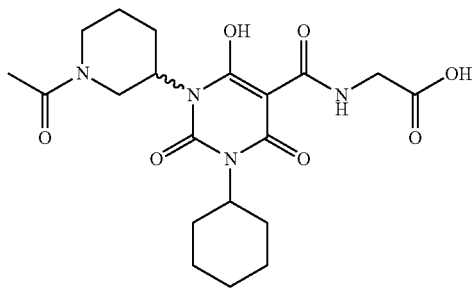 [SMILES: CC(=O)N1CCCC(n2c(O)c(C(=O)NCC(=O)O)c(=O)n(C3CCCCC3)c2=O)C1]

N-{[1-(1-Acetyl-3-piperidinyl)-3-cyclohexyl-6-hydroxy-2,4-dioxo-1,2,3,4-tetrahydro-5-pyrimidinyl]carbonyl}glycine A solution of N-{[3-cyclohexyl-6-hydroxy-2,4-dioxo-1-(3-piperidinyl)-1,2,3,4-tetrahydro-5-pyrimidinyl]carbonyl}glycine (500 mg, 1.26 mmoles) in acetic acid (5.0 mL) and acetic anhydride (5.0 mL) was heated at 130° C. for 2 hours. The mixture was cooled, diluted with ethyl acetate and washed with 1 molar hydrochloric acid (×3), dried and evaporated. Flash chromatography (dichloromethane to 4% methanol-0.1% acetic acid in dichloromethane) and recrystallization from ethanol-water gave the title compound (170 mg, 31%). 1H NMR (400 MHz, DMSO-$d_6$) δ ppm 13.10 (br. s., 1H), 10.17 (s, 1H), 4.46-4.73 (m, 2H), 4.25-4.46 (m, 1H), 4.13 (d, J=5.56 Hz, 2H), 3.67-3.92 (m, J=4.55 Hz, 1H), 3.24-3.43 (m, 1H), 2.94 (t, J=12.63 Hz, 1H), 2.34-2.48 (m, 1H), 2.25 (m, 2H), 1.97, 2.02 (2×s, 3H), 1.69-1.87 (m, 4H), 1.62 (m, 3H), 1.41-1.57 (m, 1H), 1.19-1.37 (m, 2H), 0.97-1.18 (m, 1H)

Example 120

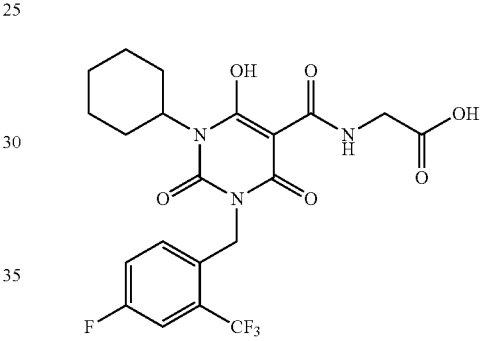

N-[(1-Cyclohexyl-3-{[4-fluoro-2-(trifluoromethyl)phenyl]methyl}-6-hydroxy-2,4-dioxo-1,2,3,4-tetrahydro-5-pyrimidinyl)carbonyl]glycine A mixture of ethyl N-[(1-cyclohexyl-6-hydroxy-2,4-dioxo-1,2,3,4-tetrahydro-5-pyrimidinyl)carbonyl]glycinate (340 mg, 1.0 mmoles), pulv. potassium carbonate (750 mg, 5.35 mmoles) and 4-fluoro-2-trifluoromethylbenzyl bromide (455 mg, 1.77 mmoles) in dimethylacetamide (6 mL) was vigorously stirred at 100° C. for 3 hours. The mixture was poured into 1 molar hydrochloric acid and extracted with ethyl acetate (×2). The combined organic solutions were washed with 1 molar hydrochloric acid and evaporated. The residue was purified by flash chromatography (10-50% ethyl acetate in hexane), the required fractions evaporated, dissolved in ethanol (5 mL) and 1 molar sodium hydroxide solution (3.0 mL) added. The mixture was stirred overnight, acidified and extracted with ethyl acetate (×2), the combined extracts washed with 1 molar hydrochloric acid, dried and evaporated. Recrystallization from hexane gave the title compound (184 mg, 38%). 1H NMR (400 MHz, DMSO-$d_6$) δ ppm 13.10 (br. s., 1H), 10.11 (br. s., 1H), 7.67 (dd, J=9.09, 2.78 Hz, 1H), 7.45 (ddd, J=8.40, 2.65 Hz, 1H), 7.29 (dd, J=8.59, 5.31 Hz, 1H), 5.13 (s, 2H), 4.64 (t, J=12.00 Hz, 1H), 4.13 (d, J=5.81 Hz, 2H), 2.24 (q, 2H), 1.78 (d, J=12.63 Hz, 2H), 1.53-1.73 (m, 3H), 1.28 (q, J=12.72 Hz, 2H), 1.10 (q, J=12.63 Hz, 1H)

Example 121

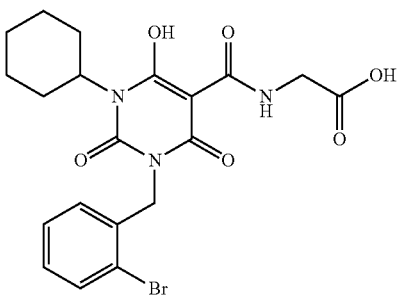 [SMILES: O=C(O)CNC(=O)c1c(O)n(C2CCCCC2)c(=O)n(Cc2ccccc2Br)c1=O]

N-({3-[(2-Bromophenyl)methyl]-1-cyclohexyl-6-hydroxy-2,4-dioxo-1,2,3,4-tetrahydro-5-pyrimidinyl}carbonyl)glycine A mixture of ethyl N-[(1-cyclohexyl-6-hydroxy-2,4-dioxo-1,2,3,4-tetrahydro-5-pyrimidinyl)carbonyl]glycinate (340 mg, 1.0 mmoles), pulv. potassium carbonate (750 mg, 5.35 mmoles) and 2-bromobenzyl bromide (480 mg, 1.92 mmoles) in dimethylacetamide (6 mL) was vigorously stirred at 100° C. for 3 hours. The mixture was poured into 1 molar hydrochloric acid and extracted with ethyl acetate (×2). The combined organic solutions were washed with 1 molar hydrochloric acid and evaporated. The residue was purified by flash chromatography (10-50% ethyl acetate in hexane), the required fractions evaporated, dissolved in ethanol (5 mL) and 1 molar sodium hydroxide solution (3.0 mL) added. The mixture was stirred overnight, acidified and extracted with ethyl acetate (×2), the combined extracts washed with 1 molar hydrochloric acid, dried and evaporated. Recrystallization from ethanol-water gave the title compound (150 mg, 38%). 1H NMR (400 MHz, DMSO-$d_6$) δ ppm 13.11 (br. s., 1H), 10.12 (br. s., 1H), 7.65 (dd, J=7.96, 1.14 Hz, 1H), 7.32 (ddd, J=7.52, 1.14 Hz, 1H), 7.22 (ddd, J=7.64, 1.64 Hz, 1H), 7.03 (dd, J=7.58, 1.26 Hz, 1H), 5.00 (s, 2H), 4.65 (t, J=12.13 Hz, 1H), 4.13 (d, J=5.81 Hz, 2H), 2.25 (q, 2H), 1.79 (d, J=12.88 Hz, 2H), 1.54-1.72 (m, 3H), 1.28 (q, J=13.14 Hz, 2H), 1.10 (q, J=12.38 Hz, 1H)

Example 122

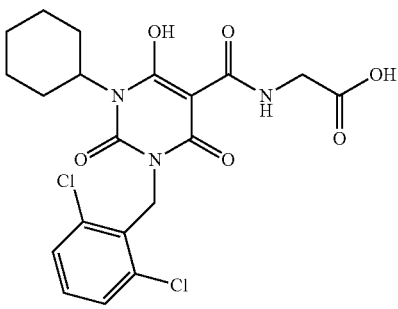 [SMILES: O=C(O)CNC(=O)c1c(O)n(C2CCCCC2)c(=O)n(Cc2c(Cl)cccc2Cl)c1=O]

N-({1-Cyclohexyl-3-[(2,6-dichlorophenyl)methyl]-6-hydroxy-2,4-dioxo-1,2,3,4-tetrahydro-5-pyrimidinyl}carbonyl)glycine A mixture of ethyl N-[(1-cyclohexyl-6-hydroxy-2,4-dioxo-1,2,3,4-tetrahydro-5-pyrimidinyl)carbonyl]glycinate (340 mg, 1.0 mmoles), pulv. potassium carbonate (750 mg, 5.35 mmoles) and 2,6-dichlorobenzyl bromide (440 mg, 2.0 mmoles) in dimethylacetamide (6 mL) was vigorously stirred at 100° C. for 3 hours. The mixture was poured into 1 molar hydrochloric acid and extracted with ethyl acetate (×2). The combined organic solutions were washed with 1 molar hydrochloric acid and evaporated. The residue was purified by flash chromatography (10-50% ethyl acetate in hexane), the required fractions evaporated, dissolved in ethanol (5 mL) and 1 molar sodium hydroxide solution (3.0 mL) added. The mixture was stirred overnight, acidified and extracted with ethyl acetate (×2), the combined extracts washed with 1 molar hydrochloric acid, dried and evaporated. Recrystallization from ethanol-water gave the title compound (150 mg, 32%). 1H NMR (400 MHz, DMSO-$d_6$) δ ppm 13.07 (br. s., 1H), 9.98 (br. s., 1H), 7.43 (dd, 2H), 7.30 (dd, 1H), 5.26 (s, 2H), 4.60 (t, J=12.00 Hz, 1H), 2.14-2.31 (m, 2H), 1.77 (d, J=12.88 Hz, 2H), 1.47-1.66 (m, 3H), 1.27 (q, 2H), 1.10 (q, 1H)

Example 123

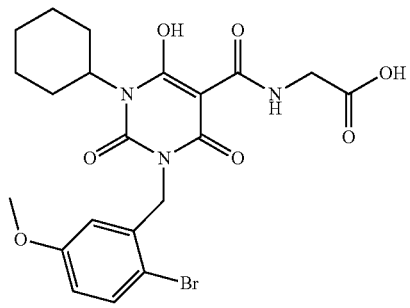 [SMILES: COc1ccc(Br)c(Cn2c(=O)c(C(=O)NCC(=O)O)c(O)n(C3CCCCC3)c2=O)c1]

N-[(3-{[2-Bromo-5-(methyloxy)phenyl]methyl}-1-cyclohexyl-6-hydroxy-2,4-dioxo-1,2,3,4-tetrahydro-5-pyrimidinyl)carbonyl]glycine A mixture of ethyl N-[(1-cyclohexyl-6-hydroxy-2,4-dioxo-1,2,3,4-tetrahydro-5-pyrimidinyl)carbonyl]glycinate (340 mg, 1.0 mmoles), pulv. potassium carbonate (750 mg, 5.35 mmoles) and 2-bromo-5-methoxybenzyl bromide (560 mg, 2.0 mmoles) in dimethylacetamide (6 mL) was vigorously stirred at 100° C. for 3 hours. The mixture was poured into 1 molar hydrochloric acid and extracted with ethyl acetate (×2). The combined organic solutions were washed with 1 molar hydrochloric acid and evaporated. The residue was purified by flash chromatography (10-50% ethyl acetate in hexane), the required fractions evaporated, dissolved in ethanol (5 mL) and 1 molar sodium hydroxide solution (3.0 mL) added. The mixture was stirred overnight, acidified and extracted with ethyl acetate (×2), the combined extracts washed with 1 molar hydrochloric acid, dried and evaporated. Recrystallization from acetic acid-water gave the title compound (150 mg, 29%). 1H NMR (400 MHz, DMSO-$d_6$) δ ppm 13.04 (br. s., 1H), 10.12 (br. s., 1H), 7.55 (d, J=8.84 Hz, 1H), 6.84 (dd, J=8.84, 3.03 Hz, 1H), 6.50 (d, J=2.78 Hz, 1H), 4.94 (s, 2H), 4.65 (t, J=11.75 Hz, 1H), 4.13 (d, J=5.81 Hz, 2H), 3.69 (s, 3H), 2.25 (q, 2H), 1.79 (d, J=13.14 Hz, 2H), 1.54-1.74 (m, 3H), 1.28 (q, J=12.72 Hz, 2H), 1.10 (q, J=12.88 Hz, 1H)

Example 124

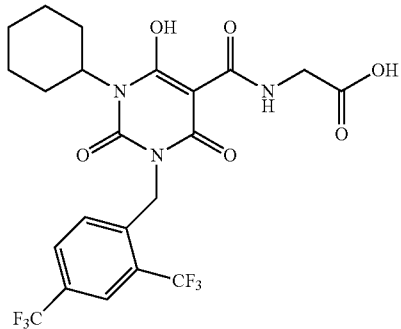 [SMILES: O=C(O)CNC(=O)c1c(O)n(C2CCCCC2)c(=O)n(Cc2ccc(C(F)(F)F)cc2C(F)(F)F)c1=O]

N-[(3-{[2,4-Bis(trifluoromethyl)phenyl]methyl}-1-cyclohexyl-6-hydroxy-2,4-dioxo-1,2,3,4-tetrahydro-5-pyrimidinyl)carbonyl]glycine A mixture of ethyl N-[(1-cyclohexyl-6-hydroxy-2,4-dioxo-1,2,3,4-tetrahydro-5-pyrimidinyl)carbonyl]glycinate (340 mg, 1.0 mmoles), pulv. potassium carbonate (750 mg, 5.35 mmoles) and 2,4-bis(trifluoromethyl)benzyl bromide (375 uL, 2.0 mmoles) in dimethylacetamide (6 mL) was vigorously stirred at 100° C. for 3 hours. The mixture was poured into 1 molar hydrochloric acid and extracted with ethyl acetate (×2). The combined organic solutions were washed with 1 molar hydrochloric acid and evaporated. The residue was purified by flash chromatography (10-50% ethyl acetate in hexane), the required fractions evaporated, dissolved in ethanol (5 mL) and 1 molar sodium hydroxide solution (3.0 mL) added. The mixture was stirred overnight, acidified and extracted with ethyl acetate (×2), the combined extracts washed with 1 molar hydrochloric acid, dried and evaporated. Recrystallization from acetic acid-water gave the title compound (180 mg, 34%). 1H NMR (400 MHz, DMSO-$d_6$) δ ppm 13.11 (br. s., 1H), 8.06 (s, 1H), 7.98 (d, J=8.59 Hz, 1H), 7.53 (d, J=8.34 Hz, 1H), 5.23 (s, 2H), 4.64 (t, J=12.00 Hz, 1H), 4.13 (d, J=5.56 Hz, 2H), 2.24 (q, 2H), 1.78 (d, J=12.63 Hz, 2H), 1.52-1.73 (m, 3H), 1.28 (q, J=13.05 Hz, 2H), 1.10 (q, 1H).

Example 125

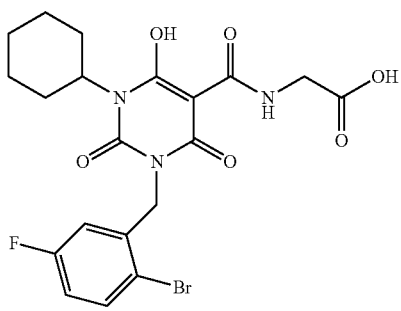 [SMILES: O=C(O)CNC(=O)c1c(O)n(C2CCCCC2)c(=O)n(Cc2cc(F)ccc2Br)c1=O]

N-({3-[(2-Bromo-5-fluorophenyl)methyl]-1-cyclohexyl-6-hydroxy-2,4-dioxo-1,2,3,4-tetrahydro-5-pyrimidinyl}carbonyl)glycine A mixture of ethyl N-[(1-cyclohexyl-6-hydroxy-2,4-dioxo-1,2,3,4-tetrahydro-5-pyrimidinyl)carbonyl]glycinate (340 mg, 1.0 mmoles), pulv. potassium carbonate (750 mg, 5.35 mmoles) and 2-bromo-5-fluorobenzyl bromide (375 uL, 2.0 mmoles) in dimethylacetamide (6 mL) was vigorously stirred at 100° C. for 3 hours. The mixture was poured into 1 molar hydrochloric acid and extracted with ethyl acetate (×2). The combined organic solutions were washed with 1 molar hydrochloric acid and evaporated. The residue was purified by flash chromatography (10-50% ethyl acetate in hexane), the required fractions evaporated, dissolved in ethanol (5 mL) and 1 molar sodium hydroxide solution (3.0 mL) added. The mixture was stirred overnight, acidified and extracted with ethyl acetate (×2), the combined extracts washed with 1 molar hydrochloric acid, dried and evaporated. Recrystallization from acetic acid-water gave the title compound (160 mg, 31%). 1H NMR (400 MHz, DMSO-$d_6$) δ ppm 13.10 (br. s., 1H), 10.10 (br. s., 1H), 7.69 (dd, J=8.59, 5.31 Hz, 1H), 7.11 (ddd, J=8.53, 3.16 Hz, 1H), 7.05 (dd, J=9.60, 2.78 Hz, 1H), 4.95 (s, 2H), 4.63 (t, J=12.38 Hz, 1H), 4.13 (d, J=5.81 Hz, 2H), 2.24 (q, 2H), 1.79 (d, J=13.14 Hz, 2H), 1.52-1.74 (m, J=27.54, 11.62 Hz, 3H), 1.28 (q, J=12.88 Hz, 2H), 1.10 (q, J=12.97 Hz, 1H).

Example 126

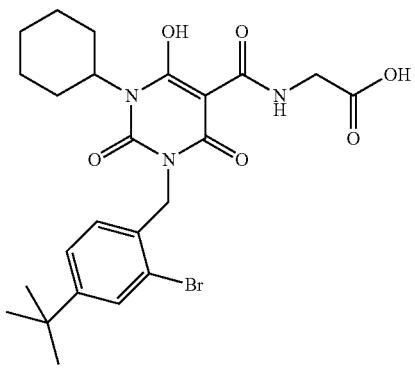 [SMILES: CC(C)(C)c1ccc(Cn2c(=O)c(C(=O)NCC(=O)O)c(O)n(C3CCCCC3)c2=O)c(Br)c1]

N-[(3-{[2-Bromo-4-(1,1-dimethylethyl)phenyl]methyl}-1-cyclohexyl-6-hydroxy-2,4-dioxo-1,2,3,4-tetrahydro-5-pyrimidinyl)carbonyl]glycine A mixture of ethyl N-[(1-cyclohexyl-6-hydroxy-2,4-dioxo-1,2,3,4-tetrahydro-5-pyrimidinyl)carbonyl]glycinate (340 mg, 1.0 mmoles), pulv. potassium carbonate (740 mg, 5.35 mmoles) and 2-bromo-1-(bromomethyl)-4-(1,1-dimethylethyl)benzene (612 mg, 2.0 mmoles) in dimethylformamide (5 mL) was vigorously stirred at 100° C. for 3 hours. The mixture was poured into 1 molar hydrochloric acid and extracted with ethyl acetate (×2). The combined organic solutions were washed with 1 molar hydrochloric acid and evaporated. The residue was purified by flash chromatography (10-50% ethyl acetate in hexane), the required fractions evaporated, dissolved in ethanol (5 mL) and 1 molar sodium hydroxide solution (1.0 mL) and 6 molar sodium hydroxide (1.0 mL) added. The mixture was stirred overnight, acidified and extracted with ethyl acetate (×2), the combined extracts washed with 1 molar hydrochloric acid, dried and evaporated. Preparative HPLC (50-90% acetonitrile-water-0.1% TFA) gave the title compound (40 mg, 7.5%). 1H NMR (400 MHz, DMSO-$d_6$) δ ppm 13.17 (br. s., 1H), 10.14 (br. s., 1H), 7.59 (d, J=1.52 Hz, 1H), 7.33 (dd, J=8.08, 1.52 Hz, 1H), 6.92 (d, J=8.08 Hz, 1H), 4.96

(s, 2H), 4.65 (t, J=11.75 Hz, 1H), 4.13 (d, J=5.56 Hz, 2H), 2.25 (q, J=11.54 Hz, 2H), 1.79 (d, J=12.13 Hz, 2H), 1.53-1.73 (m, 3H), 1.20-1.38 (m, 11H), 1.11 (q, 1H)

Example 127

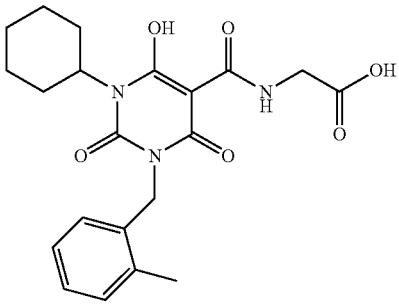 [SMILES: Cc1ccccc1Cn1c(=O)c(C(=O)NCC(=O)O)c(O)n(C2CCCCC2)c1=O]

N-({1-Cyclohexyl-6-hydroxy-3-[(2-methylphenyl)methyl]-2,4-dioxo-1,2,3,4-tetrahydro-5-pyrimidinyl}carbonyl)glycine A mixture of ethyl N-[(1-cyclohexyl-6-hydroxy-2,4-dioxo-1,2,3,4-tetrahydro-5-pyrimidinyl)carbonyl]glycinate (340 mg, 1.0 mmoles), pulv. potassium carbonate (740 mg, 5.35 mmoles) and 2-methylbenzene (268 uL, 2.0 mmoles) in dimethylformamide (5 mL) was vigorously stirred at 100° C. for 3 hours. The mixture was poured into 1 molar hydrochloric acid and extracted with ethyl acetate (×2). The combined organic solutions were washed with 1 molar hydrochloric acid and evaporated. The residue was purified by flash chromatography (10-50% ethyl acetate in hexane), the required fractions evaporated, dissolved in ethanol (5 mL) and 1 molar sodium hydroxide solution (3.0 mL) added. The mixture was stirred overnight, acidified and extracted with ethyl acetate (×2), the combined extracts washed with 1 molar hydrochloric acid, dried and evaporated. Preparative HPLC (20-90% acetonitrile-water-0.1% TFA) gave the title compound (12 mg, 3.0%). 1H NMR (400 MHz, DMSO-$d_6$) δ ppm 13.11 (br. s., 1H), 10.15 (br. s., 1H), 7.00-7.29 (m, 3H), 6.89 (d, J=6.82 Hz, 1H), 4.96 (s, 2H), 4.65 (t, J=12.25 Hz, 1H), 4.13 (d, J=5.56 Hz, 2H), 2.35 (s, 3H), 2.26 (q, 2H), 1.78 (d, J=12.13 Hz, 2H), 1.51-1.72 (m, 3H), 1.28 (q, 2H), 1.10 (q, 1H).

Example 128

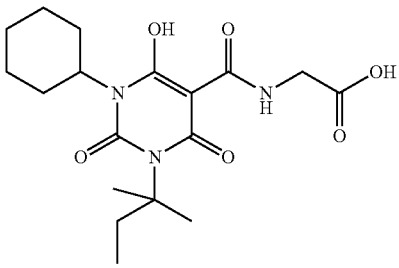 [SMILES: CCC(C)(C)n1c(=O)c(C(=O)NCC(=O)O)c(O)n(C2CCCCC2)c1=O]

N-{[1-Cyclohexyl-3-(1,1-dimethylpropyl)-6-hydroxy-2,4-dioxo-1,2,3,4-tetrahydro-5-pyrimidinyl]carbonyl}glycine 128a) 1-Cyclohexyl-3-(1,1-dimethylpropyl)-2,4,6(1H,3H,5H)-pyrimidinetrione. A mixture of t-amylamine (1.18 mL, 10 mmoles) and cyclohexyl isocyanate (1.28 mL, 10 mmoles) in chloroform (50 mL) was stirred overnight. Malonyl dichloride (1.16 mL, 12 mmoles) was added and the mixture was heated at 50° C. for 3 hours. The mixture was evaporated and flash chromatographed (ethyl acetate 10-50% in hexane) to give the title compound (1.9 g, 68%). 1H NMR (400 MHz, CHLOROFORM-d) δ ppm 4.54 (tt, J=12.25, 3.66 Hz, 1H), 3.56 (s, 2H), 2.23 (ddd, J=24.88, 12.51, 3.54 Hz, 2H), 2.06 (q, J=7.58 Hz, 2H), 1.77-1.91 (m, 2H), 1.52-1.72 (m, 9H), 1.35 (qt, J=13.09, 3.28, 3.16 Hz, 2H), 1.22 (qt, J=12.87, 12.66, 3.28 Hz, 1H), 0.83 (t, J=7.45 Hz, 3H)

128b) N-{[1-Cyclohexyl-3-(1,1-dimethylpropyl)-6-hydroxy-2,4-dioxo-1,2,3,4-tetrahydro-5-pyrimidinyl]carbonyl}glycine. A mixture of 1-cyclohexyl-3-(1,1-dimethylpropyl)-2,4,6(1H,3H,5H)-pyrimidinetrione (1.9 g, 6.8 mmoles), diisopropylethylamine (2.35 mL, 13.6 mmoles) and ethyl isocyanatoacetate (915 uL, 8.16 mmoles) in dichloromethane (60 mL) was stirred for 72 hours. The mixture was washed with 1 molar hydrochloric acid (×2) and evaporated. The residue was dissolved in ethanol (10 mL), treated with 6 molar sodium hydroxide (5 mL) and stirred overnight. The mixture was diluted with ethyl acetate, washed with 1 molar hydrochloric acid (×2), dried and evaporated. The residue was crystallized from a small amount of acetic acid to give the title compound (960 mg, 37%). 1H NMR (400 MHz, DMSO-$d_6$) δ ppm 13.06 (br. s., 1H), 10.09 (br. s., 1H), 4.54 (t, J=11.12 Hz, 1H), 4.10 (d, J=5.81 Hz, 2H), 2.22 (qd, 1H), 2.06 (q, J=7.33 Hz, 2H), 1.78 (d, J=12.38 Hz, 2H), 1.46-1.69 (m, 9H), 1.28 (q, J=13.05 Hz, 2H), 1.11 (q, J=12.88 Hz, 1H), 0.77 (t, J=7.45 Hz, 3H)

Example 129

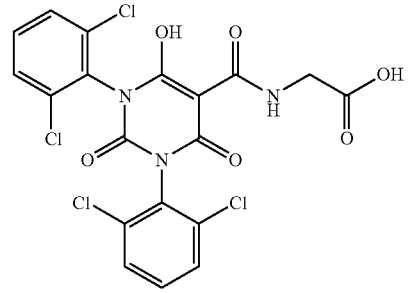 [SMILES: O=C(O)CNC(=O)c1c(O)n(-c2c(Cl)cccc2Cl)c(=O)n(-c2c(Cl)cccc2Cl)c1=O]

N-{[1,3-Bis(2,6-dichlorophenyl)-6-hydroxy-2,4-dioxo-1,2,3,4-tetrahydro-5-pyrimidinyl]carbonyl}glycine 129a) N,N'-Bis(2,6-dichlorophenyl)urea. 2,6 dichloroaniline (3.47 g, 21.4 mmoles) and carbonyldiimidazole (3.24 g, 20 mmoles) were heated together in dimethylformamide (75 mL) for 4 hours. The mixture was cooled and partitioned between ethyl acetate and 1 molar hydrochloric acid, which produced a solid. The solid was collected washed with ethyl acetate, hexane and dried to give the title compound (940 mg, 27%). 1H NMR (400 MHz, DMSO-$d_6$) δ ppm 8.44 (s, 2H), 7.52 (d, J=8.08 Hz, 4H), 7.28-7.35 (m, 2H)

129b) 1,3-Bis(2,6-dichlorophenyl)-2,4,6(1H,3H,5H)-pyrimidinetrione. A mixture of N,N'-bis(2,6-dichlorophenyl) urea (850 mg, 2.43 mmoles) and malonyl dichloride (240 uL, 2.47 mmoles) in chloroform (500 mL) was heated under reflux for 3 hours. Another aliquot of malonyl dichloride (240 uL, 2.47 mmoles) was added and heating continued for a further 2 hours. The mixture was filtered, evaporated and purified by flash chromatography (dichloromethane to 2% methanol in dichloromethane) to give the title compound (200 mg, 20%). 1H NMR (400 MHz, DMSO-$d_6$) δ ppm 7.66 (d, J=8.08 Hz, 4H), 7.53 (t, J=8.08 Hz, 2H), 4.93 (br. s, 2H)

129c) N-{[1,3-Bis(2,6-dichlorophenyl)-6-hydroxy-2,4-dioxo-1,2,3,4-tetrahydro-5-pyrimidinyl]carbonyl}glycine. A mixture of 1,3-bis(2,6-dichlorophenyl)-2,4,6(1H,3H,5H)-pyrimidinetrione (200 mg, 0.478 mmoles), diisopropylethylamine (210 uL, 0.96 mmoles) and ethyl isocyanatoacetate (126 uL, 0.574 mmoles) in dichloromethane (50 mL) was stirred overnight. Reaction was very slow, therefore additional diisopropylethylamine (1.0 mL, 3.4 mmoles) and ethyl isocyanatoacetate (500 uL, 2.6 mmoles) was added and the mixture was heated batchwise (3×20 mL) in a microwave reactor at 120° C. for 20 minutes. The combined reaction mixtures was washed with 1 molar hydrochloric acid (×2) and evaporated. The residue was dissolved in ethanol (5 mL), treated with 6 molar sodium hydroxide (5 mL) and stirred for 1 hour. The mixture was diluted with ethyl acetate, washed with 1 molar hydrochloric acid (×2), dried and evaporated. The residue was crystallized from a small amount of acetic acid to give the title compound (138 mg, 55%). 1H NMR (400 MHz, DMSO-$d_6$) δ ppm 13.25 (br. s., 1H), 10.11 (t, J=5.68 Hz, 1H), 7.67-7.76 (m, 4H), 7.59 (dd, J=8.84, 7.58 Hz, 2H), 4.18 (d, J=5.56 Hz, 2H).

BIOLOGICAL BACKGROUND

The following references set out information about the target enzymes, HIF prolyl hydroxylases, and methods and materials for measuring inhibition of same by small molecules.

M. Hirsilä, P. Koivunen, V. Günzler, K. I. Kivirikko, and J. Myllyharju "Characterization of the Human Prolyl 4-Hydroxylases That Modify the Hypoxia-inducible Factor" *J. Biol. Chem.*, 2003, 278, 30772-30780.

C. Willam, L. G. Nicholls, P. J. Ratcliffe, C. W. Pugh, P. H. Maxwell "The prolyl hydroxylase enzymes that act as oxygen sensors regulating destruction of hypoxia-inducible factor α" *Advan. Enzyme Regul.*, 2004, 44, 75-92

M. S. Wiesener, J. S. Jürgensen, C. Rosenberger, C. K. Scholze, J. H. Hörstrup, C. Warnecke, S. Mandriota, I. Bechmann, U. A. Frei, C. W. Pugh, P. J. Ratcliffe, S. Bachmann, P. H. Maxwell, and K.-U. Eckardt "Widespread hypoxia-inducible expression of HIF-2α in distinct cell populations of different organs" *FASEB J.*, 2003, 17, 271-273.

S. J. Klaus, C. J. Molineaux, T. B. Neff, V. Guenzler-Pukall, I. Lansetmo Parobok, T. W. Seeley, R. C. Stephenson "Use of hypoxia-inducible factor α (HIFα) stabilizers for enhancing erythropoiesis" PCT Int. Appl. (2004), WO 2004108121 A1

C. Warnecke, Z. Zaborowska, J. Kurreck, V. A. Erdmann, U. Frei, M. Wiesener, and K.-U. Eckardt "Differentiating the functional role of hypoxia-inducible factor (HIF)-1α and HIF-2α (EPAS-1) by the use of RNA interference: erythropoietin is a HIF-2a target gene in Hep3B and Kelly cells" *FASEB J.*, 2004, 18, 1462-1464.

For the Expression of EGLN3 See:

R. K. Bruick and S. L. McKnight "A Conserved Family of Prolyl-4-Hydroxylases That Modify HIF" *Science*, 2001, 294, 1337-1340.

For the Expression of HIF2α-CODD See:
a) P. Jaakkola, D. R. Mole, Y.-M. Tian, M. I. Wilson, J. Gielbert, S. J. Gaskell, A. von Kriegsheim, H. F. Hebestreit, M. Mukherji, C. J. Schofield, P. H. Maxwell, C. W. Pugh, P, J. Ratcliffe "Targeting of HIF-α to the von Hippel-Lindau Ubiquitylation Complex by $O_2$-Regulated Prolyl Hydroxylation" *Science*, 2001, 292, 468-472.
b) M. Ivan, K. Kondo, H. Yang, W. Kim, J. Valiando, M. Ohh, A. Salic, J. M. Asara, W. S. Lane, W. G. Kaelin Jr. "HIFα Targeted for VHL-Mediated Destruction by Proline Hydroxylation: Implications for $O_2$ Sensing" *Science*, 2001, 292, 464-468.

For the Expression of VHL, Elongin b and Elongin c See:
A. Pause, S. Lee, R. A. Worrell, D. Y. T. Chen, W. H. Burgess, W. M. Linehan, R. D. Klausner "The von Hippel-Lindau tumor-suppressor gene product forms a stable complex with human CUL-2, a member of the Cdc53 family of proteins" *Proc. Natl. Acad. Sci. USA*, 1997, 94, 2156-2161.

Biological Assay(s)

EGLN3 Assay

Materials:

His-MBP-EGLN3 (6HisMBPAttB1EGLN3(1-239)) was expressed in *E. Coli* and purified from an amylase affinity column. Biotin-VBC [6HisSumoCysVHL(2-213), 6HisSumoElonginB(1-118), and 6HisSumoElonginC(1-112)] and His-GB1-HIF2α-CODD (6HisGB1tevHIF2A (467-572)) were expressed from *E. Coli*.

Method:

Cy5-labelled HIF2a CODD, and a biotin-labeled VBC complex were used to determine EGLN3 inhibition. EGLN3 hydroxylation of the Cy5CODD substrate results in its recognition by the biotin-VBC. Addition of a Europium/streptavidin (Eu/SA) chelate results in proximity of Eu to Cy5 in the product, allowing for detection by energy transfer. A ratio of Cy5 to Eu emission (LANCE Ratio) is the ultimate readout, as this normalized parameter has significantly less variance than the Cy5 emission alone.

Then 50 nL of inhibitors in DMSO (or DMSO controls) were stamped into a 384-well low volume Corning NBS plate, followed by addition of 2.5 µL of enzyme [50 mL buffer (50 mM HEPES/50 mM KCl)+1 mL of a 10 mg/mL BSA in buffer+6.25 µL of a 10 mg/mL $FeCl_2$ solution in water+100 µL of a 200 mM solution of ascorbic acid in water+15.63 µL EGLN3] or control [50 mL buffer+1 mL of a 10 mg/mL BSA in buffer+6.25 µL of a 10 mg/mL $FeCl_2$ solution in water+100 µL of a 200 mM solution of ascorbic acid in water]. Following a 3 minutes incubation, 2.5 µL of substrate [50 mL Buffer+68.6 µL biotin-VBC+70.4 µL Eu (at 710 µg/mL stock)+91.6 µL Cy5CODD+50 µL of a 20 mM solution of 2-oxoglutaric acid in water+0.3 mM CHAPS] was added and incubated for 30 minutes. The plate was loaded into a PerkinElmer Viewlux for imaging. For dose response experiments, normalized data were fit by ABASE/XC50 using the equation y=a+(b−a)/(1+(10^x/10^c)^d), where a is the minimum % activity, b is the maximum % activity, c is the $pIC_{50}$, and d is the Hill slope.

All exemplified compounds herein (Examples 1 to 129) have demonstrated in vitro EGLN3 inhibitory activity in this assay and have $IC_{50}$'s in the range of 0.8 nanomolar to 20 micromolar. This range represents the data accumulated as of the time of filing this application. Later testing may show variations in $IC_{50}$ data due to variations in reagents, conditions and variations in the method(s) used from those given herein above. Thus, these values are to be viewed as illustrative rather than absolute.

Measure Epo Protein Produced by Hep3B Cell Line Using ELISA Method.

Hep3B cells obtained from the American Type Culture Collection (ATCC) are seeded at 2×10^4 cells/well in Dulbecco's Modified Eagle Medium (DMEM)+10% FBS in 96-well plates. Cells are incubated at 37 deg C./5% CO2/90% humidity (standard cell culture incubation conditions). After overnight adherence, medium is removed and replaced with DMEM without serum containing test compound or DMSO negative control. Following 48 hours incubation, cell culture medium is collected and assayed by ELISA to quantitate Epo protein.

Of the exemplified compounds tested to date all, except Examples 8, 9, 31, 35, 39, 88, 91, 93, and 94, have demonstrated $EC_{50}$'s in the Hep3B ELISA assay in the range of 0.4 micromolar to 100 micromolar using the reagents and under the conditions outlined herein above. Examples 8, 9, 31, 35, 39, 88, 91, 93, and 94, have demonstrated $EC_{50}$'s in the Hep3B ELISA assay of greater than 100 micromolar, the maximum concentration tested. This range represents the data accumulated as of the time of the filing of this application. Later testing may show variations in $EC_{50}$ data due to variations in reagents, conditions and variations in the method(s) used from those given herein above. Thus, these values are to be viewed as illustrative rather than absolute.

These compound are believed to be useful in therapy as defined above and to not have unacceptable or untoward effects when used in compliance with a permitted therapeutic regime.

The foregoing examples and assay have been set forth to illustrate the invention, not limit it. What is reserved to the inventors is to be determined by reference to the claims.

What is claimed is:

1. A compound according to formula (I):

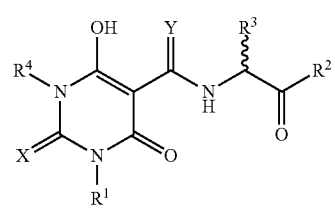

wherein:
$R^1$ and $R^4$ are each independently selected from the group consisting of hydrogen, $C_1$-$C_{10}$alkyl, $C_2$-$C_{10}$alkenyl, $C_2$-$C_{10}$alkynyl, $C_3$-$C_8$cycloalkyl, $C_3$-$C_8$cycloalkyl-$C_1$-$C_{10}$alkyl, $C_5$-$C_8$cycloalkenyl, $C_5$-$C_8$cycloalkenyl-$C_1$-$C_{10}$alkyl, $C_3$-$C_8$heterocycloalkyl, $C_3$-$C_8$heterocycloalkyl-$C_1$-$C_{10}$alkyl, aryl, aryl-$C_1$-$C_{10}$alkyl, heteroaryl and heteroaryl-$C_1$-$C_{10}$alkyl;
$R^2$ is —$OR^9$;
$R^3$ is H;
$R^9$ is H or a cation;
X is O; and
Y is O;
where any carbon or heteroatom of $R^1$, and $R^4$ is unsubstituted;
and a pharmaceutically acceptable salt thereof.

2. A method of treating anemia in a human in need thereof which comprises administering to such human a therapeutically effective amount of a compound as described in claim 1.

3. A method of treating anemia in a human in need thereof which comprises administering to such human a therapeutically effective amount of N-[(1,3-dicyclohexyl-6-hydroxy-2,4-dioxo-1,2,3,4-tetrahydro-5-pyrimidinyl)carbonyl]glycine, or a pharmaceutically acceptable salt thereof.

4. A method of treating anemia in a human in need thereof which comprises administering to such human a therapeutically effective amount of N-[(1,3-dicyclohexyl-6-hydroxy-2,4-dioxo-1,2,3,4-tetrahydro-5-pyrimidinyl)carbonyl]glycine.

* * * * *